(12) United States Patent
Guichou et al.

(10) Patent No.: US 8,901,295 B2
(45) Date of Patent: Dec. 2, 2014

(54) INHIBITORS OF CYCLOPHILINS AND USES THEREOF

(71) Applicant: Institut National de la Sante et de la Recherche Medicale (INSERM), Paris (FR)

(72) Inventors: Jean-Francois Guichou, Montpellier (FR); Lionel Colliandre, Orleans Cedex 2 (FR); Hakim Ahmed-Belkacem, Creteil (FR); Jean-Michel Pawlotsky, Creteil (FR)

(73) Assignees: Institut National de la Sante et de la Recherche Medicale (INSERM), Paris (FR); Universite Montpellier 1, Montpellier (FR); Universite Paris-EST Creteil val de Marne, Creteil (FR); Assistance Publique-Hopitaux de Paris, Paris (FR); Centre National de la Recherche Scientifique, Paris (FR)

( * ) Notice: Subject to any disclaimer, the term of this patent is extended or adjusted under 35 U.S.C. 154(b) by 0 days.

(21) Appl. No.: 14/186,432

(22) Filed: Feb. 21, 2014

(65) Prior Publication Data

US 2014/0179687 A1    Jun. 26, 2014

Related U.S. Application Data

(62) Division of application No. 13/517,148, filed as application No. PCT/EP2010/070359 on Dec. 21, 2010, now Pat. No. 8,802,666.

(30) Foreign Application Priority Data

Dec. 21, 2009  (EP) ..................................... 09306294

(51) Int. Cl.
*C07D 207/06* (2006.01)
*C07D 211/42* (2006.01)
(Continued)

(52) U.S. Cl.
CPC ............ *C07C 275/24* (2013.01); *C07D 211/42* (2013.01); *C07D 413/06* (2013.01); *C07D 307/52* (2013.01); *C07D 295/13* (2013.01); *C07D 209/08* (2013.01); *C07D 213/74* (2013.01); *C07D 277/40* (2013.01); *C07D 285/135* (2013.01); *C07D 249/08* (2013.01); *C07D 317/58* (2013.01); *C07D 401/12* (2013.01); *C07D 231/20* (2013.01); *C07D 213/72* (2013.01); *C07D 207/06* (2013.01); *C07D 213/40* (2013.01); *C07D 233/32* (2013.01); *C07D 223/04* (2013.01); *C07D 231/04* (2013.01); *C07D 413/04* (2013.01); *C07D 401/04* (2013.01); *C07D 211/56* (2013.01); *C07D 295/192* (2013.01); *C07D 513/04* (2013.01); *C07D 405/12* (2013.01); *C07D 211/60* (2013.01); *C07D 307/14* (2013.01); *C07D 309/06* (2013.01); *C07D 241/18* (2013.01); *C07C 335/12* (2013.01); *C07D 295/135* (2013.01); *C07D 413/12* (2013.01); *C07D 309/04* (2013.01); *C07D 213/73* (2013.01); *C07D 401/06* (2013.01); *C07D 211/46* (2013.01); *C07D 403/06* (2013.01); *C07C 291/02* (2013.01); *C07D 261/08* (2013.01); *C07D 295/08* (2013.01); *C07D 211/16* (2013.01); *C07D 401/14* (2013.01); *C07D 235/16* (2013.01); *C07D 319/18* (2013.01); *C07D 307/81* (2013.01); *C07D 207/10* (2013.01); *C07D 239/26* (2013.01); *C07C 307/06* (2013.01); *C07D 239/92* (2013.01); *C07D 231/12* (2013.01); *C07D 295/155* (2013.01); *C07D 213/30* (2013.01); *C07C 323/59* (2013.01); *C07D 235/14* (2013.01); *C07D 317/60* (2013.01)
USPC ........... 540/607; 544/131; 544/166; 544/168; 544/335; 548/247; 549/336; 549/426; 549/441; 560/34

(58) Field of Classification Search
None
See application file for complete search history.

(56) References Cited

FOREIGN PATENT DOCUMENTS

WO    WO 2006/117549    11/2006

OTHER PUBLICATIONS

Davidson et al., WO 2006/117549 Al (CAS Abstract).

(Continued)

*Primary Examiner* — Janet L Andres
*Assistant Examiner* — Timothy R Rozof
(74) *Attorney, Agent, or Firm* — Whitham Curtis Christofferson & Cook, PC

(57) ABSTRACT

The present invention relates to a compound of formula (I):

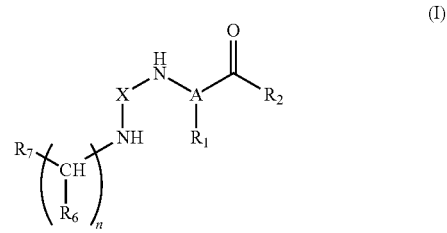

wherein:
n is 0, 1 or 2;
A is in particular CH or N;
X is in particular CO, $SO_2$, CS, and $R_1$ is in particular H,
$R_2$ is a group of formula $NR_3R_4$ or $OR_5$, $R_3$ and $R_4$ being in particular H, and $R_5$ an alkyl group,
$R_6$ is in particular H or an alkyl group, and
$R_7$ is in particular an aryl group,
for its use in the prevention and/or the treatment of viral pathologies or infections.

4 Claims, No Drawings

(51) Int. Cl.

| | |
|---|---|
| C07D 213/72 | (2006.01) |
| C07D 223/04 | (2006.01) |
| C07D 231/12 | (2006.01) |
| C07D 235/16 | (2006.01) |
| C07D 239/26 | (2006.01) |
| C07D 249/08 | (2006.01) |
| C07D 261/08 | (2006.01) |
| C07D 295/155 | (2006.01) |
| C07D 307/81 | (2006.01) |
| C07D 309/06 | (2006.01) |
| C07D 317/60 | (2006.01) |
| C07D 319/18 | (2006.01) |
| C07D 401/06 | (2006.01) |
| C07D 413/06 | (2006.01) |
| C07D 307/52 | (2006.01) |
| C07D 295/13 | (2006.01) |
| C07D 209/08 | (2006.01) |
| C07D 213/74 | (2006.01) |
| C07D 277/40 | (2006.01) |
| C07D 285/135 | (2006.01) |
| C07D 317/58 | (2006.01) |
| C07D 401/12 | (2006.01) |
| C07D 231/20 | (2006.01) |
| C07D 213/40 | (2006.01) |
| C07D 233/32 | (2006.01) |
| C07D 231/04 | (2006.01) |
| C07D 413/04 | (2006.01) |
| C07D 401/04 | (2006.01) |
| C07C 275/24 | (2006.01) |
| C07D 211/56 | (2006.01) |
| C07D 295/192 | (2006.01) |
| C07D 513/04 | (2006.01) |
| C07D 405/12 | (2006.01) |
| C07D 211/60 | (2006.01) |
| C07D 307/14 | (2006.01) |
| C07D 241/18 | (2006.01) |
| C07C 335/12 | (2006.01) |
| C07D 295/135 | (2006.01) |
| C07D 413/12 | (2006.01) |
| C07D 309/04 | (2006.01) |
| C07D 213/73 | (2006.01) |
| C07D 211/46 | (2006.01) |
| C07D 403/06 | (2006.01) |
| C07C 291/02 | (2006.01) |
| C07D 295/08 | (2006.01) |
| C07D 211/16 | (2006.01) |
| C07D 401/14 | (2006.01) |
| C07D 207/10 | (2006.01) |
| C07C 307/06 | (2006.01) |
| C07D 239/92 | (2006.01) |
| C07D 213/30 | (2006.01) |
| C07C 323/59 | (2006.01) |
| C07D 235/14 | (2006.01) |

(56) References Cited

OTHER PUBLICATIONS

Fischer et al., 11(8) Current Opinion in Investigational Drugs, 911-918 (2010).

Yang et al., 1(6) Current Opinion in Virology 607-616 (2011).

INHIBITORS OF CYCLOPHILINS AND USES THEREOF

The present invention concerns new inhibitors of cyclophilins, as well as uses thereof.

Cyclophilins (or Cyp) are members of the immunophilin class of proteins, comprising in particular cyclophilin A (CypA), cyclophilin B (CypB), and cyclophilin D (CypD). These ubiquitous cellular proteins possess cis-trans prolyl isomerase (PPIase) activities (Fischer, G., H. Bang, and C. Mech. 1984. Determination of enzymatic catalysis for the cis-trans-isomerization of peptide binding in proline-containing peptides. Biomed. Biochim. Acta 43:1101-1111) and are assumed to be involved in protein folding and to function as chaperones in intracellular transport (Snyder, S. H., and D. M. Sabatini. 1995. Immunophilins and the nervous system. Nat. Med. 1:32-37). Cyclophilins are also known to be the intracellular receptor molecules for cyclosporines (Handschumacher, R. E., M. W. Harding, J. Rice, R. J. Drugge, and D. W. Speicher. 1984. Cyclophilin: a specific cytosolic binding protein for cyclosporin A. Science 226:544-546), a class of cyclic undecapeptides produced by *Trichoderma polysporum* (Dreyfuss, M., E. Harri, H. Hoffmann, H. Kobel, W. Pache, and H. Tscherter. 1976. Cyclosporin A and C. New metabolites from *Trichoderma polysporum*. Eur. J. Appl. Microbiol, 3:125-133). Binding of cyclosporines to cyclophilins leads to the blockade of the isomerase activity.

These cyclophilins are known as drug targets for a number of diseases including HIV infection (J. Luban et al., Cell, 1993, 73, 1067-1078; Daelemans et al., Antiviral Res. 2009 Oct. 24), malaria (Bell et al., *Int J Parasitol* 2005) and ischemic (Yang Y, Moir E, Kontopidis G, Taylor P, Wear M A, Malone K, Dunsmore C J, Page A P, Turner N J, Walkinshaw M D. Biochem Biophys Res Commun. 2007 Nov. 30; 363(4) 1013-9).

Among known cyclophilin inhibitors, the [D-MeAla]$^3$-[EtVal]$^4$-cyclosporin (also known as Debio 025—Debiopharm), as well as NIM811 ([MeIle]$^4$-cyclosporin—Novartis) may be cited. The compound Debio 025 is a cyclic undecapeptide and is in particular reported by Wenger et al. in WO 00/01715 (CAS Registry Number 254435-95-5). The compound NIM811 is a cyclic undecapeptide and is in particular reported by Ko et al. in EP 0 484 281.

These known inhibitors are molecules with a high molecular weight.

The aim of the present invention is to provide new inhibitors of the cyclophilins, such as human cyclophilins A, B, and D, having an improved pharmacological profile.

The aim of the present invention is to provide new inhibitors of cyclophilins having a low molecular weight and being suitable for oral administration.

Another aim of the present invention is to provide inhibitors of cyclophilins having a selective inhibition activity for each cyclophilin.

The present invention relates to compounds having formula (I):

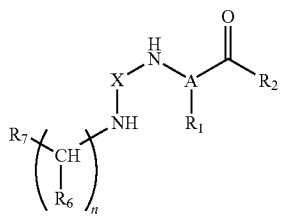

(I)

wherein:
n is 0, 1, 2 or 3;
A is CH or N, or A is C and form, together with $R_1$, $R_2$ and CO, a heterocyclyl group comprising from 5 to 20 atoms, possibly substituted;
X is CO, $SO_2$, or CS;
$R_1$ is chosen from the group consisting of: H, alkyl groups, and aralkyl groups, said alkyl or aralkyl groups being possibly substituted,
$R_2$ is a group of formula $NR_3R_4$ or $OR_5$, wherein:
$R_3$ and $R_4$ being each independently chosen from: H, $OR_a$, alkyl groups, aralkyl groups, and aryl groups, $R_a$ being chosen from the group consisting of: H, alkyl groups, aryl groups, and aralkyl groups;
wherein $R_3$ and $R_4$ may form, together with the nitrogen atom carrying them, a heterocyclyl group comprising from 5 to 20 atoms, possibly substituted,
$R_5$ is chosen from: alkyl groups, aryl groups, and aralkyl groups,
wherein $R_5$ may form, together with the oxygen atom carrying it, a heterocyclyl group from 5 to 20 atoms, possibly substituted,
$R_6$ is H or an alkyl group, or may form together with $R_2$ a heterocyclyl group from 20 to 30 atoms, preferably from 25 to 30 atoms, or may form together with $R_1$ a heterocyclyl group from 10 to 30 atoms,
$R_7$ is chosen from the group consisting of: aryl groups, heteroaryl groups,
wherein, when A is N, $R_1$ and $R_2$ may form, together with A and CO, a heterocyclyl group comprising from 5 to 20 atoms, possibly substituted,
or their pharmaceutically acceptable salts, hydrates or hydrated salts or their polymorphic crystalline structures, racemates, diastereomers or enantiomers, for their use in the prevention and/or the treatment of viral pathologies or infections.

The term "alkyl" (or "Alk") means a saturated or unsaturated aliphatic hydrocarbon group which may be straight or branched having 1 to 12 carbon atoms in the chain. Preferred alkyl groups have 1 to 6 carbon atoms in the chain. "Branched" means that one or lower alkyl groups such as methyl, ethyl or propyl are attached to a linear alkyl chain. "Lower alkyl" means 1 to 4 carbon atoms in the chain which may be straight or branched. The alkyl may be substituted with one or more "alkyl group substituents" which may be the same or different, and include for instance halo, cycloalkyl, hydroxy, alkoxy, amino, acylamino, aroylamino, carboxy.

The term "halo" (or "Hal") refers to the atoms of the group 17 of the periodic table (halogens) and includes in particular fluorine, chlorine, bromine, and iodine atom.

The terms "arylalkyl" or "aralkyl" refer to an alkyl moiety in which an alkyl hydrogen atom is replaced by an aryl group (possibly substituted). Examples of "arylalkyl" or "aralkyl" include benzyl and 9-fluorenyl groups.

The term "cycloalkyl" as employed herein includes saturated cyclic, bicyclic, tricyclic, or polycyclic hydrocarbon groups having 3 to 12 carbons, wherein any ring atom capable of substitution may be substituted by a substituent. Examples of cycloalkyl moieties include, but are not limited to, cyclohexyl and adamantyl.

The term "aryl" refers to an aromatic monocyclic, bicyclic, or tricyclic hydrocarbon ring system, wherein any ring atom capable of substitution may be substituted by a substituent. Examples of aryl moieties include, but are not limited to, phenyl, naphthyl, and anthracenyl.

The term "heterocyclyl" refers to a nonaromatic 3-10 membered monocyclic, 8-12 membered bicyclic, or 11-14 membered tricyclic ring system having 1-3 heteroatoms if monocyclic, 1-6 heteroatoms if bicyclic, or 1-9 heteroatoms if tricyclic, said heteroatoms selected from O, N, or S (e.g., carbon atoms and 1-3, 1-6, or 1-9 heteroatoms of N, O, or S if monocyclic, bicyclic, or tricyclic, respectively), wherein any ring atom capable of substitution may be substituted by a substituent.

The term "heteroaryl" refers to an aromatic 5-8 membered monocyclic, 8-12 membered bicyclic, or 11-14 membered tricyclic ring system having 1-3 heteroatoms if monocyclic, 1-6 heteroatoms if bicyclic, or 1-9 heteroatoms if tricyclic, said heteroatoms selected from O, N, or S (e.g., carbon atoms and 1-3, 1-6, or 1-9 heteroatoms of N, O, or S if monocyclic, bicyclic, or tricyclic, respectively), wherein any ring atom capable of substitution may be substituted by a substituent.

As (hetero)aryl or (hetero)cyclyl groups, the followings may be mentioned:

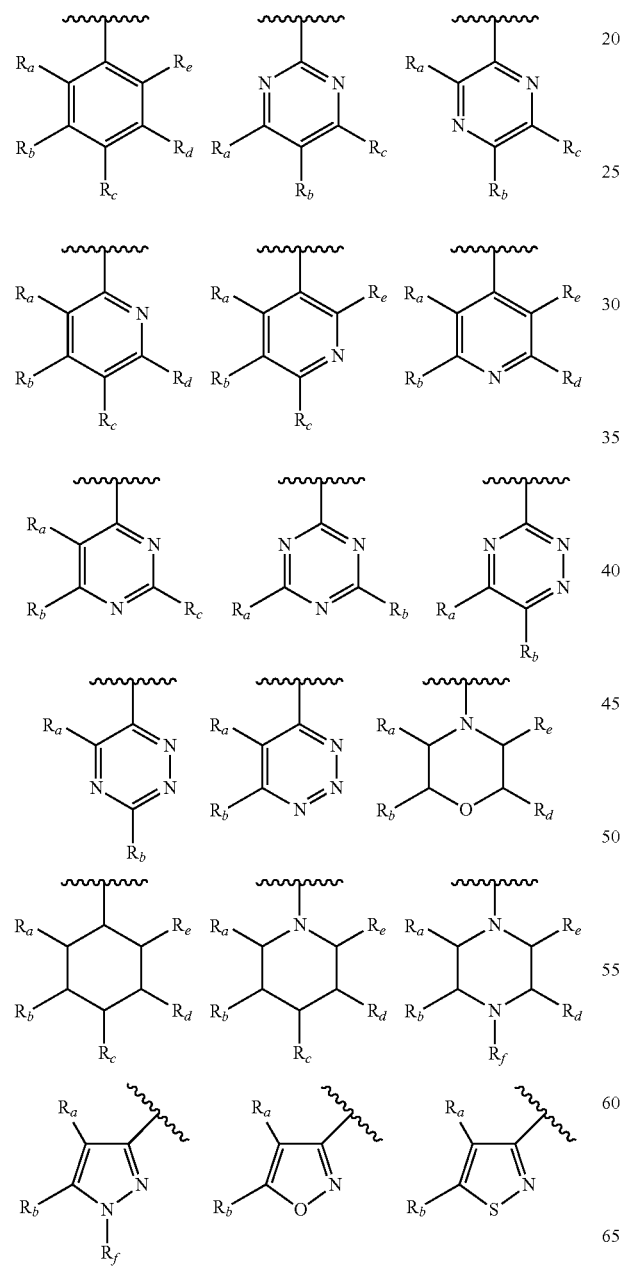
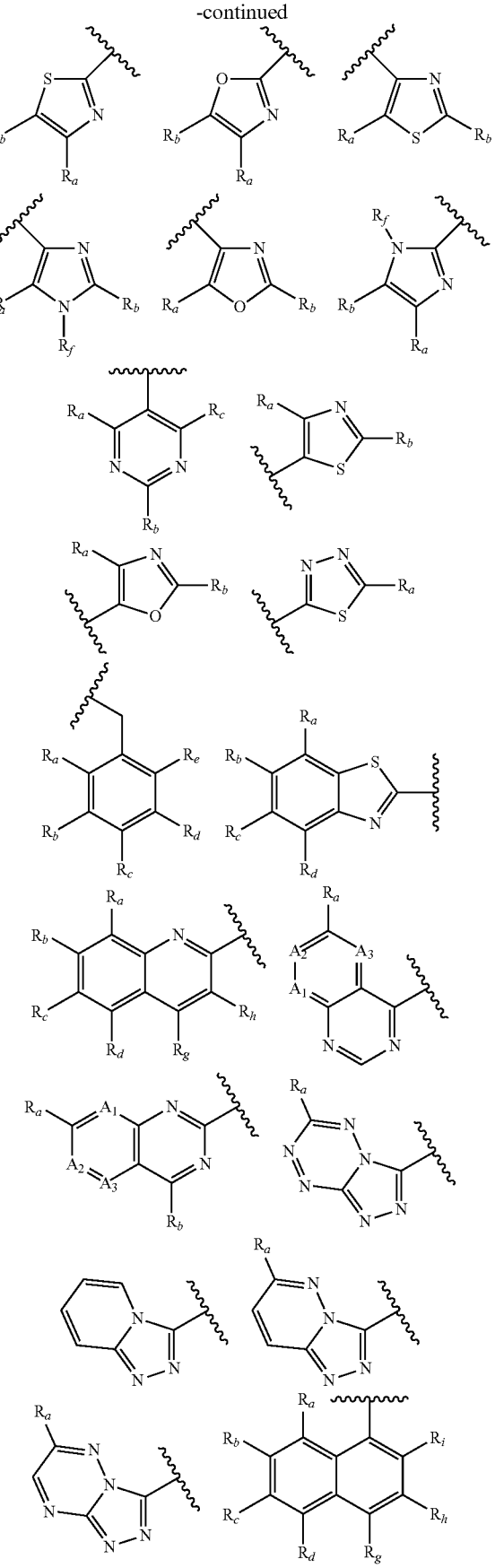

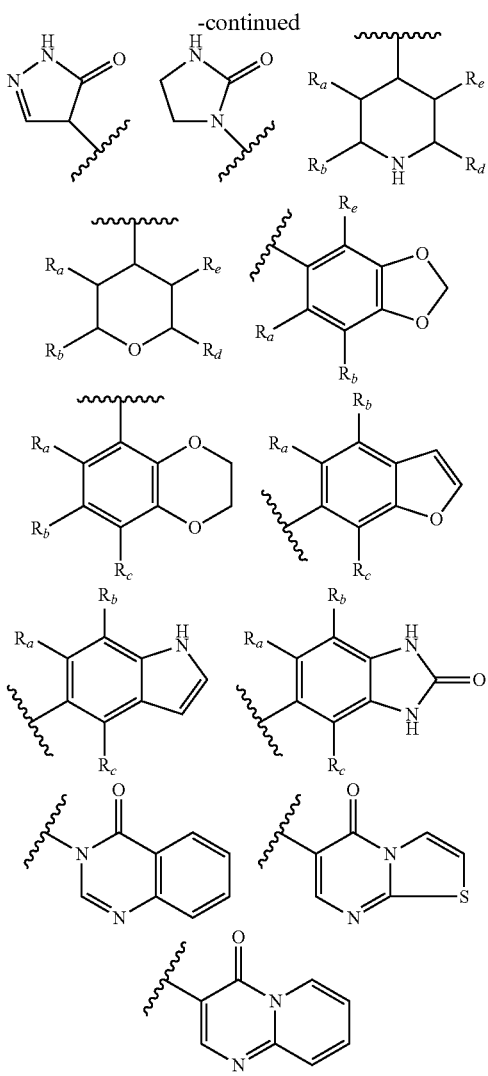

one atom among $A_1$, $A_2$ and $A_3$ representing N, and the two other atoms among $A_1$, $A_2$ and $A_3$ representing CH,
$R_f$ being H or an alkyl group,
$R_a$, $R_b$, $R_c$, $R_d$, $R_e$, $R_g$, $R_h$ and $R_i$ being chosen, independently from each other, in the group consisting of the following substituents:
H,
halogen, such as I, Br, Cl or F,
alkyl group, said alkyl group being possibly substituted in particular by one or more substituents chosen in the group consisting of the following substituents: guanidinyl, halogen, alkenyl or alkynyl groups, aryl groups, $COR_\alpha$, $COOR_\alpha$, $SR_\alpha$, $OR_\alpha$ or $NR_\alpha R_\beta$ groups, $R_\alpha$ and $R_\beta$ representing independently from each other H, an alkyl group or an aryl group,
—CHO,
—CN,
—NO$_2$,
phenyl,
(hetero)aryl or heterocyclyl, possibly substituted,
—$SR_\alpha$, $OR_\alpha$, —$NR_\alpha R_\beta$, —$CONR_\alpha R_\beta$, and —NH-$COR_\alpha$, $R_\alpha$ and $R_\beta$ being as defined above.
The term "alkoxy" refers to an —O-alkyl radical.
The term "substituents" refers to a group "substituted" on an alkyl, cycloalkyl, heterocyclyl, aryl, aralkyl or heteroaryl group at any atom of that group. Suitable substituents include, without limitation, alkyl, alkenyl, alkynyl, alkoxy, halo, hydroxy, cyano, nitro, amino, SO$_3$H, sulphate, phosphate, perfluoroalkyl, perfluoroalkoxy, methylenedioxy, ethylenedioxy, carboxyl, oxo, thioxo, imino (alkyl, aryl, aralkyl), S(O)$_n$ alkyl (where n is 0-2), S(O)$_n$ aryl (where n is 0-2), S(O)$_n$ heteroaryl (where n is 0-2), S(O)$_n$ heterocyclyl (where n is 0-2), amine (mono-, di-, alkyl, cycloalkyl, aralkyl, heteroaralkyl, and combinations thereof), ester (alkyl, aralkyl, heteroaralkyl), amide (mono-, di-, alkyl, aralkyl, heteroaralkyl, and combinations thereof), sulfonamide (mono-, di-, alkyl, aralkyl, heteroalkyl, and combinations thereof), unsubstituted aryl, unsubstituted heteroaryl, unsubstituted heterocyclyl, and unsubstituted cycloalkyl.

The preferred substituents on aryl or heteroaryl groups are amino, amine, alkoxy, halo, perfluoroalkyl such as CF$_3$, heterocyclyl, amide, and ester.

The term "acyl" refers to an alkylcarbonyl, cycloalkylcarbonyl, arylcarbonyl, heterocyclylcarbonyl, or heteroarylcarbonyl substituent, any of which may be further substituted by substituents.

The term "oxo" refers to an oxygen atom, which forms a carbonyl when attached to carbon, an N-oxide when attached to nitrogen, and a sulfoxide or sulfone when attached to sulfur.

The term "alkenyl" as employed herein includes partially unsaturated, nonaromatic, hydrocarbon groups having 2 to 12 carbons, preferably 2 to 6 carbons.

The term "alkynyl" as employed herein includes unsaturated, nonaromatic, hydrocarbon groups having 2 to 12 carbons, preferably 2 to 6 carbons, and comprising at least one triple bond.

The compounds herein described may have asymmetric centers. Compounds of the present invention containing an asymmetrically substituted atom may be isolated in optically active or racemic forms. It is well-known in the art how to prepare optically active forms, such as by resolution of racemic forms or by synthesis from optically active starting materials. All chiral, diastereomeric, racemic forms and all geometric isomeric forms of a compound are intended, unless the stereochemistry or the isomeric form is specifically indicated.

The term "pharmaceutically acceptable salt" refers to salts which retain the biological effectiveness and properties of the compounds of the invention and which are not biologically or otherwise undesirable. In many cases, the compounds of the invention are capable of forming acid and/or base salts by virtue of the presence of amino and/or carboxyl groups or groups similar thereto. Pharmaceutically acceptable acid addition salts may be prepared from inorganic and organic acids, while pharmaceutically acceptable base addition salts can be prepared from inorganic and organic bases. For a review of pharmaceutically acceptable salts see Berge, et al. ((1977) J. Pharm. Sd, vol. 66, 1). The expression "non-toxic pharmaceutically acceptable salts" refers to non-toxic salts formed with nontoxic, pharmaceutically acceptable inorganic or organic acids or inorganic or organic bases. For example, the salts include those derived from inorganic acids such as hydrochloric, hydrobromic, sulfuric, sulfamic, phosphoric, nitric, and the like, as well as salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicyclic, sulfanilic, fumaric, methanesulfonic, and toluenesulfonic acid and the like.

The compounds of the invention are inhibitors of cyclophilins A, B, and D.

Cyclophilins are known as being efficient drug targets in many diseases, including cancers (Iwona Ciechomska et al., *Int J Cancer,* 2005, 117, 59-67; Michael D Schneider, Sci STKE, 2005, pe26; and Alexis Schubert and Stefan Grimm, Cancer Res, 2004, 64, 85-93), diseases caused by flaviviruses (dengue, yellow fever, West Nile virus . . . ) (Antimicrob Agents Chemother. 2009 August; 53(8):3226-35. Epub 2009 May 18), alopecia (Iwabuchi et al., *Journal of Dermatological Science* 1995, 9, 64-69), neurodegenerative diseases (Waldmeier et al., *Curr Med Chem,* 2003, 10, 1485-1506; P. G. Sullivan and M. B. Thompson and S. W. Scheff, *Exp Neurol,* 1999, 160, 226-234; and Heng Du et al., *Neurobiol Aging,* 2009) or hepatitis C (Robert Flisiak and Jean-Maurice Dumont and Raf Crabbé, *Expert Opin Investig Drugs,* 2007, 16, 1345-1354; Robert Flisiak et al., *Hepatology,* 2008, 47, 817-826).

In particular, cyclophilin A is known as being an efficient drug target in non-small-cell lung cancer (Howard et al., *Cancer Res.* 2005, 65(19), 8853-60; and Campa et al., *Cancer research* 2003, 63, 1652-1656). Immunophilins As viral pathologies or infections, one may cite dengue, cancer (in particular breast cancer, lung cancers, pancreatic cancers, HCC (hepatocellular carcinoma) and oral squamous cell carcinoma), HIV infections, neurodegenerative diseases or hepatitis C. The compounds of formula (I) may also be used for the prevention and/or the treatment of alopecia, as well as malaria, yellow fever or West Nile virus.

In the context of the invention, the term "treating" or "treatment", as used herein, means reversing, alleviating, inhibiting the progress of, or preventing the disorder or condition to which such term applies, or one or more symptoms of such disorder or condition.

The term "neurodegenerative disease" is used throughout the specification to identify a disease which is caused by damage to the central nervous system and can be identified by neuronal death. Further, the term "neurodegenerative disease" as used herein describes "neurodegenerative diseases" which are associated with p-53 mediated cell cycle abrogation and apoptosis. Exemplary neurodegenerative diseases include HIV-associated Dementia, multiple sclerosis, Alzheimer's Disease, Parkinson's Disease, amyotrophic lateral sclerosis, and Pick's Disease.

As used herein, the term "neurodegenerative disease" shall be taken to mean a disease that is characterized by neuronal cell death. The neuronal cell death observed in a neurodegenerative disease is often preceded by neuronal dysfunction, sometimes by several years. Accordingly, the term "neurodegenerative disease" includes a disease or disorder that is characterized by neuronal dysfunction and eventually neuronal cell death. Often neurodegenerative diseases are also characterized by increased gliosis (e.g., astrocytosis or microgliosis) in the region/s of neuronal death. Cellular events observed in a neurodegenerative disease often manifest as a behavioral change (e.g., deterioration of thinking and/or memory) and/or a movement change (e.g., tremor, ataxia, postural change and/or rigidity). Examples of neurodegenerative disease include, for example, FTLD, amyotrophic lateral sclerosis, ataxia (e.g., spinocerebellar ataxia or Friedreich's Ataxia), Creutzfeldt-Jakob Disease, a polyglutamine disease (e.g., Huntington's disease or spinal bulbar muscular atrophy), Hallervorden-Spatz disease, idiopathic torsion disease, Lewy body disease, multiple system atrophy, neuroanthocytosis syndrome, olivopontocerebellar atrophy, Pelizaeus-Merzbacher disease, progressive supranuclear palsy, syringomyelia, torticollis, spinal muscular atrophy or a trinucleotide repeat disease (e.g., Fragile X Syndrome).

The compounds may be useful for the treatment of tumors, such as coronary restenosis and neoplastic diseases, particularly colon carcinoma, familiary adenomatous polyposis carcinoma and hereditary non-polyposis colorectal cancer, prostate carcinoma, melanoma, non-Hodgkin lymphoma, acute lymphatic leukemia (ALL), chronic lymphatic leukemia (CLL), acute myeolid leukemia (AML), chronic myeloid leukemia (CML), hepatocellular carcinoma, neuroblastoma, intestine carcinoma, rectum carcinoma, colon carcinoma, oesophageal carcinoma, labial carcinoma, larynx carcinoma, hypopharynx carcinoma, tong carcinoma, salivary gland carcinoma, gastric carcinoma, adenocarcinoma, medullary thyroidea carcinoma, papillary thyroidea carcinoma, renal carcinoma, kidney parenchyma carcinoma, ovarian carcinoma, cervix carcinoma, uterine corpus carcinoma, endometrium carcinoma, chorion carcinoma, pancreatic carcinoma, testis carcinoma, breast carcinoma, urinary carcinoma, brain tumors such as glioblastoma, astrocytoma, meningioma, medulloblastoma and peripheral neuroectodermal tumors, Hodgkin lymphoma, non-Hodgkin lymphoma, Burkitt lymphoma, adult T-cell leukemia lymphoma, hepatocellular carcinoma, gall bladder carcinoma, bronchial carcinoma, small cell lung carcinoma, non-small cell lung carcinoma, multiple myeloma, basalioma, teratoma, retinoblastoma, choroidea melanoma, seminoma, rhabdomyosarcoma, craniopharyngeoma, osteosarcoma, chondrosarcoma, myosarcoma, liposarcoma, fibrosarcoma, Ewing sarcoma, and plasmocytoma.

While it is possible for the compounds of the invention having formula (I) to be administered alone it is preferred to present them as pharmaceutical compositions. The pharmaceutical compositions, both for veterinary and for human use, useful according to the present invention comprise at least one compound having formula (I) as above defined, together with one or more pharmaceutically acceptable carriers and optionally other therapeutic ingredients.

In certain preferred embodiments, active ingredients necessary in combination therapy may be combined in a single pharmaceutical composition for simultaneous administration.

As used herein, the term "pharmaceutically acceptable" and grammatical variations thereof, as they refer to compositions, carriers, diluents and reagents, are used interchangeably and represent that the materials are capable of administration to or upon a mammal without the production of undesirable physiological effects such as nausea, dizziness, gastric upset and the like.

The preparation of a pharmacological composition that contains active ingredients dissolved or dispersed therein is well understood in the art and need not be limited based on formulation. Typically such compositions are prepared as injectables either as liquid solutions or suspensions; however, solid forms suitable for solution, or suspensions, in liquid prior to use can also be prepared. The preparation can also be emulsified. In particular, the pharmaceutical compositions may be formulated in solid dosage form, for example capsules, tablets, pills, powders, dragees or granules.

The choice of vehicle and the content of active substance in the vehicle are generally determined in accordance with the solubility and chemical properties of the active compound, the particular mode of administration and the provisions to be observed in pharmaceutical practice. For example, excipients such as lactose, sodium citrate, calcium carbonate, dicalcium phosphate and disintegrating agents such as starch, alginic acids and certain complex silicates combined with lubricants such as magnesium stearate, sodium lauryl sulphate and talc may be used for preparing tablets. To prepare a capsule, it is advantageous to use lactose and high molecular weight polyethylene glycols. When aqueous suspensions are used they can contain emulsifying agents or agents which facilitate suspension. Diluents such as sucrose, ethanol, polyethylene glycol, propylene glycol, glycerol and chloroform or mixtures thereof may also be used.

The pharmaceutical compositions can be administered in a suitable formulation to humans and animals by topical or systemic administration, including oral, rectal, nasal, buccal, ocular, sublingual, transdermal, rectal, topical, vaginal, parenteral (including subcutaneous, intra-arterial, intramuscular, intravenous, appreciated that the preferred route may vary with for example the condition of the recipient.

The formulations can be prepared in unit dosage form by any of the methods well known in the art of pharmacy. Such methods include the step of bringing into association the active ingredient with the carrier which constitutes one or more accessory ingredients. In general the formulations are prepared by uniformly and intimately bringing into association the active ingredient with liquid carriers or finely divided solid carriers or both, and then, if necessary, shaping the product.

Total daily dose of the compounds of the invention administered to a subject in single or divided doses may be in amounts, for example, of from about 0.001 to about 100 mg/kg body weight daily and preferably 0.01 to 10 mg/kg/day. Dosage unit compositions may contain such amounts of such submultiples thereof as may be used to make up the daily dose. It will be understood, however, that the specific dose level for any particular patient will depend upon a variety of factors including the body weight, general health, sex, diet, time and route of administration, rates of absorption and excretion, combination with other drugs and the severity of the particular disease being treated.

According to a particular embodiment, $R_6$ may form together with $R_1$ a heterocyclyl group from 10 to 30 atoms. In such an embodiment, the compounds of formula (I) contain a intramolecular cycle which is formed from $R_1$ and —CH($R_6$)—NH—X—NH-A-.

According to a particularly preferred embodiment, $R_7$ is chosen from the group consisting of: aryl groups, heteroaryl groups, —NHPh, heterocyclyl groups, and alkyl groups; wherein when $R_7$ is aryl, heteroaryl or heterocyclyl, it is substituted by at least one $NH_2$ group.

According to another preferred embodiment, $R_7$ is chosen from the group consisting of: aryl groups, heteroaryl groups, —NHPh, heterocyclyl groups, and alkyl groups; and is substituted by at least one $NH_2$ group.

According to an advantageous embodiment, in the above formula (I), $R_1$ is an alkyl group substituted by OH, in particular a group of formula —$(CH_2)_p$—OH, p being an integer from 1 to 12.

According to an advantageous embodiment, in the above formula (I), $R_3$ and $R_4$ form together with the nitrogen atom carrying them a group having the following formula:

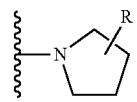

wherein R is H or a substituent in particular chosen from the group consisting of: alkyl, eventually substituted, aryl, eventually substituted, amino, hydroxy, and alcoxy.

Preferably, R is an aryl group, eventually substituted. More particularly, R is a group having the formula:

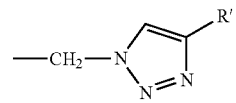

wherein R' is an alkyl group eventually substituted with substituents in particular chosen from: hydroxy, aryl, alcoxy or heterocyclyl groups.

According to an advantageous embodiment, in the above formula (I), $R_3$ is ethyl and $R_4$ is chosen from the group consisting of: —O-alkylaryl and alkyl(hetero)aryl, said alkyl (hetero)aryl group being eventually substituted.

According to an advantageous embodiment, in the above formula (I), $R_3$ is ethyl and $R_4$ is an eventually substituted benzyl group. Preferably, said benzyl group is substituted with one or two substituents chosen from alcoxy, halogen and alkylcarbonyl.

According to an advantageous embodiment, in the above formula (I), $R_3$ is ethyl and $R_4$ is —$CH_2$— (hetero)aryl, and preferably benzyl, eventually substituted. Preferably, said benzyl group is substituted with one or two substituents chosen from alcoxy, halogen, alkylcarbonyl, nitro, hydroxy, and alkyl ester.

According to an advantageous embodiment, in the above formula (I), $R_3$ and $R_4$ form together with the nitrogen atom carrying them a group having the formula:

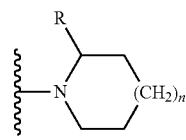

wherein n is 0, 1 or 2, and R is H or aryl, eventually substituted, and preferably, phenyl eventually substituted.

According to an advantageous embodiment, in the above formula (I), $R_7$ is chosen from the group consisting of: aryl groups, heteroaryl groups, and heterocyclyl groups.

According to an advantageous embodiment, in the above formula (I), $R_7$ is an aryl group, possibly substituted. Preferably, said substituents are heterocyclyl, amino, halo, amine, alkoxy, perfluoroalkyl such as $CF_3$, amide and ester.

According to an advantageous embodiment, in the above formula (I), $R_7$ is an aryl or heteroaryl group, possibly substituted. Preferably, said substituents are heterocyclyl, amino, halo, amine, alkoxy, perfluoroalkyl such as $CF_3$, amide and ester.

According to an advantageous embodiment, in the above formula (I), $R_7$ is a heterocyclyl group, comprising in particular from 5 to 10 atoms, and possibly substituted. Preferably, said substituents are alkyl, aryl and aralkyl.

The present invention also relates to compounds having the formula (II):

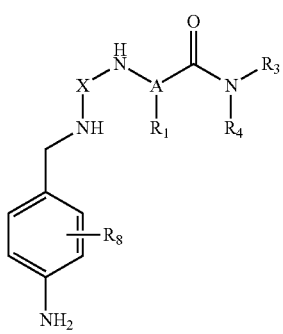

(II)

wherein:
X, A, $R_1$, $R_3$ and $R_4$ are as defined above in formula (I), and
$R_8$ is chosen from the group consisting of: H, halogen, alkyl, alkoxy, thioalkoxy (—S-alkyl), acyl groups, in particular alkylcarbonyl groups, and heteroaryl groups, in particular furanyl, oxazolyl, and isoxazolyl groups, and more particularly 2-furanyl, 5-oxazolyl, and 3-isoxazolyl groups,
for the use as mentioned above.

In formula (II), $R_8$ may also represent a group —$CH_2$—NH—C(=NH)$NH_2$.

The present invention also relates to compounds having the formula (III):

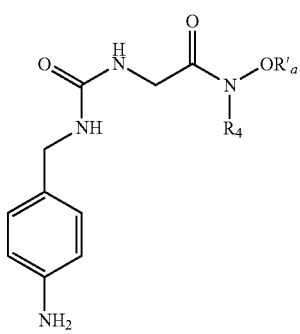

(III)

wherein $R_4$ and $R'_a$ are as defined above in formula (I),
for the use as mentioned above.

According to an advantageous embodiment, $R'_a$ is an alkyl group, possibly substituted with at least one substituent chosen from the group consisting of aryl, possibly substituted, heteroaryl, COOR, R being an alkyl or aryl group, said alkyl or aryl group being possibly substituted.

Preferably, in formula (III) as mentioned above, $R_4$ is alkyl, and preferably ethyl.

The present invention also relates to compounds having formula (III), wherein $R'_a$ is $(CH_2)_n R_9$, n being 0, 1 or 2, and $R_9$ being O-phenyl, phenyl, or heteroaryl such as pyridinyl, in particular 2-, 3- or 4-pyridinyl, or 2-pyrazinyl. When $R_9$ is phenyl, said phenyl group may be substituted by at least one substituent chosen preferably from the group consisting of: Hal, alkoxy such as OMe, $NO_2$, OPh, alkylcarbonyl such as COMe, OBn, and COOAlk, such as COOEt, for the use as mentioned above.

Preferably, in formula (III), $R'_a$ is $(CH_2)_n COR_{10}$, wherein $R_{10}$ is O-alkyl, O-phenyl, phenyl (possibly substituted), $CH_2COOAlk$, such as $CH_2COOEt$.

A preferred group of compounds of the invention is constituted by compounds having formula (III) as mentioned above, wherein $R_4$ is alkyl and $R'_a$ is $(CH_2)_n R_9$, $R_9$ and n being as defined above.

Another preferred group of compounds of the invention is constituted by compounds having formula (III) as mentioned above, wherein $R_4$ is alkyl and $R'_a$ is $(CH_2)_n COR_{10}$, $R_{10}$ and n being as defined above.

The present invention also relates to compounds having the formula (IV):

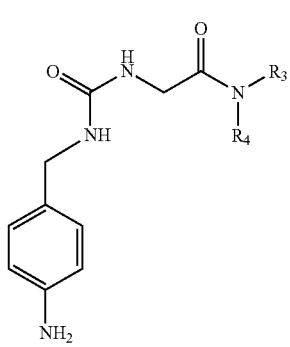

(IV)

wherein $R_3$ and $R_4$ are as defined above in formula (I), $R_3$ being preferably an alkyl group, such as ethyl, and $R_4$ being preferably a (hetero)aryl group, for the use as mentioned above.

According to a particular embodiment, in formula (IV), $R_4$ is chosen from the groups consisting of: phenyl, pyridynyl, in particular 2- or 3-pyridinyl, pyrazinyl, in particular 2-pyrazinyl, pyrimidinyl, in particular 5-pyrimidinyl, and pyridazinyl.

When $R_4$ is phenyl, said phenyl group may be substituted by at least one substituent chosen preferably from the group consisting of: alkylcarbonyl such as COMe, and $CH_2COOAlk$, such as $CH_2COOMe$ and $CH_2COOEt$.

When $R_4$ is pyridinyl, said pyridinyl group may be substituted by at least one substituent chosen preferably from alkoxy groups, such as OMe.

When $R_4$ is pyridazinyl, said pyridazinyl group may be substituted by at least one substituent chosen preferably from —S-Alk, such as $SCH_3$.

The present invention also relates to compounds having the formula (IV-1):

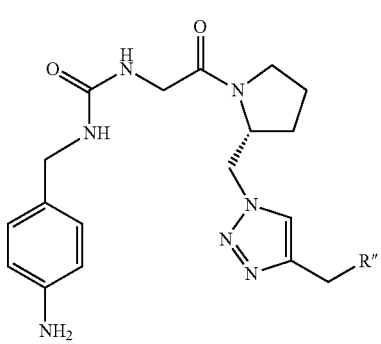

(IV-1)

wherein R" is chosen from OH, heterocyclyl, eventually substituted, such as N-phenyl-piperazinyl, alcoxy, aryl, such as phenyl, O-alkylaryl, such as benzyloxy, aryloxy, such as phenoxy, for the use as mentioned above.

The present invention also relates to compounds having the formula (IV-2):

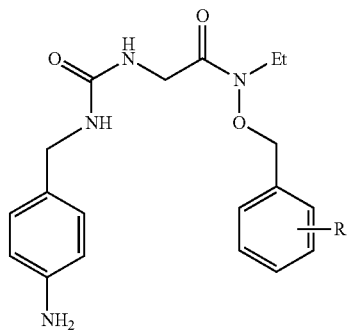

(IV-2)

wherein R is chosen from halogen such as Cl, alcoxy, such as methoxy, and alkylcarbonyl such as COMe, for the use as mentioned above.

The present invention also relates to compounds having the formula (IV-2):

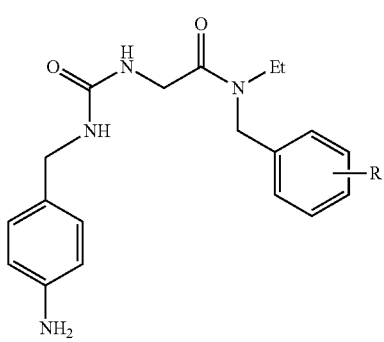

(IV-2)

wherein R is chosen from hydroxy, halogen such as F or Cl, alcoxy, such as methoxy, alkylcarbonyl such as COMe, nitro, and alkyl ester such as COOEt, for the use as mentioned above.

The present invention also relates to compounds having the formula (V):

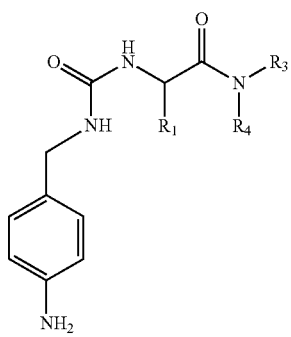

(V)

wherein $R_1$, $R_3$ and $R_4$ are as defined above in formula (I), for the use as mentioned above.

The present invention also relates to compounds having the formula (V-1):

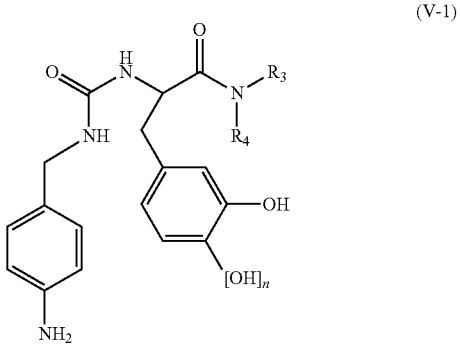

(V-1)

wherein $R_3$ and $R_4$ are as defined above in formula (I), and n is 0 or 1, for the use as mentioned above.

The present invention also relates to compounds having formula (V) or (V-1) for the use as mentioned above, wherein $R_3$ and $R_4$ form together with the nitrogen carrying them a heterocycle such as a heterocycle of six atoms comprising at least one nitrogen atom, and eventually also one other nitrogen atom and/or one oxygen atom, said heterocycle being possibly substituted, in particular by COOAlk groups, and preferably COOEt groups.

Preferably, in formula (V) or (V-1), $R_3$ is alkyl and $R_4$ is phenyl or OBn.

The present invention also relates to compounds having the formula (VI):

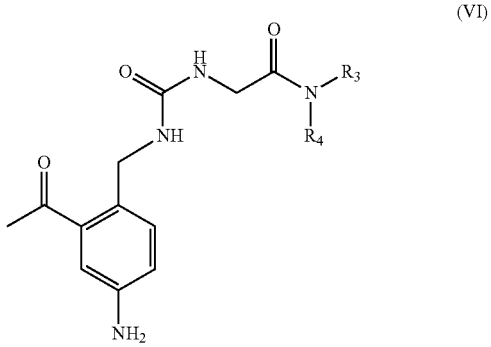

(VI)

wherein $R_3$ and $R_4$ are as defined above in formula (I), for the use as mentioned above.

The present invention also relates to compounds having formula (VI), wherein $R_3$ and $R_4$ form together with the nitrogen carrying them a heterocycle such as a heterocycle of six atoms comprising at least one nitrogen atom, and eventually also one other nitrogen atom and/or one oxygen atom, said heterocycle being possibly substituted, in particular by COOAlk groups, and preferably COOEt groups.

The present invention also relates to compounds having formula (VI), wherein $R_3$ is alkyl and $R_4$ is phenyl or OBn.

The present invention also relates to compounds having the formula (VII):

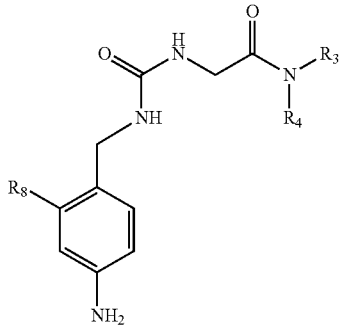

(VII)

wherein $R_3$ and $R_4$ are as defined above in formula (I), and $R_8$ is a heteroaryl group, in particular chosen from: furanyl, oxazolyl, and isoxazolyl groups, $R_8$ being more particularly 2-furanyl, 5-oxazolyl, and 3-isoxazolyl groups, for the use as mentioned above.

The present invention also relates to compounds having the formula (VIII):

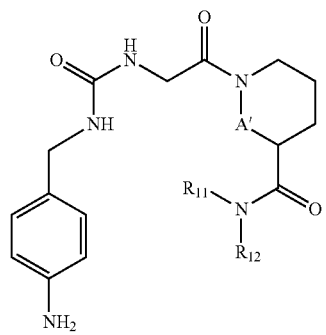

(VIII)

wherein $R_{11}$ and $R_{12}$ are, independently from each other, chosen from the group consisting of: H, alkyl, alkoxy, aryl, and aralkyl,
and A' is $CH_2$ or NH, for the use as mentioned above.

A preferred group of compounds of the invention are constituted by compounds having the following formula (VIII-1):

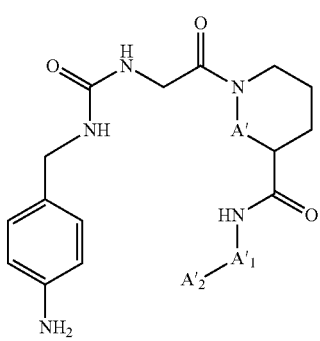

(VIII-1)

wherein:
A' is as defined above in formule (VIII),
$A'_1$ is chosen from the group consisting of: $(CH_2)_mCO$, $(CH_2)_m$, and $O(CH_2)_m$, m being an integer varying from 1 to 5, and
$A'_2$ is chosen from the aryl and heteroaryl groups, and is in particular phenyl.

A preferred group of compounds of the invention are constituted by compounds having the following formula (VIII-2):

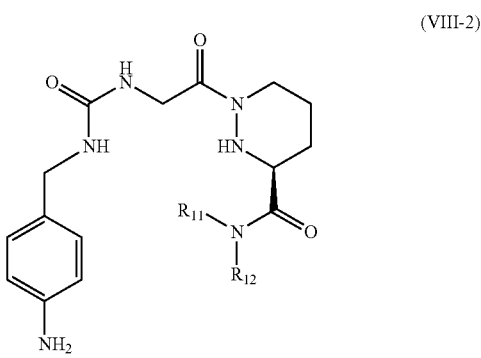

(VIII-2)

wherein $R_{11}$ and $R_{12}$ are, independently from each other, chosen from the group consisting of: H, alkyl, alkoxy, aryl, and aralkyl.

The present invention also relates to compounds having the formula (IX):

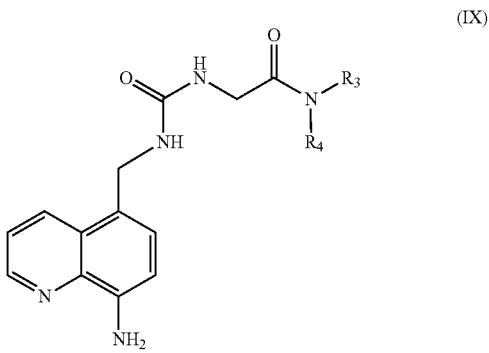

(IX)

wherein $R_3$ and $R_4$ are as defined above in formula (I), for the use as mentioned above.

A preferred group of compounds of the invention are constituted by compounds having above formula (IX), wherein $R_3$ and $R_4$ form together with the nitrogen carrying them a heterocycle such as a heterocycle of six atoms comprising at least one nitrogen atom, and eventually also one other nitrogen atom and/or one oxygen atom, said heterocycle being possibly substituted, in particular by COOAlk, preferably by COOEt.

Another preferred group of compounds of the invention are constituted by compounds having above formula (IX), wherein $R_3$ is alkyl and $R_4$ is phenyl or OBn.

The present invention also relates to compounds having the formula (X):

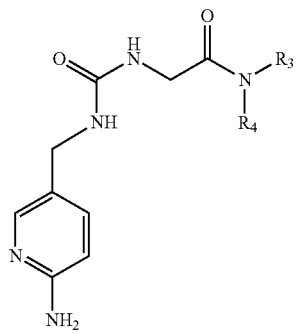
(X)

wherein $R_3$ and $R_4$ are as defined above in formula (I), for the use as defined above.

A preferred group of compounds of the invention are constituted by compounds having above formula (X), wherein $R_3$ and $R_4$ form together with the nitrogen carrying them a heterocycle such as a heterocycle of six atoms comprising at least one nitrogen atom, and eventually also one other nitrogen atom and/or one oxygen atom, said heterocycle being possibly substituted, in particular by COOAlk, preferably by COOEt.

Another preferred group of compounds of the invention are constituted by compounds having above formula (X), wherein $R_3$ is alkyl and $R_4$ is phenyl or OBn.

The present invention also relates to compounds having the formula (XI):

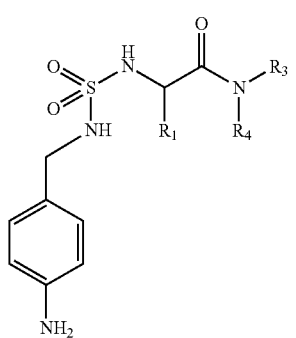
(XI)

wherein $R_1$, $R_3$ and $R_4$ are as defined above in formula (I), for the use as defined above.

A preferred group of compounds are constituted by compounds having formula (XI) wherein $R_1$ is H or

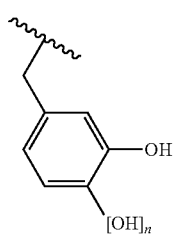

n being 0 or 1.

Thus, the present invention relates to compounds having formulae (XI-1) or (XI-2) as follows:

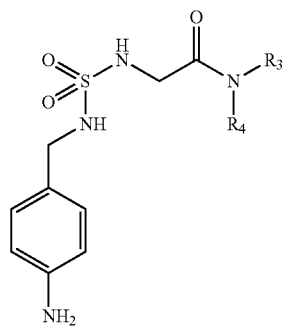
(XI-1)

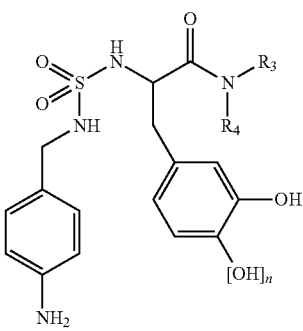
(XI-2)

for the use as defined above.

A preferred group of compounds of the invention are constituted by compounds having above formula (X), wherein $R_3$ and $R_4$ form together with the nitrogen carrying them a heterocycle such as a heterocycle of six atoms comprising at least one nitrogen atom, and eventually also one other nitrogen atom and/or one oxygen atom, said heterocycle being possibly substituted, in particular by COOAlk, preferably by COOEt.

Another preferred group of compounds of the invention are constituted by compounds having above formula (X), wherein $R_3$ is alkyl and $R_4$ is phenyl or OBn.

The present invention also relates to compounds having formula (XII):

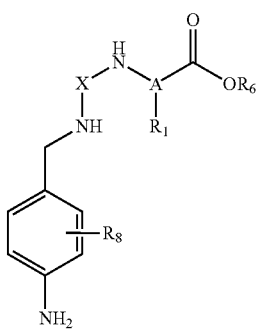
(XII)

wherein:
X, A, $R_1$, and $R_5$ are as defined above in formula (I), and
$R_6$ is chosen from the group consisting of: H, acyl groups, in particular alkylcarbonyl groups, and heteroaryl groups, in particular furanyl, oxazolyl, and isoxazolyl groups, and more particularly 2-furanyl, 5-oxazolyl, and 3-isoxazolyl groups,
for the use as defined above.

A preferred group of compounds of the invention is constituted by compounds having one of the above formulae:

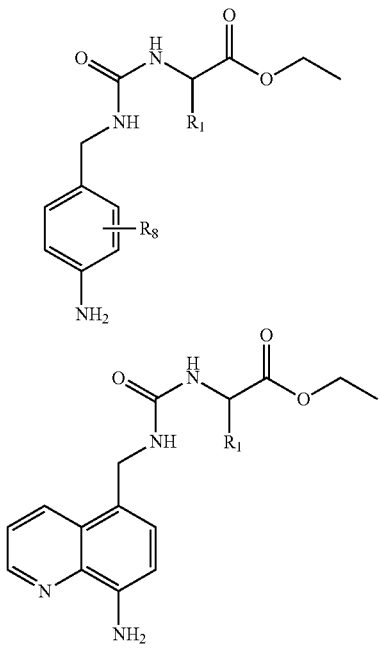

wherein:
R$_1$ is as defined above in formula (I), and
R$_8$ is H or an acyl group (such as a group COCH$_3$).

The present invention also relates to compounds having formula (XIII):

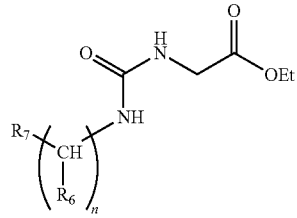
(XIII)

wherein n, R$_6$, and R$_7$ are as defined above in formula (I), R$_7$ being preferably chosen from the group consisting of: aryl groups, heteroaryl groups, and heterocyclyl groups, and n being preferably 0,
for the use as defined above.

The present invention also relates to compounds having the formula (XIV):

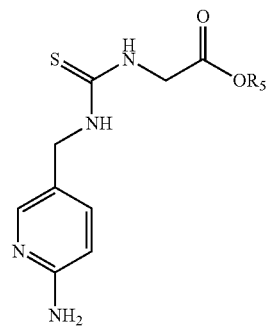
(XIV)

wherein R$_5$ is as defined above in formula (I), R$_5$ being preferably ethyl,
for the use as defined above.

The present invention also relates to compounds having the formula (XV):

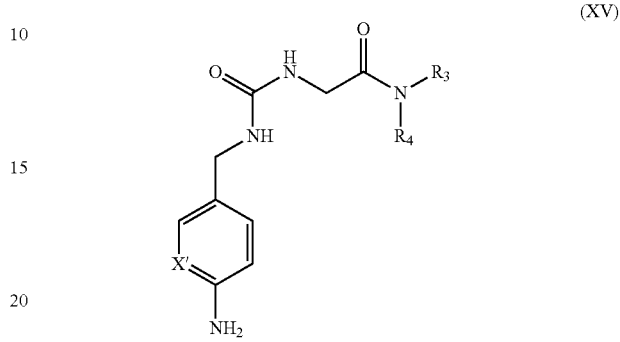
(XV)

wherein R$_3$ and R$_4$ are as defined above in formula (I), and X' is N or CH,
for the use as defined above.

The present invention also relates to compounds having the formula (XXIII):

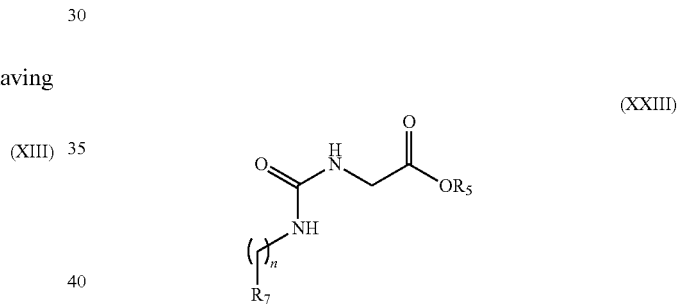
(XXIII)

wherein n and R$_5$ are as defined above in formula (I), and R$_7$ is a heteroaryl group comprising at least one nitrogen atom and one sulfur atom in the ring and comprising one NH$_2$ group as substituent, for the use as defined above.

A preferred group of compounds of the invention is constituted by compounds having one of the above formulae:

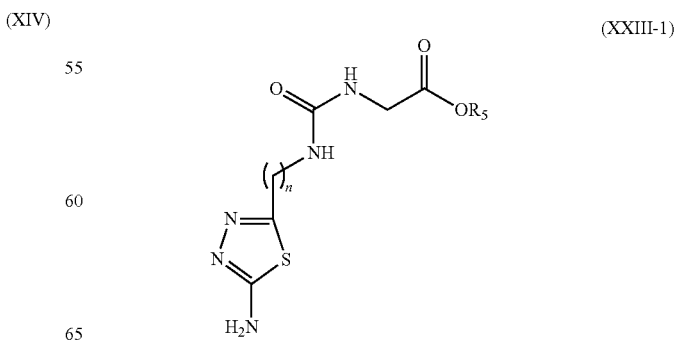
(XXIII-1)

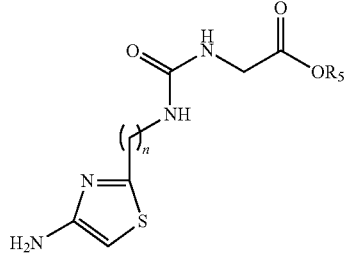
(XXIII-2)
wherein $R_5$ and n are as defined above, n being preferably 1 or 2 and $R_5$ being preferably ethyl.
The present invention relates to the following preferred compounds:
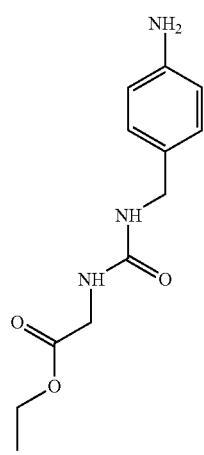
428
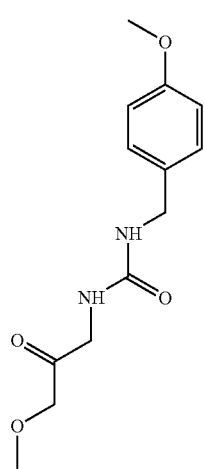
429
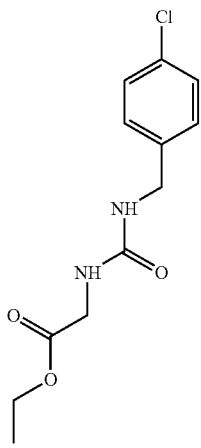
430
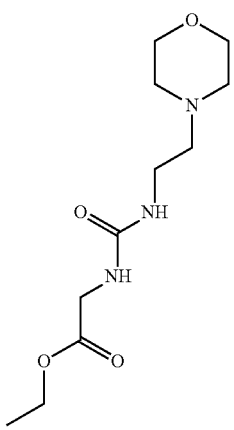
431
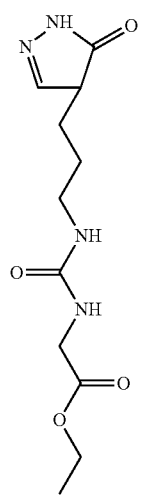
432
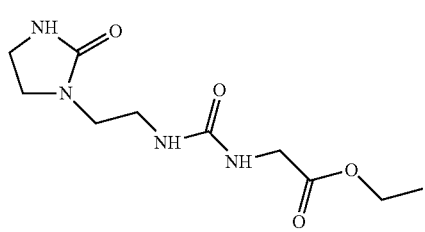
433

436
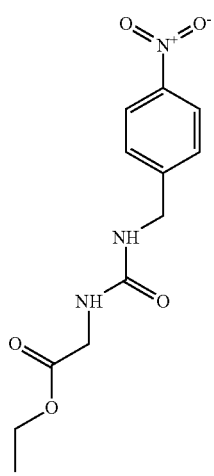
490
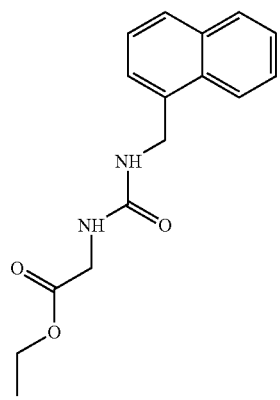
491
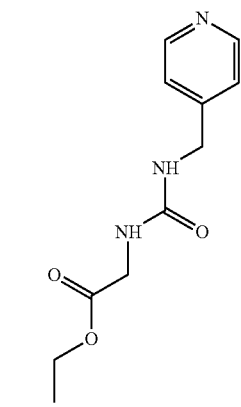
492
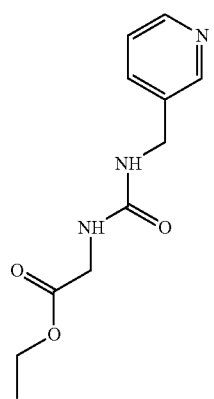
493
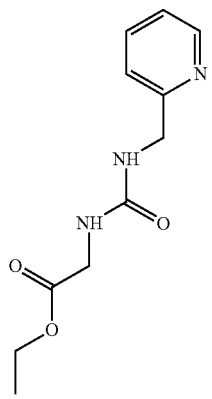
494
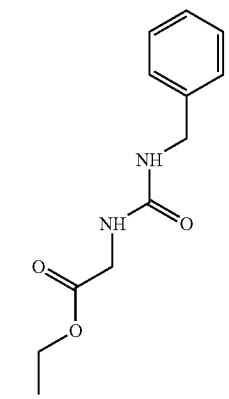
509
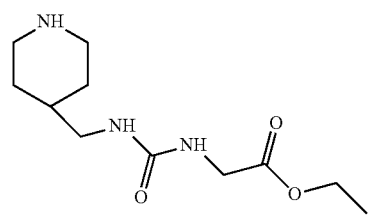
510
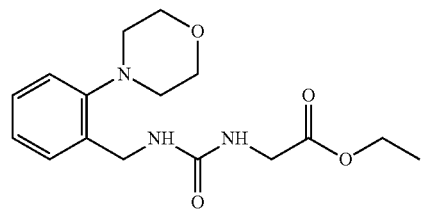
511
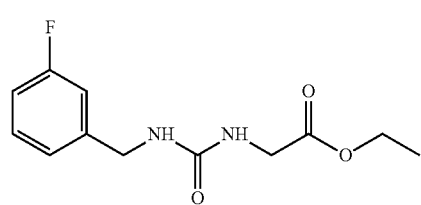

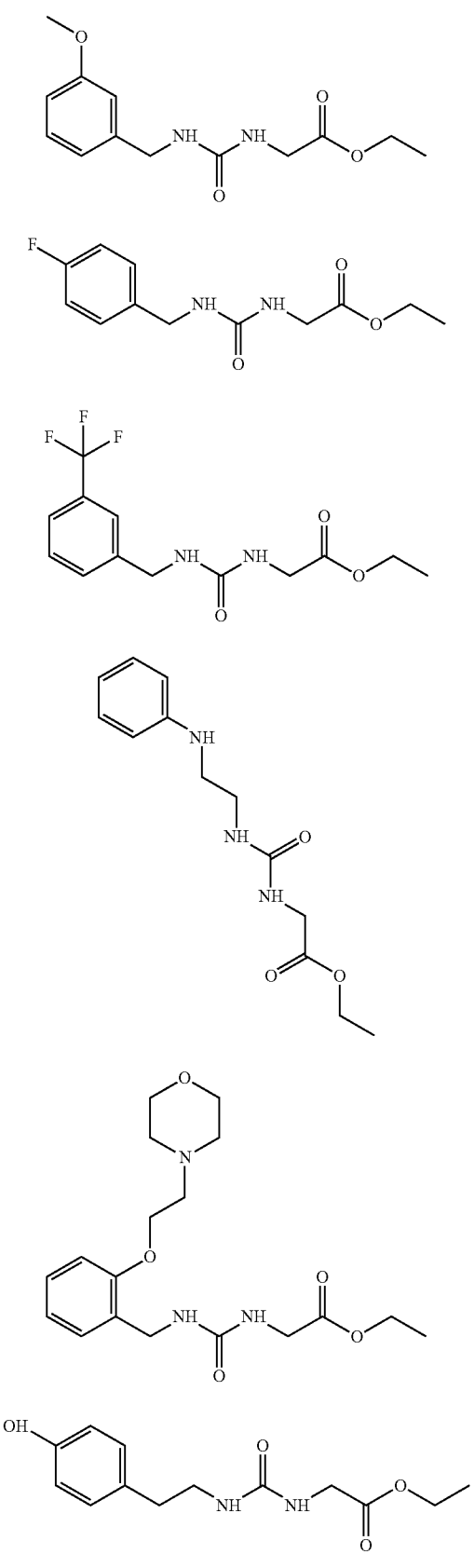
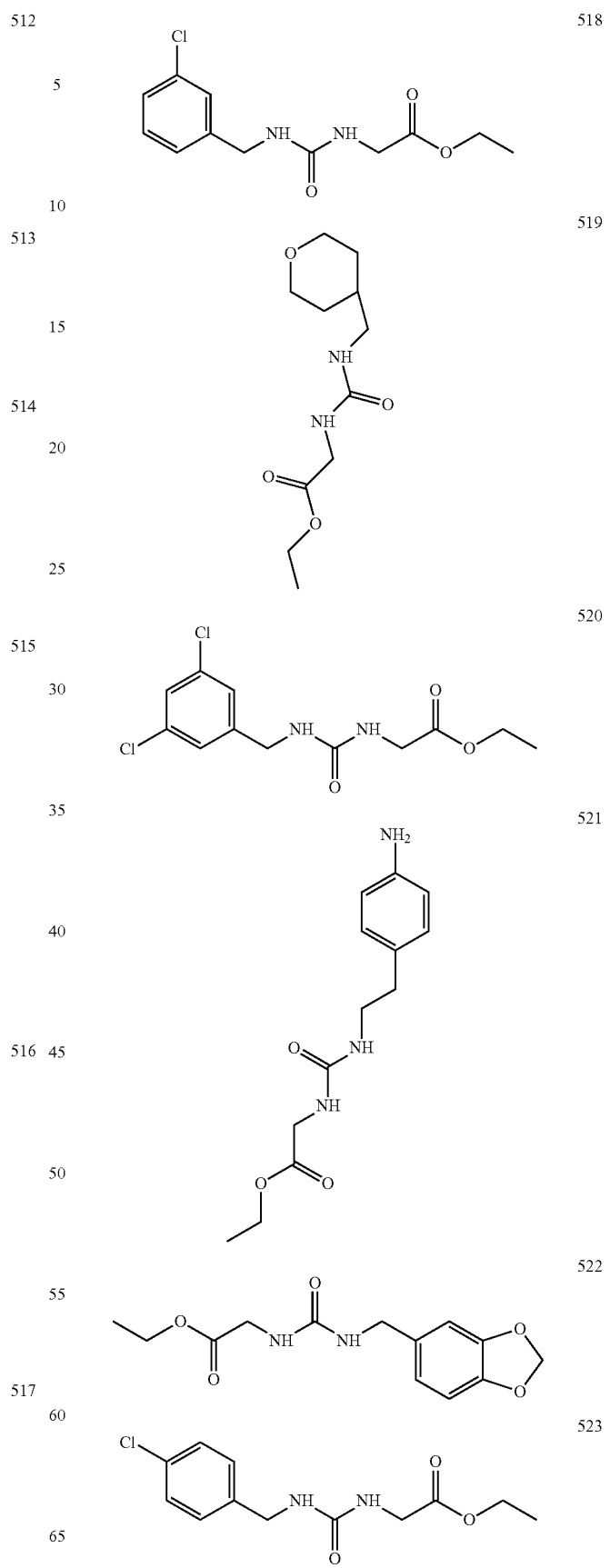

524 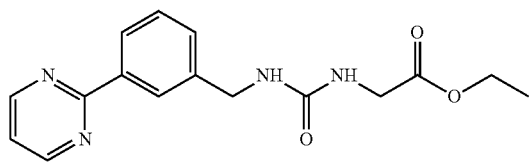
525 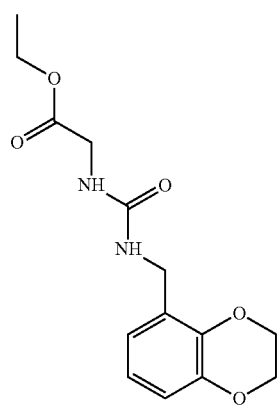
526 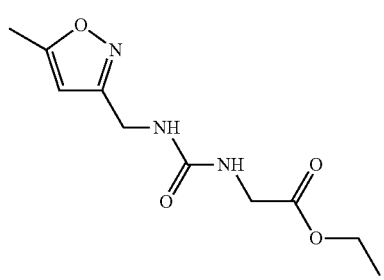
527 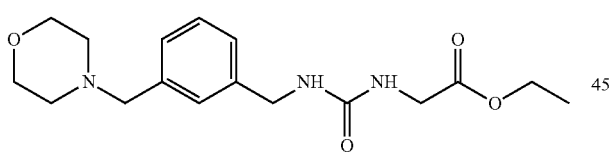
528 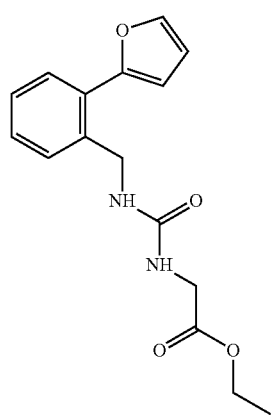
529 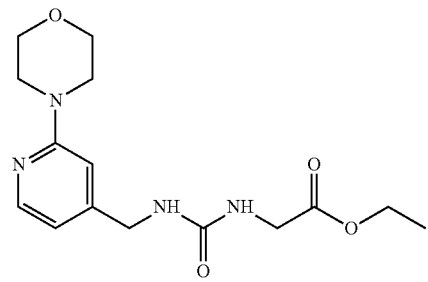
530 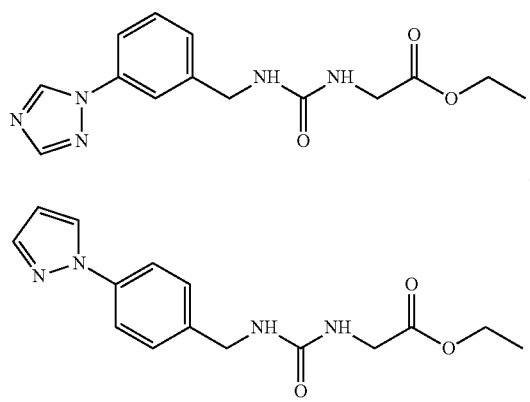
531
532 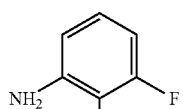
533 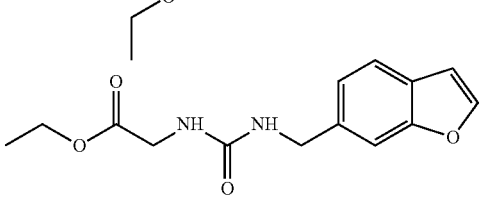
536 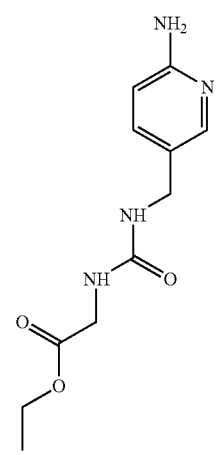

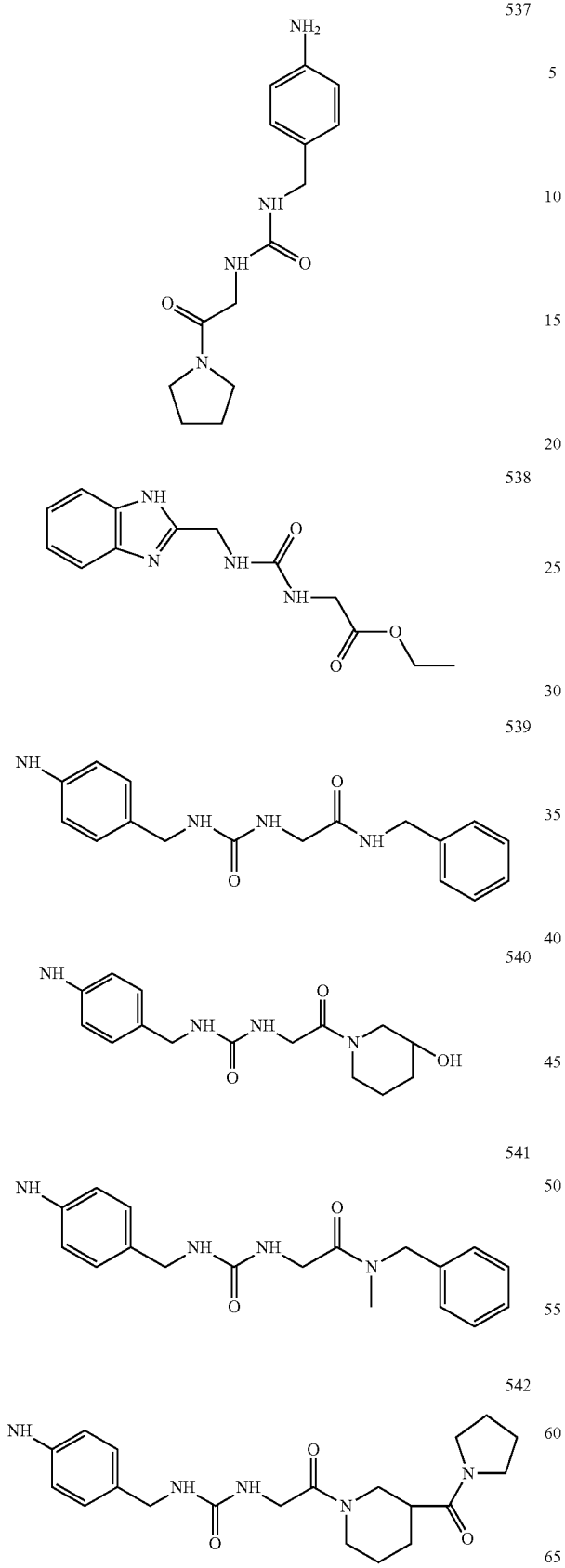

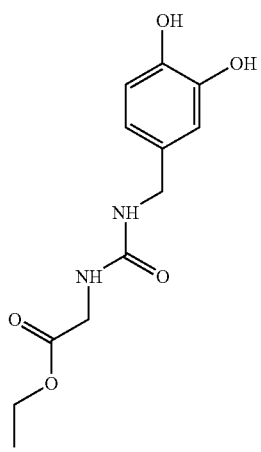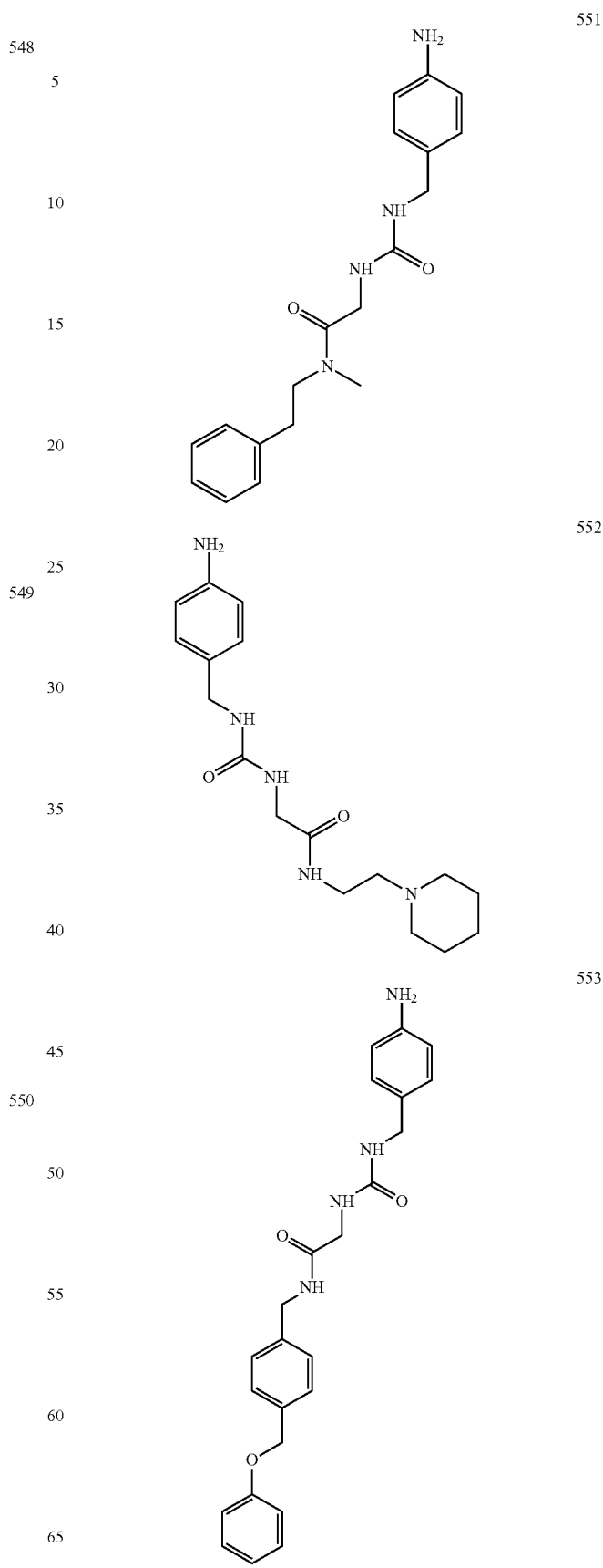

554
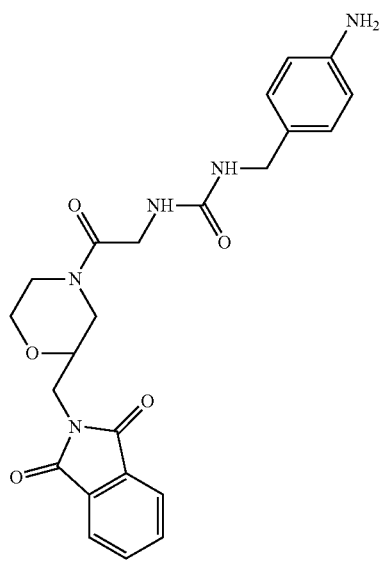
555
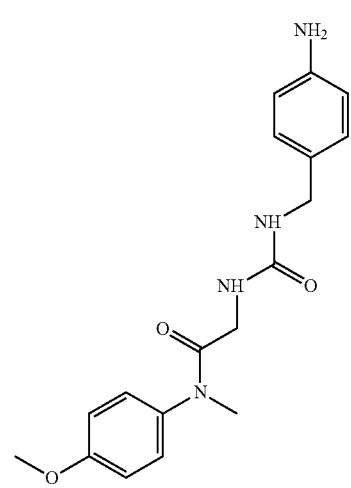
556
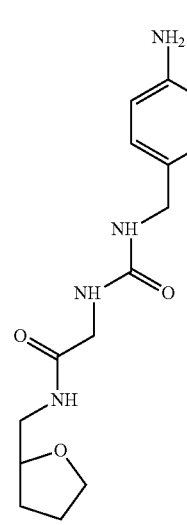
557
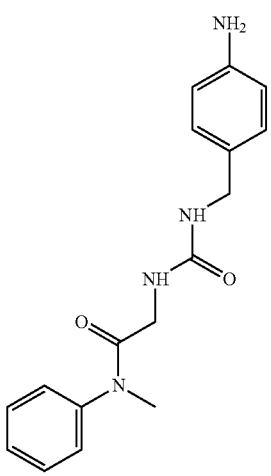
558
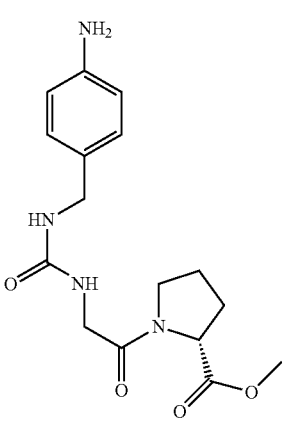
559
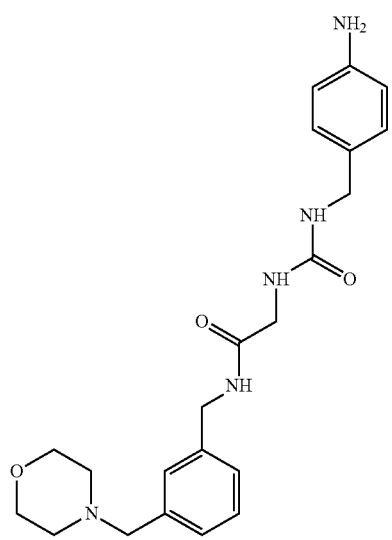

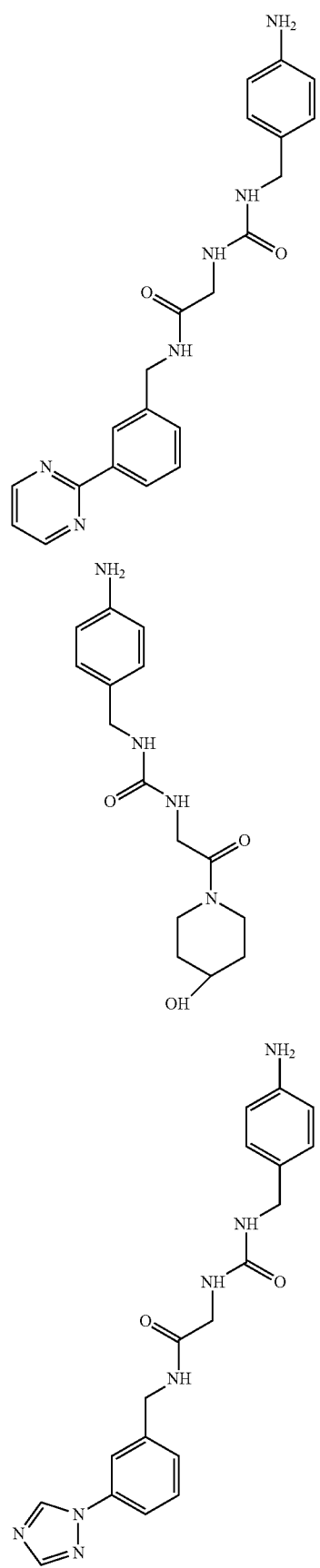
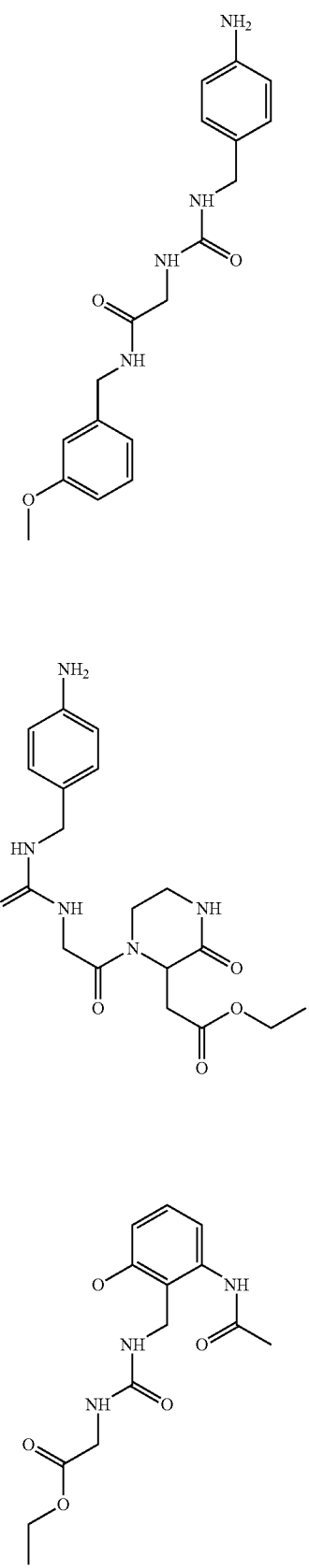

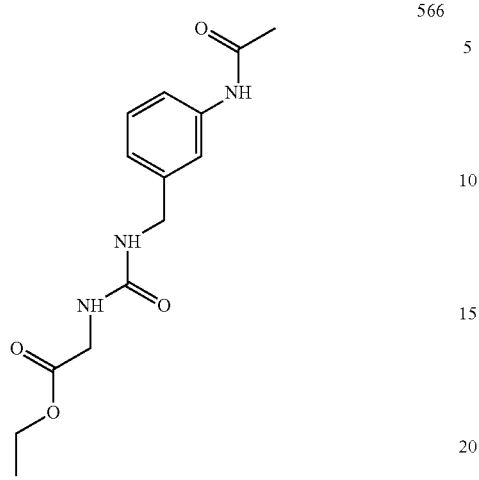
566
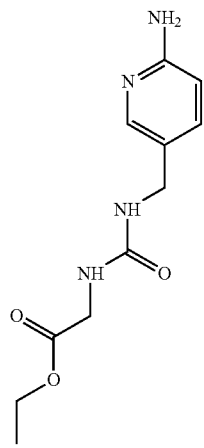
567
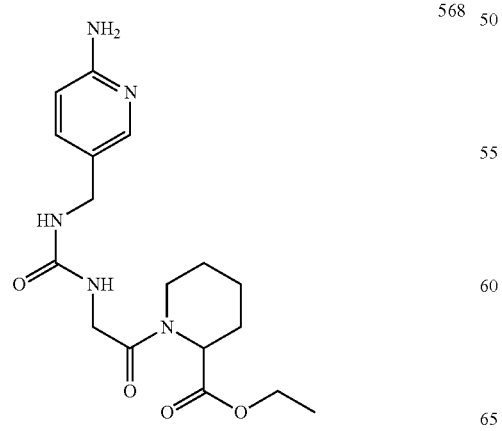
568
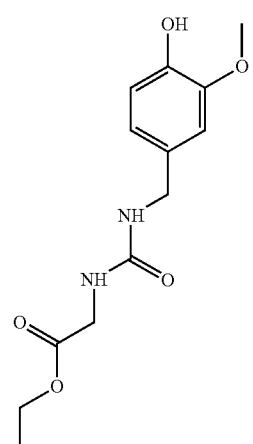
569
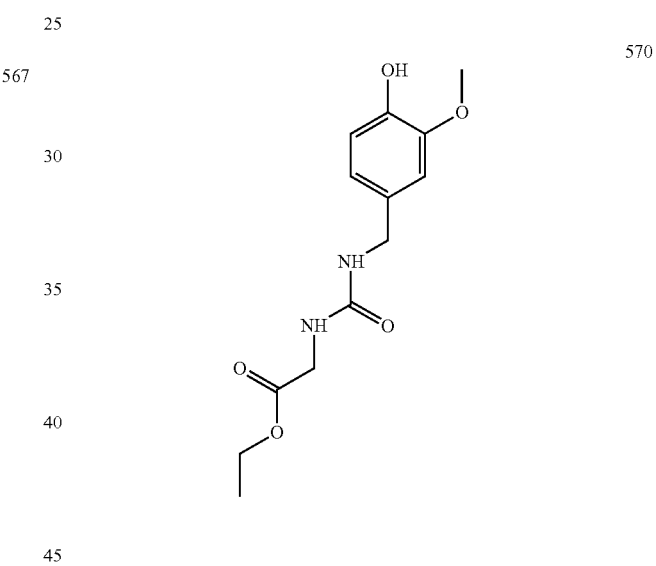
570
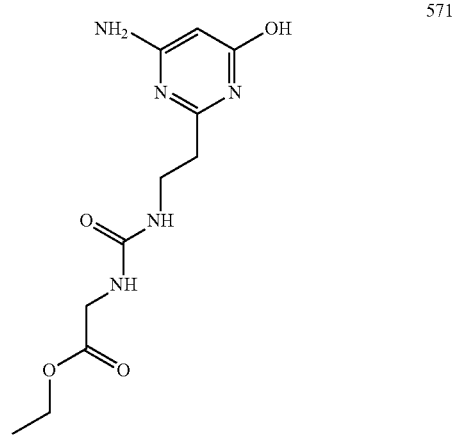
571

-continued
572
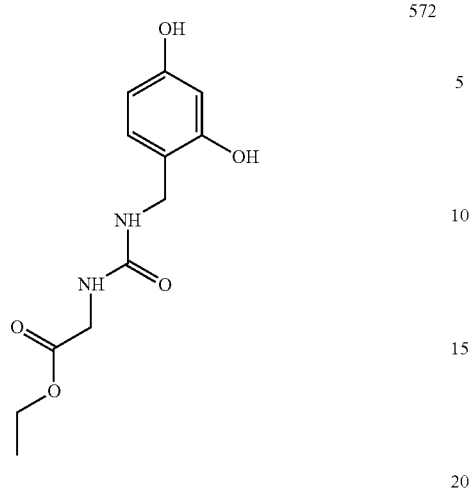
573
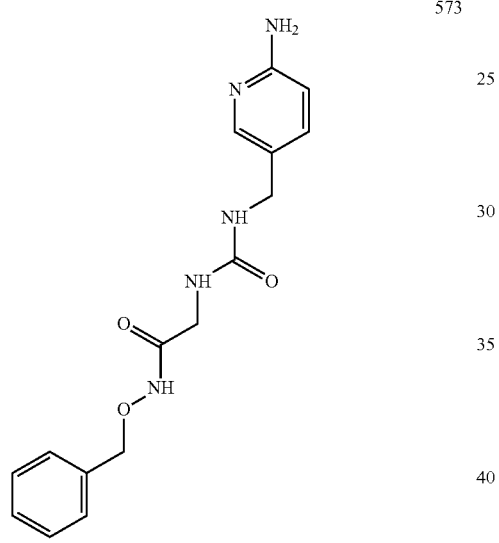
574
575
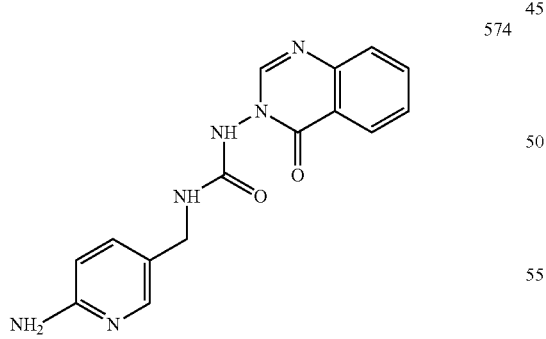
-continued
576
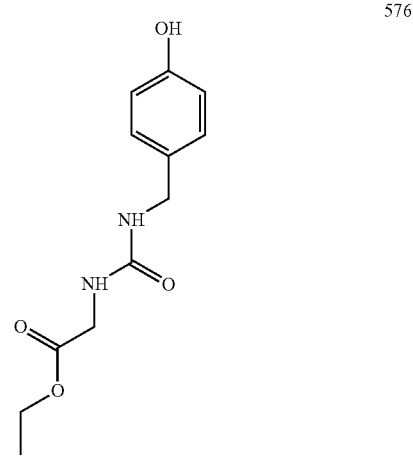
577
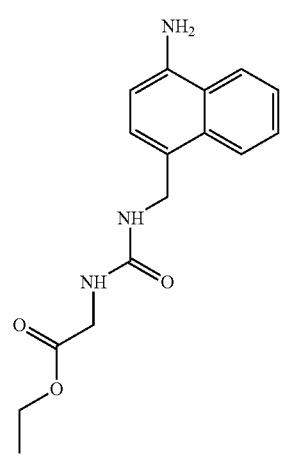
578
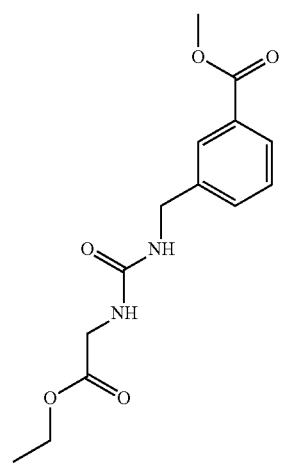

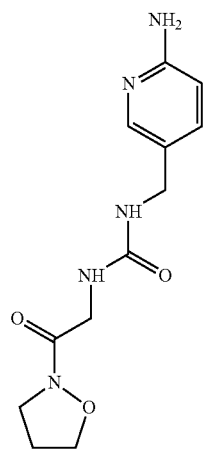
585
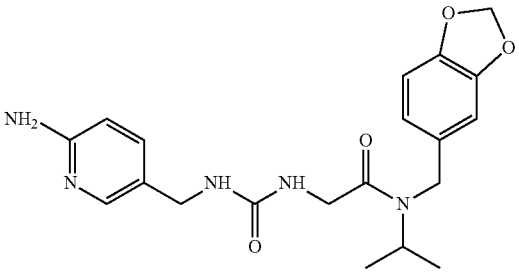
590
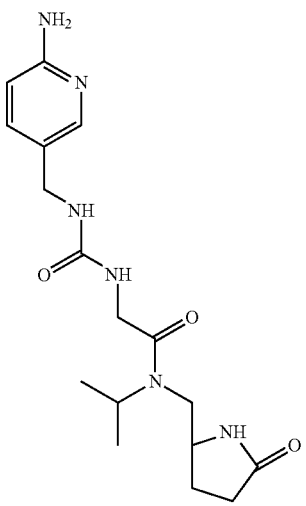
591
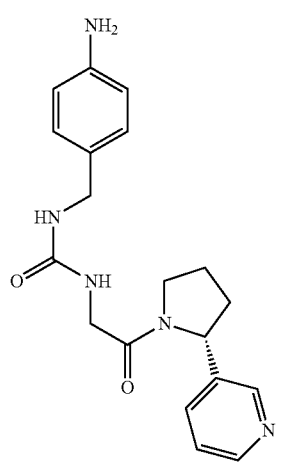
586
587
588
592

-continued
593
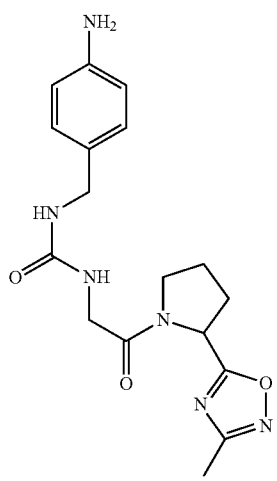
594
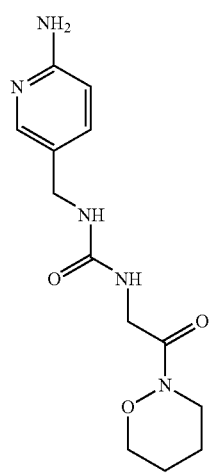
595
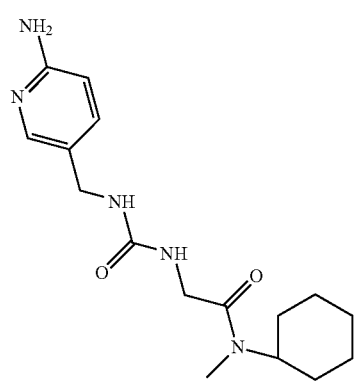
-continued
596
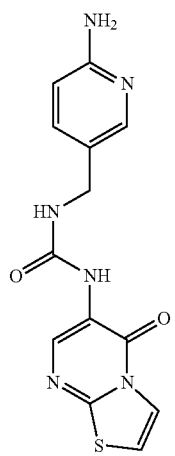
597
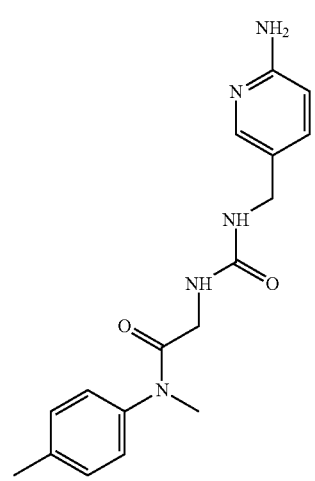
598
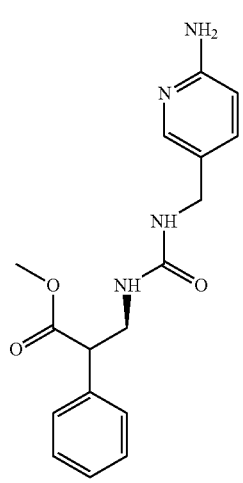
599
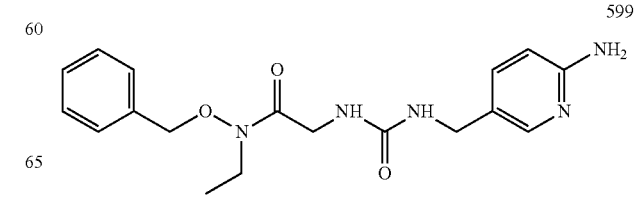

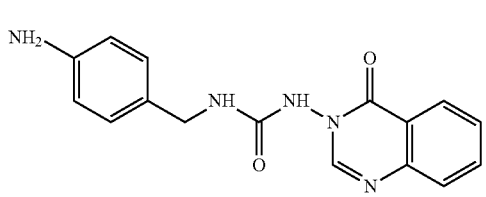
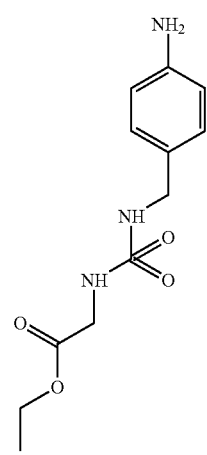
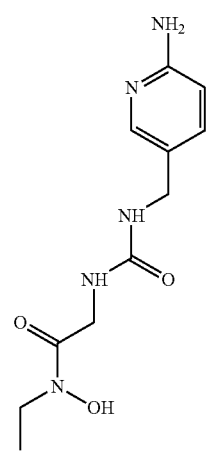
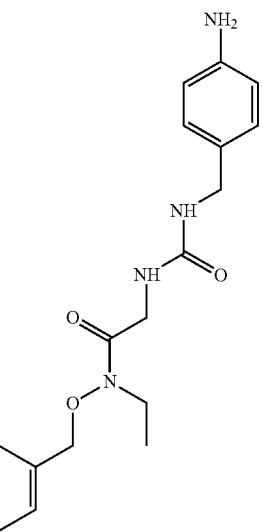
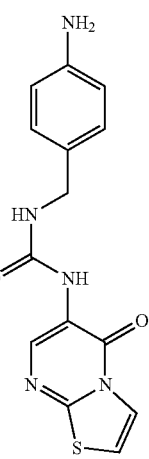
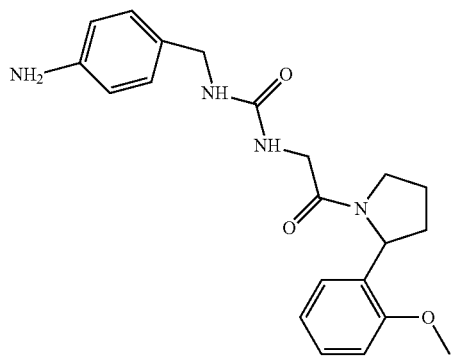
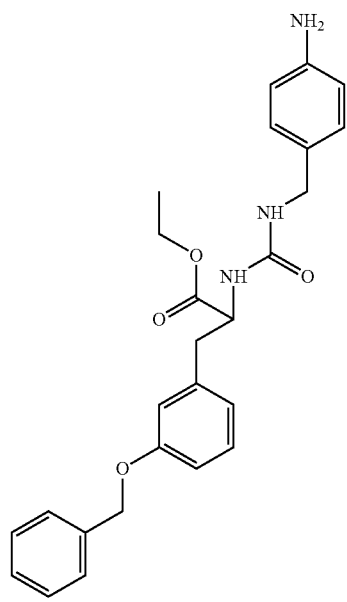

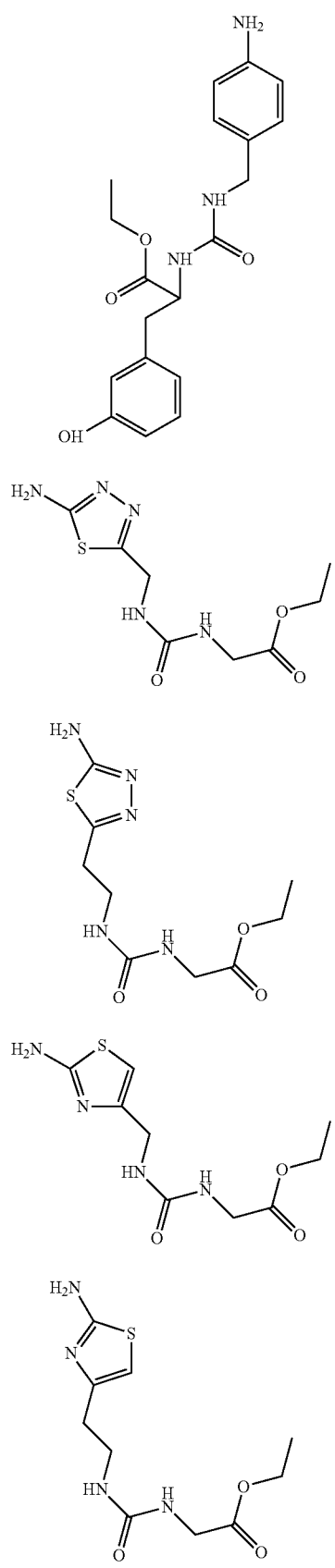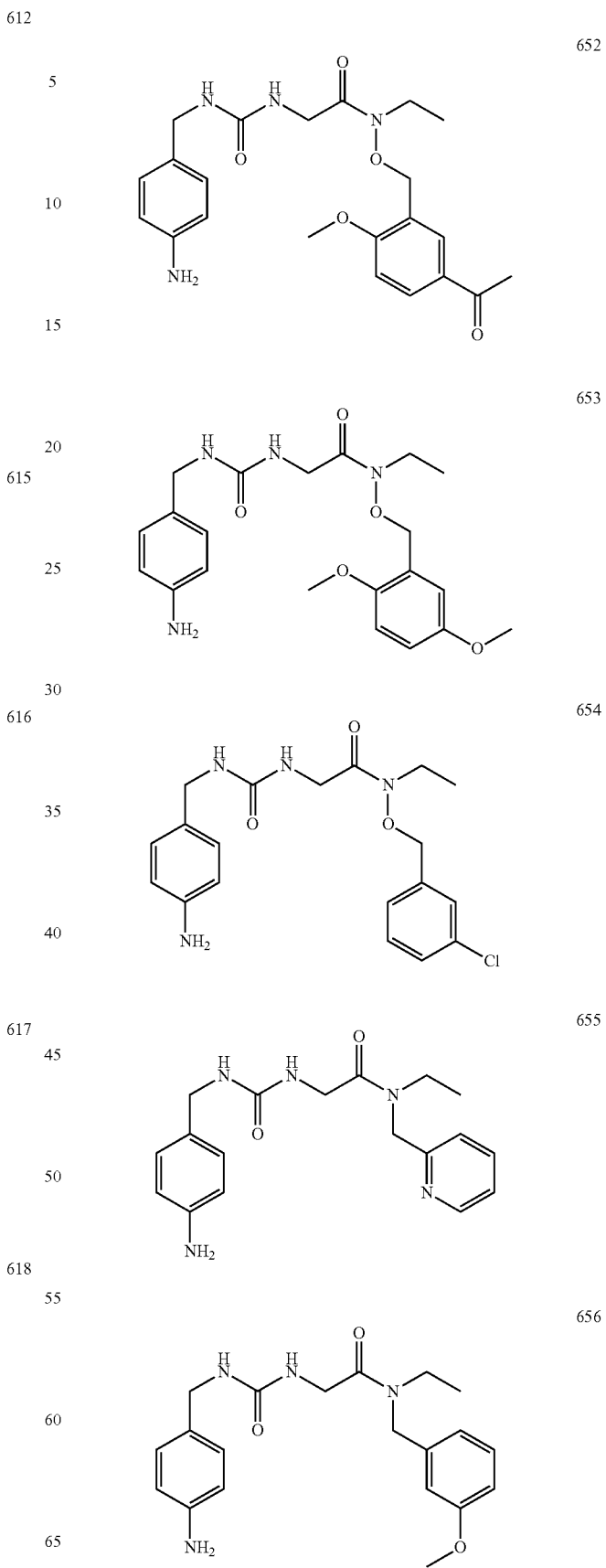

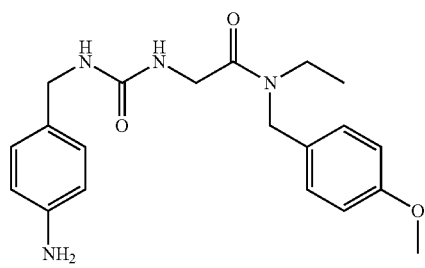
657
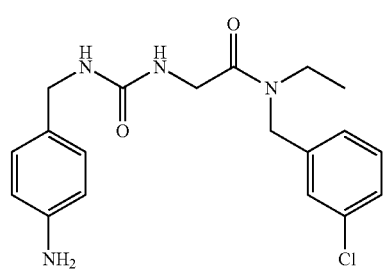
658
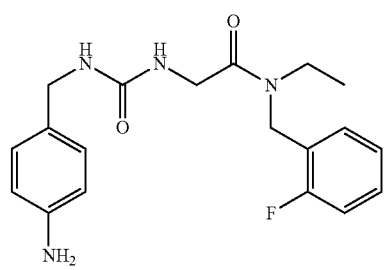
659
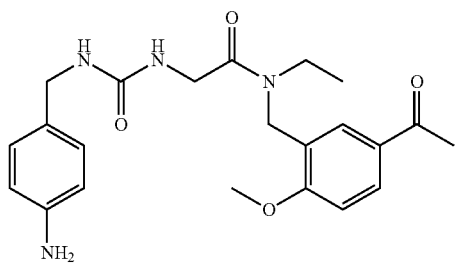
660
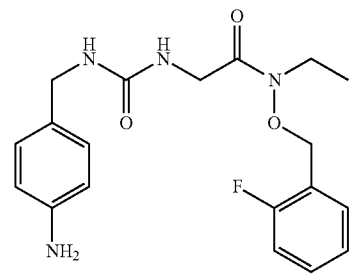
661
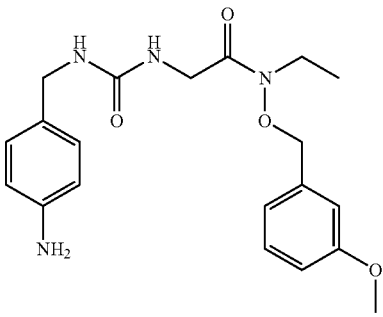
662

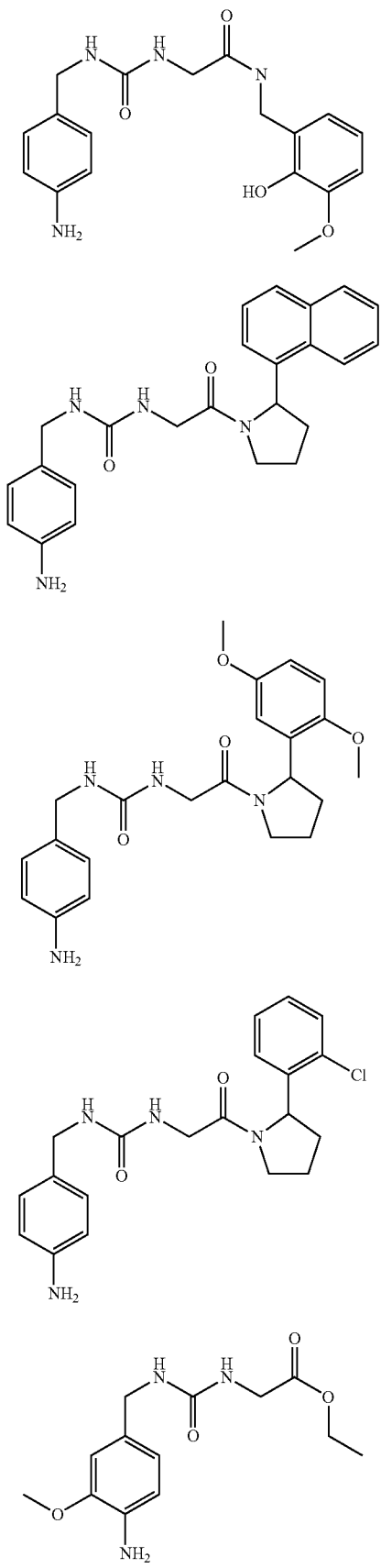
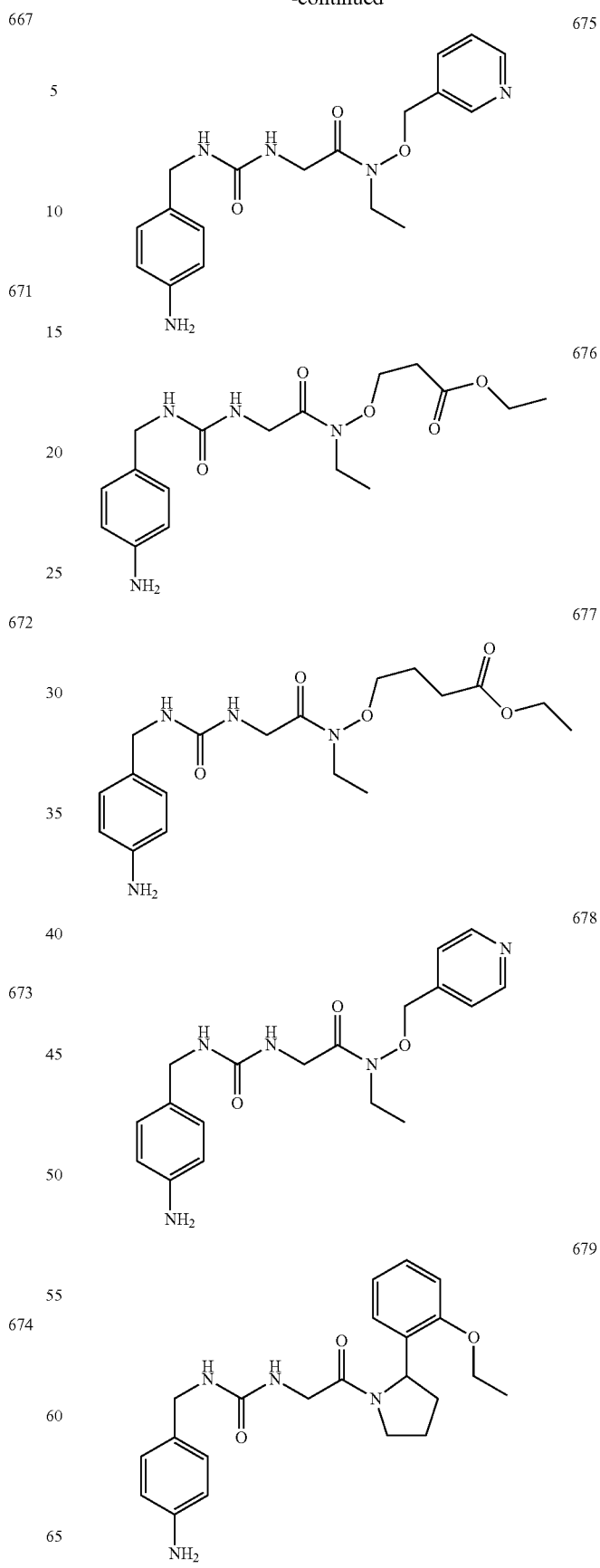

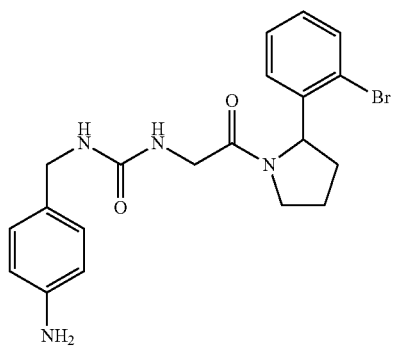
680
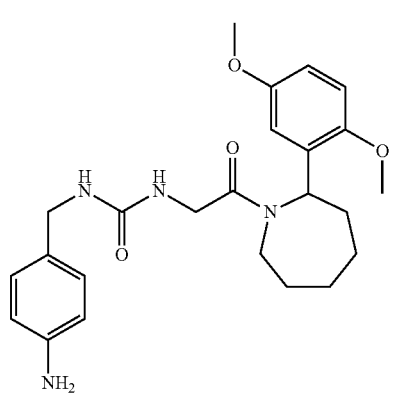
681
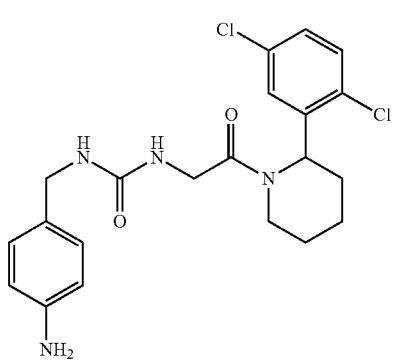
682
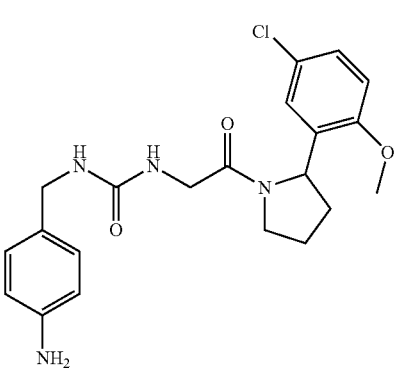
683
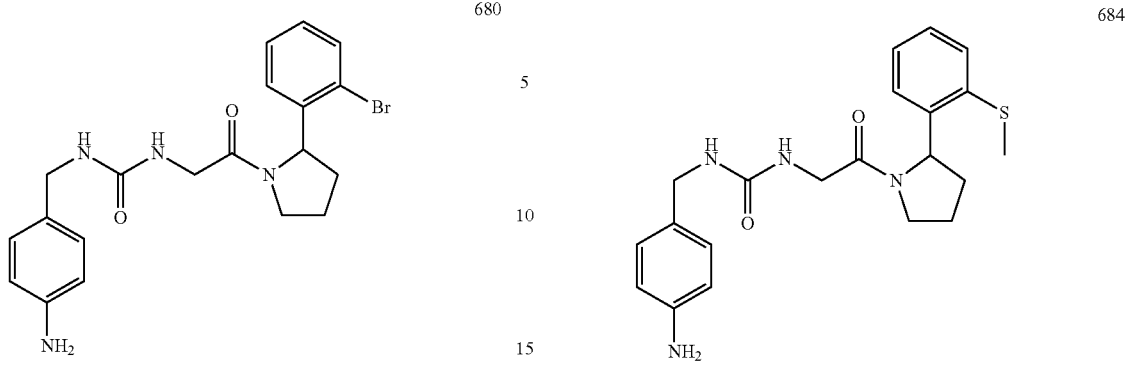
684
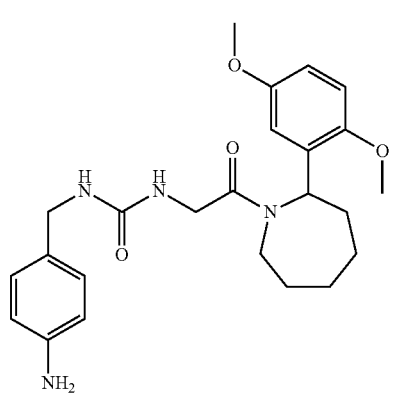
685
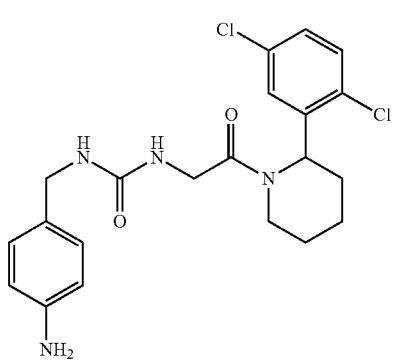
686
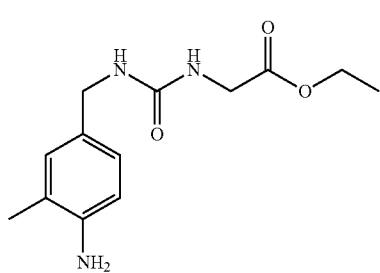
690

691 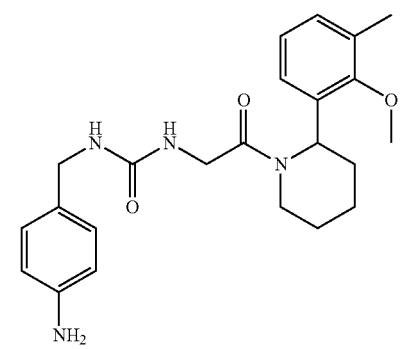
692 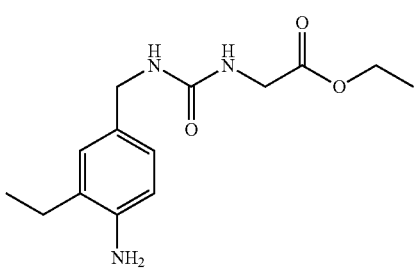
693 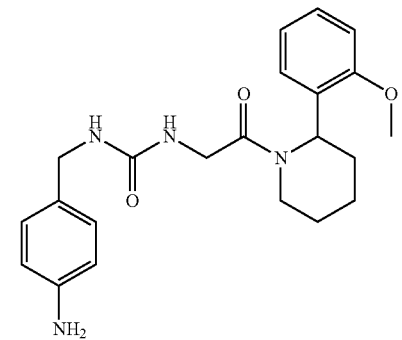
694 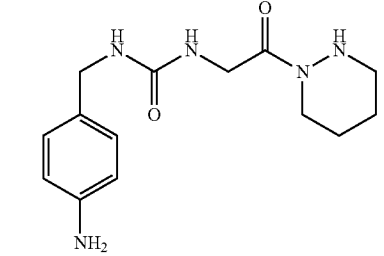
695 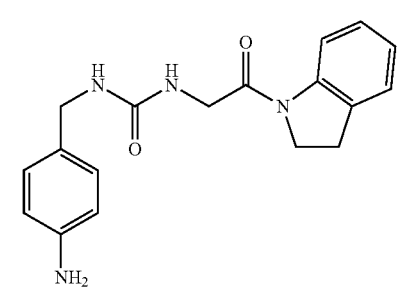
696 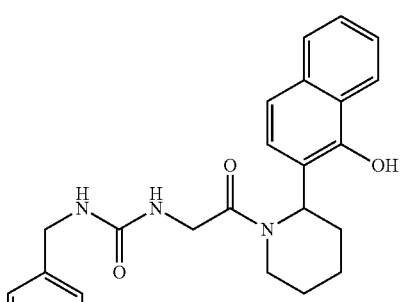
697 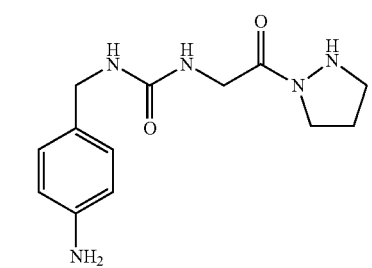
698 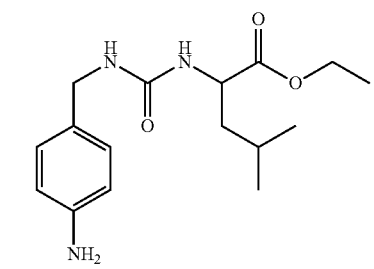
699 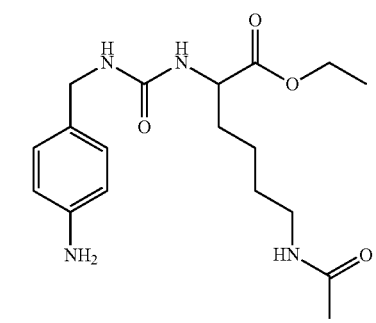
700 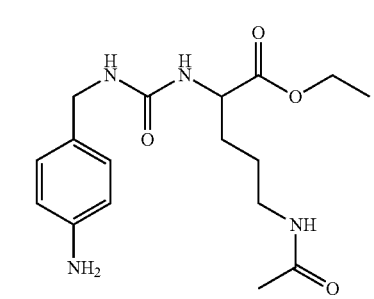

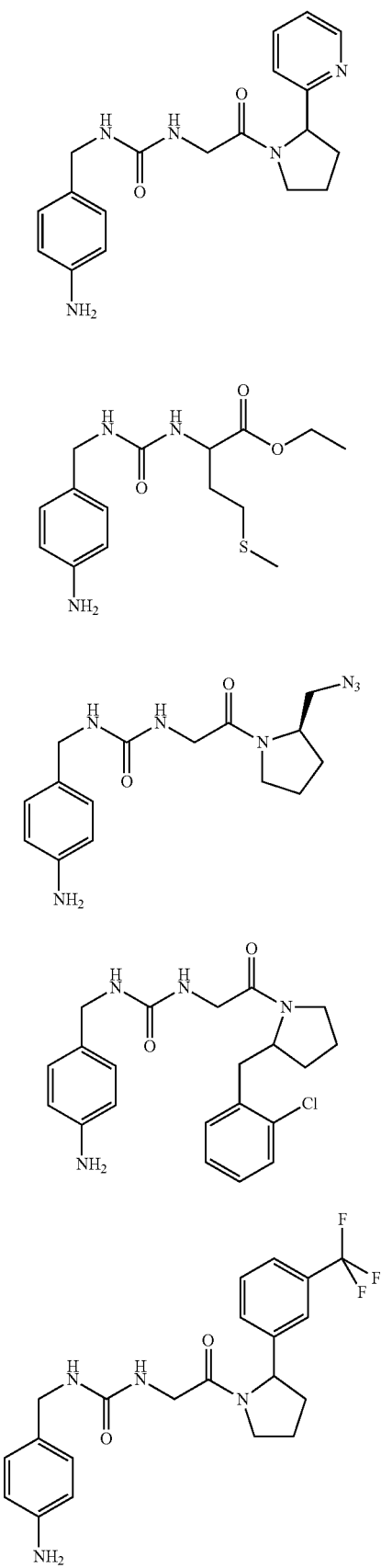
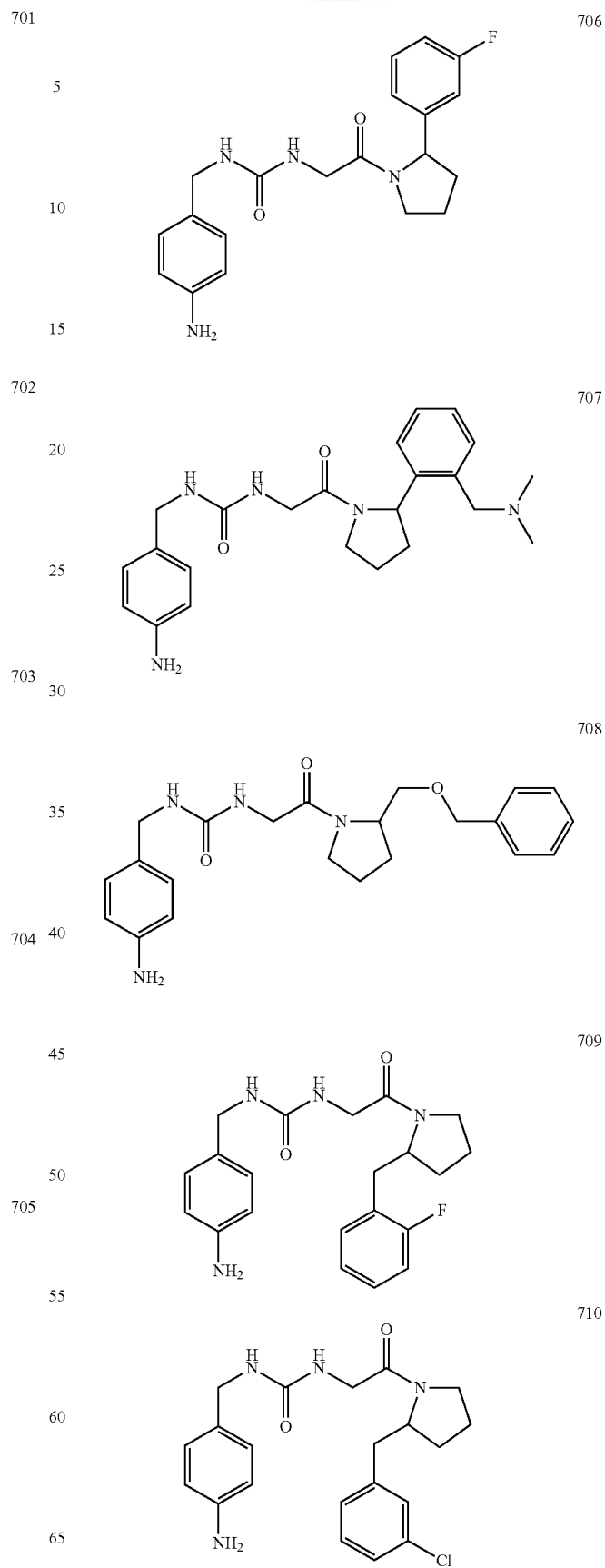

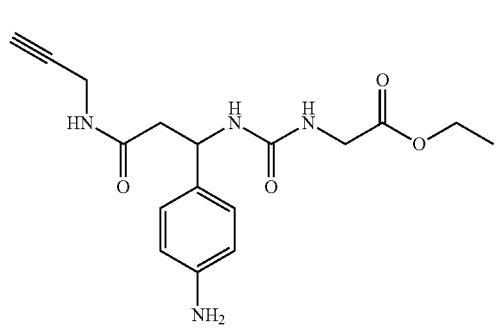
711
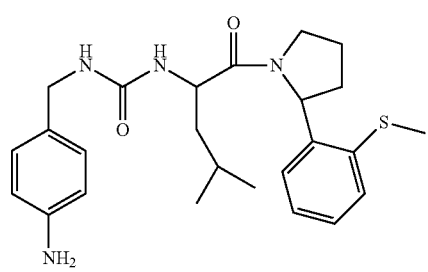
Mélange racémique (712 + 713)
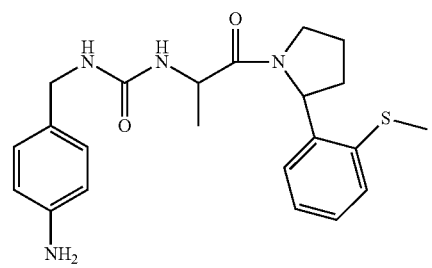
Mélange racémique (714 + 715)
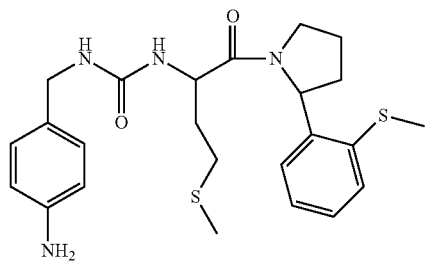
Mélange racémique (716 + 717)
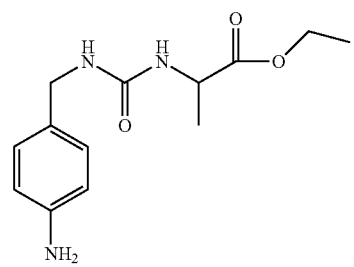
720
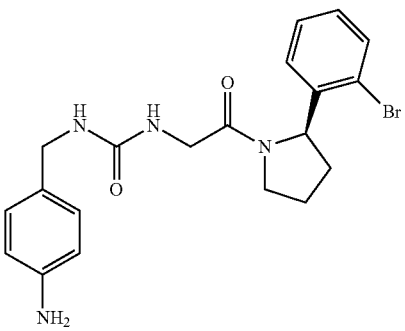
728
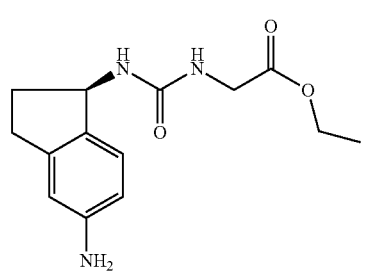
729
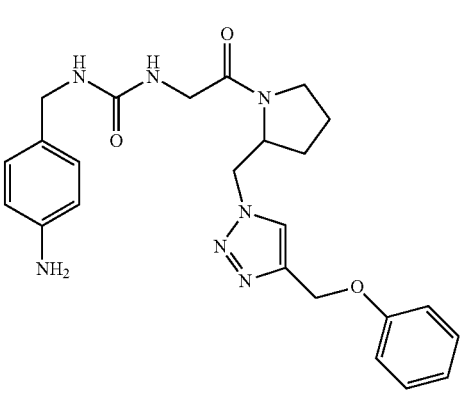
730
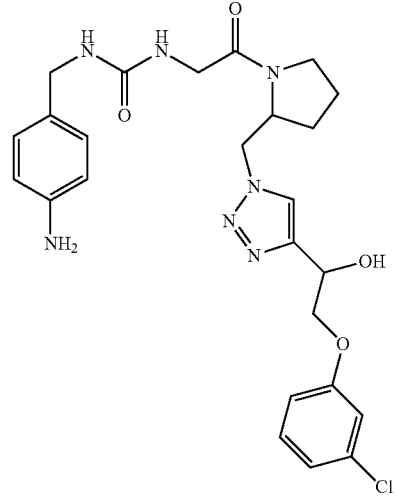
731

732 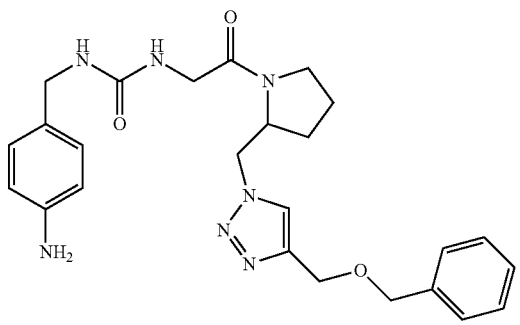

733 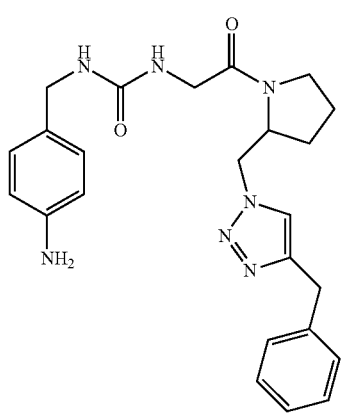

734 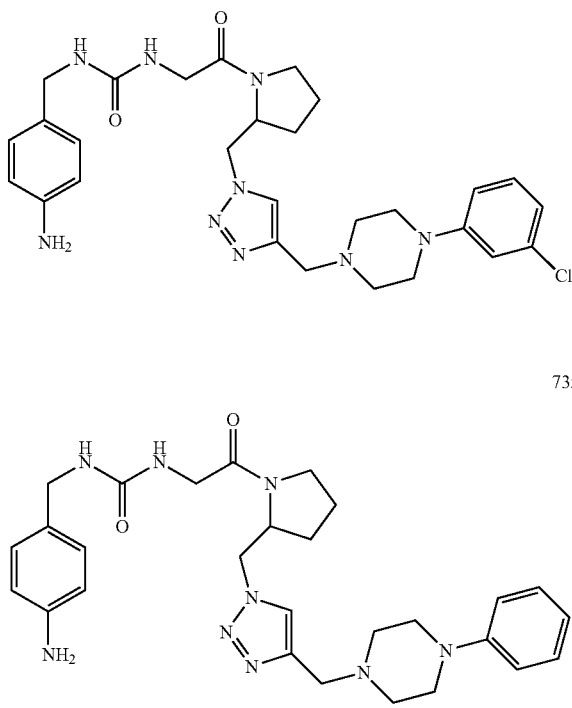

735

736 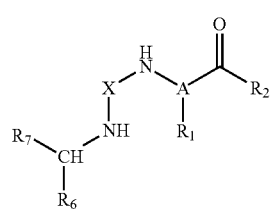

The present invention also relates to compounds having formula (I-bis):

(I-bis)

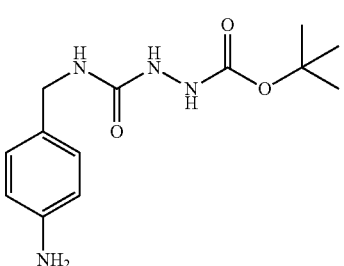

wherein:
R$_1$, R$_2$, A, X and R$_6$ are as defined above in formula (I), and
R$_7$ is chosen from the group consisting of aryl groups and heteroaryl groups comprising 5 or 6 ring atoms, substituted by at least one NH$_2$ group, or their pharmaceutically acceptable salts, hydrates or hydrated salts or its polymorphic crystalline structures, racemates, diastereomers or enantiomers, with the exclusion of the following compounds:

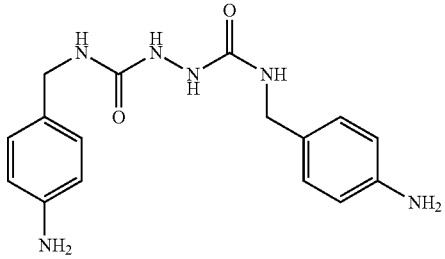

The excluded compounds are known compounds having RN 1174633-24-9 and 343823-60-9, respectively.

Preferably, in formula (I-bis), R$_6$ is H.

Preferably, in formula (I-bis), R$_7$ is an aryl or heteroaryl group comprising 6 ring atoms and substituted by one NH$_2$ group in para position.

According to a preferred embodiment, in formula (I-bis), $R_2$ is a group of formula $NR_3R_4$ as defined above in formula (I), and preferably $R_1$ is H.

According to another preferred embodiment, in formula (I-bis), $R_2$ is a group of formula $OR_5$ as defined above in formula (I), and preferably $R_1$ is H.

The present invention also relates to compounds having formula (I-ter):

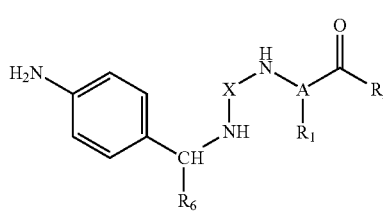
(I-ter)

wherein $R_1$, $R_2$, A, X and $R_6$ are as defined above in formula (I), with the exclusion of the above 1174633-24-9 and 343823-60-9 compounds.

Preferably, in formula (I-ter), $R_6$ is H.

According to a preferred embodiment, in formula (I-ter), $R_2$ is a group of formula $NR_3R_4$ as defined above in formula (I), and preferably $R_1$ is H.

According to another preferred embodiment, in formula (I-ter), $R_2$ is a group of formula $OR_5$ as defined above in formula (I), and preferably $R_1$ is H.

31.) The present invention also relates to compounds having formula (I-ter-1):

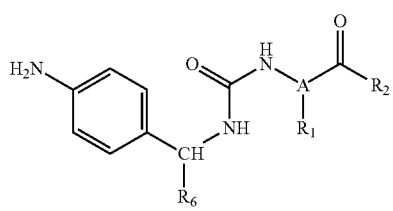
(I-ter-1)

wherein $R_1$, $R_2$, A, and $R_6$ are as defined above in formula (I), with the exclusion of the above 1174633-24-9 and 343823-60-9 compounds.

The present invention also relates to compounds having formula (I-ter-2):

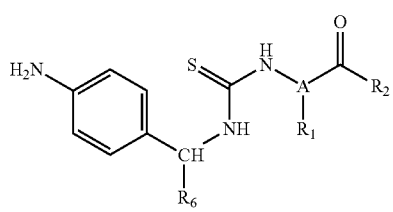
(I-ter-2)

wherein $R_1$, $R_2$, A, and $R_6$ are as defined above in formula (I).

The present invention also relates to compounds having formula (I-ter-3):

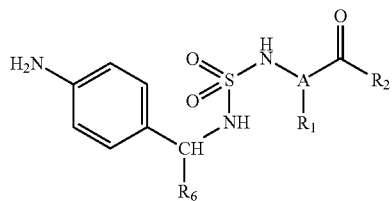
(I-ter-3)

wherein $R_1$, $R_2$, A, and $R_6$ are as defined above in formula (I).

The present invention also relates to compounds having formula (II-bis):

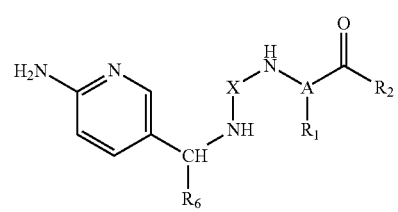
(II-bis)

wherein $R_1$, $R_2$, A, X and $R_6$ are as defined above in formula (I).

Preferably, in formula (II-bis), $R_6$ is H.

According to a preferred embodiment, in formula (II-bis), $R_2$ is a group of formula $NR_3R_4$ as defined above in formula (I), and preferably $R_1$ is H.

According to another preferred embodiment, in formula (II-bis), $R_2$ is a group of formula $OR_5$ as defined above in formula (I), and preferably $R_1$ is H.

The present invention also relates to compounds having formula (I-bis-1):

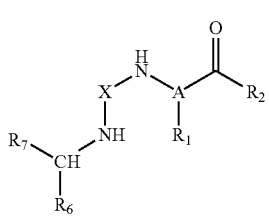
(I-bis-1)

wherein:
$R_1$, $R_2$, A, X and $R_6$ are as defined above in formula (I), and
$R_7$ is chosen from the group consisting of aryl groups and heteroaryl groups comprising 5 ring atoms, preferably substituted by at least one $NH_2$ group, or their pharmaceutically acceptable salts, hydrates or hydrated salts or its polymorphic crystalline structures, racemates, diastereomers or enantiomers.

The present invention also relates to compounds having formula (I-bis-2):

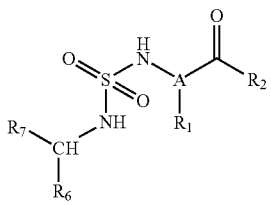
(I-bis-2)

wherein:
$R_1$, $R_2$, A, and $R_6$ are as defined above in formula (I), and
$R_7$ is chosen from the group consisting of aryl groups and heteroaryl groups comprising 5 ring atoms, preferably substituted by at least one $NH_2$ group,
or their pharmaceutically acceptable salts, hydrates or hydrated salts or its polymorphic crystalline structures, racemates, diastereomers or enantiomers.

The present invention also relates to compounds having formula (I-bis-3):

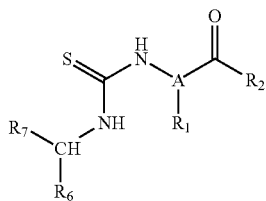
(I-bis-3)

wherein:
$R_1$, $R_2$, A, and $R_6$ are as defined above in formula (I), and
$R_7$ is chosen from the group consisting of aryl groups and heteroaryl groups comprising 5 ring atoms, preferably substituted by at least one $NH_2$ group,
or their pharmaceutically acceptable salts, hydrates or hydrated salts or its polymorphic crystalline structures, racemates, diastereomers or enantiomers.

The present invention also relates to compounds having formula (I-bis-4):

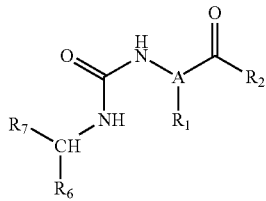
(I-bis-4)

wherein:
$R_1$, $R_2$, A, and $R_6$ are as defined above in formula (I), and
$R_7$ is chosen from the group consisting of aryl groups and heteroaryl groups comprising 5 ring atoms, preferably substituted by at least one $NH_2$ group,
or their pharmaceutically acceptable salts, hydrates or hydrated salts or its polymorphic crystalline structures, racemates, diastereomers or enantiomers.

Preferably in formulae (I-bis-1), (I-bis-2), (I-bis-3) and (I-bis-4), A is CH and $R_1$ is H.

The present invention also relates to compounds having formula (I-1):

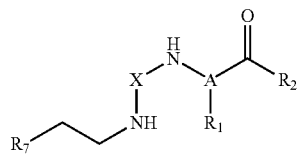
(I-1)

wherein:
$R_1$, $R_2$, X, and A are as defined above in formula (I), and
$R_7$ is chosen from the group consisting of aryl groups and heteroaryl groups comprising 5 ring atoms, preferably substituted by at least one $NH_2$ group,
or their pharmaceutically acceptable salts, hydrates or hydrated salts or its polymorphic crystalline structures, racemates, diastereomers or enantiomers.

The present invention also relates to compounds having formula (XIII-bis):

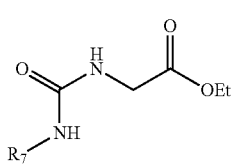
(XIII-bis)

wherein $R_7$ is chosen from the group consisting of aryl groups and heteroaryl groups comprising 5 or 6 ring atoms, substituted by at least one $NH_2$ group.

The present invention also relates to compounds having the formula (XXIII):

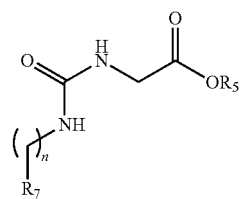
(XXIII)

wherein n and $R_5$ are as defined above in formula (I), and $R_7$ is a heteroaryl group comprising at least one nitrogen atom and one sulfur atom in the ring and comprising one $NH_2$ group as substituent.

Among those compounds of formula (MI), one may cite the preferred compounds having formula (XXIII-1) or (XXIII-2) as defined above.

The present invention also relates as such to compounds having one of the formulae (II), (III), (IV), (1V-1), (1V-2), (V), (VI), (VII), (VIII), (VIII-1), (VIII-2), (IX), (X), (XI), (XI-1), (XI-2), (XII), (XIII-bis), (XIV), and (XV), said formulae being as defined above.

The present invention also relates to a pharmaceutical composition comprising a compound of formula (I-bis), (I-ter), (II-bis), (II), (III), (IV), (IV-1), (IV-2), (V), (VI), (VII), (VIII), (VIII-1), (VIII-2), (IX), (X), (XI), (XI-1), (XI-2), (XII), (XIII-bis), (XIV), and (XV) as defined above, in association with a pharmaceutically acceptable vehicle.

"Pharmaceutically acceptable" means it is, within the scope of sound medical judgment, suitable for use in contact with the cells of humans and lower animals without undue toxicity, irritation, allergic response and the like, and are commensurate with a reasonable benefit/risk ratio.

The present invention also relates as such to compounds 428 to 433, 436, 490 to 494, 509 to 533, 536 to 578, 585 to 588, 590 to 600, 604, 606 to 609, 611, and 612, as well as pharmaceutical compositions comprising at least one of these compounds. The present invention also relates as such to compounds 652 to 667, 671 to 686, 690 to 717, 720, and 730 to 736, as well as pharmaceutical compositions comprising at least one of these compounds.

The present invention also relates to a method for preparing compounds having formula (III) as defined above, said method comprising the reaction of a compound $HN(R_4)(OR'_a)$ (having the formula (XVI)) with a compound having the following formula (XVII):

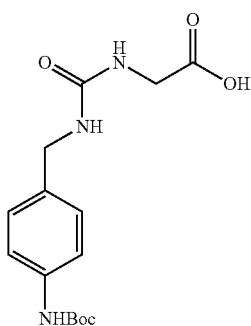

(XVII)

This method comprises two steps, the first one being carried out in the presence of EDAP (1-[3-(Dimethylamino)propyl]-3-ethylcarbodiimide), 1-hydroxybenzotriazole (HOBt), diisopropylethylamine (DIEA) and dichloromethane (DCM), and the second one in the presence of trifluoroacetic acid (TFA) and dichloromethane (DCM).

The compounds having formula (XVII) are prepared according the following reaction scheme:

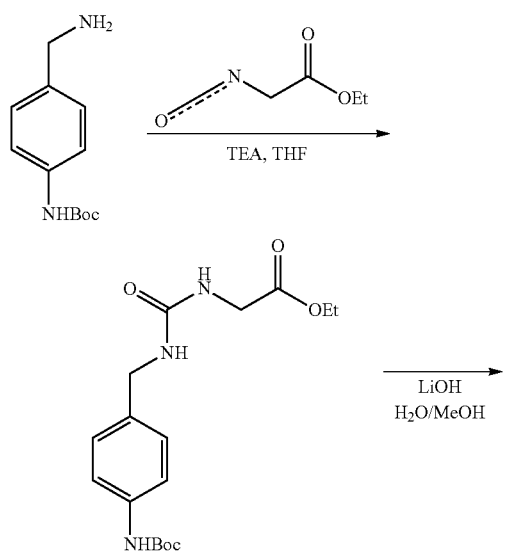

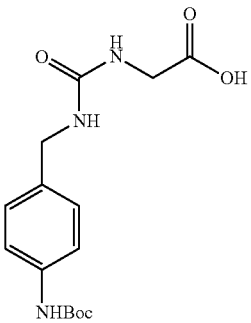

The compounds having formula (XVI) are prepared according one of both below reaction schemes:

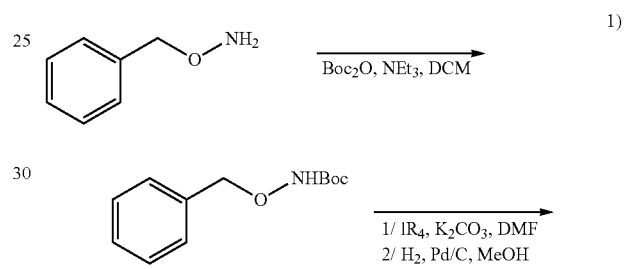

1)

2)

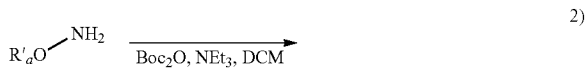

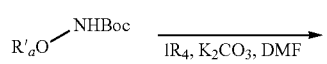

The present invention also relates to a method for preparing compounds having formula (IV) as defined above, said method comprising the reaction of a compound $HN(R_4)(R_3)$ (having the formula (XVIII)) with a compound having the formula (XVII) as mentioned above.

The compounds of formula (XVII) may be obtained by a reducing amination from compounds of formula $NH_2(R_4)$.

The present invention also relates to a method for preparing compounds having formula (V) as defined above, according to the following reaction scheme:

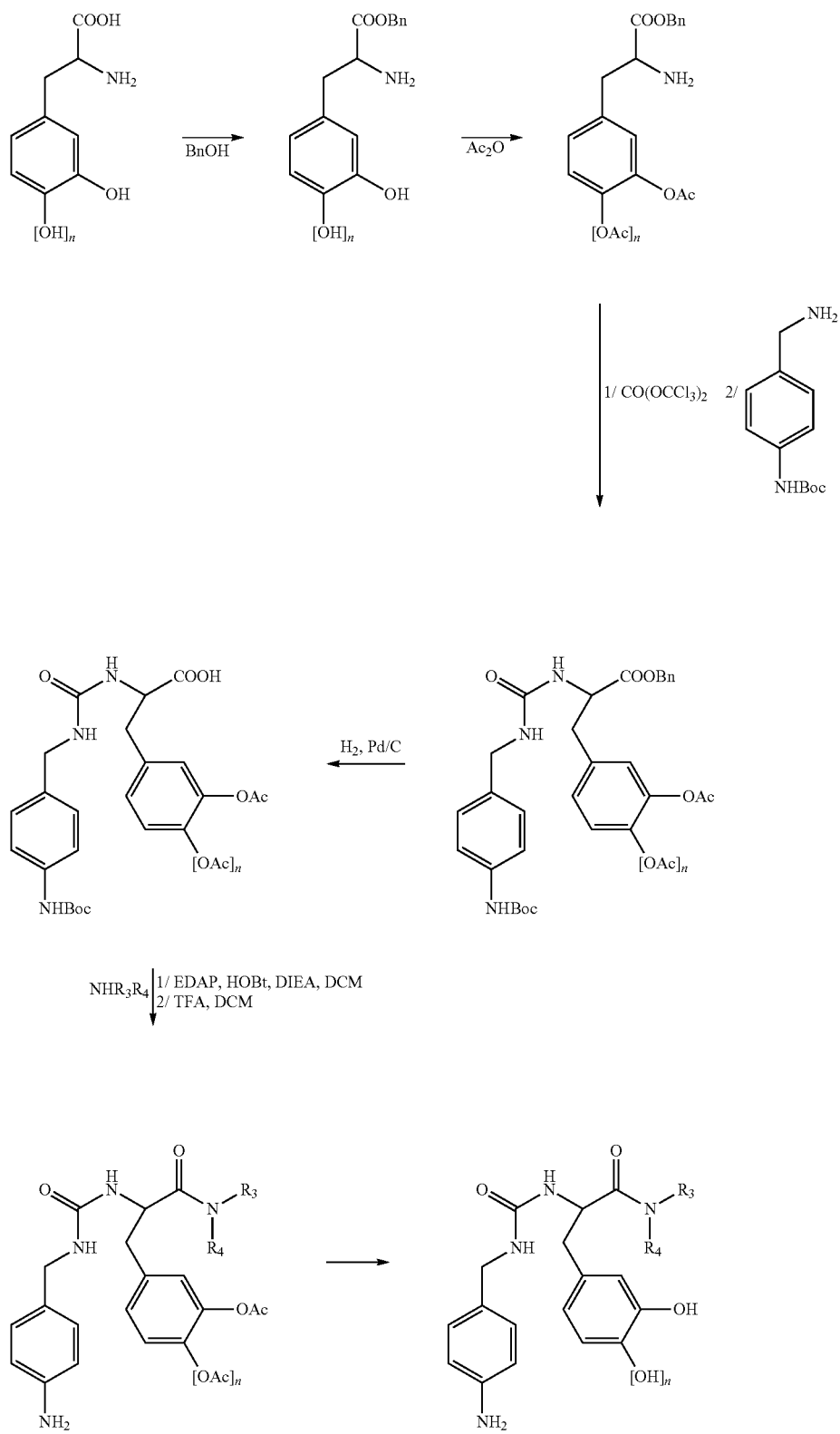
The present invention also relates to a method for preparing compounds having formula (VI) as defined above, according to the following reaction scheme:

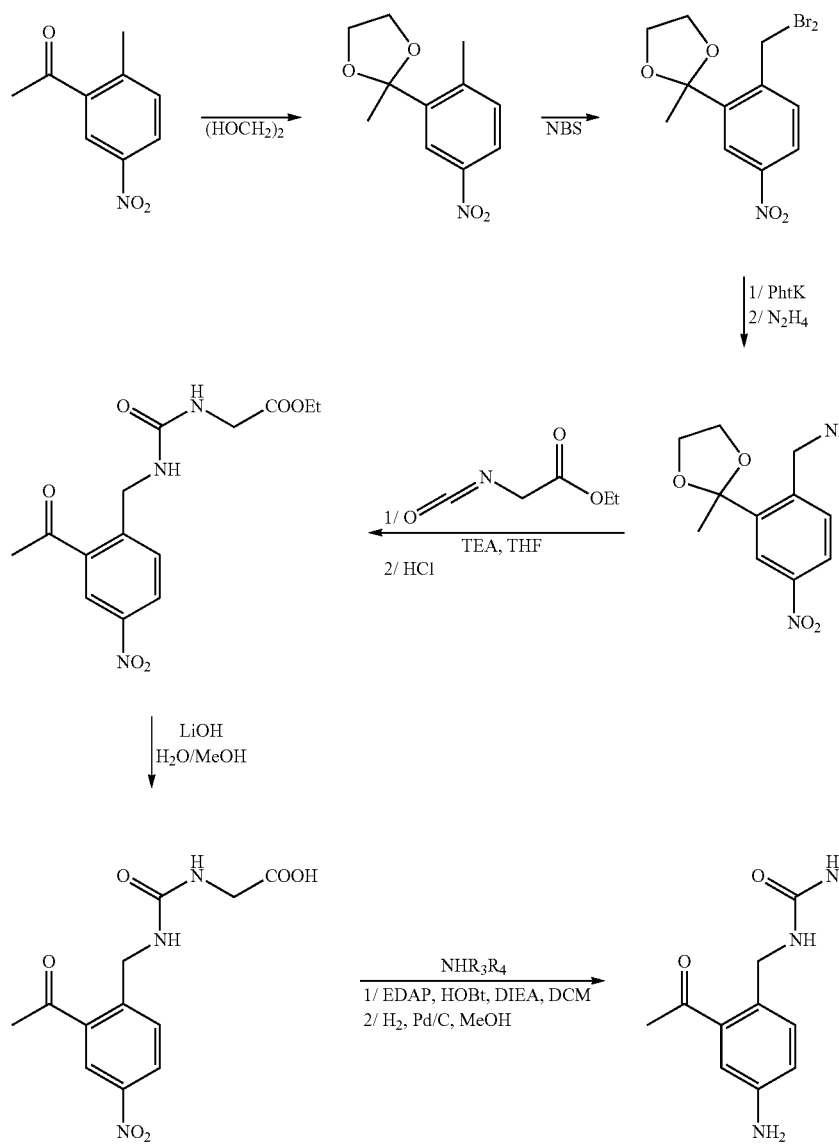
The present invention also relates to a method for preparing compounds having formula (VU) as defined above, according to the following reaction scheme:
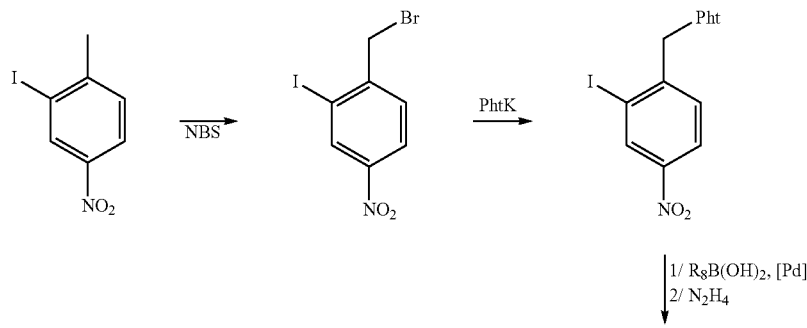

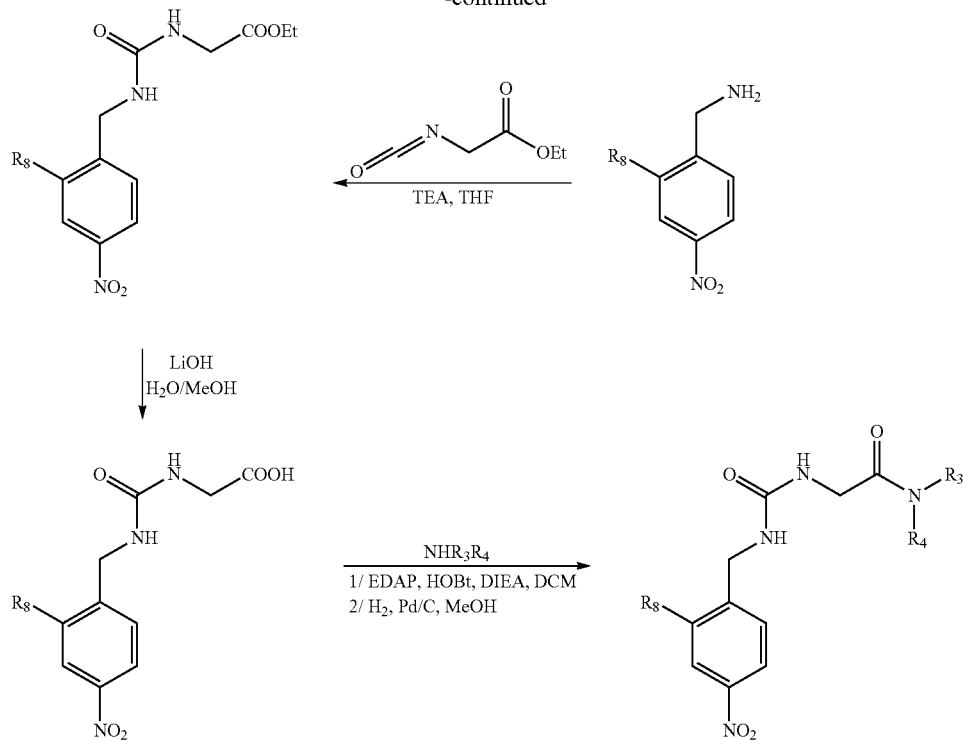

The present invention also relates to a method for preparing compounds having formula (VIII) as defined above, said method comprising the reaction of a compound having the above formula (XVII) with a compound having (XIX):

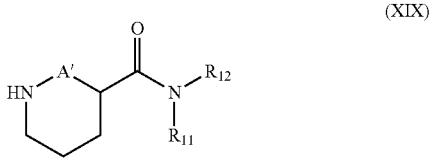
(XIX)

A', $R_{11}$ and $R_{12}$ being as defined above in formula (VIII).

This method comprises two steps, the first one being carried out in the presence of EDAP, HOBt, DIEA and DCM, and the second one in the presence of TFA and DCM.

The compounds having formula (XIX) are prepared from a compound having the following formula:

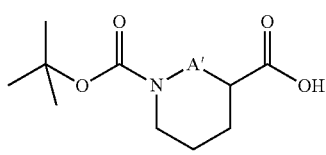

in the presence of EDAP, HOBt, DIEA and DCM, and then in the presence of TFA and DCM.

The present invention also relates to a method for preparing compounds having formula (VIII-2) as defined above, said method comprising the reaction of a compound having the above formula (XVII) with a compound having (XX):

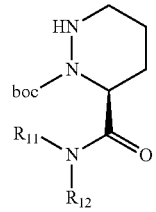
(XX)

$R_{11}$ and $R_{12}$ being as defined above in formula (VIII).

This method comprises two steps, the first one being carried out in the presence of EDAP, HOBt, DIEA and DCM, and the second one in the presence of TFA and DCM.

The present invention also relates to a method for preparing compounds having formula (VIII-2) as defined above, said method comprising the reaction of a compound having the above formula (XVII) with a compound having (XXI):

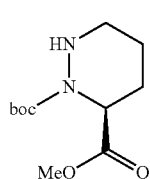
(XXI)

and in the presence of an amine $NH(R_{11})(R_{12})$.

The compounds of formula (XX) and (XXI) are prepared according to the following reaction scheme:

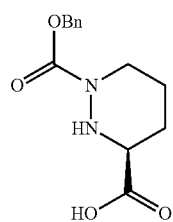
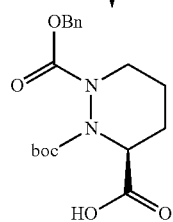
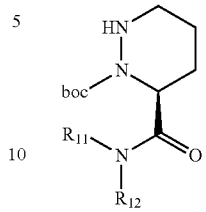
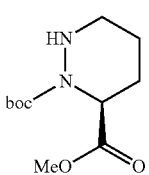
The present invention also relates to a method for preparing compounds having formula (IX) as defined above, according to the following reaction scheme:
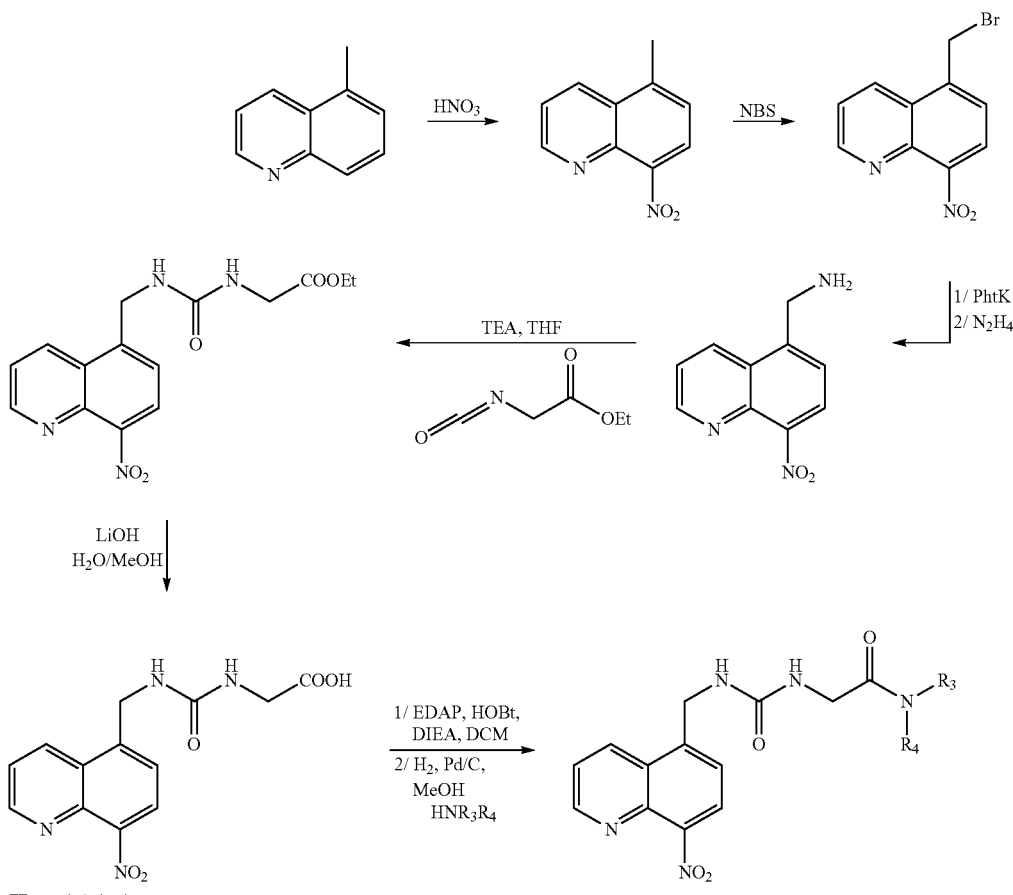
TEA = triethylamine The present invention also relates to a method for preparing compounds having formula (X) as defined above, according to the following reaction scheme:
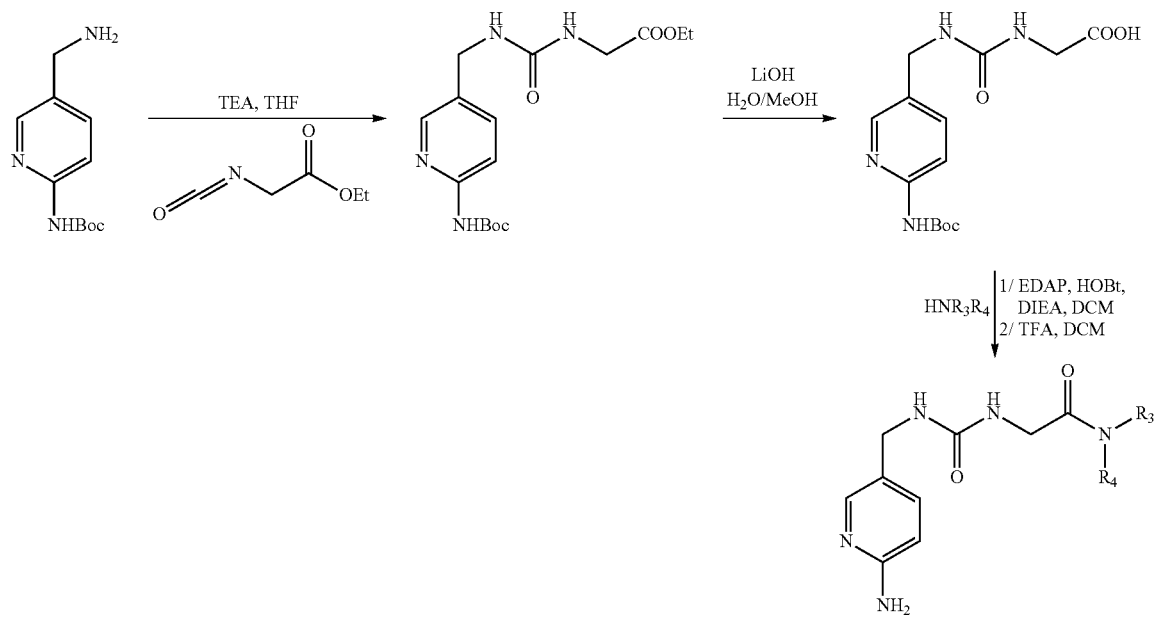
The present invention also relates to a method for preparing compounds having formula (XI-1) as defined above, according to the following reaction scheme:
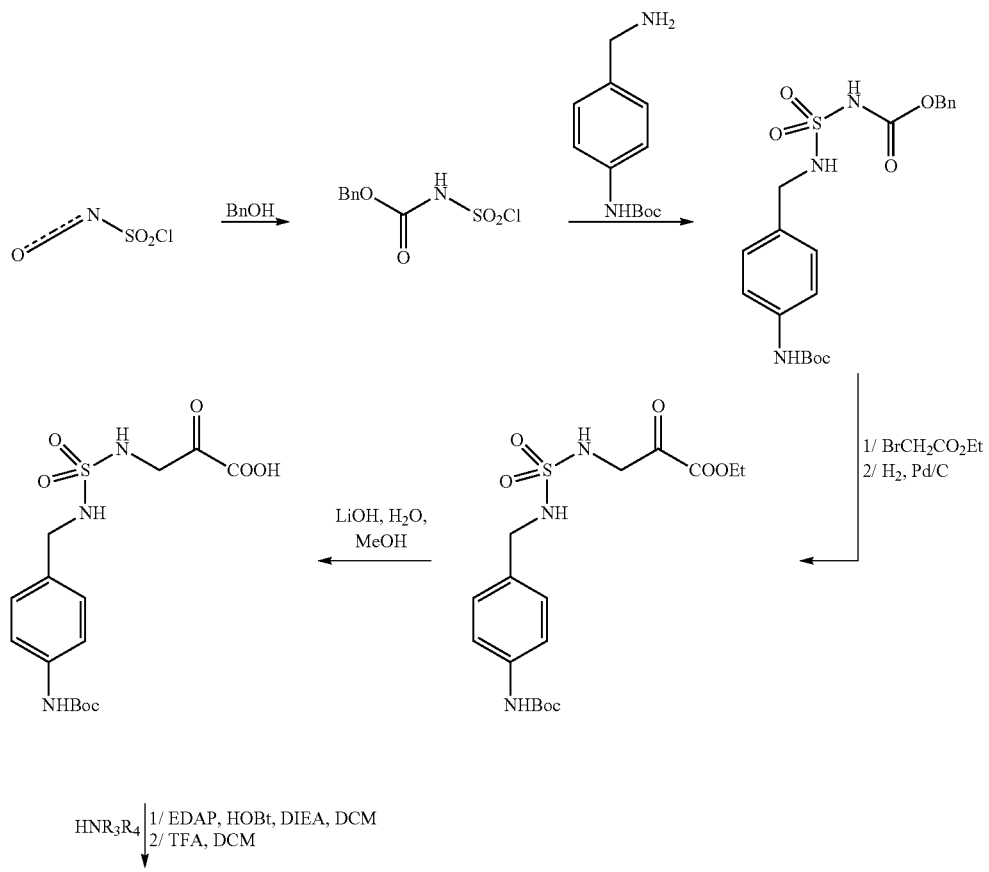

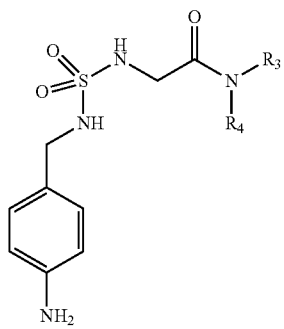
The present invention also relates to a method for preparing compounds having formula (XI-2) as defined above, according to the following reaction scheme:
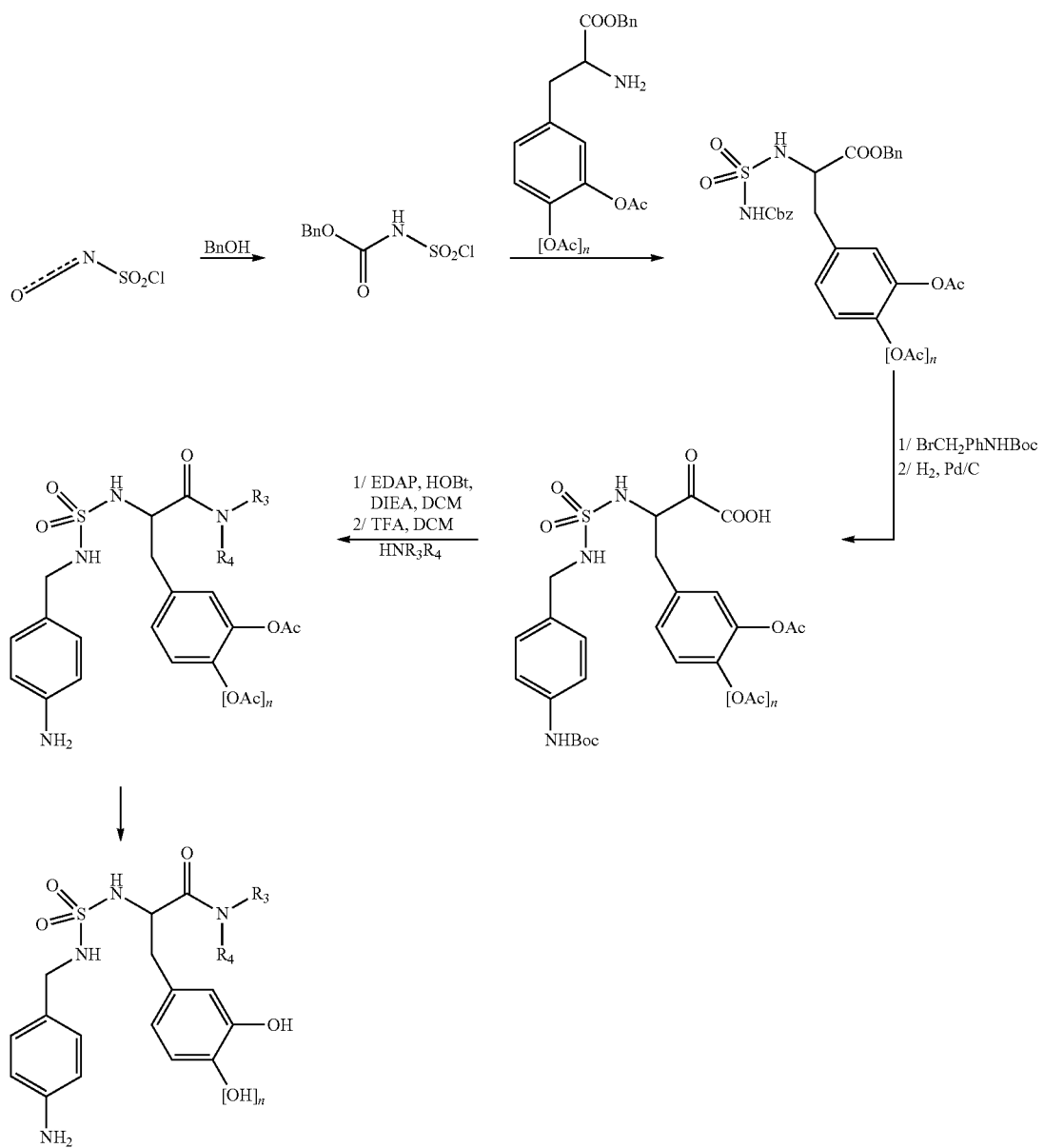

81

The compound having formula

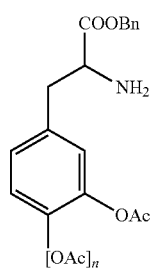

may be obtained according to the below reaction scheme:

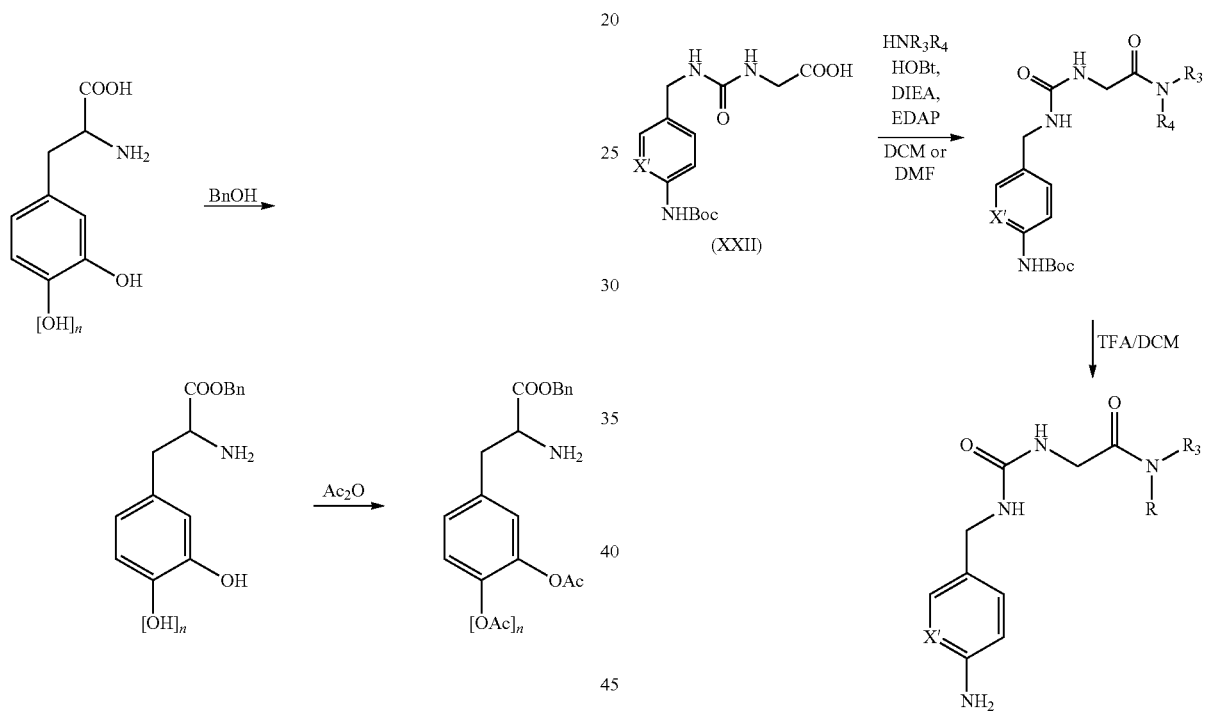

The present invention also relates to a method for preparing compounds having formula (XIII) as defined above, comprising the reaction of ethyl isocyanatoacetate with an amine having formula $H_2N-(CH(R_6))_n-R_7$, n, $R_6$ and $R_7$ being as defined in formula (XIII).

This reaction is carried out in a solvent such as tetrahydrofuran (THF) or dimethylformamide (DMF).

The present invention also relates to a method for preparing compounds having formula (XIV) as defined above, comprising the reaction of an isothiocyanatoacetate having formula (XIV-1):

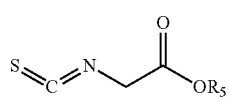

82 with an amine having formula

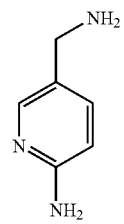

The present invention also relates to a method for preparing compounds having formula (XV) as defined above, according to the following reaction scheme:

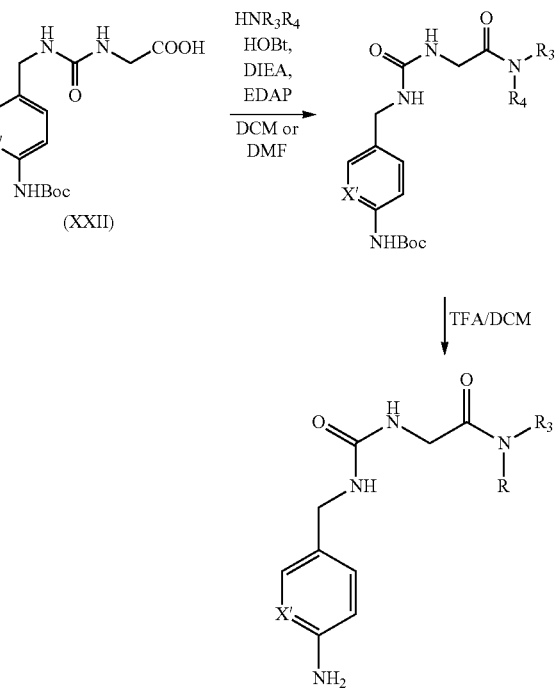

The above-mentioned compounds having formula (XXII) are prepared according to the below reaction scheme:

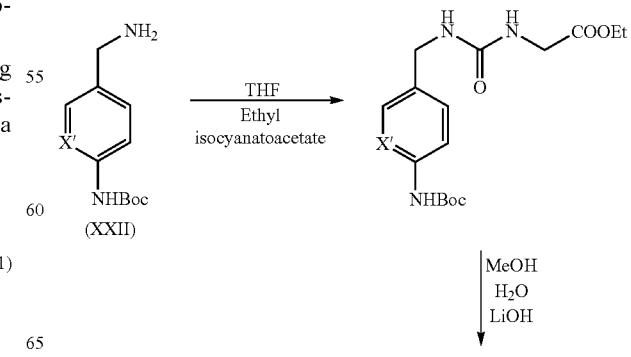

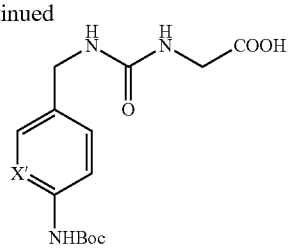

The present invention also relates to a method for preparing compounds having formula (XXIII) as defined above, comprising the reaction of a compound having formula $R_7$—$(CH_2)_n$—$NH_2$, wherein $R_7$ and n are as defined above in formula (XXIII), with a isocyanatoacetate compound of formula $R_{50}$—CO—$CH_2$—NCO, $R_5$ being as defined above in formula (I).

EXPERIMENTAL PART

A—Synthesis of Compounds

General Methods.

All commercial reagents (Aldrich, Acros, Chembridge, Chemivate) and solvents (SOS) were used without further purification. Mass spectra were acquired under ESI conditions using a Micromass Q-Tof. The $^1$H NMR spectra of all the compounds were recorder on Bruker 200, 300, 400, 500 and 600 MHz spectrometers using tetramethylsilane (TMS) as an internal standard, and chemical shift (δ) data for the proton resonance were reported in parts per million (ppm) relative to internal standard TMS. Thin-layer chromatography (TLC) was performed using Silica gel 60 $F_{254}$ plates from Macherey-Nagel and visualized by UV light. Flash chromatography was carried out using SOS silica gel 60 (35-70 mesh) with hexane, ethyl acetate (EtOAc), dichloromethane (DCM), petroleum ether (EDP) and methanol (MeOH) as eluents with chromatographic solvent proportion expressed on a volume:volume basis. The reported chemical yields were not optimized. HPLC chromatography was performed using a Waters Alliance 2790 (detector UV); method A: Column Thermo Hypersil C18 (50×2.1 mm), gradient of elution water/acetonitril/trifluoroacetic acid (99.9%10%/0.1% to 19.9%/80%/0.1% in 15 nm); method B: Column Waters Atlantis C18 (250×5 mm), gradient of elution water/acetonitril/trifluoroacetic acid (99.9%/0%/0.1% to 9.9%/90%/0.1% in 30 nm). Mass spectra was determined using an Micromass Q-T of in ElectroSpray (ESI) from Bruker.

I—Synthesis of Ureas (1-46)

General Procedure

Ethyl isocyanatoacetate (1 equivalent, 100 mg, 87 µl, 0.77 mmol) was dissolved in THF (0.4 M) or in DMF (0.4M). One equivalent of triethylamine was added if the amine is a salt form of HCl, then the amine (1 equivalent) was added in one portion and the reaction mixture was let 2 h at room temperature. After the reaction was complete (TLC control), the reaction mixture was concentrated and purified with different procedures.

The compounds 1-46 are prepared according the following reaction scheme:

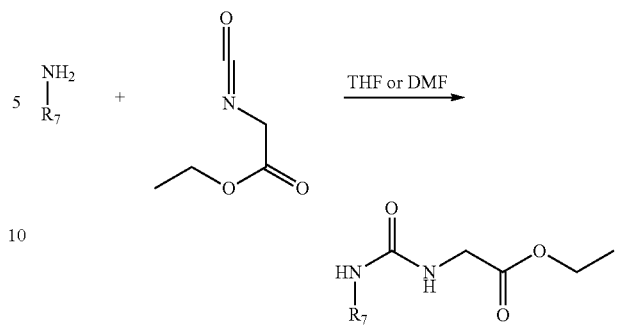

They correspond to compounds having formula (XIII) wherein n is 0.

Example 1

Preparation of ethyl 2-(3-(2-morpholinobenzyl)ureido)acetate (F510)(1)

1 was purified by precipitation in AcOEt/EDP to afford 200 mg of a white solid (87%) Rf=0.52 (AcOEt). $^1$H NMR (DMSO): δ 1.19 (t, 3H, J=7.1 Hz), 2.82 (t, 4H, J=4.3 Hz), 3.74 (t, 4H, J=4.3 Hz), 3.79 (d, 2H, J=6.0 Hz), 4.08 (q, 2H, J=7.1 Hz), 4.28 (d, 2H, J=5.8 Hz), 6.32 (t, 1H, J=6.0 Hz), 6.56 (t, 1H, J=5.8 Hz), 7.05 (d, 1H, J=7.4 Hz), 7.11 (d, 1H, J=7.3 Hz), 7.22 (d, 1H, J=7.4 Hz), 7.27 (d, 1H, J=7.3 Hz). HPLC method A tr=8.34 nm (100%). ESI-MS m/z: 322.2 [M+H]$^+$.

Example 2

Preparation of ethyl 2-(3-(3-fluorobenzyl)ureido)acetate (F511)(2)

2 was purified by precipitation in EDP to afford 194 mg of a white solid (98%) Rf=0.55 (AcOEt). $^1$H NMR (DMSO): δ 1.19 (t, 3H, J=7.1 Hz), 3.78 (d, 2H, J=6.0 Hz), 4.08 (q, 2H, J=7.1 Hz), 4.23 (d, 2H, J=6.0 Hz), 6.36 (t, 1H, J=6.0 Hz), 6.75 (t, 1H, J=6.0 Hz), 7.05 (m, 3H), 7.35 (m, 1H). HPLC method A tr=8.98 nm (97.5%). ESI-MS m/z: 255.2 [M+H]$^+$.

Example 3

Preparation of ethyl 2-(3-(3-methoxybenzyl)ureido)acetate (F512)(3)

3 was purified by precipitation in EDP to afford 199 mg of a white solid (97%) Rf=0.71 (AcOEt). $^1$H NMR (DMSO): δ 1.19 (t, 3H, J=7.1 Hz), 3.73 (s, 3H), 3.78 (d, 2H, J=6.0 Hz), 4.08 (q, 2H, J=7.1 Hz), 4.18 (d, 2H, J=6.0 Hz), 6.29 (t, 1H, J=6.0 Hz), 6.66 (t, 1H, J=6.0 Hz), 6.81 (m, 3H), 7.22 (t, 1H, J=8.0 Hz). HPLC method A tr=8.92 nm (100%). ESI-MS m/z: 267.2 [M+H]$^+$.

Example 4

Preparation of ethyl 2-(3-(4-fluorobenzyl)ureido)acetate (F513)(4)

4 was purified by precipitation in AcOEt/EDP to afford 177 mg of a white solid (90%) Rf=0.55 (AcOEt). $^1$H NMR (DMSO): δ 1.19 (t, 3H, J=7.1 Hz), 3.78 (d, 2H, J=6.0 Hz), 4.08 (q, 2H, J=7.1 Hz), 4.19 (d, 2H, J=6.0 Hz), 6.30 (t, 1H, J=6.0 Hz), 6.69 (t, 1H, J=6.0 Hz), 7.14 (m, 2H), 7.29 (m, 2H). HPLC method A tr=8.97 nm (98.1%). ESI-MS m/z: 255.2 [M+H]$^+$.

Example 5

Preparation of ethyl 2-(3-(3-trifluoromethylbenzyl) ureido)acetate (F514)(5)

5 was purified by precipitation in EDP to afford 213 mg of a white solid (90%) Rf=0.53 (AcOEt). $^1$H NMR (DMSO): δ 0.95 (t, 3H, J=7.1 Hz), 3.54 (d, 2H, J=6.1 Hz), 3.85 (q, 2H, J=7.1 Hz), 4.06 (d, 2H, J=6.1 Hz), 6.14 (t, 1H, J=6.1 Hz), 6.58 (t, 1H, J=6.1 Hz), 7.64 (m, 4H). HPLC method A tr=11.45 nm (91.2%). ESI-MS m/z: 305.2 [M+H]$^+$.

Example 6

Preparation of ethyl 2-(3-(2-(phenylamino)ethyl) ureido)acetate (F515)(6)

6 was purified by precipitation in EDP to afford 199 mg of a white solid (97%) Rf=0.43 (AcOEt). $^1$H NMR (CDCl$_3$): δ 1.19 (t, 3H, J=7.1 Hz), 1.66 (sl, 1H), 3.15 (t, 2H, J=4.5 Hz), 3.36 (q, 2H, J=5.5 Hz), 3.91 (d, 2H, J=5.5 Hz), 4.07 (q, 2H, J=7.1 Hz), 5.15 (t, 1H, J=5.5 Hz), 5.25 (t, 1H, J=5.5 Hz), 6.53 (d, 2H, J=7.5 Hz), 6.62 (t, 1H, J=7.5 Hz), 7.09 (t, 2H, J=7.5 Hz). HPLC method A tr=7.30 nm (96.1%). ESI-MS m/z: 266.2 [M+H]$^+$.

Example 7

Preparation of ethyl 2-(3-(2-(2-morpholinoethoxy) benzyl) ureido)acetate (F516)(7)

7 was purified by precipitation in EDP to afford 282 mg of a white solid (99%) Rf=0.14 (AcOEt). $^1$H NMR (CDCl$_3$): δ 1.19 (t, 3H, J=7.1 Hz), 2.51 (t, 4H, J=4.7 Hz), 2.74 (t, 2H, J=5.3 Hz), 3.66 (t, 4H, J=4.7 Hz), 3.89 (d, 2H, J=5.3 Hz), 4.08 (m, 4H), 4.28 (d, 2H, J=6.0 Hz), 5.12 (sl, 1H), 5.53 (sl, 1H), 6.77 (d, 1H, J=8.2 Hz), 6.83 (t, 1H, J=7.4 Hz), 7.16 (m, 2H). HPLC method A tr=8.70 nm (96.9%). ESI-MS m/z: 366.2 [M+H]$^+$.

Example 8

Preparation of ethyl 2-(3-(4-hydroxyphenylethyl) ureido)acetate (F517)(8)

8 was purified by precipitation in EDP to afford 201 mg of a white solid (98%) Rf=0.32 (AcOEt). $^1$H NMR (DMSO): δ 1.19 (t, 3H, J=7.1 Hz), 2.55 (t, 2H, J=7.3 Hz), 3.15 (q, 2H, J=6.8 Hz), 3.75 (d, 2H, J=6.0 Hz), 4.08 (q, 2H, J=7.1 Hz), 6.11 (t, 1H, J=6.0 Hz), 6.21 (t, 1H, J=6.0 Hz), 6.68 (d, 2H, J=8.3 Hz), 6.99 (d, 1H, J=8.3 Hz), 9.16 (s, 1H). HPLC method A tr=7.64 nm (99.4%). ESI-MS m/z: 267.2 [M+H]$^+$.

Example 9

Preparation of ethyl 2-(3-(3-chlorobenzyl)ureido) acetate (F518)(9)

9 was purified by precipitation in EDP to afford 209 mg of a white solid (99%) Rf=0.48 (AcOEt). $^1$H NMR (DMSO): δ 1.19 (t, 3H, J=7.1 Hz), 3.78 (d, 2H, J=6.0 Hz), 4.09 (q, 2H, J=7.1 Hz), 4.22 (d, 2H, J=6.0 Hz), 6.36 (t, 1H, J=6.0 Hz), 6.75 (t, 1H, J=6.0 Hz), 7.05 (d, 1H, J=7.3 Hz), 7.27 (m, 3H). HPLC method A tr=10.37 nm (99.0%). ESI-MS m/z: 271.3/273.1 [M+H]$^+$.

Example 10

Preparation of ethyl 2-(3-((tetrahydro-2H-pyran-4-yl)methyl) ureido)acetate (F519)(10)

10 was purified by precipitation in EDP to afford 66 mg of a white solid (35%) Rf=0.83 (AcOEt). $^1$H NMR (DMSO): δ 1.05 (m, 2H), 1.19 (t, 3H, J=7.1 Hz), 1.51 (m, 3H), 2.89 (t, 2H, J=6.0 Hz), 3.24 (t, 2H, J=11.3 Hz), 3.75 (d, 2H, J=6.0 Hz), 3.83 (dd, 2H, J=10.3; 3.4 Hz), 4.08 (q, 2H, J=7.1 Hz), 6.11 (t, 1H, J=6.0 Hz), 6.22 (t, 1H, J=6.0 Hz). HPLC method A tr=6.54 nm (92.2%). ESI-MS m/z: 245.2 [M+H]$^+$.

Example 11

Preparation of ethyl 2-(3-(3,5-dichlorobenzyl)ureido) acetate (F520)(11)

11 was purified by precipitation in EDP to afford 217 mg of a white solid (92%) Rf=0.75 (AcOEt). $^1$H NMR (DMSO): δ 1.19 (t, 3H, J=7.1 Hz), 3.32 (d, 2H, J=6.0 Hz), 4.09 (q, 2H, J=7.1 Hz), 4.22 (d, 2H, J=6.1 Hz), 6.44 (t, 1H, J=6.1 Hz), 6.81 (t, 1H, J=6.0 Hz), 7.29 (d, 2H, J=1.9 Hz), 7.46 (t, 1H, J=1.9 Hz). HPLC method A tr=12.08 nm (96.1%). ESI-MS m/z: 305.11307.1 [M+H]$^+$.

Example 12

Preparation of ethyl 2-(3-(2-(4-aminophenyl)ethyl) ureido)acetate (F521)(12)

12 was purified by precipitation in AcOEt/EDP to afford 63 mg of a white solid (31%) Rf=0.36 (AcOEt). $^1$H NMR (DMSO): δ 1.19 (t, 3H, J=7.1 Hz), 2.48 (m, 2H), 3.12 (m, 2H), 3.91 (d, 2H, J=6.0 Hz), 4.07 (q, 2H, J=7.1 Hz), 4.84 (s, 2H), 6.08 (t, 1H, J=5.5 Hz), 6.21 (d, 2H, J=5.9 Hz), 6.48 (d, 2H, J=8.2 Hz), 6.84 (d, 2H, J=8.2 Hz). HPLC method A tr=6.12 nm (97.1%). ESI-MS m/z: 266.2 [M+H]$^+$.

Example 13

Preparation of ethyl 2-(3-(benzo[d][1,3]dioxol-5-ylmethyl) ureido)acetate (F522)(13)

13 was purified by precipitation in EDP to afford 142 mg of a white solid (65%) Rf=0.32 (AcOEt). $^1$H NMR (DMSO): δ 1.19 (t, 3H, J=7.1 Hz), 3.77 (d, 2H, J=6.0 Hz), 4.09 (m, 4H), 5.97 (s, 1H), 6.25 (t, 1H, J=6.0 Hz), 6.62 (t, 1H, J=6.0 Hz), 6.75 (d, 1H, J=8.3; 1.9 Hz), 7.80 (m, 2H). HPLC method A tr=8.76 nm (99.6%). ESI-MS m/z: 281.2 [M+H]$^+$.

Example 14

Preparation of ethyl 2-(3-(4-bromobenzyl)ureido) acetate (F523)(14)

14 was purified by precipitation in EDP to afford 100 mg of a white solid (41%) Rf=0.70 (AcOEt). $^1$H NMR (DMSO): δ 1.19 (t, 3H, J=7.1 Hz), 3.78 (d, 2H, J=6.0 Hz), 4.08 (q, 2H, J=7.1 Hz), 4.18 (d, 2H, J=6.0 Hz), 6.30 (t, 1H, J=6.0 Hz), 6.72 (t, 1H, J=6.0 Hz), 7.20 (d, 2H, J=8.1 Hz), 7.50 (d, 2H, J=8.1 Hz). HPLC method A tr=10.95 nm (98.4%). ESI-MS m/z: 315.1/317.1 [M+H]$^+$.

Example 15

Preparation of ethyl 2-(3-(3-pyrimidin-2-yl)benzyl) ureido)acetate (F524)(15)

15 was purified by precipitation in EDP to afford 158 mg of a white solid (65%) Rf=0.22 (AcOEt). $^1$H NMR (DMSO): δ 1.25 (t, 3H, J=7.1 Hz), 3.85 (d, 2H, J=6.0 Hz), 4.15 (q, 2H, J=7.1 Hz), 4.37 (d, 2H, J=6.0 Hz), 6.40 (t, 1H, J=5.8 Hz), 6.85 (t, 1H, J=5.8 Hz), 7.50 (m, 3H), 8.32 (dd, 1H, J=7.4, 1.2 Hz), 8.38 (s, 1H), 8.95 (dd, 2H, J=4.8, 1.2 Hz). HPLC method A tr=9.07 nm (93.1%). ESI-MS m/z: 315.2 [M+H]$^+$.

Example 16

Preparation of ethyl 2-(3-((2,3-dihydrobenzo[b][1,4] dioxin-5-yl)methyl)ureido)acetate (F525)(16)

The residue was taking up with AcOEt, the organic phase was washed with a solution of 10% citric acid and brine, dried over Na$_2$SO$_4$, filtrated and concentrated to afford 16 as a white solid (148 mg; 66%) Rf=0.47 (AcOEt). $^1$H NMR (DMSO): δ 1.24 (t, 3H, J=7.1 Hz), 3.84 (d, 2H, J=6.0 Hz), 4.16 (q, 2H, J=7.1 Hz), 4.21 (d, 2H, J=6.0 Hz), 4.33 (m, 4H), 6.37 (t, 1H, J=6.0 Hz), 6.55 (t, 1H, J=6.0 Hz), 6.81 (m, 3H). HPLC method A tr=9.35 nm (99.6%). ESI-MS m/z: 295.2 [M+H]$^+$.

Example 17

Preparation of ethyl 2-(3-((5-methylisoxazol-3-yl) methyl) ureido)acetate (F526)(17)

17 was purified by precipitation in EDP to afford 196 mg of a white solid (95%) Rf=0.47 (AcOEt). $^1$H NMR (DMSO): δ 1.19 (t, 3H, J=7.1 Hz), 2.36 (s, 3H), 3.77 (d, 2H, J=6.0 Hz), 4.10 (q, 2H, J=7.1 Hz), 4.19 (d, 2H, J=6.0 Hz), 6.07 (s, 1H), 6.38 (t, 1H, J=6.0 Hz), 6.70 (t, 1H, J=6.0 Hz). HPLC method A tr=6.72 nm (99.3%). ESI-MS m/z: 242.2 [M+H]$^+$.

Example 18

Preparation of ethyl 2-(3-(3-(morpholinomethyl) benzyl) ureido)acetate (F527)(18)

The crude product was purified by flash chromatography (EtOAc/MeOH 98/2) to afford the urea 18 (210 mg; 81%) as a white solid Rf=0.31 (AcOEt). $^1$H NMR (CDCl$_3$): δ 1.17 (t, 3H, J=7.1 Hz), 2.34 (d, 4H, J=4.2 Hz), 3.37 (s, 2H), 3.61 (m, 4 Hz), 3.87 (m, 2H), 4.06 (q, 2H, J=7.1 Hz), 4.24 (d, 2H, J=5.7 Hz), 5.40 (sl, 2H), 7.13 (m, 4H). HPLC method A tr=7.02 nm (93.5%). ESI-MS m/z: 336.2 [M+H]$^+$.

Example 19

Preparation of ethyl 2-(3-((2-furfur2-yl)benzyl)ureido)acetate (F528)(19)

19 was purified by precipitation in EDP to afford 230 mg of a white solid (98%) Rf=0.71 (AcOEt). $^1$H NMR (DMSO): δ 1.19 (t, 3H, J=7.1 Hz), 3.79 (d, 2H, J=6.0 Hz), 4.08 (q, 2H, J=7.1 Hz), 4.38 (d, 2H, J=5.8 Hz), 6.39 (t, 1H, J=5.8 Hz), 6.63 (m, 1H), 6.68 (t, 1H, J=5.8 Hz), 6.75 (d, 1H, J=3.3 Hz), 7.33 (m, 3H), 7.65 (m, 1H), 7.81 (s, 1H). HPLC method A tr=11.72 nm (91.7%). ESI-MS m/z: 303.2 [M+H]$^+$.

Example 20

Preparation of ethyl 2-(3-((2-morpholino-pyridin-4-yl)methyl) ureido)acetate (F529)(20)

20 was purified by precipitation in EDP to afford 133 mg of a white solid (53%) Rf=0.19 (AcOEt). $^1$H NMR (DMSO): δ 1.19 (t, 3H, J=7.1 Hz), 3.42 (t, 4H, J=4.9 Hz), 3.69 (t, 4H, J=4.9 Hz), 3.78 (d, 2H, J=6.1 Hz), 4.08 (q, 2H, J=7.1 Hz), 4.15 (d, 2H, J=6.0 Hz), 6.33 (t, 1H, J=6.1 Hz), 6.57 (d, 1H, J=5.0 Hz), 6.68 (s, 1H), 6.72 (t, 1H, J=6.1 Hz), 8.03 (d, 1H, J=5.0 Hz). HPLC method A tr=6.72 nm (100%). ESI-MS m/z: 323.2 [M+H]$^+$.

Example 21

Preparation of ethyl 2-(3-(3-(1H-1,2,4-triazol-1-yl) benzyl) ureido)acetate (F530)(21)

21 was purified by precipitation in EDP to afford 208 mg of a white solid (89%) Rf=0.11 (AcOEt). $^1$H NMR (DMSO): δ 1.18 (t, 3H, J=7.1 Hz), 3.79 (d, 2H, J=6.0 Hz), 4.08 (q, 2H, J=7.1 Hz), 4.31 (d, 2H, J=6.0 Hz), 6.38 (t, 1H, J=6.0 Hz), 6.81 (t, 1H, J=6.0 Hz), 7.30 (d, 1H, J=7.6 Hz), 7.50 (t, 1H, J=7.7 Hz), 7.73 (m, 2H), 8.24 (s, 1H), 9.27 (s, 1H). HPLC method A tr=8.16 nm (98.7%). ESI-MS m/z: 304.2 [M+H]$^+$.

Example 22

Preparation of ethyl 2-(3-(3-(1H-pyrazol-1-yl)benzyl)ureido)acetate (F531)(22)

22 was purified by precipitation in EDP to afford 224 mg of a white solid (95%) Rf=0.38 (AcOEt). $^1$H NMR (DMSO): δ 1.21 (t, 3H, J=7.1 Hz), 3.77 (d, 2H, J=6.0 Hz), 4.08 (q, 2H, J=7.1 Hz), 4.14 (d, 2H, J=6.0 Hz), 6.47 (t, 1H, J=6.0 Hz), 6.52 (s, 1H), 6.61 (t, 1H, J=6.0 Hz), 7.39 (m, 4H), 7.75 (s, 1H), 8.09 (s, 1H). HPLC method A tr=9.16 nm (96.6%). ESI-MS m/z: 303.2 [M+H]$^+$.

Example 23

Preparation of ethyl 2-(3-(2-fluoro-6-aminobenzyl) ureido)acetate (F532)(23)

The crude product was purified by HPLC preparative to afford the urea 23 (182 mg; 43%) as a white solid Rf=0.76 (AcOEt). $^1$H NMR (DMSO): δ 1.19 (t, 3H, J=7.1 Hz), 3.78 (d, 2H, J=6.0 Hz), 4.11 (m, 4H), 5.58 (s, 2H), 6.19 (t, 1H, J=6.0 Hz), 6.29 (t, 1H, J=8.1 Hz), 6.43 (d, 1H, J=8.1 Hz), 6.69 (t, 1H, J=6.0 Hz), 6.95 (m, 1H). HPLC method A tr=7.26 nm (99.5%). ESI-MS m/z: 270.2 [M+H]$^+$.

Example 24

Preparation of ethyl 2-(3-(benzofuran-5-ylmethyl) ureido)acetate (F533)(24)

The crude product was purified by flash chromatography (EtOAc) and finally precipitated in EDP to afford the urea 24 (29 mg; 14%) as a white solid Rf=0.55 (AcOEt). $^1$H NMR (DMSO): δ 1.19 (t, 3H, J=7.1 Hz), 3.79 (d, 2H, J=5.7 Hz), 4.08 (q, 2H, J=7.1 Hz), 4.29 (d, 2H, J=5.9 Hz), 6.28 (t, 1H, J=5.7 Hz), 6.70 (t, 2H, J=5.9 Hz), 6.93 (s, 1H), 7.21 (d, 1H, J=8.7 Hz), 7.53 (m, 2H), 8.00 (s, 1H). HPLC method A tr=9.95 nm (98.5%). ESI-MS m/z: 277.2 [M+H]$^+$.

Example 25

Preparation of ethyl 2-(3-((1H-benzo[d]imidazol-2-yl)methyl) ureido)acetate (F538)(25)

The residue was taking up with AcOEt, the organic phase was washed with a solution of 10% citric acid and brine, dried over $Na_2SO_4$, filtrated and concentrated. 25 was purified by precipitation in EDP to afford 95 mg of a yellow solid (44%) Rf=0.89 (AcOEt). $^1H$ NMR (DMSO): δ 1.19 (t, 3H, J=7.1 Hz), 3.82 (d, 2H, J=5.9 Hz), 4.08 (q, 2H, J=7.1 Hz), 4.43 (d, 2H, J=5.7 Hz), 6.52 (t, 1H, J=5.9 Hz), 6.83 (t, 1H, J=5.7 Hz), 7.13 (m, 2H), 7.45 (d, 1H, J=5.7 Hz), 7.54 (d, 1H, J=5.7 Hz), 12.16 (s, 1H). HPLC method A tr=6.48 nm (98.9%). ESI-MS m/z: 277.2 $[M+H]^+$.

Example 26

Preparation of ethyl 2-(3-(3,4-dihydroxybenzyl)ureido)acetate (F548)(26)

The crude product was purified by HPLC preparative to afford the urea 26 (81 mg; 36%) as a white solid. $^1H$ NMR ($CDCl_3$): δ 1.17 (t, 3H, J=7.1 Hz), 2.34 (d, 4H, J=4.2 Hz), 3.37 (s, 2H), 3.61 (m, 4 Hz), 3.87 (m, 2H), 4.06 (q, 2H, J=7.1 Hz), 4.24 (d, 2H, J=5.7 Hz), 5.40 (sl, 2H), 7.13 (m, 4H). HPLC method A tr=5.64 nm (100%). ESI-MS m/z: 269.2 $[M+H]^+$.

Example 27

Preparation of ethyl 2-(3-(3-aminobenzyl)ureido)acetate (F549)(27)

The crude product was purified by HPLC preparative to afford the urea 27 (160 61 mg; 31%) as a white solid. $^1H$ NMR ($CDCl_3$): δ 1.21 (t, 3H, J=7.1 Hz), 3.80 (d, 2H, J=6.0 Hz), 4.10 (m, 4H), 5.03 (s, 2H), 6.25 (t, 1H, J=6.0 Hz), 6.45 (m, 3H), 6.53 (t, 1H, J=6.0 Hz), 6.95 (t, 1H, J=7.5 Hz). HPLC method A tr=5.02 mn (99.9%). ESI-MS m/z: 252.2 $[M+H]^+$.

Example 28

Preparation of ethyl 2-(3-(3-methoxy-4-hydroxybenzyl) ureido)acetate (F570)(28)

The crude product was purified by flash chromatography (EtOAc/EDP 8/2) to afford the urea 28 (30 mg; 17%) as a white solid Rf=0.14 (AcOEt/EDP 8/2). $^1H$ NMR (DMSO): δ 1.21 (t, 3H, J=7.1 Hz), 3.76 (s, 3H), 3.80 (d, 2H, J=6.0 Hz), 4.10 (m, 4H), 6.24 (t, 1H, J=6.0 Hz), 6.56 (t, 1H, J=6.0 Hz), 6.70 (m, 2H), 6.84 (s, 1H), 8.83 (sl, 1H). HPLC method A tr=6.98 nm (98.0%). ESI-MS m/z: 283.2 $[M+H]^+$.

Example 29

Preparation of ethyl 2-(3-(2-(4-amino-6-hydroxypyrimidin-2-yl)ethyl)ureido)acetate (F571)(29)

The reaction mixture was heat at 70° C. for 2 hours in DMF. The crude product was purified by flash chromatography (EtOAc/MeOH 7/3) to afford the urea 29 (52 mg; 33%) as a white solid Rf=0.24 (AcOEt/MeOH 7/3). $^1H$ NMR (DMSO): δ 1.19 (t, 3H, J=7.1 Hz), 2.54 (m, 2H), 3.08 (m, 2H), 3.75 (d, 2H, J=6.0 Hz), 4.07 (q, 2H, J=7.1 Hz), 4.86 (s, 1H), 6.33 (m, 2H), 6.36 (s, 2H), 11.35 (s, 1H). HPLC method A tr=5.78 nm (99.4). ESI-MS m/z: 284.3 $[M+H]^+$.

Example 30

Preparation of ethyl 2-(3-(2,4-dihydroxybenzyl)ureido)acetate (F572)(30)

The residue was taking up with AcOEt, the organic phase was washed with a solution of 10% citric acid and brine, dried over $Na_2SO_4$, filtrated and concentrated. The crude product was purified by flash chromatography (EtOAc) to afford the urea 30 (28 mg; 19%) as a white solid Rf=0.44 (AcOEt). $^1H$ NMR (DMSO): δ 1.20 (t, 3H, J=7.1 Hz), 3.78 (d, 2H, J=6.0 Hz), 4.01 (d, 2H, J=6.0 Hz), 4.11 (q, 2H, J=7.1 Hz), 6.16 (dd, 1H, J=8.1; 2.3 Hz), 6.25 (d, 1H, J=2.3 Hz), 6.40 (t, 1H, J=6.0 Hz), 6.53 (t, 1H, J=6.0 Hz), 6.89 (d, 1H, J=8.1 Hz), 9.14 (s, 1H), 9.62 (s, 1H). HPLC method A tr=6.88 nm (98.7%). ESI-MS m/z: 269.2 $[M+H]^+$.

Example 31

Preparation of ethyl 3-((3-(2-ethoxy-2-oxoethyl)ureido)methyl)benzoate (F578)(31)

The crude product was purified by flash chromatography (EtOAc) to afford the urea 31 (41 mg; 29%) as a white solid Rf=0.55 (AcOEt). NMR (DMSO): δ 1.20 (t, 3H, J=7.1 Hz), 3.80 (d, 2H, J=6.1 Hz), 3.87 (s, 3H), 4.10 (q, 2H, J=7.1 Hz), 4.29 (d, 2H, J=6.1 Hz), 6.38 (t, 1H, J=6.1 Hz), 6.81 (t, 1H, J=6.1 Hz), 7.52 (m, 2H), 7.86 (m, 2H). HPLC method A tr=9.09 nm (100%). ESI-MS m/z: 295.2 $[M+H]^+$.

Example 32

Preparation of ethyl 2-(3-(4-aminobenzyl)ureido)acetate (F428)(32)

32 was purified by precipitation in EDP to afford 221 mg of a white solid (92%). $^1H$ NMR (DMSO): δ 1.21 (t, 3H, J=7.1 Hz), 3.77 (d, 2H, J=6.0 Hz), 4.08 (q, 2H, J=7.1 Hz), 4.14 (d, 2H, J=6.0 Hz), 6.47 (t, 1H, J=6.0 Hz), 6.52 (s, 1H), 6.61 (t, 1H, J=6.0 Hz), 7.39 (m, 4H), 7.75 (s, 1H), 8.09 (s, 1H). ESI-MS m/z: 252.2 $[M+H]^+$.

Example 33

Preparation of ethyl 2-(3-(4-methoxybenzyl)ureido)acetate (F429)(33)

33 was purified by precipitation in EDP to afford 182 mg of a white solid (83%). NMR (DMSO): δ 1.21 (t, 3H, J=7.1 Hz), 3.77 (d, 2H, J=6.0 Hz), 4.08 (q, 2H, J=7.1 Hz), 4.14 (d, 2H, J=6.0 Hz), 6.47 (t, 1H, J=6.0 Hz), 6.52 (s, 1H), 6.61 (t, 1H, J=6.0 Hz), 7.39 (m, 4H), 7.75 (s, 1H), 8.09 (s, 1H). ESI-MS m/z: 267.2 $[M+H]^+$.

Example 34

Preparation of ethyl 2-(3-(4-chlorobenzyl)ureido)acetate (F430)(34)

34 was purified by precipitation in EDP to afford 205 mg of a white solid (98%) Rf=0.48 (AcOEt). NMR (DMSO): δ 1.19 (t, 3H, J=7.1 Hz), 3.78 (d, 2H, J=6.0 Hz), 4.09 (q, 2H, J=7.1 Hz), 4.22 (d, 2H, J=6.0 Hz), 6.36 (t, 1H, J=6.0 Hz), 6.75 (t, 1H, J=6.0 Hz), 7.05 (d, 1H, J=7.3 Hz), 7.27 (m, 3H). ESI-MS m/z: 271.3/273.1 $[M+H]^+$.

Example 35

Preparation of ethyl 2-(3-(2-morpholinoethyl)ureido)acetate (F431)(35)

35 was purified by precipitation in EDP to afford 201 mg of a white solid (93%). $^1$H NMR (DMSO): δ 1.21 (t, 3H, J=7.1 Hz), 3.77 (d, 2H, J=6.0 Hz), 4.08 (q, 2H, J=7.1 Hz), 4.14 (d, 2H, J=6.0 Hz), 6.47 (t, 1H, J=6.0 Hz), 6.52 (s, 1H), 6.61 (t, 1H, J=6.0 Hz), 7.39 (m, 4H), 7.75 (s, 1H), 8.09 (s, 1H). ESI-MS m/z: 260.2 [M+H]$^+$.

Example 36

Preparation of ethyl 2-(3-(3-(5-oxo-4,5-dihydro-1H-pyrazol-4-yl)propyl)ureido)acetate (F432)(36)

36 was purified by precipitation in EDP to afford 208 mg of a white solid (96%). $^1$H NMR (DMSO): δ 1.21 (t, 3H, J=7.1 Hz), 3.77 (d, 2H, J=6.0 Hz), 4.08 (q, 2H, J=7.1 Hz), 4.14 (d, 2H, J=6.0 Hz), 6.47 (t, 1H, J=6.0 Hz), 6.52 (s, 1H), 6.61 (t, 1H, J=6.0 Hz), 7.39 (m, 4H), 7.75 (s, 1H), 8.09 (s, 1). ESI-MS m/z: 271.2 [M+H]$^+$.

Example 37

Preparation of ethyl 2-(3-(2-(2-oxoimidazolidin-1yl)ethyl)ureido)acetate (F433)(37)

37 was purified by precipitation in EDP to afford 198 mg of a white solid (89%). $^1$H NMR (DMSO): δ 1.21 (t, 3H, J=7.1 Hz), 3.77 (d, 2H, J=6.0 Hz), 4.08 (q, 2H, J=7.1 Hz), 4.14 (d, 2H, J=6.0 Hz), 6.47 (t, 1H, J=6.0 Hz), 6.52 (s, 1H), 6.61 (t, 1H, J=6.0 Hz), 7.39 (m, 4H), 7.75 (s, 1H), 8.09 (s, 1H). ESI-MS m/z: 259.2 [M+H]$^+$.

Example 38

Preparation of ethyl 2-(3-(4-nitrobenzyl)ureido)acetate (F436)(38)

38 was purified by precipitation in EDP to afford 205 mg of a white solid (94%). $^1$H NMR (DMSO): δ 1.21 (t, 3H, J=7.1 Hz), 3.77 (d, 2H, J=6.0 Hz), 4.08 (q, 2H, J=7.1 Hz), 4.14 (d, 2H, J=6.0 Hz), 6.47 (t, 1H, J=6.0 Hz), 6.52 (s, 1H), 6.61 (t, 1H, J=6.0 Hz), 7.39 (m, 4H), 7.75 (s, 1H), 8.09 (s, 1H). ESI-MS m/z: 282.2 [M+H]$^+$.

Example 39

Preparation of ethyl 2-(3-benzyl)ureido)acetate (F494)(39)

39 was purified by precipitation in EDP to afford 222 mg of a white solid (99%). $^1$H NMR (DMSO): δ 1.21 (t, 3H, J=7.1 Hz), 3.77 (d, 2H, J=6.0 Hz), 4.08 (q, 2H, J=7.1 Hz), 4.14 (d, 2H, J=6.0 Hz), 6.47 (t, 1H, J=6.0 Hz), 6.52 (s, 1H), 6.61 (t, 1H, J=6.0 Hz), 7.39 (m, 4H), 7.75 (s, 1H), 8.09 (s, 1H). ESI-MS m/z: 237.2 [M+H]$^+$.

Example 40

Preparation of ethyl 2-(3-(piperidin-4-ylmethyl)ureido)acetate (F509)(40)

The crude product was purified by HPLC preparative to afford the urea 39 (92 mg; 39%) as a white solid. $^1$H NMR (DMSO): δ 1.19 (t, 3H, J=7.1 Hz), 3.78 (d, 2H, J=6.0 Hz), 4.11 (m, 4H), 5.58 (s, 2H), 6.19 (t, 1H, J=6.0 Hz), 6.29 (t, 1H, J=8.1 Hz), 6.43 (d, 1H, J=8.1 Hz), 6.69 (t, 1H, J=6.0 Hz), 6.95 (m, 1H). HPLC method A tr=7.26 nm (99.5%). ESI-MS m/z: 244.2 [M+H]$^+$.

Example 41

Preparation of ethyl 2-(3-((napht-1-yl)methyl)ureido)acetate (F490)(41)

41 was purified by precipitation in EDP to afford 197 mg of a white solid (92%). NMR (DMSO): δ 1.21 (t, 3H, J=7.1 Hz), 3.77 (d, 2H, J=6.0 Hz), 4.08 (q, 2H, J=7.1 Hz), 4.14 (d, 2H, J=6.0 Hz), 6.47 (t, 1H, J=6.0 Hz), 6.52 (s, 1H), 6.61 (t, 1H, J=6.0 Hz), 7.39 (m, 4H), 7.75 (s, 1H), 8.09 (s, 1H). ESI-MS m/z: 287.2 [M+H]$^+$.

Example 42

Preparation of ethyl 2-(3-(pyridin-4-ylmethyl)ureido)acetate (F491)(42)

42 was purified by precipitation in EDP to afford 202 mg of a white solid (93%). $^1$H NMR (DMSO): δ 1.21 (t, 3H, J=7.1 Hz), 3.77 (d, 2H, J=6.0 Hz), 4.08 (q, 2H, J=7.1 Hz), 4.14 (d, 2H, J=6.0 Hz), 6.47 (t, 1H, J=6.0 Hz), 6.52 (s, 1H), 6.61 (t, 1H, J=6.0 Hz), 7.39 (m, 4H), 7.75 (s, 1H), 8.09 (s, 1H). ESI-MS m/z: 238.2 [M+H]$^+$.

Example 43

Preparation of ethyl 2-(3-(pyridin-3-ylmethyl)ureido)acetate (F492)(43)

43 was purified by precipitation in EDP to afford 208 mg of a white solid (94%). $^1$H NMR (DMSO): δ 1.21 (t, 3H, J=7.1 Hz), 3.77 (d, 2H, J=6.0 Hz), 4.08 (q, 2H, J=7.1 Hz), 4.14 (d, 2H, J=6.0 Hz), 6.47 (t, 1H, J=6.0 Hz), 6.52 (s, 1H), 6.61 (t, 1H, J=6.0 Hz), 7.39 (m, 4H), 7.75 (s, 1H), 8.09 (s, 1H). ESI-MS m/z: 238.2 [M+H]$^+$.

Example 44

Preparation of ethyl 2-(3-((6-aminopyridin-3-yl)methyl)ureido)acetate (F536)(44)

The crude product was purified by flash chromatography (EtOAc/MeOH 7/3) to afford the urea 44 (90 mg; 71%) as a white solid Rf=0.28 (AcOEt/MeOH 7/3). $^1$H NMR (DMSO): δ 0.97 (t, 3H, J=7.1 Hz), 3.54 (d, 2H, J=6.0 Hz), 3.77 (d, 2H, J=5.7 Hz), 3.84 (q, 2H, J=7.1 Hz), 5.55 (s, 2H), 5.97 (t, 1H, J=6.0 Hz), 6.16 (d, 1H, J=8.4 Hz), 6.25 (t, 1H, J=5.7 Hz), 7.03 (d, 1H, J=8.4 Hz), 7.56 (s, 1H). HPLC method A tr=5.65 nm (100%). ESI-MS m/z: 253.2 [M+H]$^+$.

Example 45

Preparation of ethyl 2-(3-(pyridin-2-ylmethyl)ureido)acetate (F493)(45)

45 was purified by precipitation in EDP to afford 201 mg of a white solid (92%). $^1$H NMR (DMSO): δ 1.21 (t, 3H, J=7.1 Hz), 3.77 (d, 2H, J=6.0 Hz), 4.08 (q, 2H, J=7.1 Hz), 4.14 (d, 2H, J=6.0 Hz), 6.47 (t, 1H, J=6.0 Hz), 6.52 (s, 1H), 6.61 (t, 1H, J=6.0 Hz), 7.39 (m, 4H), 7.75 (s, 1H), 8.09 (s, 1H). ESI-MS m/z: 238.2 [M+H]$^+$.

Example 46

Preparation of (R)-ethyl 2-(3-(6-amino-2,3-dihydro-1H-inden-1-yl)ureido)acetate (F729)(46)

(R)-2,3-dihydro-1H-indene-1,6-diamine (1 eq, 100 mg, 0.46 mmol) and triethylamine (2.5 eq, 158 μL, 1.15 mmol) were dissolved in 2 mL of DMF. The reaction mixture was cooled at 0° C. and ethyl isocyanatoacetate (1 eq, 59 mg, 51 μL, 0.46 mmol) was added dropwise and stirred for 2 hours at 0° C. The reaction mixture was concentrated and purified on reverse phase (H$_2$O/MeCN) to afford the compound 46 (26 mg, 21%) as a white solid Rf=0.26. $^1$H NMR (300 MHz, DMSO): δ 6.91 (d, J=7.8, 1H), 6.47-6.39 (m, 2H), 6.36 (d, J=8.3 Hz, 1H), 6.11 (t, J=5.9 Hz, 1H), 5.02-4.88 (m, 3H), 4.13 (q, J=7.1 Hz, 2H), 3.83 (d, J=6.0, Hz 2H), 2.87-2.57 (m, 2H), 2.40-2.25 (m, 1H), 1.72.1.56 (m, 1H), 1.31-1.17 (t, J=7.2 Hz, 3H). HPLC method A tr=5.60 m (93.4%). ESI-MS m/z: 278.2 [M+H]$^+$.

II—Synthesis of Ureas (47-52)

General Procedure

Cyano derivative (N≡C—R$_7$) (0.3 g, 1 équivalent) was dissolved in 100 ml of MeOH, then a 40 bar pression of hydrogen is applied in the presence of Ni/Raney for 20 h. The reaction mixture is filtered through celite and concentrated. The crude product was purified by flash chromatography to afford the amine. The amine (1 equivalent) was dissolved in DMF (0.4M), then the ethyl isocyanatoacetate (1 equivalent) was added in one portion and the reaction mixture was let 2 h at room temperature. After the reaction was complete (TLC control), the reaction mixture was concentrated and purified by flash chromatography to afford the urea.

The compounds 47-52 are prepared according the following reaction scheme:

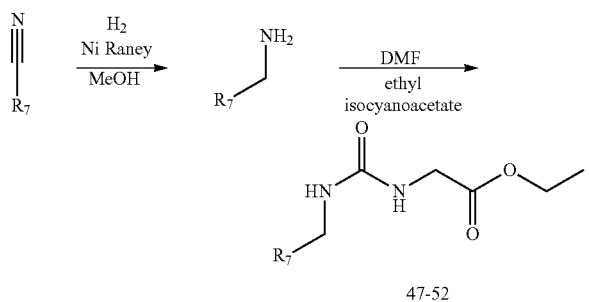

Example 47

Preparation of ethyl 2-(3-((indol-5-yl)methyl)ureido)acetate (F575)(47)

5-cyano-indole (0.3 g, 2.11 mmol) was reduced to obtain the 5-aminomethylindole (0.18 g, 59%) after purification by flash chromatography (AcOEt/MeOH 7/3 then MeOH) Rf=0.09 (MeOH). $^1$H NMR (DMSO): δ 2.40 (s, 2H), 3.78 (s, 2H), 6.38 (m, 1H), 7.10 (d, 1H, J=8.3 Hz), 7.29 (m, 1H), 7.33 (d, 1H, J=8.3 Hz), 7.49 (s, 1H), 11.00 (s, 1H). The 5-aminomethylindole (57 mg, 0.39 mmol) was used to obtain urea 47 (63 mg, 66%) after treatment of the crude product by EDP Rf=0.57 (AcOEt). $^1$H NMR (DMSO): δ 1.21 (t, 3H, J=7.1 Hz), 3.81 (d, 2H, J=6.0 Hz), 4.11 (q, 2H, J=7.1 Hz), 4.28 (d, 2H, J=5.7 Hz), 6.24 (t, 1H, J=6.0 Hz), 6.39 (s, 1H), 6.58 (t, 1H, J=5.7 Hz), 7.01 (d, 1H, J=8.3 Hz), 7.38 (m, 3H), 11.03 (s, 1H). HPLC method A tr=8.37 nm (97.3%). ESI-MS m/z: 276.2 [M+H]$^+$.

Example 48

Preparation of ethyl 2-(3-(4-hydroxybenzyl)ureido)acetate (F576)(48)

4-cyano-phenol (0.3 g, 2.52 mmol) was reduced to obtain the 4-aminomethylphenol (0.13 g, 43%) after purification by flash chromatography (AcOEt/MeOH 7/3) Rf=0.09 (AcOEt/MeOH 7/3). $^1$H NMR (DMSO): δ 2.40 (s, 2H), 3.53 (s, 2H), 6.69 (d, 2H, J=8.4 Hz), 7.11 (d, 2H, J=8.4 Hz), 9.20 (s, 1H). The 4-aminomethylphenol (48 mg, 0.39 mmol) was used to obtain urea 48 (23 mg, 26%, yellow solid) after purification of the crude product by flash chromatography (DCM/MeOH 95/5 Rf=0.34). $^1$H NMR (DMSO): δ 1.19 (t, 3H, J=7.1 Hz), 3.77 (d, 2H, J=6.0 Hz), 4.08 (m, 4H), 6.20 (t, 1H, J=6.0 Hz), 6.51 (t, 1H, J=5.6 Hz), 6.69 (d, 2H, J=8.4 Hz), 7.05 (d, 2H, J=8.4 Hz), 9.25 (s, 1H). HPLC method A tr=6.39 nm (92.6%). ESI-MS m/z: 253.2 [M+H]$^+$.

Example 49

Preparation of ethyl 2-(3-((4-aminonapht-1-yl)methyl)ureido)acetate (F577)(49)

4-Amino-1-naphthalenecarbonitrile (0.5 g, 2.98 mmol) was reduced to obtain the 4-aminomethyl-1-amino-naphthalene (0.22 g, 43%) after purification by flash chromatography (AcOEt/MeOH 7/3) Rf=0.09 (AcOEt/MeOH 7/3). $^1$H NMR (DMSO): δ 1.99 (s, 2H), 4.05 (s, 2H), 5.62 (s, 2H), 6.60 (d, 1H, J=9.6 Hz), 7.20 (d, 1H, J=7.6 Hz), 7.35 (m, 2H), 8.08 (m, 2H). The 4-aminomethyl-1-aminonaphthalene (154 mg, 0.89 mmol) was used to obtain urea 49 (12 mg, 5%, yellow solid) after purification of the crude product by flash chromatography (AcOEt Rf=0.52). $^1$H NMR (DMSO): δ 1.19 (t, 3H, J=7.1 Hz), 3.79 (d, 2H, J=6.0 Hz), 4.08 (q, 2H, J=7.1 Hz), 4.49 (d, 2H, J=5.2 Hz), 5.66 (s, 2H), 6.12 (t, 1H, J=6.0 Hz), 6.42 (t, 1H, J=5.2 Hz), 6.61 (d, 1H, J=7.6 Hz), 7.15 (d, 1H, J=7.6 Hz), 7.45 (m, 2H), 7.91 (d, 1H, J=8.1 Hz), 8.09 (d, 1H, J=8.1 Hz). HPLC method A tr=7.06 nm (89.7%). ESI-MS m/z: 302.3 [M+H]$^+$.

Example 50 ethyl 2-(3-(4-amino-3-methoxybenzyl)ureido)acetate (F674) (50)

4-amino-3-methoxybenzonitrile (0.2 g, 1.12 mmol) was reduced to obtain the 4-(aminomethyl)-2-methoxyaniline (m$_{theo}$=202 mg). The crude (202 mg, 1.1 mmol) was used to obtain urea (34 mg, two step global yield=10%, white solid) after purification of the crude product by flash chromatography (EDP/EtOAc), Rf=0.14 (EDP/EtOAc 30/70). $^1$H NMR (300 MHz, DMSO): δ 6.74 (s, 1H), 6.62-6.58 (m, 2H), 6.47 (t, J=5.7 Hz, 1H), 6.21 (t, J=6.1 Hz, 1H), 4.62 (broad s, 2H), 4.12 (q, J=7.2 Hz, 2H), 4.09 (d, J=5.7 Hz, 2H), 3.81 (d, J=6.1 Hz, 2H), 3.77 (s, 3H), 1.22 (t, J=7.1 Hz, 3H). HPLC method A tr=5.11 nm (94.1%). ESI-MS m/z: 282.2 [M+H]$^+$.

Example 51 ethyl 2-(3-(4-amino-3-methylbenzyl)ureido)acetate (F690) (51)

4-amino-3-methylbenzonitrile (0.2 g, 1.5 mmol) was reduced to obtain the 4-(aminomethyl)-2-methylaniline ($m_{theo}$=206 mg) as a yellow oil. The crude (206 mg, 1.5 mmol) was used to obtain urea (108 mg, two step global yield=27%, white solid) after purification of the crude product by flash chromatography (EDP/EtOAc), Rf=0.18 (EDP/EtOAc 30/70). $^1$H NMR (200 MHz, DMSO): δ 6.88-6.96 (m, 2H), 6.56 (d, J=7.9 Hz, 1H), 6.47-6.37 (m, 1H), 6.18 (t, J=5.9 Hz, 1H), 4.75 (broad s, 2H), 4.12 (q, J=7.0 Hz, 2H), 4.03 (d, J=6.2 Hz, 2H), 3.80 (d, J=6.0 Hz, 2H), 2.06 (s, 3H), 1.23 (t, J=7.1 Hz, 3H). HPLC method A tr=5.07 nm (90.5%). ESI-MS m/z: 266.2 [M+H]$^+$.

Example 52 ethyl 2-(3-(4-amino-3-ethylbenzyl)ureido)acetate (F692)(52)

4-amino-3-ethylbenzonitrile (0.2 g, 1.37 mmol) was reduced to obtain the 4-(aminomethyl)-2-ethylaniline ($m_{theo}$=205 mg) as a yellow oil. The crude (205 mg, 1.37 mmol) was used to obtain urea (92 mg, two step global yield=24%, white solid) after purification of the crude product by flash chromatography (EDP/EtOAc), Rf=0.3 (EDP/EtOAc 30/70). $^1$H NMR (200 MHz, CDCl$_3$): δ 7.02-6.88 (m, 2H), 6.61 (d, J=7.8 Hz, 1H), 5.02 (t, J=5.2 Hz, 1H), 4.89 (t, J=5.4 Hz, 1H), 4.23 (d, J=5.5 Hz, 1H), 4.15 (q, J=7.2 Hz, 2H), 3.97 (d, J=5.3 Hz, 2H), 3.62 (broad s, 2H), 2.48 (q, J=7.5 Hz, 2H), 1.25 (t, J=7.1 Hz, 3H), 1.22 (t, J=7.4 Hz, 3H). HPLC method A tr=5.86 nm (86.4%). ESI-MS m/z: 280.2 [M+H]$^+$.

III—Synthesis of Thioureas

Thioureas are synthesised according to the following reaction scheme:

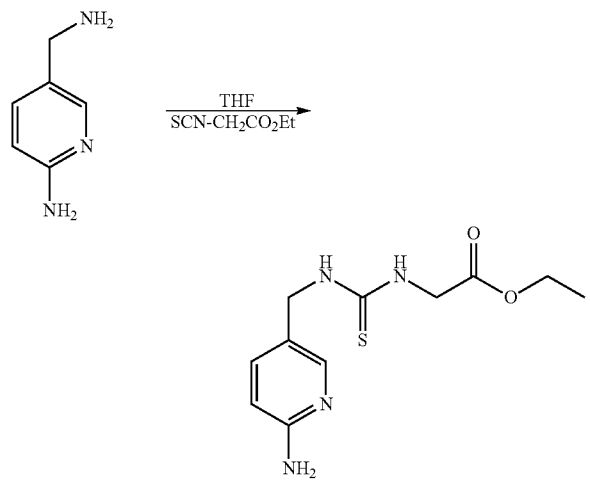

Example 53

Preparation of ethyl 2-(3-((6-aminopyridin-3-yl)methyl)thioureido)acetate (F569)(53)

Ethyl isothiocyanatoacetate (1 equivalent) was dissolved in THF (0.4 M), then the amine (1 equivalent, 181 mg) was added in one portion and the reaction mixture was let 2 h at room temperature. After the reaction was complete (TLC control), the reaction mixture was concentrated and purified by precipitation in diethylether/hexane to obtain thiourea 50 as white solid (264 mg, 89%). HPLC method B tr=14.43 nm (92.4%). ESI-MS m/z: 269.2 [M+H]$^+$.

IV—Synthesis of Amides (58-145)

General Procedure

IV-1—Synthesis of Carboxylic Acids

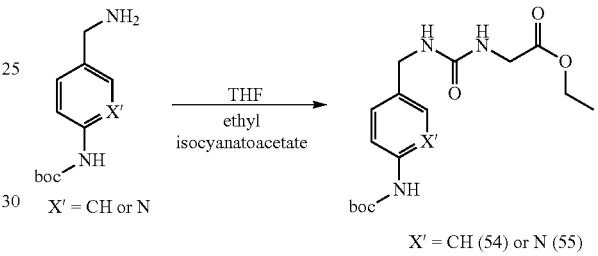

X' = CH or N

X' = CH (54) or N (55)

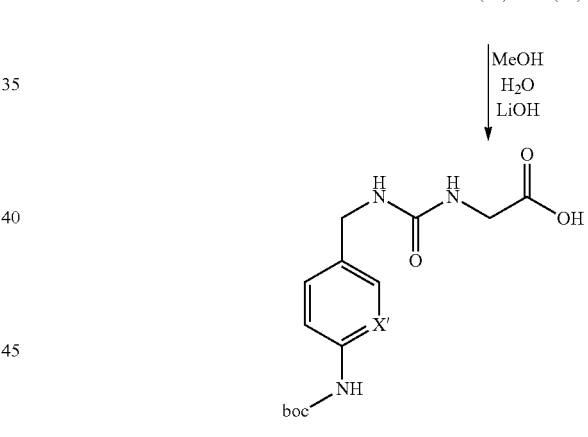

X' = CH (56) or N (57)

Synthesis of Ester 54 and 55

General Procedure

Ethyl isocyanatoacetate (1 equivalent, 100 mg, 87 µA, 0.77 mmol) was dissolved in THF (0.4 M), then the amine (1 equivalent) was added in one portion and the reaction mixture was let 2 h at room temperature. After the reaction was complete (TLC control), the reaction mixture was concentrated and purified by precipitation in diethyl ether.

Ethyl 2-(3-(4-(tert-butoxycarbonylamino)benzyl)ureido)acetate (54)

white solid (7.82 g, 99%). $^1$H NMR (DMSO): δ 1.20 (t, 3H, J=7.1 Hz), 1.48 (s, 9H), 3.78 (d, 2H, J=5.8 Hz), 4.08 (q, 2H, J=7.1 Hz), 4.13 (d, 2H, J=5.5 Hz), 6.26 (t, 1H, J=5.5 Hz), 6.58 (t, 1H, J=5.8 Hz), 7.12 (d, 2H, J=8.4 Hz), 7.37 (d, 2H, J=8.4 Hz), 9.27 (s, 1H).

Ethyl 2-(3-((6-(certbutoxycarbonylamino)pyridin-3-yl)methyl)ureido)acetate (55)

white solid (7.66 g, 97%). $^1$H NMR (DMSO): δ 1.18 (t, 3H, J=7.3 Hz), 1.46 (s, 9H), 3.76 (d, 2H, J=5.8 Hz), 4.08 (q, 2H, J=7.3 Hz), 4.15 (d, 2H, J=5.3 Hz), 6.37 (t, 1H, J=5.3 Hz), 6.73 (t, 1H, J=5.8 Hz), 7.60 (d, 1H, J=8.4 Hz), 7.71 (d, 1H, J=8.4 Hz), 8.12 (s, 1H), 9.70 (s, 1H).

2-(3-(4-(tert-butoxycarbonylamino)benzyl)ureido)acetic acid (56)

50 (7.5 g, 21.3 mmol) was dissolved in 50 nil of MeOH and 50 ml of water, LiOH (4 équivalent, 2.0 g) was added and the reaction mixture was heated to 50° C. for 2 h. The reaction mixture is concentrated and 200 ml of water are added, then extracted twice with AcOEt. The water is acidified to pH 3 with concentrated HCl 36%, then extracted twice with AcOEt. The combine organic phase are dried over $Na_2SO_4$, filtered and concentrated to afford 56 (6.81 g, 99%) as a white solid.

$^1$H NMR (DMSO): δ 1.47 (s, 9H), 3.72 (d, 2H, J=5.7 Hz), 4.13 (d, 2H, J=5.6 Hz), 6.14 (t, 1H, J=5.6 Hz), 6.54 (t, 1H, J=5.7 Hz), 7.13 (d, 2H, J=8.5 Hz), 7.37 (d, 2H, J=8.5 Hz), 9.26 (s, 1H), 12.21 (s, 1H).

2-(3-((6-(tert-butoxycarbonylamino)pyridin-3-yl)methyl)ureido)acetic acid (57)

51 (7.5 g, 21.3 mmol) was dissolved in 50 ml of MeOH and 50 ml of water, LiOH (4 équivalent, 2.0 g) was added and the reaction mixture was heated to 50° C. for 2 h. The reaction mixture is concentrated and 200 ml of water are added, then extracted twice with AcOEt. The water is acidified to pH 5 with concentrated HCl 36%, then extracted twice with AcOEt. The combine organic phase are dried over $Na_2SO_4$, filtered and concentrated to afford 57 (6.74 g, 98%) as a white solid.

$^1$H NMR (DMSO): δ 1.47 (s, 9H), 3.97 (s, 2H), 4.16 (d, 2H, J=5.6 Hz), 6.09 (t, 1H, J=5.0 Hz), 6.71 (t, 1H, J=5.6 Hz), 7.60 (d, 1H, J=8.7 Hz), 7.72 (d, 1H, J=8.7 Hz), 8.12 (s, 1H), 9.66 (s, 1H).

IV-2—Synthesis of Amides (58-145)

General Procedure.

Acid derivative 56 or 57 (1 equivalent) was dissolved in 2 ml of DCM or DMF. Amine (1.1 equivalent), Hydroxybenzotriazole (HOBt) (1.2 equivalent), diisopropylethylamine (DIEA) (2.2 equivalent) and 1-[3-(Dimethylamino)propyl]-3-ethylcarbodiimide (EDAP) (1.2 equivalent) were added successively and the reaction mixture is stirred for 20 h at room temperature. The reaction mixture is concentrated and 100 ml of AcOEt are added. The organic phase are washed with $NaHCO_3$ saturated, 10% citric acid and brine then dried over $Na_2SO_4$, filtered and concentrated. The crude product was purified by flash chromatography to afford the amide. Finally, the amide was dissolved in 2 ml of DCM and 2 ml of TFA was added then the reaction mixture was let 1 h at room temperature. The reaction mixture was concentrated and purified by precipitation using AcOEt/Hexane to afford the amide deprotected 58-94bis.

The amides 58-145 are prepared according the following reaction scheme:

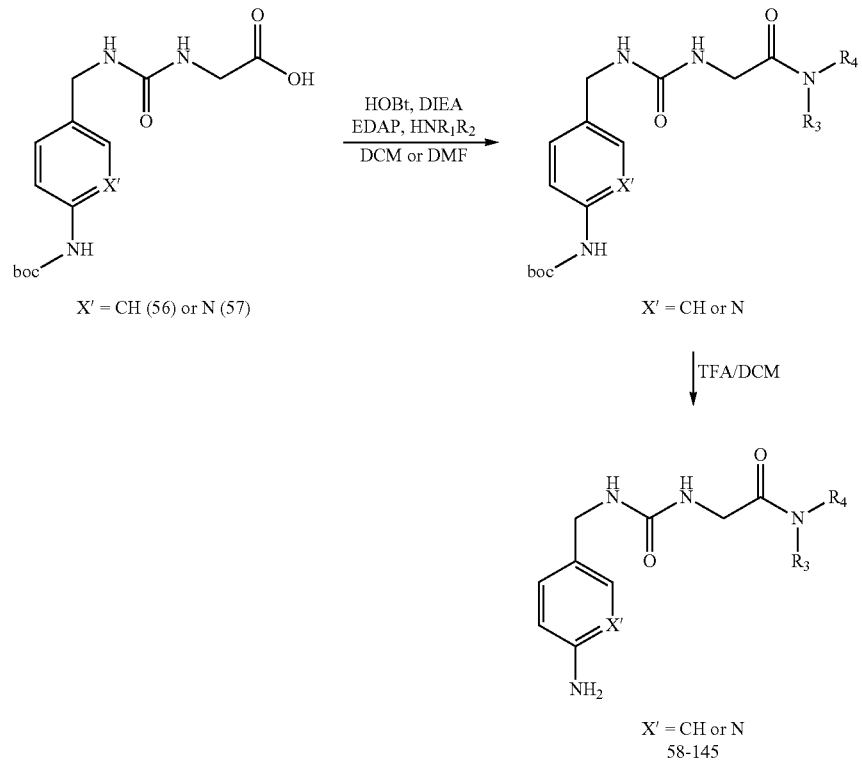

Example 54

Preparation of 1-(4-aminobenzyl)-3-(2-pyrrolidin-1-yl-2-oxoethyl)urea (F537)(58)

The crude product was purified by flash chromatography (AcOEt) to afford the amide protected (100 mg; 44%) as a white solid Rf=0.09 (AcOEt). $^1$H NMR (DMSO): δ 1.47 (s, 9H), 1.78 (m, 2H), 1.90 (m, 4H), 3.30 (m, 4H), 3.81 (d, 2H, J=4.9 Hz), 4.12 (d, 2H, J=5.8 Hz), 6.06 (t, 1H, J=4.9 Hz), 6.66 (t, 1H, J=5.8 Hz), 7.12 (d, 2H, J=8.5 Hz), 7.37 (d, 2H, J=8.5 Hz), 9.27 (s, 1H). The amide was deprotected to afford compound 58 as yellow solid (73 mg, 70%). HPLC method A tr=5.60 nm (95.8%). ESI-MS m/z: 277.2 [M+H]$^+$.

Example 55

Preparation of 2-(3-(4-aminobenzyl)ureido)-N-benzyl-acetamide (F539)(59)

The crude product was purified by flash chromatography (DCM/MeOH 9/1) to afford the amide protected (100 mg; 40%) as a white solid Rf=0.47 (DCM/MeOH 9/1). $^1$H NMR (DMSO): δ 1.47 (s, 9H), 3.71 (d, 2H, J=5.5 Hz), 4.13 (d, 2H, J=5.7 Hz), 4.29 (d, 2H, J=5.9 Hz), 6.18 (t, 1H, J=5.7 Hz), 6.55 (t, 1H, J=5.9 Hz), 7.13 (d, 2H, J=6.0 Hz), 7.13 (m, 7H), 8.32 (t, 1H, J=5.5 Hz), 9.27 (s, 1H). The amide was deprotected to afford compound 59 as yellow solid (64 mg, 61%). HPLC method A tr=6.33 nm (99.5%). ESI-MS m/z: 313.3 [M+H]$^+$.

Example 56

Preparation of 1-(4-aminobenzyl)-3-(2-(3-hydroxy-piperidin-1-yl)-2-oxoethyl)urea (F540)(60)

The crude product was purified by flash chromatography (DCM/MeOH 9/1) to afford the amide protected (84 mg; 34%) as a white solid Rf=0.32 (DCM/MeOH 9/1). $^1$H NMR (DMSO): δ 1.47 (s, 9H), 1.80 (m, 4H), 3.40 (m, 4H), 3.89 (d, 2H, J=5.1 Hz), 4.12 (d, 2H, J=5.8 Hz), 4.89 (s, 1H), 6.05 (t, 1H, J=5.8 Hz), 6.68 (t, 1H, J=5.1 Hz), 7.12 (d, 2H, J=8.4 Hz), 7.37 (d, 2H, J=8.4 Hz), 9.27 (s, 1H). The amide was deprotected to afford compound 60 as yellow solid (53 mg, 59%). HPLC method A tr=4.92 m (94.0%). ESI-MS m/z: 307.3 [M+H]$^+$.

Example 57

Preparation of 2-(3-(4-aminobenzyl)ureido)-N-benzyl-N-methylacetamide (F541)(61)

The crude product was purified by flash chromatography (DCM/MeOH 9/1) to afford the amide protected (107 mg; 41%) as a white oil Rf=0.28 (DCM/MeOH 9/1). NMR (DMSO): δ 1.47 (s, 9H), 2.90 (s, 3H), 3.98 (d, 2H, J=4.9 Hz), 4.14 (d, 2H, J=6.0 Hz), 4.54 (d, 2H, J=5.0 Hz), 6.11 (t, 1H, J=4.9 Hz), 6.68 (t, 1H, J=5.0 Hz), 7.30 (m, 10H), 9.27 (s, 1H). The amide was deprotected to afford compound 61 as yellow solid (78 mg, 68%). HPLC method A tr=8.52 nm (97.2%). ESI-MS m/z: 327.3 [M+H]$^+$.

Example 58

Preparation of 1-(4-aminobenzyl)-3-(2-oxo-2-(pyrrolidine-1-carbonyl)piperidin-1-yl)ethyl)urea (F542)(62)

The crude product was purified by flash chromatography (DCM/MeOH 9/1) to afford the amide protected (120 mg; 48%) as a white solid Rf=0.39 (DCM/MeOH 9/1). $^1$H NMR (DMSO): δ 1.47 (s, 9H), 1.85 (m, 8H), 3.35 (m, 8H), 3.90 (m, 1H), 4.10 (m, 4H), 6.04 (m, 1H), 6.67 (m, 1H), 7.12 (d, 2H, J=8.4 Hz), 7.37 (d, 2H, J=8.4 Hz), 9.27 (s, 1H). The amide was deprotected to afford compound 62 as yellow solid (95 mg, 73%). HPLC method A tr=6.62 nm (99.0%). ESI-MS m/z: 388.3 [M+H]$^+$.

Example 59

Preparation of 1-(4-aminobenzyl)-3-(2-oxo-2-(piperin-1-yl)ethyl)urea (F543)(63)

The crude product was purified by flash chromatography (DCM/MeOH 9/1) to afford the amide protected (105 mg; 44%) as a white solid Rf=0.55 (DCM/MeOH 9/1). NMR (DMSO): δ 1.47 (s, 9H), 1.52 (m, 6H), 3.40 (m, 4H), 3.88 (d, 2H, J=4.8 Hz), 4.10 (d, 2H, J=6.3 Hz), 6.05 (t, 1H, J=4.8 Hz), 6.66 (t, 1H, J=6.3 Hz), 7.12 (d, 2H, J=8.5 Hz), 7.37 (d, 2H, J=8.5 Hz), 9.27 (s, 1H). The amide was deprotected to afford compound 63 as yellow solid (64 mg, 61%). HPLC method A tr=5.86 nm (99.1%). ESI-MS m/z: 291.3 [M+H]$^+$.

Example 60

Preparation of 1-(4-aminobenzyl)-3-(2-morpholino-2-oxoethyl)urea (F544)(64)

The crude product was purified by flash chromatography (DCM/MeOH 9/1) to afford the amide protected (110 mg; 46%) as a white solid Rf=0.33 (DCM/MeOH 9/1). $^1$H NMR (DMSO): δ 1.47 (s, 9H), 3.30 (m, 4H), 3.56 (m, 4H), 3.91 (d, 2H, J=4.9 Hz), 4.12 (d, 2H, J=5.7 Hz), 6.08 (t, 1H, J=4.9 Hz), 6.67 (t, 1H, J=5.7 Hz), 7.12 (d, 2H, J=8.5 Hz), 7.37 (d, 2H, J=8.5 Hz), 9.27 (s, 1H). The amide was deprotected to afford compound 64 as yellow solid (58 mg, 48%). HPLC method A tr=5.05 nm (99.1%). ESI-MS m/z: 2912 [M+H]$^+$.

Example 61

Preparation of ethyl 1-(2-(3-(4-aminobenzyl)ureido)acetyl)piperidine-3-carboxylate (F545)(65)

The crude product was purified by flash chromatography (DCM/MeOH 9/1) to afford the amide protected (158 mg; 56%) as a white solid Rf=0.54 (DCM/MeOH 9/1). $^1$H NMR (DMSO): δ 1.16 (t, 3H, J=6.8 Hz), 1.43 (s, 9H), 1.80 (m, 4H), 3.65 (m, 4H), 4.10 (m, 7H), 6.01 (t, 1H, J=4.0 Hz), 6.64 (t, 1H, J=5.4 Hz), 7.08 (d, 2H, J=8.3 Hz), 7.33 (d, 2H, J=8.3 Hz), 9.23 (s, 1H). The amide was deprotected to afford compound 65 as yellow solid (73 mg, 43%). HPLC method A tr=6.97 nm (98.6%). ESI-MS m/z: 363.3 [M+H]$^+$.

Example 62

Preparation of (S)-methyl 1-(2-(3-(4-aminobenzyl)ureido)acetyl)pyrrolidine-2-carboxylate (F546)(66)

The crude product was purified by flash chromatography (DCM/MeOH 9/1) to afford the amide protected (110 mg; 41%) as a white solid Rf=0.37 (DCM/MeOH 9/1). The amide was deprotected to afford compound 66 as white solid (93 mg, 81%). $^1$H NMR (DMSO): δ 2.00 (m, 4H), 3.52 (m, 2H), 3.64 (s, 3H), 3.90 (d, 2H, J=5.0 Hz), 4.05 (sl, 2H), 4.21 (d, 2H, J=5.1 Hz), 4.35 (m, 1H), 6.17 (m, 1H), 6.76 (t, 1H, J=5.1 Hz), 7.17 (d, 2H, J=8.1 Hz), 7.30 (d, 2H, J=8.1 Hz). HPLC method A tr=5.49 nm (97.7%). ESI-MS m/z: 335.3 [M+H]⁺.

Example 63

Preparation of 2-(3-(4-aminobenzyl)ureido)-N-2-phenyl-ethylacetamide (F547)(67)

The crude product was purified by flash chromatography (DCM/MeOH 9/1) to afford the amide protected (115 mg; 44%) as a white solid Rf=0.47 (DCM/MeOH 9/1). ¹H NMR (DMSO): δ 1.47 (s, 9H), 2.70 (t, 2H, J=7.0 Hz), 3.61 (d, 2H, J=5.7 Hz), 4.10 (m, 4H), 6.12 (t, 1H, J=5.3 Hz), 6.55 (t, 1H, J=5.7 Hz), 7.12 (d, 2H, J=8.5 Hz), 7.21 (m, 3H), 7.30 (t, 2H, J=8.2 Hz), 7.38 (d, 2H, J=8.5 Hz), 9.28 (s, 1H). The amide was deprotected to afford compound 67 as yellow solid (93 mg, 78%). HPLC method A tr=6.95 nm (99.3%). ESI-MS m/z: 327.3 [M+H]⁺.

Example 64

Preparation of 2-(3-(4-aminobenzyl)ureido)-N-methyl-N-((tetrahydrofuran-3-yl)methyl)acetamide (F550)(68)

The crude product was purified by flash chromatography (DCM/MeOH 9/1) to afford the amide protected (52 mg; 40%) as an orange solid Rf=0.31 (DCM/MeOH 9/1). ¹H NMR (DMSO): δ 1.47 (s, 9H), 1.52 (m, 1H), 1.95 (m, 2H), 2.94 (s, 3H), 3.28 (m, 2H), 3.70 (m, 4H), 3.88 (d, 2H, J=4.8 Hz), 4.12 (d, 2H, J=5.9 Hz), 6.05 (t, 1H, J=4.8 Hz), 6.67 (t, 1H, J=5.9 Hz), 7.12 (d, 2H, J=8.5 Hz), 7.37 (d, 2H, J=8.5 Hz), 9.27 (s, 1H). The amide was deprotected and precipitated in ether to afford compound 63 as yellow solid (17 mg, 31%). HPLC method A tr=6.34 nm (88.2%). ESI-MS m/z: 321.3 [M+H]⁺.

Example 65

Preparation of 2-(3-(4-aminobenzyl)ureido)-N-2-phenyl-ethyl-N-methylacetamide (F551)(69)

The crude product was purified by flash chromatography (DCM/MeOH 9/1) to afford the amide protected (108 mg; 43%) as a white solid Rf=0.49 (DCM/MeOH 9/1). ¹H NMR (DMSO) (major conformer): δ 1.47 (s, 9H), 2.73 (m, 2H), 2.88 (s, 3H), 3.45 (m, 2H), 3.85 (d, 1H, J=4.8 Hz), 4.13 (d, 1H, J=6.2 Hz), 6.04 (t, 1H, J=4.8 Hz), 6.68 (t, 1H, J=6.2 Hz), 7.10 (m, 2H), 7.30 (m, 7H), 9.27 (s, 1H). The amide was deprotected to afford compound 69 as yellow solid (90 mg, 78%). HPLC method A tr=8.99 nm (97.5%). ESI-MS m/z: 288.4 [M+H]⁺.

Example 66

Preparation of 2-(3-(4-aminobenzyl)ureido)-N-(2-(piperidin-1-yl)ethyl)acetamide (F552)(70)

The crude product was purified by flash chromatography (DCM/MeOH 9/1) to afford the amide protected (110 mg; 46%) as an orange solid Rf=0.14 (DCM/MeOH 9/1). ¹H NMR (DMSO): δ 1.47 (s, 9H), 2.30 (m, 6H), 3.18 (m, 2H), 3.35 (m, 6H), 3.66 (d, 2H, J=5.5 Hz), 4.12 (d, 2H, J=5.8 Hz), 6.14 (t, 1H, J=5.5 Hz), 6.56 (t, 1H, J=5.8 Hz), 7.12 (d, 2H, J=8.3 Hz), 7.38 (d, 2H, in ether to afford compound 70 as yellow solid (67 mg, 58%). HPLC method A tr=5.67 nm (87.4%). ESI-MS m/z: 334.3 [M+H]⁺.

Example 67

Preparation of 2-(3-(4-aminobenzyl)ureido)-N-(4-(phenoxymethyl)benzyl)acetamide (F553)(71)

The crude product was purified by flash chromatography (DCM/MeOH 911) to afford the amide protected (82 mg; 51%) as a white solid Rf=0.42 (DCM/MeOH 9/1). ¹H NMR (DMSO): δ 1.47 (s, 9H), 3.70 (d, 2H, J=4.5 Hz), 4.13 (d, 2H, J=5.5 Hz), 4.29 (d, 2H, J=5.8 Hz), 5.08 (s, 2H), 6.08 (t, 1H, J=5.5 Hz), 6.55 (t, 1H, J=5.8 Hz), 6.93 (t, 1H, J=7.3 Hz), 6.99 (d, 2H, J=8.1 Hz), 7.13 (d, 2H, J=8.4 Hz), 7.28 (m, 4H), 7.38 (m, 4H), 8.31 (t, 1H, J=4.5 Hz), 9.27 (s, 1H). The amide was deprotected to afford compound 71 as yellow solid (63 mg, 74%). HPLC method A tr=11.54 nm (89.2%). ESI-MS m/z: 419.3 [M+1-1]⁺.

Example 68

Preparation of 1-(4-aminobenzyl)-3-(2-(2-((1,3-dioxoisoindolin-2-yl)methyl)morpholino)-2-oxoethyl)urea (F554)(72)

The crude product was purified by flash chromatography (DCM/MeOH 9/1) to afford the amide protected (135 mg; 77%) as a white solid Rf=0.39 (DCM/MeOH 9/1). ¹H NMR (DMSO): δ 1.47 (s, 9H), 3.80 (m, 8H), 4.05 (m, 5H), 6.05 (t, 1H, J=4.7 Hz), 6.65 (t, 1H, J=5.9 Hz), 7.10 (d, 2H, J=8.3 Hz), 7.35 (d, 2H, J=8.3 Hz), 7.89 (m, 4H), 9.27 (s, 1H). The amide was deprotected to afford compound 72 as yellow solid (104 mg, 74%). HPLC method A tr=8.91 nm (95.5%). ESI-MS m/z: 452.3 [M+H]⁺.

Example 69

Preparation of 2-(3-(4-aminobenzyl)ureido)-N-4-methoxyphenyl-N-methylacetamide (F555)(73)

The crude product was purified by flash chromatography (DCM/MeOH 9/1) to afford the amide protected (82 mg; 58%) as a white oil Rf=0.45 (DCM/MeOH 9/1). ¹H NMR (DMSO): δ 1.47 (s, 9H), 3.13 (s, 3H), 3.50 (d, 2H, J=4.7 Hz), 3.79 (s, 3H), 4.14 (d, 2H, J=6.0 Hz), 6.05 (t, 1H, J=4.7 Hz), 6.64 (t, 1H, J=6.0 Hz), 7.02 (d, 2H, J=9.1 Hz), 7.08 (d, 2H, J=8.3 Hz), 7.29 (d, 2H, J=9.1 Hz), 7.36 (d, 2H, J=8.3 Hz), 9.27 (s, 1H). The amide was deprotected to afford compound 73 as yellow solid (59 mg, 69%). HPLC method A tr=8.33 nm (96.5%). ESI-MS m/z: 343.3 [M+H]⁺.

Example 70

Preparation of 2-(3-(4-aminobenzyl)ureido)-N-((tetrahydrofuran-3-yl)methyl)acetamide (F556)(74)

The crude product was purified by flash chromatography (DCM/MeOH 9/1) to afford the amide protected (54 mg; 37%) as a white solid Rf=0.26 (DCM/MeOH 914 ¹H NMR (DMSO): δ 1.47 (s, 9H), 1.85 (m, 4H), 3.13 (m, 2H), 3.64 (d, 2H, J=5.5 Hz), 3.80 (m, 3H), 4.12 (d, 2H, J=5.7 Hz), 6.14 (t, 1H, J=5.5 Hz), 6.55 (t, 1H, J=5.7 Hz), 7.12 (d, 2H, J=8.3 Hz), 7.37 (d, 2H, J=8.3 Hz), 7.80 (t, 1H, J=4.5 Hz), 9.27 (s, 1H). The amide was deprotected to afford compound 74 as yellow solid (30 mg, 53%). HPLC method A tr=5.52 nm (93.8%). ESI-MS m/z: 307.3 [M+H]⁺.

Example 71

Preparation of 2-(3-(4-aminobenzyl)ureido)-N-phenyl-N-methylacetamide (F557)(75)

The crude product was purified by flash chromatography (DCM/MeOH 9/1) to afford the amide protected (62 mg; 48%) as a white solid Rf=0.55 (DCM/MeOH 9/1). $^1$H NMR (DMSO): δ 1.47 (s, 9H), 3.18 (s, 3H), 3.54 (d, 2H, J=4.6 Hz), 4.07 (d, 2H, J=5.4 Hz), 6.07 (t, 1H, J=4.6 Hz), 6.65 (t, 1H, J=5.4 Hz), 7.08 (d, 2H, J=8.2 Hz), 7.37 (m, 5H), 7.47 (d, 2H, J=8.3 Hz), 9.27 (s, 1H). The amide was deprotected to afford compound 75 as yellow solid (24 mg, 34%). HPLC method A tr=7.82 nm (92.2%). ESI-MS m/z: 313.3 [M+H]$^+$.

Example 72

Preparation of (R)-methyl 1-(2-(3-(4-aminobenzyl)ureido)acetyl)pyrrolidine-2-carboxylate (F558)(76)

The crude product was purified by flash chromatography (DCM/MeOH 9/1) to afford the amide protected (57 mg; 53%) as a white solid Rf=0.29 (DCM/MeOH 9/1). $^1$H NMR (DMSO) major conformer: δ 1.47 (s, 9H), 1.90 (m, 4H), 3.52 (m, 2H), 3.62 (s, 3H), 3.91 (d, 2H, J=5.2 Hz), 4.12 (d, 2H, J=5.6 Hz), 4.32 (m, 1H), 6.08 (t, 1H, J=5.2 Hz), 6.61 (t, 1H, J=5.6 Hz), 7.12 (d, 2H, J=8.4 Hz), 7.37 (d, 2H, J=8.4 Hz), 9.27 (s, 1H). The amide was deprotected to afford compound 76 as yellow solid (35 mg, 59%). HPLC method A tr=6.30 nm (96.6%). ESI-MS m/z: 335.3 [M+H]$^+$.

Example 73

Preparation of 2-(3-(4-aminobenzyl)ureido)-N-(3-(morpholinomethyl)benzylacetamide (F559)(77)

The crude product was purified by flash chromatography (DCM/MeOH 9/1) to afford the amide protected (42 mg; 34%) as a white solid Rf=0.24 (DCM/MeOH 9/1). $^1$H NMR (DMSO): δ 1.47 (s, 9H), 2.37 (m, 4H), 3.44 (s, 2H), 3.58 (m, 4H), 3.72 (d, 2H, J=5.7 Hz), 4.14 (d, 2H, J=5.8 Hz), 4.30 (d, 2H, J=5.7 Hz), 6.19 (t, 1H, J=5.8 Hz), 6.55 (t, 1H, J=5.7 Hz), 7.20 (m, 6H), 7.40 (d, 2H, J=8.4 Hz), 8.35 (t, 1H, J=5.7 Hz), 9.27 (s, 1H). The amide was deprotected to afford compound 77 as yellow solid (18 mg, 40%). HPLC method A tr=6.16 nm (96.7%). ESI-MS m/z: 412.4 [M+H]$^+$.

Example 74

Preparation of 2-(3-(4-aminobenzyl)ureido)-N-(3-(pyrimidin-2-yl)benzyl)acetamide (F560)(78)

The crude product was purified by flash chromatography (DCM/MeOH 9/1) to afford the amide protected (82 mg; 73%) as a white solid Rf=0.46 (DCM/MeOH 9/1). $^1$H NMR (DMSO): δ 1.48 (s, 9H), 3.75 (d, 2H, J=5.5 Hz), 4.15 (d, 2H, J=6.0 Hz), 4.41 (d, 2H, J=5.8 Hz), 6.21 (t, 1H, J=5.5 Hz), 6.58 (t, 1H, J=5.8 Hz), 7.14 (d, 2H, J=8.5 Hz), 7.38 (d, 2H, J=8.5 Hz), 7.50 (m, 3H), 8.34 (m, 2H), 8.98 (d, 2H, J=5.0 Hz), 9.30 (s, 1H). The amide was deprotected to afford compound 78 as yellow solid (64 mg, 76%). HPLC method A tr=8.11 nm (97.0%). ESI-MS m/z: 391.3 [M+H]$^+$.

Example 75

Preparation of 1-(4-aminobenzyl)-3-(2-(4-hydroxypiperidin-1-yl)-2-oxoethyl)urea (F561)(79)

The crude product was purified by flash chromatography (DCM/MeOH 9/1) to afford the amide protected (46 mg; 51%) as a white solid Rf=0.18 (DCM/MeOH 9/1). $^1$H NMR (DMSO): δ 1.47 (s, 9H), 1.75 (m, 4H), 3.10 (m, 4H), 3.68 (m, 1H), 3.89 (d, 2H, J=4.9 Hz), 4.12 (d, 2H, J=5.6 Hz), 4.75 (d, 1H, J=4.0 Hz), 6.03 (t, 1H, J=4.9 Hz), 6.67 (t, 1H, J=5.6 Hz), 7.12 (d, 2H, J=8.5 Hz), 7.37 (d, 2H, J=8.5 Hz), 9.27 (s, 1H). The amide was deprotected to afford compound 79 as yellow solid (23 mg, 48%). HPLC method A tr=4.92 nm (91.0%). ESI-MS m/z: 307.3 [M+H]$^+$.

Example 76

Preparation of 2-(3-(4-aminobenzyl)ureido)-N-(3-(1H,1,2,4-triazol-1-yl)benzyl)acetamide (F562)(80)

The crude product was purified by flash chromatography (DCM/MeOH 9/1) to afford the amide protected (52 mg; 47%) as a white solid Rf=0.29 (DCM/MeOH 9/1). $^1$H NMR (DMSO): δ 1.47 (s, 9H), 3.72 (d, 2H, J=5.6 Hz), 4.14 (d, 2H, J=5.8 Hz), 4.39 (d, 2H, J=6.0 Hz), 6.25 (t, 1H, J=5.6 Hz), 6.58 (t, 1H, J=5.8 Hz), 7.13 (d, 2H, J=8.5 Hz), 7.31 (d, 1H, J=7.8 Hz), 7.36 (d, 2H, J=8.5 Hz), 7.50 (t, 1H, J=7.8 Hz), 7.73 (d, 1H, J=7.8 Hz), 7.77 (s, 1H), 8.24 (s, 1H), 8.44 (t, 1H, J=6.0 Hz), 9.26 (s, 1H), 9.36 (s, 1H). The amide was deprotected to afford compound 80 as yellow solid (23 mg, 42%). HPLC method A tr=7.20 nm (98.5%). ESI-MS m/z: 380.3 [M+H]$^+$.

Example 77

Preparation of 2-(3-(4-aminobenzyl)ureido)-N-3-methoxybenzylacetamide (F563)(81)

The crude product was purified by flash chromatography (DCM/MeOH 9/1) to afford the amide protected (61 mg; 61%) as a white solid Rf=0.37 (DCM/MeOH 911). $^1$H NMR (DMSO): δ 1.47 (s, 9H), 3.70 (d, 2H, J=5.6 Hz), 3.73 (s, 3H), 4.13 (d, 2H, J=5.8 Hz), 4.26 (d, 2H, J=6.0 Hz), 6.19 (t, 1H, J=5.6 Hz), 6.55 (t, 1H, J=6.0 Hz), 6.83 (m, 3H), 7.13 (d, 2H, J=8.5 Hz), 7.22 (t, 1H, J=8.0 Hz), 7.36 (d, 2H, J=8.5 Hz), 8.32 (d, 1H, J=5.8 Hz), 9.27 (s, 1H). The amide was deprotected to afford compound 81 as orange solid (33 mg, 51%). HPLC method A tr=7.69 nm (91.3%). ESI-MS m/z: 343.3 [M+H]$^+$.

Example 78

Preparation of ethyl 1-(2-(3-(4-aminobenzyl)ureido)acetyl)-3-oxopiperazine-2-carboxylate (F564)(82)

The crude product was purified by flash chromatography (DCM/MeOH 9/1) to afford the amide protected (51 mg; 57%) as a white solid Rf=0.27 (DCM/MeOH 9/1). $^1$H NMR (DMSO): δ 1.16 (t, 3H, J=7.1 Hz), 1.47 (s, 9H), 2.72 (d, 2H, J=5.7 Hz), 3.55 (m, 4H), 3.90 (m, 4H), 4.12 (d, 2H, J=5.7 Hz), 4.83 (t, 1H, J=6.0 Hz), 6.09 (m, 1H), 6.65 (t, 1H, J=5.7 Hz), 7.12 (d, 2H, J=8.5 Hz), 7.35 (d, 2H, J=8.5 Hz), 8.13 (s, 1H), 9.27 (s, 1H). The amide was deprotected to afford compound 82 as orange solid (24 mg, 44%). HPLC method A tr=6.34 nm (97.3%). ESI-MS m/z: 392.3 [M+H]$^+$.

Example 79

Preparation of 2-(3-((6-aminopyridin-3-yl)methyl)ureido)-N-methoxy-N-methylacetamide (F567)(83)

The crude product was purified by flash chromatography (AcOEt/MeOH 95/5) to afford the amide protected (72 mg; 88%) as a white solid. $^1$H NMR (DMSO): δ 1.47 (s, 9H), 3.70 (d, 2H, J=5.6 Hz), 3.73 (s, 3H), 4.13 (d, 2H, J=5.8 Hz), 4.26

(d, 2H, J=6.0 Hz), 6.19 (t, 1H, J=5.6 Hz), 6.55 (t, 1H, J=6.0 Hz), 6.83 (m, 3H), 7.13 (d, 2H, J=8.5 Hz), 7.22 (t, 1H, J=8.0 Hz), 7.36 (d, 2H, J=8.5 Hz), 8.32 (d, 1H, J=5.8 Hz), 9.27 (s, 1H). The amide was deprotected to afford compound 83 as yellow solid (68 mg, 96%). HPLC method B tr=12.41 nm (98.4%). ESI-MS m/z: 267.2 [M+H]$^+$.

Example 80

Preparation of ethyl 1-(2-(3-((6-aminopyridin-3-yl)methyl)ureido)acetyl)piperidine-2-carboxylate (F568)(84)

The crude product was purified by flash chromatography (AcOEt/MeOH 95/5) to afford the amide protected (72 mg; 74%) as a white solid. The amide was deprotected to afford compound 84 as yellow solid (71 mg, 94%). HPLC method B tr=8.47 m (99.0%). ESI-MS m/z: 364.3 [M+H]$^+$.

Example 81

Preparation of 2-(3-((6-aminopyridin-3-yl)methyl)ureido)-N-benzyloxy)acetamide (F573)(85)

The crude product was purified by flash chromatography (AcOEt/MeOH 95/5) to afford the amide protected (74 mg; 78%) as a white solid. $^1$H NMR (DMSO): δ 1.47 (s, 9H), 3.70 (d, 2H, J=5.6 Hz), 3.73 (s, 3H), 4.13 (d, 2H, J=5.8 Hz), 4.26 (d, 2H, J=6.0 Hz), 6.19 (t, 1H, J=5.6 Hz), 6.55 (t, 1H, J=6.0 Hz), 6.83 (m, 3H), 7.13 (d, 2H, J=8.5 Hz), 7.22 (t, 1H, J=8.0 Hz), 7.36 (d, 2H, J=8.5 Hz), 8.32 (d, 1H, J=5.8 Hz), 9.27 (s, 1H). The amide was deprotected to afford compound 85 as yellow solid (68 mg, 94%). HPLC method B tr=14.01 nm (100%). ESI-MS m/z: 330.2 [M+H]$^+$.

Example 82

Preparation of 1-((6-aminopyridin-3-yl)methyl-3-(2-isoxazolidin-2-yl)-2-oxoethyl)urea (F585)(86)

The crude product was purified by precipitation in acetone/hexane to afford the amide protected (31 mg; 54%) as a white solid. The amide was deprotected to afford compound 86 as yellow solid (18 mg, 51%). HPLC method B tr=13.07 nm (93.0%). ESI-MS m/z: 280.0 [M+H]$^+$.

Example 83

Preparation of 1-β6-aminopyridin-3-yl)methyl-3-(2-morpholino-2-oxoethyl)urea (F594)(87)

The crude product was purified by precipitation in acetone/hexane to afford the amide protected (55 mg; 82%) as a white solid. The amide was deprotected to afford compound 87 as yellow solid (47 mg, 78%). HPLC method B tr=13.62 nm (97.1%). ESI-MS m/z: 294.3 [M+H]$^+$.

Example 84

Preparation of 1-((6-aminopyridin-3-yl)methyl)-3-(2-oxo-2-(2-(pyridin-2-yl)pyrrolidin-1-yl)ethyl)urea (F586)(88)

The crude product was purified by precipitation in acetone/hexane to afford the amide protected (83 mg; 95%) as a white solid. The amide was deprotected to afford compound 88 as yellow solid (79 mg, 88%). HPLC method B tr=13.92 nm (99.4%). ESI-MS m/z: 355.3 [M+H]$^+$.

Example 85

Preparation of (S)-1-((6-aminopyridin-3-yl)methyl)-3-(2-oxo-2-(2-(pyridin-3-yl)pyrrolidin-1-yl)ethyl)urea (F588)(89)

The crude product was purified by flash chromatography (AcOEt/MeOH 98/2) to afford the amide protected (81 mg; 85%) as a white solid. The amide was deprotected to afford compound 89 as yellow solid (64 mg, 75%). HPLC method B tr=12.19 nm (97.6%). ESI-MS m/z: 369.2 [M+H]$^+$.

Example 86

Preparation of 1-((6-aminopyridin-3-yl)methyl)-3-(2-(2-(2-methoxyphenyl)pyrrolidin-1-yl)-2-oxoethyl)urea (F587)(90)

The crude product was purified by flash chromatography (AcOEt/MeOH 95/5) to afford the amide protected (66 mg; 87%) as a white solid. The amide was deprotected to afford compound 90 as yellow solid (53 mg, 76%). HPLC method B tr=23.57 nm (99.8%). ESI-MS m/z: 384.4 [M+H]$^+$.

Example 87

Preparation of 1-((6-aminopyridin-3-yl)methyl)-3-(2-(2-(3-methyl-1,2,4-oxadiazol-5-yl)pyrrolidin-1-yl)-2-oxoethyl)urea (F593)(91)

The crude product was purified by precipitation in AcOEt/hexane to afford the amide protected (80 mg; 75%) as a white solid. The amide was deprotected to afford compound 91 as yellow solid (62 mg, 73%). HPLC method B tr=17.19 nm (99.1%). ESI-MS m/z: 360.3 [M+H]$^+$.

Example 88

Preparation of 1-(4-aminobenzyl)-3-(2-(2-(2-methoxyphenyl) pyrrolidin-1-yl)-2-oxoethyl)urea (F609) (92)

The crude product was purified by flash chromatography (AcOEt/MeOH 9/1) to afford the amide protected (210 mg; 88%) as a white solid. The amide was deprotected to afford compound 92 as yellow solid (198 mg, 88%). HPLC method B tr=23.47 nm (99.5%). ESI-MS m/z: 383.4 [M+H]$^+$.

Example 89

Preparation of 1-(((6-aminopyridin-3-yl)methyl)ureido)-N-(benzo[d][1,3]dioxol-4-ylmethyl)-N-isopropylacetamide (F590)(93)

The crude product was purified by precipitation in acetone/hexane to afford the amide protected (80 mg; 82%) as a white solid. The amide was deprotected to afford compound 94 as yellow solid (69 mg, 81%). HPLC method B tr=19.53 nm (91.5%). ESI-MS m/z: 400.1 [M+H]$^+$.

Example 90

Preparation of 2-(3-((6-aminopyridin-3-yl)methyl) ureido)-N-isopropyl-N-(3-(methylthio)benzyl)acetamide (F592)(94)

The crude product was purified by flash chromatography (AcOEt/MeOH 95/5) to afford the amide protected (84 mg; 84%) as a white solid. The amide was deprotected to afford compound 94 as yellow solid (78 mg, 87%). HPLC method B tr=22.31 nm (96.9%). ESI-MS m/z: 402.2 [M+H]$^+$.

Example 91

Preparation of 2-(3-((6-aminopyridin-3-yl)methyl) ureido)-N-isopropyl-N-((5-oxopyrrolidin-2-yl)methyl)acetamide (F591)(95)

The crude product was purified by flash chromatography (AcOEt/MeOH 8/2) to afford the amide protected (26 mg; 32%) as a white solid. The amide was deprotected to afford compound 95 as yellow solid (16 mg, 53%). HPLC method B tr=15.07 nm (94.5%). ESI-MS m/z: 363.1 [M+H]$^+$.

Example 92

Preparation of 2-(3-((6-aminopyridin-3-yl)methyl) ureido)-N-cyclohexyl-N-methylacetamide (F595) (96)

The crude product was purified by flash chromatography (AcOEt/MeOH 95/5) to afford the amide protected (67 mg; 90%) as a white solid. The amide was deprotected to afford compound 96 as yellow solid (21 mg, 28%). HPLC method B tr=18.86 nm (97.9%). ESI-MS m/z: 320.3 [M+H]$^+$.

Example 93

Preparation of 2-(3-((6-aminopyridin-3-yl)methyl) ureido)-N-(4-fluorophenyl)-N-methylacetamide (F597)(97)

The crude product was purified by flash chromatography (AcOEt) to afford the amide protected (36 mg; 60%) as a white solid. The amide was deprotected to afford compound 97 as yellow solid (12 mg, 30%). HPLC method B tr=17.17 nm (94.3%). ESI-MS m/z: 332.1 [M+H]$^+$.

Example 94

Preparation of 2-(3-((6-aminopyridin-3-yl)methyl) ureido)-N-(benzyloxy)-N-ethylacetamide (F599)(98)

The crude product was purified by flash chromatography (AcOEt/MeOH 95/5) to afford the amide protected (105 mg; 89%) as a white solid. $^1$H NMR (DMSO): δ 1.10 (t, 3H, J=6.7 Hz), 1.47 (s, 9H), 3.64 (q, 2H, J=6.7 Hz), 3.99 (d, 2H, J=4.4 Hz), 4.16 (d, 2H, J=5.8 Hz), 4.92 (s, 2H), 6.10 (t, 1H, J=4.4 Hz), 6.71 (t, 1H, J=5.8 Hz), 7.45 (m, 5H), 7.60 (d, 1H, J=8.6 Hz), 7.73 (d, 1H, J=8.6 Hz), 8.13 (s, 1H), 9.67 (s, 1H). The amide was deprotected to afford compound 98 as yellow solid (107 mg, 97%). HPLC method B tr=17.49 nm (94.5%). ESI-MS m/z: 358.2 [M+H]$^+$.

Example 95

Preparation of 2-(3-((4-aminobenzyl)ureido)-N-(benzyloxy)-N-ethylacetamide (F607)(99)

The crude product was purified by flash chromatography (AcOEt) to afford the amide protected (312 mg; 77%) as a white solid. The amide was deprotected to afford compound 99 as yellow solid (307 mg, 91%). $^1$H NMR (DMSO): δ 1.10 (m, 3H), 3.45 (s, 2H), 3.65 (m, 2H), 4.00 (s, 2H), 4.14 (s, 2H), 4.93 (s, 2H), 6.08 (s, 1H), 6.63 (s, 1H), 6.92 (m, 2H), 7.15 (m, 2H), 7.45 (m, 5H). HPLC method B tr=18.32 nm (96.5%). ESI-MS m/z: 357.2 [M+H]$^+$.

Example 96

N-(5-acetyl-2-methoxybenzyloxy)-2-(3-(4-aminobenzyl) ureido)-N-ethylacetamide (F652)(100)

The crude product (amide; Rf=0.43 (EtOAc)) was deprotected and purified by flash chromatography (EDP/EtOAc) to afford the amine (20 mg; two step global yield=8%) Rf=0.09 (EDP/EtOAC 30/70). $^1$H NMR (300 MHz, DMSO): δ 8.12-8.05 (m, 2H), 7.22 (d, J=8.4 Hz, 1H), 6.94 (d, J=8.3 Hz, 2H), 6.53 (d, J=8.3 Hz, 2H), 6.50 (t, J=5.3 Hz, 1H), 5.99 (t, J=5.2 Hz, 1H), 5.00-4.93 (m, 4H), 4.06 (s, 2H), 4.04 (s, 2H), 4.00 (s, 3H), 3.69 (q, J=6.8 Hz, 2H), 2.58 (s, 3H), 1.13 (t, J=7.0 Hz, 3H). HPLC method A tr=9.52 nm (93.6%). ESI-MS m/z: 429.2 [M+H]$^+$.

Example 97

2-(3-(4-aminobenzyl)ureido)-N-(2,5-dimethoxybenzyloxy)-N-ethylacetamide (F653)(101)

The crude product (amide; Rf=0.43 (EDP/EtOAc 30/70)) was deprotected and purified by flash chromatography (EDP/EtOAc) to afford the amine (10 mg; two step global yield=10%) Rf=0.14 (EDP/EtOAC 30/70). $^1$H NMR (300 MHz, DMSO) δ 7.03-6.95 (m, 3H), 6.90 (d, J=8.4 Hz, 2H), 6.50 (d, J=8.3 Hz, 2H), 6.45 (t, J=5.7 Hz, 1H), 5.95 (t, J=5.4 Hz, 1H), 4.97 (broad s, 2H), 4.84 (s, 2H), 4.03-3.97 (m, 4H), 3.80 (s, 3H), 3.72 (s, 3H), 3.63 (q, J=7.2 Hz, 2H), 1.09 (t, J=7.0 Hz, 3H). HPLC method A tr=10.15 nm (90.4%). ESI-MS m/z: 417.2 [M+H]$^+$.

Example 98

2-(3-(4-aminobenzyl)ureido)-N-(3-chlorobenzyloxy)-N-ethyl-acetamide (F654)(102)

The crude product (amide; Rf=0.31 (EDP/EtOAc 30/70)) was deprotected and purified by flash chromatography (EDP/EtOAc) to afford the amine (56 mg; two step global yield=25%) as a white solid Rf=0.4 (EtOAC). $^1$H NMR (300 MHz, DMSO): δ 7.61-7.46 (m, 4H), 6.94 (d, J=8.3 Hz, 2H), 6.53 (d, J=8.3 Hz, 2H), 6.48 (t, J=5.9 Hz, 1H), 6.03 (1, J=5.4 Hz, 1H), 4.99-4.93 (m, 4H), 4.08-3.98 (m, 4H), 3.67 (q, J=7.1 Hz, 2H), 1.12 (t, J=6.9 Hz, 3H). HPLC method A tr=10.97 nm (97.3%). ESI-MS m/z: 391.2/393.2 [M+H]$^+$.

Example 99

1-((N-ethyl-N-((pyridin-2-yl)methyl)carbamoyl) methyl)-3-(4-aminobenzyl)urea (F655)(103)

The crude product was purified by flash chromatography (EtOAc/MeOH) to afford the amide protected (56 mg; 47%)

as a colourless oil Rf=0.38 (EtOAc/MeOH 95/5). $^1$H NMR (300 MHz, CDCl$_3$): δ 8.46-8.56 (m, 1H), 7.77-7.55 (m, 1H), 7.25-7.11 (m, 5H), 6.61 (s, 1H), 5.97 (s, 1H), 5.55 (s, 1H), 4.65-4.52 (m, 2H), 4.31-4.23 (m, 2H), 4.21-4.10 (m, 2H), 3.35 (q, J=6.9 Hz, 2H), 1.50 (s, 9H), 1.15 (t, J=6.3 Hz, 3H). The amide was deprotected to afford the amine (30 mg; 70%) as a yellow oil Rf=0.2 (EtOAc/MeOH 90/10). $^1$H NMR (300 MHz, DMSO): δ 8.56 (dd, J=4.1 Hz, 16.3 Hz, 1H), 7.89-7.72 (m, 1H), 7.42-7.22 (m, 2H), 6.99-6.90 (m, 2H), 6.58-6.50 (m, 3H), 6.12-6.02 (m, 1H), 5.08 (broad s, 2H), 4.63 (d, J=6.9 Hz, 2H), 4.06 (d, J=5.3 Hz, 2H), 4.04-3.96 (m, 2H), 3.48-3.28 (m, 2H) 1.19-0.96 (m, 3H). HPLC method A tr=4.42 mn (88.4%). ESI-MS m/z: 342.3 [M+H]$^+$.

Example 100

1-((N-(3-methoxybenzyl)-N-ethylcarbamoyl)methyl)-3-(4-aminobenzyl)urea (F656)(104)

The crude product was purified by flash chromatography (EDP/EtOAc) to afford the amide protected (35 mg; 43%) as a white solid Rf=0.6 (EtOAc). $^1$H NMR (200 MHz, CDCl$_3$): δ 7.31-7.09 (m, 6H), 6.86-6.62 (m, 3H), 6.58-6.46 (m, 1H), 4.48-4.40 (m, 2H), 4.30-4.22 (m, 2H), 4.18-4.05 (m, 4H), 3.78 (d, J=5.1 Hz, 3H), 3.39-3.13 (m, 2H), 1.50 (s, 9H), 1.20-0.94 (m, 3H). The amide was deprotected to afford the amine (15 mg; 53%) as a white solid Rf=0.29 (EtOAc). $^1$H NMR (300 MHz, DMSO) δ 7.30 (dt, J=8.0 Hz, 19.2 Hz, 1H), 6.98-6.89 (m, 2H), 6.89-6.79 (m, 3H), 6.58-6.49 (m, 3H), 6.14-6.03 (m, 1H), 4.97 (broad s, 2H), 4.57-4.50 (m, 2H), 4.10-3.89 (m, 4H), 3.81-3.74 (m, 3H), 3.47-3.22 (m, 2H), 1.13 (t, J=7.0 Hz, 3H). HPLC method A tr=9.46 nm (96.3%). ESI-MS m/z: 371.2 [M+H]$^+$.

Example 101

1-((N-(4-methoxybenzyl)-N-ethylcarbamoyl)methyl)-3-(4-aminobenzyl)urea (F657)(105)

The crude product was purified by flash chromatography (EDP/EtOAc) to afford the amide protected (48 mg; 34%) as a white solid Rf=0.66 (EtOAc). $^1$H NMR (200 MHz, CDCl$_3$): δ 7.35-6.73 (m, 9H), 6.49 (s, 1H), 4.47-4.35 (m, 2H), 4.32-4.23 (m, 2H), 4.16-4.11 (m, 2H), 3.80-3.77 (m, 3H), 3.24 (dq, J=7 Hz, 20.6 Hz, 2H), 1.51 (s, 9H), 1.06 (dt, J=7.1 Hz, 21.6 Hz, 3H). The amide was deprotected to afford the amine (31 mg; 81%) as a yellow solid Rf=0.27 (EtOAc). $^1$H NMR (300 MHz, DMSO): δ 7.26-7.17 (m, 2H), 7.05-6.86 (m, 4H), 6.69-6.54 (m, 3H), 6.11 (s, 1H), 4.48 (broad s, 2H), 4.12-4.04 (m, 2H), 4.04-3.90 (m, 2H), 3.79-3.74 (m, 3H), 3.54-318 (m, 4H), 1.13 (t, J=6.9 Hz, 3H). HPLC method A tr=8.42 nm (96.3%). ESI-MS m/z: 371.2 [M+H]$^+$.

Example 102

1 1-((N-(3-chlorobenzyl)-N-ethylcarbamoyl)methyl)-3-(4-aminobenzyl)urea (F658)(106)

The crude product was purified by flash chromatography (EDP/EtOAc) to afford the amide protected (50 mg; 52%) as a colourless oil Rf=0.17 (EDP/EtOAc 50/50). $^1$H NMR (300 MHz, CDCl$_3$): δ 7.30-7.07 (m, 8H), 7.05-6.96 (m, 1H), 6.57 (broad s, 1H), 4.45-4.36 (m, 2H), 4.29-4.21 (m, 2H), 4.19-4.04 (m, 2H), 3.25 (dq, J=7.1 Hz, 14.3 Hz, 2H), 1.50 (s, 9H), 1.17-0.95 (m, 3H). The amide was deprotected to afford the amine (10 mg; 24%) as a yellow solid Rf=0.41 (EtOAc). HPLC method A tr=10.06 nm (98.5%). ESI-MS m/z: 375.2/377.2 [M+H]$^+$.

Example 103

2-(3-(4-aminobenzyl)ureido)-N-ethyl-N-(2-fluorobenzyl)acetamide (F659)(107)

The crude product was purified by flash chromatography (EDP/EtOAc) to afford the amide protected, Rf=0.37 (EtOAc). The amide was deprotected and purified by flash chromatography (EDP/EtOAc) to afford the amine (36 mg; two step global yield=30%) as a yellow solid, Rf=0.3 (EtOAc). HPLC method A tr=9.05 nm (97.5%). ESI-MS m/z: 359.2 [M+H]$^+$.

Example 104

1-((N-(5-acetyl-2-methoxybenzyl)-N-ethylcarbamoyl)methyl)-3-(4-aminobenzyl)urea (F660)(108)

The crude product was purified by flash chromatography (EDP/EtOAc) to afford the amide protected (10 mg; 25%) Rf=0.11 (EDP/EtOAc 30/70). $^1$H NMR (300 MHz, CDCl3) δ 7.96-785 (m, 1H), 7.75-7.65 (m, 1H), 7.33-7.14 (m, 6H), 6.95-6.85 (m, 1H), 6.53-6.43 (m, 1H), 4.59-4.53 (m, 1H), 4.44 (broad s, 1H), 4.34-4.26 (m, 2H), 4.19-4.11 (m, 2H), 3.94-3.85 (m, 3H), 3.43-3.23 (m, 2H), 2.59-2.49 (m, 3H), 1.50 (s, 9H), 1.21-0.98 (m, 3H). The amide was deprotected to afford the amine (5 mg; 63%) as a yellow oil Rf=0.22 (EtOAc). HPLC method A tr=9.11 nm (92.2%). ESI-MS m/z: 413.2 [M+H]$^+$.

Example 105

2-(3-(4-aminobenzyl)ureido)-N-ethyl-N-(2-fluorobenzyloxy) acetamide (F661)(109)

The crude product was purified by flash chromatography (EDP/EtOAc) to afford the amine protected (88 mg; 42%) as a white solid Rf=0.34 (EDP/EtOAc 30/70). The amide was deprotected and purified by flash chromatography (EDP/EtOAc) to afford the amine (15 mg; 21%) Rf=0.33 (ETOAc). $^1$H NMR (300 MHz, DMSO) δ 7.65-7.47 (m, 2H), 7.37-7.26 (m, 2H), 6.94 (d, J=8.3 Hz, 2H), 6.53 (d, J=8.3 Hz, 2H), 6.47 (t, J=5.7 Hz, 1H), 6.01 (t, J=5.5 Hz, 1H), 5.01 (s, 2H), 4.97 (s, 2H), 4.04 (d, J=5.7 Hz, 2H), 4.00 (d, J=5.5 Hz, 2H), 3.66 (q, J=7.0 Hz, 2H), 1.11 (t, J=7.0 Hz, 3H). HPLC method A tr=9.76 nm (98.3%). ESI-MS m/z: 375.2 [M+H]$^+$.

Example 106

2-(3-(4-aminobenzyl)ureido)-N-ethyl-N-(3-methoxybenzyl-oxy)acetamide (F662)(110)

The crude product (amide; Rf=0.34 (EDP/EtOAc 30/70)) was deprotected and purified by flash chromatography (EDP/EtOAc) to afford the amine (20 mg; two step global yield=12%) Rf=0.06 (EDP/EtOAC 30/70). $^1$H NMR (300 MHz, DMSO) δ 7.45-7.34 (m, 1H), 7.11-7.05 (m, 2H), 7.06-6.99 (m, 1H), 6.96 (d, J=8.3 Hz, 2H), 6.56 (d, J=8.3 Hz, 2H), 6.51 (t, J=5.7 Hz, 1H), 6.04 (t, J=5.4 Hz, 1H), 4.99 (broad s, 2H), 4.94 (s, 2H), 4.09-4.01 (m, 4H), 3.83 (s, 3H), 3.69 (q, J=7.0 Hz, 2H), 1.15 (t, J=7.2 Hz 3H). HPLC method A tr=9.75 nm (97.8%). ESI-MS m/z: 387.2 [M+H]$^+$.

Example 107 ethyl 3-(9-(4-aminophenyl)-3-ethyl-4,7-dioxo-2-oxa-3,6,8-triazanonyl)benzoate (F663)(111)

The crude product (amide; Rf=0.28 (EDP/EtOAc 30/70)) was deprotected and purified by flash chromatography (EDP/EtOAc) to afford the amine (25 mg; two step global yield=13%); Rf=0.09 (EDP/EtOAC30/70). $^1$H NMR (300 MHz, DMSO) δ 8.09 (s, 1H), 8.02 (d, J=7.8 Hz, 1H), 7.79 (d, J=7.7 Hz, 1H), 7.63 (t, J=7.7 Hz, 1H), 6.94 (d, J=8.4 Hz, 2H), 6.53 (d, J=8.4 Hz, 2H), 6.49 (t, J=5.9 Hz, 1H), 6.03 (t, J=5.5 Hz, 1H), 5.05 (s, 2H), 4.98 (broad s, 2H), 4.38 (q, J=6.9 Hz, 2H), 4.10-3.98 (m, 4H), 3.68 (q, J=7.0, 2H), 1.37 (t, J=7.1, 3H), 1.13 (t, J=7.0, 3H). HPLC method A tr=10.76 nm (96.8%). ESI-MS m/z: 429.2 [M+H]$^+$.

Example 108

2-(3-(4-aminobenzyl)ureido)-N-ethyl-N-(3-nitrobenzyloxy) acetamide (F664)(112)

The crude product was purified by flash chromatography (EDP/EtOAc) to afford the amine protected (32 mg; 12%) as a white solid Rf=0.13 (EDP/EtOAc 30/70). The amide was deprotected and purified by flash chromatography (EDP/EtOAc) to afford the amine (10 mg; 38%) Rf=0.24 (EtOAc). $^1$H NMR (300 MHz, DMSO): δ 8.39 (s, 1H), 8.31 (d, J=7.3 Hz, 1H), 7.98 (d, J=7.8 Hz, 1H), 7.78 (t, J=7.9 Hz, 1H), 6.94 (d, J=8.3 Hz, 2H), 6.53 (d, J=8.4 Hz, 2H), 6.48 (t, J=5.7 Hz, 1H), 6.03 (t, J=5.3 Hz, 1H), 5.12 (s, 2H), 4.97 (s, 2H), 4.08-4.01 (m, 4H), 3.70 (q, J=6.8 Hz, 2H), 1.14 (t, J=7.0 Hz, 3H). HPLC method A tr=9.67 nm (97.6%). ESI-MS m/z: 402.2 [M+H]$^+$.

Example 109

2-(3-(4-aminobenzyl)ureido)-N-ethyl-N-(4-nitrobenzyloxy) acetamide (F665)(113)

The crude product was purified by flash chromatography (EDP/EtOAc) to afford the amine protected (71 mg; 42%) as a white solid Rf=0.13 (EDP/EtOAc 30/70). The amide was deprotected and purified by flash chromatography (EDP/EtOAc) to afford the amine (26 mg; 46%) Rf=0.3 (EtOAc). $^1$H NMR (300 MHz, DMSO): δ 8.33 (d, J=8.8 Hz, 2H), 7.78 (d, J=8.7 Hz, 2H), 6.93 (d, J=8.3 Hz, 2H), 6.53 (d, J=8.4 Hz, 2H), 6.48 (t, J=6.1 Hz, 1H), 6.04 (t, J=5.5 Hz, 1H), 5.13 (s, 2H), 4.97 (s, 2H), 4.07-4.00 (m, 4H), 3.69 (q, J=7.1 Hz, 2H), 1.14 (1, J=7.0 Hz, 3H). HPLC method A tr=9.78 nm (95.4%). ESI-MS m/z: 402.2 [M+H]$^+$.

Example 110

2-(3-(4-aminobenzyl)ureido)-N-ethyl-N-(pyridin-2-yl-methoxy)acetamide (F666)(114)

The crude product (amide) was deprotected and purified by flash chromatography (EtOAc/MeOH) to afford the amine (50 mg; two step global yield=30%). $^1$H NMR (300 MHz, DMSO): δ 8.69-8.61 (m, 1H), 7.90 (t, J=7.3 Hz, 1H), 7.59 (d, J=7.4 Hz, 1H), 7.50-7.40 (m, 1H), 6.93 (d, J=7.8 Hz, 2H), 6.53 (d, J=8.1, 2H), 6.48 (s, 1H), 6.01 (s, 1H), 5.04 (s, 2H), 4.96 (s, 2H), 4.09-3.98 (m, 4H), 3.67 (q, J=6.9 Hz, 2H), 1.13 (t, J=7.0 Hz, 3H). HPLC method A tr=6.22 nm (99.1%). ESI-MS m/z: 358.2 [M+H]$^+$.

Example 111

1-((N-(2-hydroxy-3-methoxybenzyl)-N-ethylcarbamoyl)methyl)-3-(4-aminobenzyl)urea (F667)(115)

The crude product was purified by flash chromatography (EDP/EtOAc) to afford the amide protected. The amide was deprotected and purified by flash chromatography (EtOAc/MeOH) to afford the amine (14 mg; two step global yield=7%) Rf=0.3 (EtOAc/MeOH 98/2). $^1$H NMR (300 MHz, DMSO): δ 8.22 (s, 1H), 6.94 (d, J=8.3 Hz, 2H), 6.91-6.85 (m, 1H), 6.79-6.73 (m, 2H), 6.53 (d, J=8.4 Hz, 2H), 6.42 (t, J=5.8 Hz, 1H), 6.14 (t, J=5.3 Hz, 1H), 4.96 (broad s, 2H), 4.26 (d, J=5.8 Hz, 2H), 4.05 (d, J=5.3 Hz, 2H), 3.81 (s, 3H), 3.73 (d, J=5.7 Hz, 2H). HPLC method A tr=6.38 nm (79.6%). ESI-MS m/z: 359.2 [M+H]$^+$.

Example 112

1-(4-aminobenzyl)-3-(2-(2-(naphthalen-1-yl)pyrrolidin-1-yl)-2-oxoethyl)urea (F671)(116)

The crude product was purified by flash chromatography (EDP/EtOAc) to afford the amide protected Rf=0.16 (EtOAc). The amide was deprotected and precipitated in ether to afford the amine (TFA salt; 22.7 mg; two step global yield=14%) as a white solid Rf=0.14 (EtOAc). HPLC method A tr=9.89 nm (92.3%). ESI-MS m/z: 403.2 [M+H]$^+$.

Example 113

1-(4-aminobenzyl)-3-(2-(2-(2,5-dimethoxyphenyl)pyrrolidin-1-yl)-2-oxoethyl)urea (F672)(117)

The crude product was purified by flash chromatography (EDP/EtOAc) to afford the amide protected Rf=0.22 (EtOAc). The amide was deprotected and precipitated in ether to afford the amine (TFA salt; 54 mg; two step global yield=33%) as a white solid Rf=0.47 (CH$_2$Cl$_2$/MeOH 95/5). $^1$H NMR (300 MHz, CDCl$_3$); δ 7.29-7.21 (m, 2H), 7.20-7.11 (m, 2H), 6.80-6.61 (m, 3H), 3.64 (m, 6H), 3.56-3.04 (m, 2H), 2.25-2.06 (m, 1H), 1.98-1.54 (m, 4H), 1.47 (d, J=2.1, 9H). HPLC method A tr=8.73 nm (99.7%). ESI-MS m/z: 413.3 [M+H]$^+$.

Example 114

1-(4-aminobenzyl)-3-(2-(2-(2-chlorophenyl)pyrrolidin-1-yl)-2-oxoethyl)urea (F673)(118)

The crude product was purified by flash chromatography (EDP/EtOAc then EtOAc/MeOH) to afford the amide protected Rf=0.26 (EtOAc). $^1$H NMR (300 MHz, CDCl$_3$): δ 7.43-6.80 (m, 8H), 6.67 (s, 1H), 5.42-5.13 (m, 1H), 4.23-4.16 (m, 2H), 4.16-4.02 (m, 1H), 3.79-3.20 (m, 3H), 2.40-2.07 (m, 1H), 2.00-1.53 (m, 4H), 1.50-1.46 (m, 9H). The amide was deprotected and precipitated in ether to afford the amine (TFA salt; 90 mg; two step global yield=58%) as a yellow solid Rf=0.37 (CH$_2$Cl$_2$/MeOH 95/5), HPLC method A tr=10.16 nm (83.5%). ESI-MS m/z: 387.2 [M+H]$^+$.

Example 115

2-(3-(4-aminobenzyl)ureido)-N-ethyl-N-(pyridin-3-yl-115 methoxy)acetamide (F675)(119)

The crude product (amide; Rf=0.22 (EtOAc/MeOH 90/10)) was deprotected and purified by flash chromatography (EtOAc/MeOH) to afford the amine (18 mg; two step global yield=12%) Rf=0.16 (EtOAc/MeOH 90/10). $^1$H NMR (300 MHz, DMSO): δ 8.73-8.68 (m, 1H), 8.67-8.60 (m, 1H), 7.93 (d, J=7.7 Hz, 1H), 7.54-7.46 (m, 1H), 6.94 (d, J=8.3 Hz, 2H), 6.53 (d, J=8.3 Hz, 2H), 6.48 (t, J=5.5 Hz, 1H), 6.03 (t, J=5.4 Hz, 1H), 5.07-4.93 (m, 4H), 4.09-3.97 (m, 4H), 3.68 (q, J=6.9 Hz, 2H), 1.13 (t, J=7.0 Hz, 3H). HPLC method A tr=4.47 nm (86.5%). ESI-MS m/z: 358.2 [M+H]$^+$.

Example 116 ethyl 1-(4-aminophenyl)-7-ethyl-3,6-dioxo-8-oxa-2,4,7-triazaundecan-1'-oate (F676)(120)

The crude product (amide; Rf=0.32 (EtOAc)) was deprotected and purified by flash chromatography (EDP/EtOAc) to afford the amine (17 mg; two step global yield=17%) Rf=0.15 (EtOAc). $^1$H NMR (200 MHz, CDCl$_3$): δ 7.08 (d, J=8.3 Hz, 2H), 6.69 (d, J=8.3 Hz, 2H), 5.45 (s, 1H), 5.16 (s, 1H), 4.30-4.05 (m, 8H), 3.62 (q, J=7.1 Hz, 2H), 2.63 (t, J=5.9 Hz, 2H), 1.27 (t, J=7.1 Hz, 3H), 1.13 (t, J=7.1 Hz, 3H). HPLC method A tr=6.97 nm (92.6%). ESI-MS m/z: 367.2 [M+H]$^+$.

Example 117 ethyl 1-(4-aminophenyl)-7-ethyl-3,6-dioxo-8-oxa-2,4,7-triazadodecan-12-oate (F677(121))

The crude product (amide; Rf=0.08 (EtOAc)) was deprotected and purified by flash chromatography (EDP/EtOAc) to afford the amine (13 mg; two step global yield=11%) Rf=0.12 (EtOAc). $^1$H NMR (200 MHz, CDCl$_3$) δ 7.08 (d, J=8.4 Hz, 2H), 6.71 (d, J=8.4 Hz, 2H), 5.50 (s, 1H), 5.24 (s, 1H), 4.30-4.06 (m, 6H), 3.90 (t, J=6.2 Hz, 2H), 3.59 (q, J=7.1 Hz, 2H), 2.44 (t, J=7.3 Hz, 2H), 2.08-1.88 (m, 2H), 1.25 (t, J=7.2 Hz, 4H), 1.14 (t, J=7.1 Hz, 3H). HPLC method A tr=7.61 nm (93.6%). ESI-MS m/z: 381.3 [M+H]$^+$.

Example 118

2-(3-(4-aminobenzyl)ureido)-N-ethyl-N-(pyridin-4-yl-methoxy)acetamide (F678)(122)

The crude product (amide; Rf=0.46 (EtOAc)) was deprotected and purified by flash chromatography (EtOAc/MeOH) to afford the amine (31 mg; two step global yield=21%) Rf=0.06 (EtOAc/MeOH 9812). $^1$H NMR (300 MHz, CDCl$_3$): δ 8.66-8.55 (m, 2H), 7.80-7.65 (m, 3H), 7.49-7.36 (m, 3H), 7.32-7.27 (m, 1H), 7.24-7.16 (m, 1H), 4.97 (5, 4H), 4.87 (s, 2H), 3.03 (q, J=7.1 Hz, 2H), 1.11 (t, J=7.1 Hz, 3H). HPLC method A tr=4.46 nm (95.3%). ESI-MS m/z: 358.2 [M+H]$^+$.

Example 119

1-(4-aminobenzyl)-3-(2-(2-(2-ethoxyphenyl)pyrrolidin-1-yl)-2-oxoethyl)urea (F679)(123)

The crude product was purified by flash chromatography (EDP/EtOAc) to afford the amide protected Rf=0.26 (EtOAc). The amide was deprotected and precipitated in ether to afford the amine as a yellow solid (TFA salt; 16 mg; two step global yield=20%) Rf=0.08 (EtOAc). HPLC method A tr=9.46 nm (99.6%). ESI-MS m/z: 397.3 [M+H]$^+$.

Example 120

1-(4-aminobenzyl)-3-(2-(2-(2-bromophenyl)pyrrolidin-1-yl)-2-oxoethyl)urea (F680)(124)

The crude product was purified by flash chromatography (EDP/EtOAc then EtOAc/MeOH) to afford the amide protected Rf=0.28 (EtOAc). NMR (300 MHz, CDCl$_3$): δ 7.58-7.45 (m, 1H), 7.35-6.98 (m, 6H), 6.92-6.86 (m, 1H), 6.54 (broad s, 1H), 5.98 (t, J=4.3 Hz, 1H), 5.86 (t, J=4.4 Hz, 1H), 5.67-5.53 (m, 1H), 5.41-5.09 (m, 1H), 4.27-4.18 (m, 2H), 4.17-3.23 (m, 4H), 2.44-2.18 (m, 1H), 2.01-1.54 (m, 3H), 1.49 (m, 9H). The amide was deprotected and precipitated in ether to afford the amine (TFA salt; 16 mg; two step global yield=19%) as a brown solid Rf=0.08 (EtOAc). HPLC method A tr=9.29 nm (96.1%). ESI-MS m/z: 431.2/433.2 [M+H]$^+$.

Example 121

1-(4-aminobenzyl)-3-(2-(2-(2,5-dimethoxyphenyl)azepan-1-yl)-2-oxoethyl)urea (F681)(125)

The crude product was purified by flash chromatography (EDP/EtOAc) to afford the amide protected Rf=0.43 (EtOAc). The amide was deprotected and precipitated in ether to afford the amine (TFA salt; 30.2 mg; two step global yield=18%) as a white solid Rf=0.32 (EtOAc). HPLC method A tr=10.15 nm (96.8%). ESI-MS m/z: 441.3 [M+H]$^+$.

Example 122

1-(4-aminobenzyl)-3-(2-(2-(2,5-dichlorophenyl)piperidin-1-yl)-2-oxoethyl)urea (F682)(126)

The crude product was purified by flash chromatography (EDP/EtOAc) to afford the amide protected Rf=0.41 (EtOAc). $^1$H NMR (300 MHz, CDCl$_3$): δ 7.39-7.01 (m, 7H), 6.82-6.56 (m, 1H), 6.04-5.80 (m, 1H), 5.68-5.44 (m, 1H), 4.46-4.13 (m, 4H), 3.80-2.85 (m, 2H), 2.03-1.53 (m, 6H), 1.50 (s, 9H). The amide was deprotected and precipitated in ether to afford the amine (TFA salt; 34.7 mg; two step global yield=21%) as a yellow solid Rf=0.33 (EtOAc). HPLC method A tr=10.66 nm (90.6%). ESI-MS m/z: 435.2/437.2 [M+H]$^+$.

Example 123

1-(4-aminobenzyl)-3-(2-(2-(5-chloro-2-methoxyphenyl) pyrrolidin-1-yl)-2-oxoethyl)urea (F683)(127)

The crude product was purified by flash chromatography (EDP/EtOAc) to afford the amide protected Rf=0.33 (EtOAc). $^1$H NMR (300 MHz, CDCl$_3$) δ 7.34-6.52 (m, 9H), 5.35-5.06 (m, 1H), 4.23 (m, 2H), 4.14-4.08 (m, 1H), 3.80 et 3.68 (2s, 3H), 3.77-3.10 (m, 3H), 2.27-2.05 (m, 1H), 1.98-1.53 (m, 3H), 1.48 (s, 9H). The amide was deprotected and precipitated in ether to afford the amine (TFA salt; 62 mg; two step global yield=38%) as a yellow solid Rf=0.4 (EtOAc). HPLC method A tr=10.64 nm (98.6%). ESI-MS m/z: 417.2/419.2 [M+H]$^+$.

Example 124

1-(4-aminobenzyl)-3-(2-(2-(2-(methylthio)phenyl) pyrrolidin-1-yl)-2-oxoethyl)urea (F684)(128)

The crude product was purified by flash chromatography (EDP/EtOAc then EtOAc/MeOH) to afford the amide protected Rf=0.38 (EtOAc). $^1$H NMR (300 MHz, CDCl$_3$): δ 7.33-6.97 (m, 8H), 6.88-6.76 (m, 1H), 6.68-6.54 (m, 1H), 5.58-5.06 (m, 1H), 4.29-4.16 (m, 2H), 3.84-3.14 (m, 4H), 2.52-2.35 (m, 3H), 2.34-2.09 (m, 1H), 2-1.63 (m, 3H), 1.48 (m, 9H). The amide was deprotected and precipitated in ether to afford the amine (TFA salt; 77.3 mg; two step global yield=49%) as a yellow solid Rf=0.32 (CH$_2$Cl$_2$/MeOH 95/5). HPLC method A tr=10.25 nm (97.8%). ESI-MS m/z: 399.2 [M+H]$^+$.

Example 125

1-(4-aminobenzyl)-3-(2-(2-(biphenyl)piperidin-1-yl)-2-oxoethyl)urea (F685)(129)

The crude product was purified by flash chromatography (EDP/EtOAc) to afford the amide protected Rf=0.54 (EtOAc). $^1$H NMR (200 MHz, CDCl$_3$) δ 7.51-7.02 (m, 13H), 6.52 (s, 1H), 5.70 (broad s, 1H), 5.20 (broad s, 1H), 4.26 (d, J=5.6 Hz, 2H), 4.00-2.91 (m, 4H), 1.96-1.37 (m, 7H), 1.50 (s, 9H). The amide was deprotected and precipitated in ether to afford the amine (TFA salt; 32 mg; two step global yield=19%) as a yellow solid Rf=0.32 (EtOAc). HPLC method A tr=11.48 nm (83.1%). ESI-MS m/z: 443.3 [M+H]$^+$.

Example 126

1-(4-aminobenzyl)-3-(2-(2-benzhydrylpiperidin-1-yl)-2-oxoethyl)urea (F686)(130)

The crude product was purified by flash chromatography (EDP/EtOAc) to afford the amide protected Rf=0.51 (EtOAc). The amide was deprotected and precipitated in ether to afford the amine (TFA salt; 10.6 mg; two step global yield=6%) as a yellow solid Rf=0.4 (EtOAc). $^1$H NMR (300 MHz, CDCl$_3$): δ 7.45-7.04 (m, 14H), 6.69 (broad s, 1H), 5.75-5.65 (m, 1H), 5.56-5.46 (m, 1H), 5.32 (t, J=5.7 Hz, 1H), 4.29 (d, J=5.7 Hz, 2H), 4.07-3.95 (m, 1H), 3.58-3.46 (m, 1H), 3.44-2.98 (m, 2H), 2.00-1.30 (m, 6H), 1.51 (s, 9H). HPLC method A tr=11.25 nm (91.9%). ESI-MS m/z: 457.3 [M+H]$^+$.

Example 127

1-(4-aminobenzyl)-3-(2-(2-(2-methoxy-3-methylphenyl) piperidin-1-yl)-2-oxoethyl)urea (F691) (131)

The crude product was purified by flash chromatography (EDP/EtOAc) to afford the amide protected Rf=0.68 (EtOAc). $^1$H NMR (300 MHz, CDCl$_3$): δ 7.25 (d, J=8.4 Hz, 2H), 7.14 (d, J=8.4 Hz, 2H), 7.11-6.82 (m, 3H), 6.53 (broad s, 1H), 5.90 (broad s, 1H), 5.55-5.00 (m, 1H), 4.50-3.95 (m, 4H), 3.90-2.70 (m, 5H), 2.27 (s, 3H), 2.15-1.35 (m, 6H), 1.50 (s, 9H). The amide was deprotected and purified on reverse phase (H$_2$O/MeCN) to afford the amine (8 mg; two step global yield=6%) Rf=0.4 (EtOAc). HPLC method A tr=9.89 nm (70.3%). ESI-MS m/z: 411.3 [M+H]$^+$.

Example 128

1-(4-aminobenzyl)-3-(2-(2-(2-methoxyphenyl)piperidin-1-yl)-2-oxoethyl)urea (F693)(132)

The crude product was purified by flash chromatography (EDP/EtOAc) to afford the amide protected Rf=0.59 (EtOAc). $^1$H NMR (300 MHz, CDCl$_3$): δ 7.24 (d, J=8.4 Hz, 2H), 7.15 (d, J=8.4 Hz, 2H), 7.05-6.97 (m, 1H), 6.92-6.78 (m, 2H), 6.51 (s, 1H), 6.10-5.80 (m, 1H), 5.75-5.35 (m, 1H), 5.55-5.10 (m, 1H), 4.40-4.20 (m, 4H), 3.81 (s, 3H), 3.78-3.55 (m, 2H), 2.25-1.35 (m, 6H), 1.50 (s, 9H). The amide was deprotected and purified on reverse phase (H$_2$O/MeCN) to afford the amine (8 mg; two step global yield=7%) Rf=0.36 (EtOAc). HPLC method A tr=9.56 nm (89.1%). ESI-MS m/z: 397.2 [M+H]$^+$.

Example 129

1-(4-aminobenzyl)-3-(2-oxo-2-(piperazin-1-yl)-2-oxoethyl) urea (F694)(133)

The crude product was purified by flash chromatography (EDP/EtOAc) to afford the amide protected (18 mg, 15%) as a colourless oil Rf=0.5 (EtOAc). $^1$H NMR (300 MHz, CDCl$_3$): δ 7.29 (d, J=8.5 Hz, 2H), 7.21 (d, J=8.5 Hz, 2H), 6.53 (s, 1H), 5.50 (s, 1H), 5.18 (s, 1H), 4.36-4.20 (m, 4H), 4.19-3.71 (m, 2H), 3.05-2.55 (m, 2H), 1.73-1.53 (m, 4H), 1.52-1.44 (m, 18H). The amide was deprotected and purified on reverse phase (H$_2$O/MeCN) to afford the amine (6 mg; two step global yield=61%); Rf=0.49 (MeOH). HPLC method A tr=4.46 nm (100%). ESI-MS m/z: 292.2 [M+H]$^+$.

Example 130

1-(4-aminobenzyl)-3-(2-(indolin-1-yl)-2-oxoethyl) urea (F695)(134)

The crude product was purified by flash chromatography (EDP/EtOAc) to afford the amide protected Rf=0.3 (EDP/EtOAc 30/70). $^1$H NMR (200 MHz, CDCl$_3$): δ 8.08 (d, J=7.3 Hz, 1H), 7.35-6.93 (m, 7H), 6.55 (s, 1H), 5.94 (t, J=4.5 Hz, 1H), 5.49 (t, J=5.8 Hz, 1H), 4.28 (d, J=5.7 Hz, 2H), 4.12 (d, J=4.6 Hz, 2H), 3.97 (t, J=8.4 Hz, 2H), 3.17 (t, J=8.3 Hz, 2H), 1.50 (s, 9H). The amide was deprotected and precipitated in ether to afford the amine (TFA salt; 10.6 mg; two step global yield=8%) as a yellow solid Rf=0.33 (EtOAc). $^1$H NMR (300 MHz, DMSO): δ 8.10 (d, J=7.7 Hz, 1H), 7.29 (d, J=8.3 Hz, 2H), 7.21 (1, J=7.6 Hz, 1H), 7.10 (d, J=8.3 Hz, 2H), 7.04 (t, J=7.5 Hz, 1H), 6.80 (s, 1H), 6.30 (s, 1H), 4.23 (d, J=5.2 Hz, 2H), 4.11 (t, J=8.5 Hz, 2H), 4.04 (broad s, 2H), 3.20 (t, J=8.3 Hz, 2H). HPLC method A tr=7.63 nm (95.5%). ESI-MS m/z: 325.2 [M+H]$^+$.

Example 131

1-(4-aminobenzyl)-3-(2-(2-(1-hydroxynaphthalen-2-yl) piperazin-1-yl)-2-oxoethyl)urea (F696)(135)

The crude product was purified by flash chromatography (EDP/EtOAc) to afford the amide protected (18 mg, 15%) as a colourless oil Rf=0.53 (EtOAc). The amide was deprotected and purified on reverse phase (H$_2$O/MeCN) to afford the amine (6 mg; 61%) Rf=0.48 (EtOAc). HPLC method A tr=10.28 nm (86.2%). ESI-MS m/z: 433.2.2 [M+H]$^+$.

Example 132

1-(4-aminobenzyl)-3-(2-oxo-2-(pyrazolidin-1-yl) ethyl)urea (F697)(136)

The crude product was purified by flash chromatography (EDP/EtOAc) to afford the amide protected (80 mg, 54%) as a colourless oil Rf=0.26 (EtOAc). The amide was deprotected and purified on reverse phase (H$_2$O/MeCN) to afford the amine (12 mg; two step global yield=26%) Rf=0.38 (MeOH). $^1$H NMR (300 MHz, DMSO): δ 6.93 (d, J=8.3 Hz, 2H), 6.53 (d, J=8.4 Hz, 2H), 6.50 (t, J=5.7 Hz, 1H), 5.95 (t, J=5.1 Hz, 1H), 5.12 (t, J=8.6 Hz, 1H), 5.00 (broad s, 2H), 4.03 (d, J=5.7 Hz, 2H), 3.98 (d, J=5.1 Hz, 2H), 3.45-3.29 (m, 2H), 2.86 (q, J=6.6 Hz, 2H), 2.05-1.84 (qn, J=6.6 Hz, 2H). ESI-MS m/z: 278.1 [M+H]$^+$.

Example 133

(R)-1-(4-aminobenzyl)-3-(2-(2-(azidomethyl)pyrrolidin-1-yl)-2-oxoethyl)urea (F703)(137)

(R)-2-(Azidomethyl)-1-Boc-pyrrolidine (70 mg, 0.3 mmol) was dissolved in 2 ml of DCM and 2 ml of TFA was added, then the reaction mixture was let 1 h at room temperature to afford the amine as a TFA salt (m$_{theo}$=73 mg). The solvent was evaporated and the next step was did as the description. The crude product was purified by flash chromatography (CH$_2$Cl$_2$/MeOH) to afford the amide protected (100 mg, 75%) Rf=0.54 (CH$_2$Cl$_2$/MeOH 90/10). $^1$H NMR (200 MHz, CDCl$_3$): δ 7.30 (d, J=8.6 Hz, 2H), 7.20 (d, J=8.6 Hz, 2H), 6.57 (broad s, 1H), 5.82 (t, J=4.1 Hz, 1H), 5.45 (t, J=5.4 Hz, 1H), 4.31 (d, J=5.6 Hz, 2H), 4.17-3.17 (m, 7H), 2.15-1.76 (m, 4H), 1.50 (s, 9H). The amide was deprotected and purified on reverse phase (H$_2$O/MeCN) to afford the amine (62 mg; 80%) Rf=0.48 (CH$_2$Cl$_2$/MeOH 90/10). HPLC method A tr=6.60 nm (99.6%). ESI-MS m/z: 332.3 [M+H]$^+$.

Example 134

1-(4-aminobenzyl)-3-(2-(2-(2-chlorobenzyl)pyrrolidin-1-yl)-2-oxoethyl)urea (F704)(138)

The crude product was purified by flash chromatography (EDP/EtOAc) to afford the amide protected (107 mg, 69%) as a white solid Rf=0.24 (EtOAc). $^1$H NMR (300 MHz, CDCl$_3$): δ 7.40-7.08 (m, 8H), 6.55 (s, 1H), 6.15-5.90 (m, 1H), 5.80-5.45 (m, 1H), 4.42-3.90 (m, 5H), 3.85-2.65 (m, 4H), 1.99-1.56 (m, 4H), 1.50 (s, 9H). The amide was deprotected and purified on reverse phase (H$_2$O/MeCN) to afford the amine (73 mg; 85%) as an orange solid Rf=0.8 (MeOH). HPLC method A tr=9.78 nm (96.0%). ESI-MS m/z: 401.2/403.2 [M+H]$^+$.

Example 135

1-(4-aminobenzyl)-3-(2-oxo-2-(2-(3-(trifluoromethyl)phenyl) pyrrolidin-1-yl)ethyl)urea (F705)(139)

The crude product was purified by flash chromatography (EDP/EtOAc) to afford the amide protected (120 mg, 75%) as a white solid Rf=0.18 (EtOAc). $^1$H NMR (300 MHz, CDCl$_3$): δ 7.62-7.02 (m, 8H), 6.57 (broad s, 1H), 5.98-5.82 (m, 1H), 5.66-5.46 (m, 1H), 5.12-4.92 (m, 1H), 4.33-3.99 (m, 4H), 3.83-3.14 (m, 2H), 2.43-1.64 (m, 4H), 1.49 (s, 9H). The amide was deprotected and purified on reverse phase (H$_2$O/MeCN) to afford the amine (64 mg; 66%) as an orange solid Rf=0.77 (MeOH). HPLC method A tr=9.77 nm (96.5%). ESI-MS m/z: 421.2 [M+H]$^+$.

Example 136

1-(4-aminobenzyl)-3-(2-(2-(3-fluorophenyl)pyrrolidin-1-yl)-2-oxoethyl)urea (F706)(140)

The crude product was purified by flash chromatography (EDP/EtOAc) to afford the amide protected (120 mg, 82%) as a white solid Rf=0.24 (EtOAc). $^1$H NMR (300 MHz, CDCl$_3$): δ 7.35-7.08 (m, 5H), 7.00-6.63 (m, 3H), 6.59 (broad s, 1H), 6.02 (broad s, 1H), 5.69 (broad s, 1H), 5.05-4.85 (m, 1H), 4.34-3.99 (m, 4H), 3.78-3.16 (m, 2H), 2.40-1.60 (m, 4H), 1.49 (s, 9H). The amide was deprotected and purified on reverse phase (H$_2$O/MeCN) to afford the amine (51 mg; 54%) as a white solid Rf=0.70 (MeOH). HPLC method A tr=8.39 nm (95.4%). ESI-MS m/z: 371.2 [M+H]$^+$.

Example 137

1-(4-aminobenzyl)-3-(2-(2-(2-((dimethylamino)methyl)phenyl)pyrrolidin-1-yl)-2-oxoethyl)urea (F707)(141)

The crude product was purified by flash chromatography (EtOAc/MeOH) to afford the amide protected (120 mg, 76%) as a white solid Rf=0.22 (EtOAc/MeOH 60/40). The amide was deprotected and purified on reverse phase (H$_2$O/MeCN) to afford the amine (64 mg; 67%) as an orange solid Rf=0.23 (MeOH). HPLC method A tr=6.17 nm (94.8%). ESI-MS m/z: 410.3 [M+H]$^+$.

Example 138

1-(4-aminobenzyl)-3-(2-(2-(benzyloxymethyl)pyrrolidin-1-yl)-2-oxoethyl)urea (F708)(142)

The crude product was purified by flash chromatography (EtOAc/MeOH) to afford the amide protected (60 mg, 40%) as a white solid Rf=0.35 (EtOAc/MeOH 90/10). $^1$H NMR (300 MHz, CDCl$_3$) δ 7.36-7.06 (m, 9H), 6.50 (broad s, 1H), 5.00 (broad s, 1H), 4.90 (broad s, 1H), 4.30-4.19 (m, 2H), 4.15-3.89 (m, 4H), 3.46-3.33 (m, 1H), 2.96-2.71 (m, 2H), 2.31-2.14 (m, 1H), 1.98-1.54 (m, 3H), 1.48 (s, 9H). The amide was deprotected and purified on reverse phase (H$_2$O/MeCN) to afford the amine (18 mg; 38%) as an orange oil Rf=0.61 (MeOH). HPLC method A tr=5.94 nm (85.1%). ESI-MS m/z: 397.2 [M+H]$^+$.

Example 139

1-(4-aminobenzyl)-3-(2-(2-(2-fluorobenzyl)pyrrolidin-1-yl)-2-oxoethyl)urea (F709)(143)

The crude product was purified by flash chromatography (EDP/EtOAc) to afford the amide protected (94 mg, 63%) as a colourless oil Rf=0.46 (EtOAc). $^1$H NMR (300 MHz, CDCl$_3$): δ 7.40-6.90 (m, 8H), 6.55 (broad s, 1H), 6.19-5.92 (m, 1H), 5.82-5.49 (m, 1H), 4.38-4.27 (m, 2H), 4.26-4.05 (m, 3H), 3.47-3.10 (m, 2H), 3.05-2.60 (m, 2H), 1.92-1.62 (m, 4H), 1.50 (s, 9H). The amide was deprotected and purified on reverse phase (H$_2$O/MeCN) to afford the amine (58 mg, 76%) as an orange solid Rf=0.23 (EtOAc). HPLC method A tr=9.17 nm (97.1%). ESI-MS m/z: 385.2 [M+H]$^+$.

Example 140

1-(4-aminobenzyl)-3-(2-(2-(3-chlorobenzyl)pyrrolidin-1-yl)-2-oxoethyl)urea (F710)(144)

The crude product was purified by flash chromatography (EDP/EtOAc) to afford the amide protected Rf=0.5 (EtOAc).

The amide was deprotected and purified on reverse phase (H₂O/MeCN) to afford the amine (36 mg; two step global yield=29%) as a white solid Rf=0.28 (EtOAc). ¹H NMR (300 MHz, CDCl₃): δ 7.32-6.96 (m, 8H), 6.59 (s, 2H), 6.12-5.72 (m, 1H), 5.60-5.16 (m, 1H), 4.26 (s, 2H), 4.15 (s, 1H), 4.01 (s, 2H), 3.53-3.28 (m, 2H), 3.14-2.95 (m, 1H), 2.66-2.38 (m, 1H), 1.99-1.57 (m, 4H). HPLC method A tr=10.04 nm (96.7%). ESI-MS m/z: 401.2/403.2 [M+H]⁺.

Example 141

(R)-1-(4-aminobenzyl)-3-(2-(2-(2-bromophenyl) pyrrolidin-1-yl)-2-oxoethyl)urea (F728)(145)

The crude product was purified by flash chromatography (EDP/EtOAc) to afford the amide protected (98 mg, 60%) as a white solid Rf=0.51 (EtOAc). The amide was deprotected and purified on reverse phase (H₂O/MeCN) to afford the amine (24 mg, 31%) Rf=0.05 (EtOAc). HPLC method A tr=9.31 nm (96.9%). ESI-MS m/z: 431.2/433.2 [M+H]⁺.

IV-3—Synthesis of Amides (146-147

General Procedure.

Amine derivative 21 or 25 (1 equivalent) was dissolved in 2 ml of DCM. Acetyl chloride (1 equivalent) was added and the reaction mixture is stirred for 20 h at room temperature. The reaction mixture is concentrated and 50 ml of AcOEt are added. The organic phase are washed with NaHCO₃ saturated, 10% citric acid and brine then dried over Na₂SO₄, filtered and concentrated. The crude product was purified by flash chromatography to afford the amide.

Example 142

Preparation of ethyl 2-(3-(2-acetamido-6-fluorobenzyl) ureido)acetate (F565)(146)

The crude product was purified by flash chromatography (AcOEt/EDP 5/5) to afford the amide 146 (37 mg; 67%) as a white solid Rf=0.59 (AcOEt/EDP 5/5). ¹H NMR (DMSO): δ 1.18 (t, 3H, J=7.1 Hz), 2.03 (s, 3H), 3.82 (d, 2H, J=6.0 Hz), 4.08 (q, 2H, J=7.1 Hz), 4.22 (d, 2H, J=6.4 Hz), 6.42 (t, 1H, J=6.0 Hz), 6.95 (t, 1H, J=9.0 Hz), 7.13 (t, 2H, J=6.4 Hz), 7.30 (q, 1H, J=8.2 Hz), 7.78 (d, 1H, J=8.2 Hz), 10.52 (s, 1H). HPLC method A tr=8.90 nm (94.7%). ESI-MS m/z: 312.3 [M+H]⁺.

Example 143

Preparation of 2-(3-(3-acetamidobenzyl)ureido)acetate (F566)(147)

The crude product was purified by flash chromatography (AcOEt/MeOH 95/5) to afford the amide 147 (17 mg; 17%) as a white solid Rf=0.16 (AcOEt/MeOH 95/5). ¹H NMR (DMSO): δ 1.18 (t, 3H, J=7.1 Hz), 2.03 (s, 3H), 3.82 (d, 2H, J=6.0 Hz), 4.08 (q, 2H, J=7.1 Hz), 4.22 (d, 2H, J=6.4 Hz), 6.42 (t, 1H, J=6.0 Hz), 6.95 (t, 1H, J=9.0 Hz), 7.13 (t, 2H, J=6.4 Hz), 7.30 (q, 1H, J=8.2 Hz), 7.78 (d, 1H, J=8.2 Hz), 10.52 (s, 1H). HPLC method A tr=7.38 nm (97.7%). ESI-MS m/z: 294.3 [M+H]⁺.

V—Synthesis of Urea 149

Urea 149 is prepared according to the following reaction scheme:

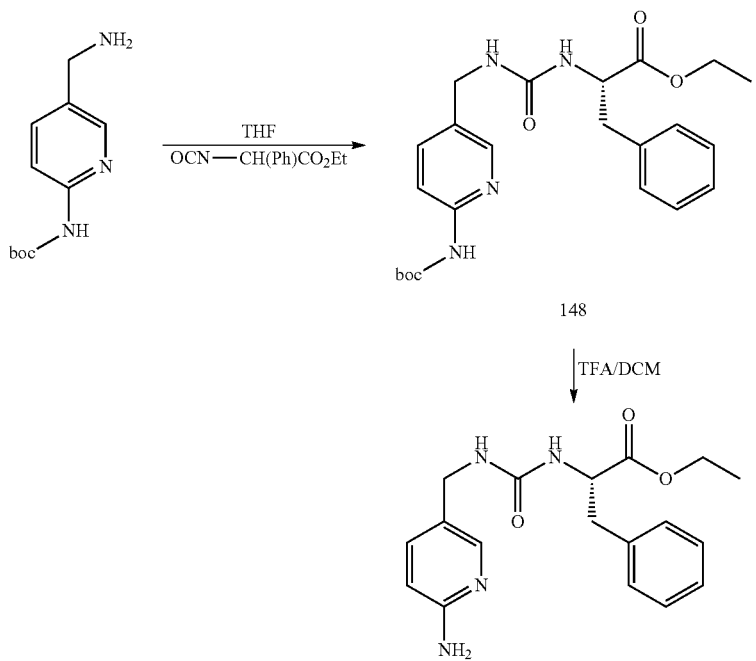

(S)-methyl 2-(3-((6-terbutyloxycarbonylaminopyridin-3-yl)methyl)ureido)-3-phenylpropanoate (148)

Methyl (S)-2-isocyanato-3-phenylpropionate (1 equivalent, 463 μl) was dissolved in THF (0.4 M), then the amine (1 equivalent, 474 mg) was added in one portion and the reaction mixture was let 2 h at room temperature. After the reaction was complete (TLC control), the reaction mixture was concentrated and purified by precipitation in hexane to afford the urea 148 (860 mg, 96%). $^1$H NMR (DMSO): δ 1.47 (s, 9H), 2.90 (dd, 1H, J=13.5, 5.5 Hz), 2.99 (dd, 1H, J=13.5, 5.5 Hz), 3.61 (s, 3H), 4.12 (s, 2H), 4.43 (dd, 1H, J=13.5, 5.5 Hz), 6.35 (d, 1H, J=7.8 Hz), 6.57 (t, 1H, J=5.9 Hz), 7.16 (d, 2H, J=7.0 Hz), 7.23 (m, 1H), 7.29 (m, 2H), 7.53 (d, 1H, J=8.1 Hz), 7.71 (d, 1H, J=8.9 Hz), 8.09 (s, 1H), 9.66 (s, 1H).

Example 144

Preparation of (S)-methyl 2-(3-((6-aminopyridin-3-yl)methyl)ureido)-3-phenylpropanoate (F598)(149)

The urea 148 (210 mg) was dissolved in 2 ml of DCM and 2 ml of TFA was added then the reaction mixture was let 1 h at room temperature. The reaction mixture was concentrated and purified by precipitation using AcOEt/Hexane to afford the urea deprotected 149 as yellow solid (204 mg, 89%). HPLC method B tr=17.99 nm (95.8%). ESI-MS m/z: 329.3 [M+H]$^+$.

VI—Synthesis of Sulfonylurea 156

VI.1. Synthesis of Amine 152

The amine 152 is prepared according to the following reaction scheme:

tert-butyl benzyloxycarbamate (150)

N-hydroxybenzyl-amine (1 equivalent, 1.62 g) was dissolved in 30 ml of THF. Boc$_2$O (1 equivalent, 2.87 g) was added and the reaction mixture is stirred for 20 h at room temperature. The reaction mixture is concentrated and 50 ml of AcOEt are added. The organic phase are washed with 10% citric acid and brine then dried over Na$_2$SO$_4$, filtered and concentrated to afford 150 as an oil (2.92 g, 99%). $^1$H NMR (CDCl$_3$): δ 1.42 (s, 9H), 4.73 (s, 2H), 7.37 (m, 5H), 10.03 (s, 1H).

tert-butyl benzyloxy(ethyl)carbamate (151)

150 (1.66 g, 1 équivalent) was dissolved in 20 ml of DMF and this solution was cool to 0° C., then NaH (1 équivalent, 180 mg) was added in one portion. The reaction mixture was let at 0° for 5 min, then ethyl iodide was added (1.2 equivalent, 1.40 g) and the reaction mixture was let at room temperature overnight. 100 ml of AcOEt was added to the reaction mixture. The organic phase are washed with 10% citric acid, saturated NaHCO$_3$ and brine then dried over Na$_2$SO$_4$, filtered and concentrated. The crude product was purified by flash chromatography (AcOEt/Hexane 1/9) to afford 151 as an oil (1.67 g, 90%). $^1$H NMR (CDCl$_3$): δ 1.31 (t, 3H, J=7.0 Hz), 1.66 (s, 9H), 3.61 (q, 2H, J=7.0 Hz), 4.99 (s, 2H), 7.50 (m, 3H), 7.57 (m, 2H).

O-benzyl-Methylhydroxylamine (152)

151 (616 mg) was dissolved in 4 ml of DCM and 4 ml of TFA was added then the reaction mixture was let 1 h at room temperature. The reaction mixture is concentrated and 50 ml of AcOEt are added. The organic phase are washed with saturated NaHCO$_3$ and brine then dried over Na$_2$SO$_4$, filtered and concentrated to afford 152 as an oil (324 mg, 88%). $^1$H NMR (DMSO): δ 0.99 (t, 3H, J=7.3 Hz), 2.82 (m, 2H), 4.61 (s, 2H), 6.50 (t, 1H, J=5.8 Hz), 7.32 (m, 5H).

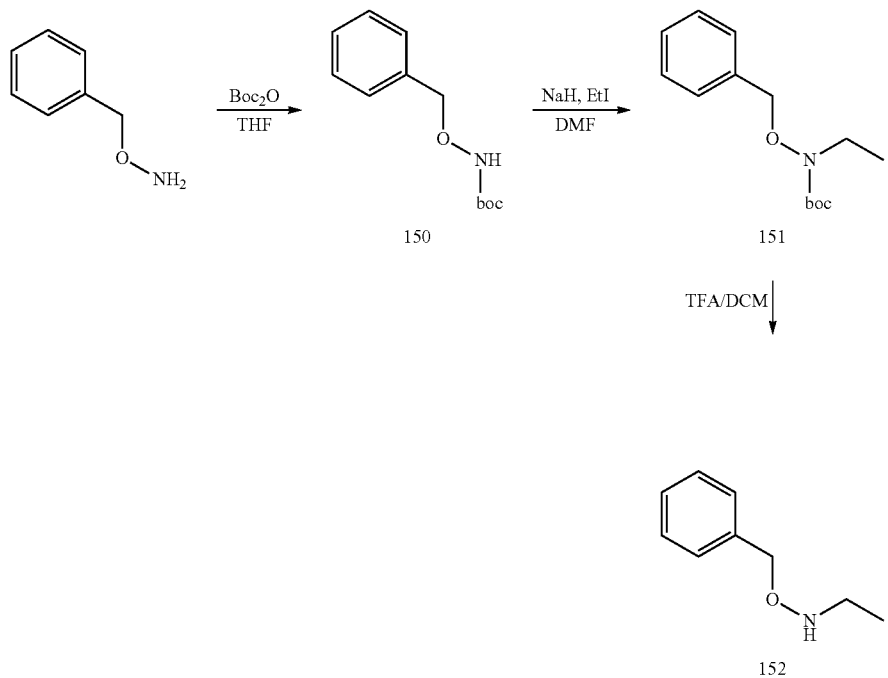

VI.2. Synthesis of Sulfonylurea 156

This sulfonylurea is prepared according to the following reaction scheme:

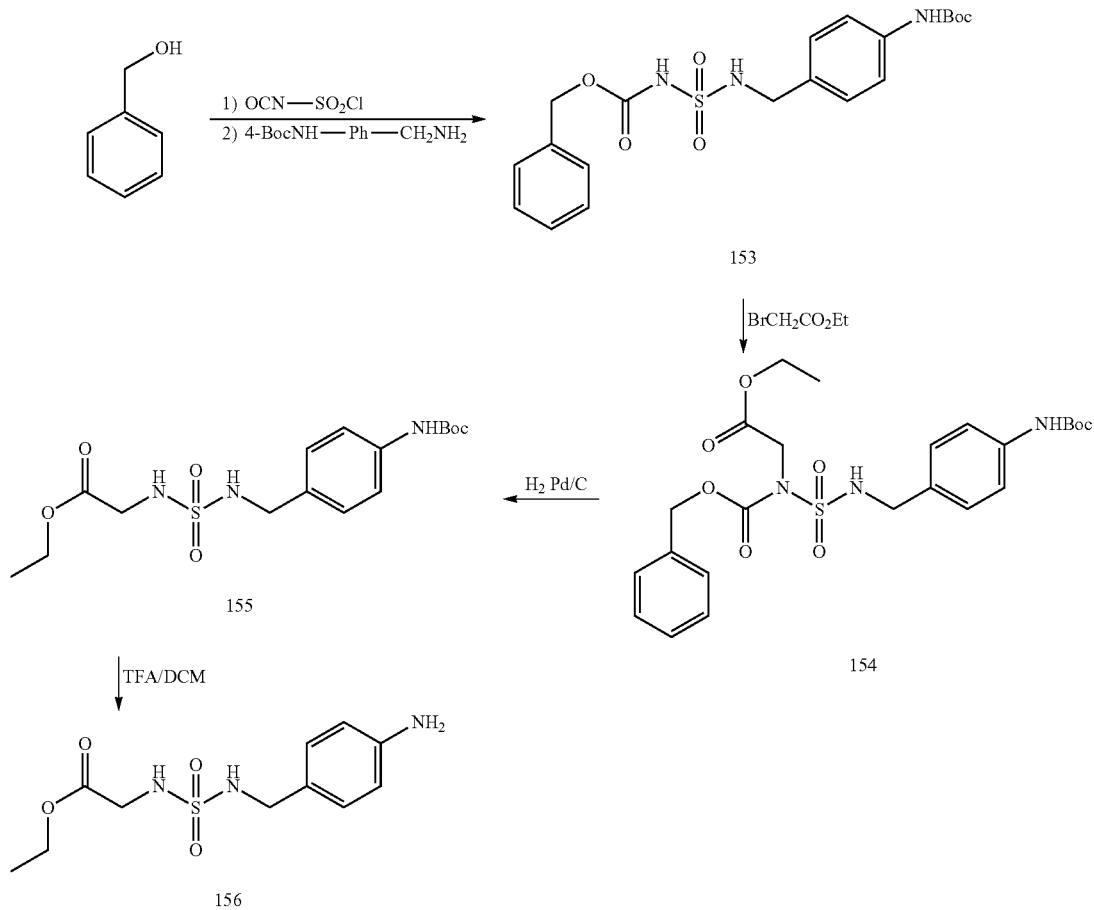

Benzyl-N-((4-tert-butoxycarbonylamino)benzyl)sulfamoylcarbamate (153)

Benzyl alcohol (259 µl, 1 equivalent was added slowly at 0° C. to the stirring chlorosulfonyl isocyanate (218 µl, 1 equivalent) solution in DCM (20 ml), and the stirring was continued for 30 min at 0° C. Triethylamine (2 ml) in DCM (10 ml) was added to the solution. The resulting mixture was then added dropwise to an ice-chilled suspension of 4-(tert-butoxycarbonylamino)benzylamine (0.56 g, 1 equivalent) in DCM (40 ml). The solution thus obtained was stirred for 2 h and evaporated under reduced pressure. The residue was dissolved in AcOEt (100 ml). The organic phase are washed with 10% citric acid and brine then dried over $Na_2SO_4$, filtered and concentrated. The crude product was recrystallized in DCM to afford 153 as white solid (720 mg, 66%). $^1$H NMR (DMSO): δ 1.48 (s, 9H), 4.03 (d, 2H, J=5.2 Hz), 5.03 (s, 2H), 7.17 (d, 2H, J=8.3 Hz), 7.37 (m, 7H), 8.25 (s, 1H), 9.33 (s, 1H), 11.21 (s, 1H).

Ethyl 2-(benzyloxycarbonyl)(N-(4-tert-butoxycarbonylamino)benzyl) sulfamoyl)amino)acetate (154)

153 (253 mg, 1 equivalent) was dissolved in 5 ml of DMF, then potassium carbonate (39 mg, 0.5 equivalent) and ethyl bromoacetate (1 equivalent, 62 µl) were added successively. The reaction mixture was let 2 days at room temperature. 50 ml of AcOEt was added to the reaction mixture. The organic phase are washed with 10% citric acid, saturated $NaHCO_3$ and brine then dried over $Na_2SO_4$, filtered and concentrated. The crude product was purified by flash chromatography (AcOEt/Hexane 5/5) to afford 154 as white solid (200 mg, 69%). %). $^1$H NMR ($CDCl_3$): δ 1.26 (t, 3H, J=7.0 Hz), 1.55 (s, 9H), 4.21 (q, 2H, J=7.0 Hz), 4.25 (s, 2H), 4.46 (s, 2H), 5.25 (s, 2H), 6.48 (s, 1H), 7.19 (m, 3H), 7.37 (m, 5H).

Ethyl 2-(N-(4-(tert-butoxycarbonylamino)benzyl) sulfamoylamino)acetate (155)

A solution of 154 (190 mg) in AcOEt (20 ml) was stirred for 1 h under hydrogen atmosphere in the presence of 10% Pd/C. The resulting mixture was filtered through celite and the filtrate was evaporated under reduced pressure to give 155 as white solid (162 mg, 96%). $^1$H NMR ($CDCl_3$): δ 1.31 (t, 3H, J=7.3 Hz), 1.54 (s, 9H), 3.82 (m, 2H), 4.22 (d, 2H, J=5.8 Hz), 4.24 (q, 2H, J=7.3 Hz), 4.53 (t, 1H, J=5.8 Hz), 4.82 (m, 1H), 6.51 (s, 1H), 7.25 (d, 2H, J=7.0 Hz), 7.37 (d, 2H, J=7.0 Hz).

Example 145

Preparation of ethyl 2-(N-(4-aminobenzyl)sulfamoyl-amino)acetate (F604)(156)

155 (96 mg) was dissolved in 2 ml of DCM and 2 ml of TFA was added then the reaction mixture was let 1 h at room temperature. The reaction mixture is concentrated and purified by precipitation using AcOEt/Hexane to afford the sulfonylurea deprotected 156 as yellow solid (92 mg, 88%). HPLC method B tr=12.01 nm (94.3%). ESI-MS m/z: 288.2 [M+H]$^+$.
VII—Synthesis of Ureas 162-163
The ureas 162 and 163 are prepared according to the following reaction scheme:
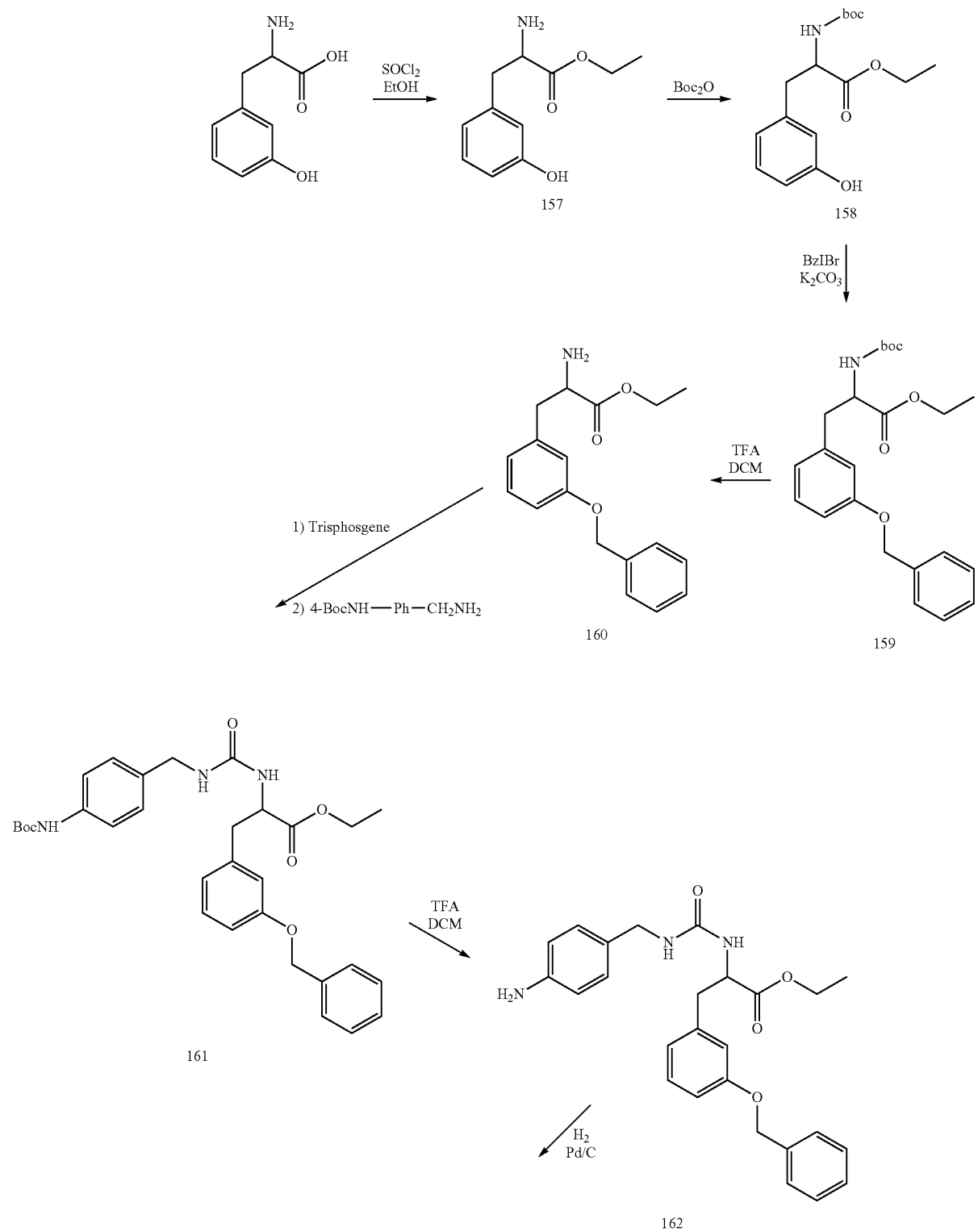

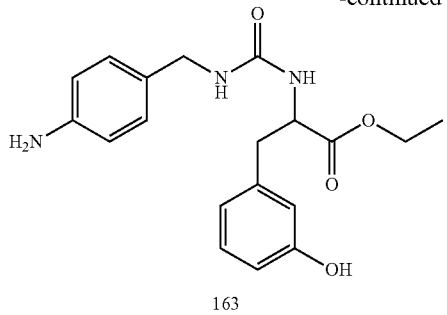

163

Ethyl 2-amino-3-(3-hydroxyphenyl)propanoate (157)

To 20 mL of EtOH at −5° C. was added, with stirring, 0.2 mL of SOCl₂ slowly. The clear colorless solution was cooled to −5° C. and 510 mg of meta-Tyrosine was added. After 5 min, the resulting solution was refluxed overnight. The solution was concentrated to afford 157 as HCl salt (690 mg, 99%).

Ethyl 2-(tert-butoxycarbonylamino)-3-(3-hydroxyphenyl)propanoate (158)

157 (1 equivalent, 2.81 mmol) was dissolved in 10 ml of DCM. Diisopropylethylamine (6 equivalent) and Boc₂O (1 equivalent, 2.87 g) were added successively and the reaction mixture is stirred for 2 h at room temperature. The reaction mixture is concentrated and 50 ml of AcOEt are added. The organic phase are washed with 10% citric acid and brine then dried over Na₂SO₄, filtered and concentrated. The crude product was purified by flash chromatography (AcOEt/Hexane 8/2) to afford 158 as white solid (770 mg, 89%).

Ethyl 3-(3-(benzyloxy)phenyl)-2-(tert-butoxycarbonylamino)propanoate (159)

158 (760 mg, 1 equivalent) was dissolved in 15 ml of acetone, then potassium carbonate (373 mg, 1.1 equivalent) and benzylbromide (1.1 équivalent, 323 µl) were added successively. The reaction mixture was let overnight at room temperature. The reaction mixture is concentrated and 50 ml of AcOEt are added. The organic phase are washed with 10% citric acid, saturated NaHCO₃ and brine then dried over Na₂SO₄, filtered and concentrated. The crude product was purified by flash chromatography (AcOEt/Hexane 2/8) to afford 159 as white solid (860 mg, 88%). ¹H NMR (CDCl₃): δ 1.38 (t, 3H, J=7.4 Hz), 1.69 (s, 9H), 3.22 (m, 2H), 4.31 (q, 2H, J=7.4 Hz), 4.71 (s, 2H), 5.13 (m, 1H), 5.20 (s, 2H), 6.90 (d, 1H, J=7.1 Hz), 6.94 (s, 1H), 7.01 (d, 1H, J=8.2 Hz), 7.36 (t, 1H, J=7.7 Hz), 7.49 (m, 1H), 7.56 (m, 4H).

Ethyl 2-amino-3-(3-(benzyloxy)phenyl)propanoate (160)

159 (850 mg) was dissolved in 4 ml of DCM and 4 ml of TFA was added then the reaction mixture was let 1 h at room temperature. The reaction mixture is concentrated and 50 ml of AcOEt are added. The organic phase are washed with saturated NaHCO₃ and brine then dried over Na₂SO₄, filtered and concentrated to afford 160 as a white solid (540 mg, 86%), ¹H NMR (DMSO): δ 1.26 (t, 3H, J=6.5 Hz), 1.89 (s, 2H), 2.89 (dd, 1H, J=6.5 Hz), 5.21 (s, 2H), 6.90 (d, 1H, J=7.6 Hz), 6.99 (s, 2H), 7.32 (t, 1H, J=7.8 Hz), 7.47 (m, 1H), 7.53 (t, 2H, J=7.0 Hz), 7.58 (d, 2H, J=7.6 Hz).

Ethyl 3-(3-(benzyloxy)phenyl)-2-(3-(4-(tert-butoxycarbonylamino)benzyl) ureido)propanoate (161)

160 (530 mg, 1.76 mmol) was dissolved in AcOEt (30 mL) and trisphosgene (0.33 equivalent, 173 mg) was added while stirring at −10° C. The mixture was allowed to warm to room temperature, then refluxed for 1 h. 4-(tert-butoxycarbonylamino)benzylamine (391 mg, 1 equivalent) and triethylamine (2 equivalent) were added successively and the resulting solution was stirring at room temperature overnight. 100 ml of AcOEt are added. The organic phase are washed with 10% citric acid, saturated NaHCO₃ and brine then dried over Na₂SO₄, filtered and concentrated. The crude product was purified by flash chromatography (AcOEt/Hexane 5/5) to afford 161 as white solid (960 mg, 99%). ¹H NMR (DMSO): δ 1.28 (t, 3H, J=6.5 Hz), 1.61 (s, 9H), 3.01 (dd, 1H, J=13.8, 8.3 Hz), 3.09 (dd, 1H, J=13.8, 5.0 Hz), 4.19 (q, 2H, J=6.5 Hz), 4.24 (d, 2H, J=5.1 Hz), 4.57 (s, 1H), 5.20 (s, 2H), 6.38 (d, 1H, J=7.8 Hz), 6.61 (t, 1H, J=5.1 Hz), 6.90 (d, 1H, J=7.1 Hz), 7.02 (d, 1H, J=8.7 Hz), 7.21 (d, 2H, J=8.1 Hz), 7.33 (t, 1H, J=7.8 Hz), 7.50 (m, 5H), 7.57 (d, 2H, J=8.1 Hz), 9.35 (s, 1H).

Example 146

Preparation of ethyl 2-(3-(4-aminobenzyl)ureido)-3-(3-(benzyloxy)phenyl)propanoate (F611)(162)

161 (469 mg) was dissolved in 4 ml of DCM and 4 ml of TEA was added then the reaction mixture was let 1 h at room temperature. The reaction mixture is concentrated and 50 ml of AcOEt are added. The organic phase are washed with saturated NaHCO₃ and brine then dried over Na₂SO₄, filtered and concentrated to afford 162 as a white solid (350 mg, 91%). ¹H NMR (DMSO): δ 1.28 (t, 3H, J=6.5 Hz), 3.04 (m, 2H), 4.13 (d, 2H, J=4.1 Hz), 4.19 (q, 2H, J=6.5 Hz), 4.56 (m, 1H), 5.02 (s, 2H), 5.21 (s, 2H), 6.29 (d, 1H, J=8.3 Hz), 6.45 (m, 1H), 6.62 (d, 2H, J=7.3 Hz), 6.89 (d, 1H, J=7.3 Hz), 7.00 (m, 3H), 7.33 (t, 1H, J=7.3 Hz), 7.53 (t, 1H, J=7.3 Hz), 7.57 (d, 1H, J=6.7 Hz). HPLC method B tr=21.65 mn (97.4%). ESI-MS m/z: 448.3 [M+H]⁺.

Example 147

Preparation of ethyl 2-(3-(4-aminobenzyl)ureido)-3-(3-hydroxyphenyl)propanoate (F612)(163)

A solution of 162 (205 mg) in MeOH (20 ml) was stirred for 1 h under hydrogen atmosphere in the presence of 10% Pd/C. The resulting mixture was filtered through celite and the filtrate was evaporated under reduced pressure to give 163 as white solid (160 mg, 98%). ¹H NMR (DMSO): δ 1.28 (t, 3H, J=6.4 Hz), 2.97 (m, 2H), 4.12 (m, 2H), 4.19 (q, 2H, J=6.4

Hz), 4.51 (m, 1H), 5.02 (s, 2H), 6.24 (d, 1H, J=8.3 Hz), 6.46 (m, 1H), 6.63 (d, 2H, J=7.5 Hz), 6.71 (s, 2H), 6.75 (d, 1H, J=7.5 Hz), 7.00 (d, 2H, J=7.5 Hz), 7.19 (t, 1H, J=7.5 Hz), 9.42 (s, 1H). HPLC method B tr=17.75 nm (96.3%). ESI-MS m/z: 358.2 [M+H]$^+$.
VIII—Synthesis of Urea 169
The urea 169 is prepared according to the following reaction scheme:
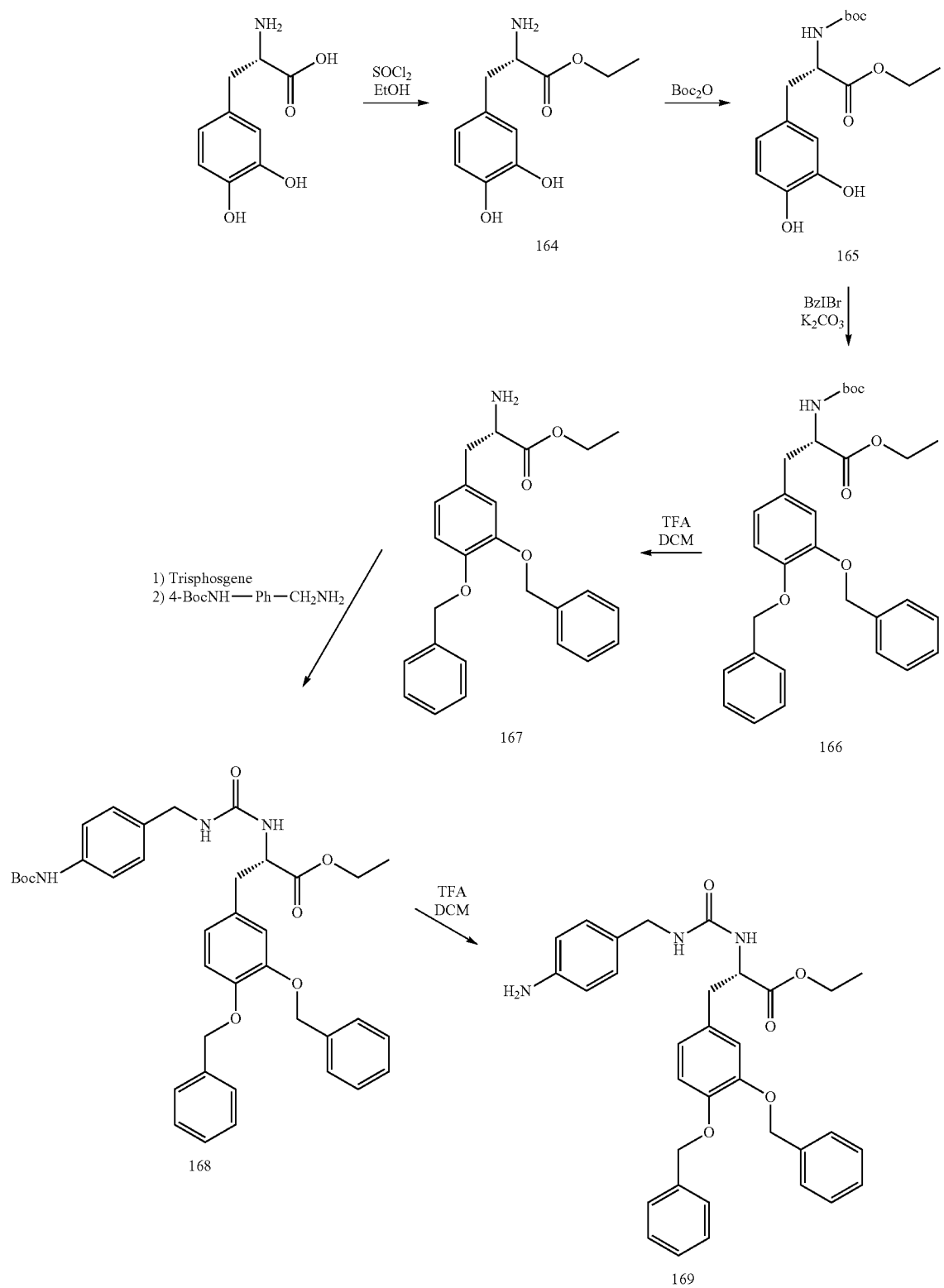

Ethyl 2-amino-3-(3,4-dihydroxyphenyl)propanoate (164)

To 30 mL of EtOH at −5° C. was added, with stirring, 0.37 mL of SOCl₂ slowly. The clear colorless solution was cooled to −5° C. and 1 g of L-Dopa was added. After 5 min, the resulting solution was refluxed overnight. The solution was concentrated to afford 164 as HCl salt (1.30 g, 99%). ¹H NMR (DMSO): δ 1.29 (t, 3H, J=7.4 Hz), 3.03 (m, 1H), 3.15 (m, 1H), 4.21 (m, 1H), 4.27 (m, 2H), 4.35 (sl, 3H), 6.60 (d, 1H, J=7.9 Hz), 6.74 (s, 1H), 6.82 (d, 1H, J=7.9 Hz), 8.63 (s, 2H).

Ethyl 2-(tert-butoxycarbonylamino)-3-(3,4-dihydroxyphenyl)propanoate (165)

164 (1 equivalent, 5.07 mmol) was dissolved in 20 ml of DCM. Diisopropylethylamine (6 equivalent) and Boc₂O (1 equivalent, 1.25 g) were added successively and the reaction mixture is stirred for 2 h at room temperature. The reaction mixture is concentrated and 50 ml of AcOEt are added. The organic phase are washed with 10% citric acid and brine then dried over Na₂SO₄, filtered and concentrated. The crude product was purified by flash chromatography (AcOEt/Hexane 5/5) to afford 165 as white solid (1.26 g, 76%). ¹H NMR (DMSO): δ 1.27 (t, 3H, J=7.2 Hz), 1.49 (s, 9H), 2.82 (m, 1H), 2.90 (m, 1H), 4.18 (m, 3H), 6.59 (d, 1H, J=7.4 Hz), 6.74 (m, 2H), 7.26 (s, 1H), 8.88 (s, 2H).

Ethyl 3-(3,4-(dibenzyloxy)phenyl)-2-(tert-butoxycarbonylamino)propanoate (166)

165 (1.25 g, 1 equivalent) was dissolved in 20 ml of acetone, then potassium carbonate (1.27 g, 2.2 equivalent) and benzylbromide (2.2 equivalent, 920 µl) were added successively. The reaction mixture was let overnight at room temperature. The reaction mixture is concentrated and 50 ml of AcOEt are added. The organic phase are washed with 10% citric acid, saturated NaHCO₃ and brine then dried over Na₂SO₄, filtered and concentrated. The crude product was purified by flash chromatography (AcOEt/Hexane 2/8) to afford 166 as white solid (1.82 g, 94%). ¹H NMR (DMSO): δ 1.25 (t, 3H, J=7.2 Hz), 1.48 (s, 9H), 2.91 (m, 1H), 3.02 (m, 1H), 4.18 (q, 2H, J=7.2 Hz), 4.25 (m, 1H), 5.22 (s, 4H), 6.89 (d, 1H, 7.9 Hz), 7.09 (d, 1H, J=8.7 Hz), 7.15 (s, 1H), 7.36 (d, 1H, J=8.2 Hz), 7.53 (m, 10H).

Ethyl 2-amino-3-(3,4-(dibenzyloxy)phenyl)propanoate (167)

166 (1.80 g) was dissolved in 4 ml of DCM and 4 ml of TFA was added then the reaction mixture was let 1 h at room temperature. The reaction mixture is concentrated and 50 ml of AcOEt are added. The organic phase are washed with saturated NaHCO₃ and brine then dried over Na₂SO₄, filtered and concentrated to afford 167 as a white solid (1.33 g, 92%). ¹H NMR (DMSO): δ 1.25 (t, 3H, J=7.1 Hz), 2.65 (s, 2H), 2.84 (dd, 1H, J=13.2, 6.5 Hz), 2.92 (dd, 1H, J=13.2, 6.5 Hz), 3.69 (t, 1H, J=6.5 Hz), 4.15 (q, 2H, J=7.1 Hz), 5.24 (s, 4H), 6.83 (d, 1H, J=8.1 Hz), 7.06 (s, 1H), 7.09 (d, 1H, J=81 Hz), 7.46 (t, 1H, J=7.0 Hz), 7.51 (m, 4H), 7.58 (m, 5H).

Ethyl 3-(3,4-(dibenzyloxy)phenyl)-2-(3-(4-(tert-butoxycarbonylamino)benzyl)ureido)propanoate (168)

167 (1.32 g, 3.26 mmol) was dissolved in AcOEt (60 mL) and trisphosgene (0.33 equivalent, 320 mg) was added while stirring at −10° C. The mixture was allowed to warm to room temperature, then refluxed for 1 h. 4-(tert-butoxycarbonylamino)benzylamine (725 mg, 1 equivalent) and triethylamine (2 equivalent) were added successively and the resulting solution was stirring at room temperature overnight. 100 ml of AcOEt are added. The organic phase are washed with 10% citric acid, saturated NaHCO₃ and brine then dried over Na₂SO₄, filtered and concentrated. The crude product was purified by flash chromatography (AcOEt/Hexane 5/5) to afford 168 as white solid (1.35 g, 63%). ¹H NMR (DMSO): δ 1.27 (t, 3H, J=6.8 Hz), 1.60 (s, 9H), 2.99 (m, 2H), 4.19 (q, 2H, J=6.8 Hz), 4.24 (d, 2H, J=5.7 Hz), 4.52 (dd, 1H, J=13.7, 6.0 Hz), 5.22 (m, 4H), 6.36 (d, 1H, J=8.1 Hz), 6.62 (t, 1H, J=5.7 Hz), 6.81 (d, 1H, J=7.6 Hz), 7.05 (s, 1H), 7.09 (d, 1H, J=7.6 Hz), 7.23 (d, 2H, J=7.8 Hz), 7.46 (t, 1H, J=6.9 Hz), 7.51 (m, 5H), 7.57 (m, 6H), 9.39 (s, 1H).

Example 148

Preparation of ethyl 2-(3-(4-aminobenzyl)ureido)-3-(3,4-(dibenzyloxy)phenyl)propanoate (169)

168 (600 mg) was dissolved in 4 ml of DCM and 4 ml of TFA was added then the reaction mixture was let 1 h at room temperature. The reaction mixture is concentrated and 50 ml of AcOEt are added. The organic phase are washed with saturated NaHCO₃ and brine then dried over Na₂SO₄, filtered and concentrated to afford 169 as a white solid (480 mg, 94%). ¹H NMR (DMSO): δ 1.27 (t, 3H, J=7.4 Hz), 2.95 (m, 2H), 4.15 (m, 4H), 4.51 (m, 1H), 5.09 (s, 2H), 5.22 (s, 4H), 6.22 (d, 1H, J=7.1 Hz), 6.27 (d, 1H, J=7.6 Hz), 6.37 (m, 1H), 6.47 (m, 1H), 6.63 (m, 2H), 6.81 (d, 1H, J=7.4 Hz), 7.00 (m, 2H), 7.05 (s, 1H), 7.09 (d, 1H, J=8.1 Hz), 7.24 (t, 1H, J=8.1 Hz), 7.35 (m, 2H), 7.52 (m, 4H), 7.64 (t, 1H, J=8.0 Hz).

IX—Synthesis of Urea 176

This compound is prepared according to the following reaction scheme:

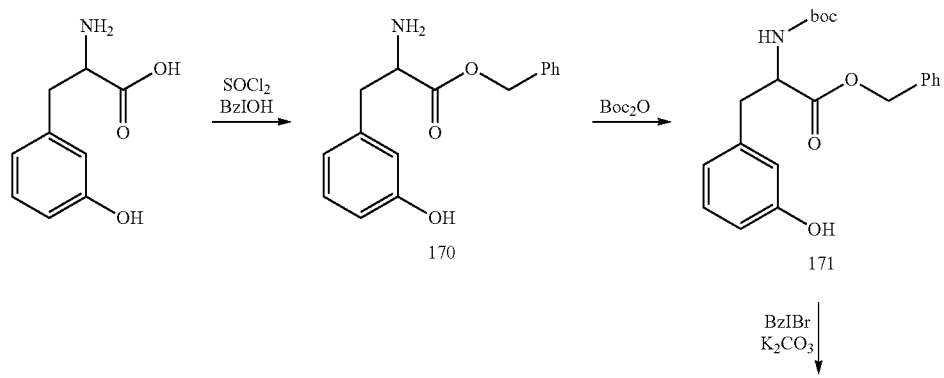

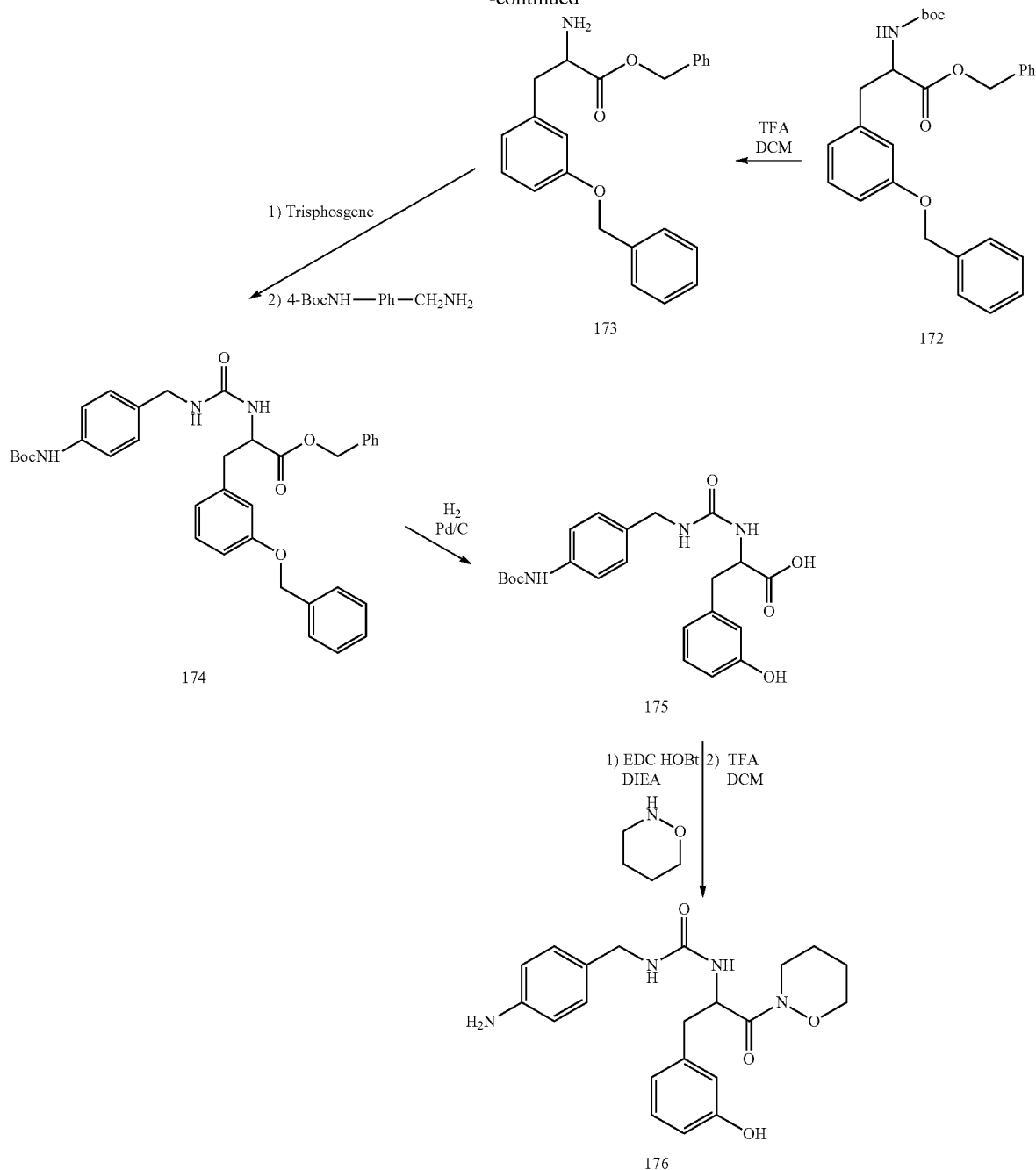

Benzyl 2-amino-3-(3-hydroxyphenyl)propanoate (170)

To 10 mL of benzyl alcohol at −5° C. was added, with stirring, 0.2 mL of SOCl₂ slowly. The clear colorless solution was cooled to −5° C. and 490 mg of meta-Tyrosine was added. After 5 min, the resulting solution was heated to 120° C. overnight. 100 ml of AcOEt are added. The organic phase are washed with saturated NaHCO₃ and brine then dried over Na₃SO₄, filtered and concentrated to afford 170 as a white solid (430 mg, 59%). ¹H NMR (DMSO): δ 1.90 (s, 3H), 2.87 (dd, 1H, J=13.1, 6.5 Hz), 2.94 (dd, 1H, J=13.1, 6.5 Hz), 3.73 (t, 1H, J=6.5 Hz), 5.19 (s, 2H), 6.70 (d, 1H, J=7.7 Hz), 6.75 (s, 1H), 7.17 (t, 1H, J=7.7 Hz), 7.41 (d, 1H, J=7.0 Hz), 7.48 (m, 5H), 9.37 (s, 1H).

Benzyl 2-(tert-butoxycarbonylamino)-3-(3-hydroxyphenyl)propanoate (171)

170 (1 equivalent, 425 mg) was dissolved in 10 ml of DCM. Diisopropylethylamine (2 equivalent) and Boc₂O (1 equivalent) were added successively and the reaction mixture is stirred for 2 h at room temperature. The reaction mixture is concentrated and 50 ml of AcOEt are added. The organic phase are washed with 10% citric acid and brine then dried over Na$_2$SO$_4$, filtered and concentrated. The crude product was purified by flash chromatography (AcOEt/Hexane 5/5) to afford 171 as white solid (580 mg, 99%). $^1$H NMR (CDCl$_3$): 1.67 (s, 9H), 3.19 (m, 2H), 4.77 (m, 1H), 4.87 (s, 1H), 5.12 (s, 1H), 5.26 (d, 1H, J=12.2 Hz), 5.38 (d, 1H, J=12.2 Hz), 6.54 (s, 1H), 6.77 (d, 1H, J=7.0 Hz), 6.84 (d, 1H, J=7.0 Hz), 7.26 (t, 1H, J=7.3 Hz), 7.51 (m, 5H).

Benzyl 3-(3-(benzyloxy)phenyl)-2-(tert-butoxycarbonylamino)propanoate (172)

171 (580 mg, 1 equivalent) was dissolved in 15 ml of acetone, then potassium carbonate (238 mg, 1.1 equivalent) and benzylbromide (1.1 équivalent, 206 µl) were added successively. The reaction mixture was let overnight at room temperature. The reaction mixture is concentrated and 50 ml of AcOEt are added. The organic phase are washed with 10% citric acid, saturated NaHCO$_3$ and brine then dried over Na$_2$SO$_4$, filtered and concentrated. The crude product was purified by flash chromatography (AcOEt/Hexane 2/8) to afford 172 as white solid (513 mg, 71%). $^1$H NMR (CDCl$_3$): δ 1.46 (s, 9H), 2.64 (s, 1H), 3.05 (m, 1H), 3.18 (m, 1H), 4.39 (m, 1H), 5.20 (s, 1H), 5.25 (s, 4H), 6.95 (d, 1H, J=7.1 Hz), 7.00 (d, 1H, J=7.9 Hz), 7.07 (s, 1H), 7.20 (m, 2H), 7.27 (d, 2H, J=7.4 Hz), 7.32 (t, 1H, J=7.9 Hz), 7.50 (m, 6H).

Benzyl 2-amino-3-(3-(benzyloxy)phenyl)propanoate (173)

172 (610 mg) was dissolved in 4 ml of DCM and 4 ml of TFA was added then the reaction mixture was let 1 h at room temperature. The reaction mixture is concentrated and 50 ml of AcOEt are added. The organic phase are washed with saturated NaHCO$_3$ and brine then dried over Na$_2$SO$_4$, filtered and concentrated. The crude product was purified by flash chromatography (AcOEt/Hexane 2/8) to afford 173 as white solid (480 mg, 85%). $^1$H NMR (DMSO): δ 2.90 (m, 2H), 3.73 (t, 1H, J=7.4 Hz), 5.19 (s, 4H), 6.70 (d, 1H, J=7.3 Hz), 6.74 (m, 2H), 6.97 (m, 1H), 7.17 (t, 1H, J=7.9 Hz), 7.41 (d, 2H, J=6.5 Hz), 7.48 (m, 2H), 9.37 (s, 2H).

Benzyl 3-(3-(benzyloxy)phenyl)-2-(3-(4-(tert-butoxycarbonylamino)benzyl) ureido)propanoate (174)

173 (470 mg, 1.3 mmol) was dissolved in AcOEt (30 mL) and trisphosgene (0.33 equivalent, 128 mg) was added while stirring at −10° C. The mixture was allowed to warm to room temperature, then refluxed for 1 h. 4-(tert-butoxycarbonylamino)benzylamine (289 mg, 1 equivalent) and triethylamine (2 equivalent) were added successively and the resulting solution was stirring at room temperature overnight. 100 ml of AcOEt are added. The organic phase are washed with 10% citric acid, saturated NaHCO$_3$ and brine then dried over Na$_2$SO$_4$, filtered and concentrated. The crude product was purified by flash chromatography (AcOEt/Hexane 5/5) to afford 174 as white solid (540 mg, 68%). $^1$H NMR (DMSO): δ 1.61 (s, 9H), 3.02 (m, 2H), 4.24 (s, 2H), 4.60 (m, 1H), 5.22 (s, 4H), 6.38 (d, 1H, J=7.6 Hz), 6.62 (m, 1H), 6.70 (d, 1H, J=8.0 Hz), 6.75 (m, 2H), 7.21 (m, 4H), 7.47 (m, 11H), 9.35 (s, 1H).

2-(3-(4-(tert-butoxycarbonylamino)benzyl)ureido)-3-(3-hydroxyphenyl) propanoic acid (175)

A solution of 174 (410 mg) in MeOH (20 ml) was stirred for 1 h under hydrogen atmosphere in the presence of 10% Pd/C. The resulting mixture was filtered through celite and the filtrate was evaporated under reduced pressure to give 175 as white solid (280 mg, 97%). $^1$H NMR (DMSO): δ 1.61 (s, 9H), 2.93 (m, 1H), 3.05 (m, 1H), 4.23 (m, 2H), 4.38 (m, 1H), 6.17 (d, 1H, J=8.0 Hz), 6.66 (t, 1H, J=5.9 Hz), 7.16 (t, 1H, J=7.3 Hz), 7.22 (d, 2H, J=7.6 Hz), 7.50 (d, 2H, J=7.6 Hz), 9.38 (s, 1H).

Example 149

Preparation of 1-(4-aminobenzyl)-3-(3-(3-hydroxyphenyl)-1-morpholino-1-oxopropan-2-yl)urea (176)

Acid derivative 175 (1 equivalent) was dissolved in 2 ml of DMF. Amine (1.1 equivalent), Hydroxybenzotriazole (HOBO (1.2 equivalent), diisopropylethylamine (DIEA) (2.2 equivalent) and 1-[3-(Dimethylamino)propyl]-3-ethylcarbodiimide (EDAP) (1.2 equivalent) were added successively and the reaction mixture is stirred for 20 h at room temperature. The reaction mixture is concentrated and 100 ml of AcOEt are added. The organic phase are washed with NaHCO$_3$ saturated, 10% citric acid and brine then dried over Na$_2$SO$_4$, filtered and concentrated. The crude product was purified by flash chromatography (AcOEt) to afford the amide as white solid (80 mg, 73%). $^1$H NMR (DMSO): δ 1.48 (s, 9H), 1.60 (m, 2H), 1.72 (m, 2H), 2.62 (m, 1H), 2.80 (dd, 1H, J=13.4, 5.2 Hz), 3.77 (m, 2H), 3.98 (m, 2H), 4.08 (d, 2H, J=5.3 Hz), 4.90 (m, 1H), 6.14 (d, 1H, J=8.8 Hz), 6.43 (t, 1H, J=5.3 Hz), 6.60 (m, 3H), 7.05 (d, 1H, J=8.5 Hz), 7.08 (d, 2H, J=8.2 Hz), 7.36 (d, 2H, J=8.2 Hz), 9.25 (s, 1H), 9.27 (s, 1H). The protected urea (78 mg) was dissolved in 2 µl of DCM and 2 ml of TFA was added then the reaction mixture was let 1 h at room temperature. The reaction mixture was concentrated and purified by precipitation using AcOEt/Hexane to afford the urea deprotected 176 as yellow solid (75 mg, 92%). HPLC method B tr=15.77 mn (92.3%). ESI-MS m/z: 399.4 [M+H]$^+$.

X—Synthesis of Ureas 177-180

General Protocol:

bicyclic amine (1 equivalent) was dissolved in AcOEt (30 mL) and trisphosgene (0.33 equivalent) was added while stirring at −10° C. The mixture was allowed to warm to room temperature, then refluxed for 1 h. 4-(tert-butoxycarbonylamino)benzylamine or 2-(tert-butoxycarbonylamino)-5-(2-aminomethyl)pyridine (1 equivalent) and triethylamine (2 equivalent) were added successively and the resulting solution was stirring at room temperature overnight. 100 ml of AcOEt are added. The organic phase are washed with 10% citric acid, saturated NaHCO$_3$ and brine then dried over Na$_2$SO$_4$, filtered and concentrated. The crude product was purified by flash chromatography to afford the urea protected. Finally, the urea was dissolved in 2 ml of DCM and 2 ml of TFA was added then the reaction mixture was let 1 h at room temperature. The reaction mixture was concentrated and purified by precipitation using AcOEt/Hexane to afford the urea deprotected 177-180.

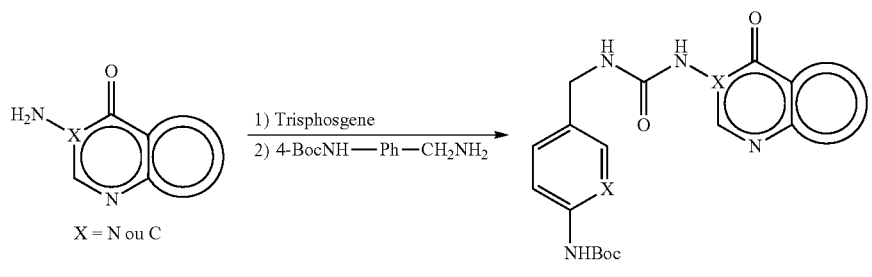

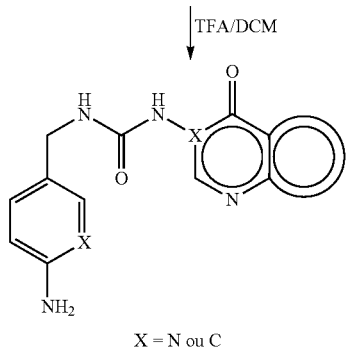

X = N ou C
177-180

Example 150

Preparation of 1-(4-aminobenzyl)-3-(5-oxo-5H-thiazolo[3,2-a]pyrimidin-6-yl)urea (F608)(177)

The crude product was purified by flash chromatography (AcOEt) to afford the urea protected (123 mg; 62%) as a white solid. $^1$H NMR (DMSO): δ 1.61 (s, 9H), 4.36 (d, 2H, J=5.1 Hz), 7.31 (d, 2H, J=7.5 Hz), 7.40 (t, 1H, J=5.1 Hz), 7.54 (d, 2H, J=7.5 Hz), 7.68 (d, 1H, J=5.0 Hz), 8.15 (d, 1H, J=5.0 Hz), 8.32 (s, 1H), 8.96 (s, 1H), 9.39 (s, 1H). The urea was deprotected to afford compound 177 as yellow solid (112 mg, 86%). HPLC method B tr=13.67 nm (97.3%). ESI-MS m/z: 316.1 [M+H]$^+$.

Example 151

Preparation of 1-((6-aminopyridin-3-yl)methyl)-3-(5-oxo-5H-thiazolo[3,2-c]pyrimidin-6-yl)urea (F596)(178)

The crude product was purified by flash chromatography (AcOEt/MeOH 95/5) to afford the urea protected (103 mg; 57%) as a white solid. $^1$H NMR (DMSO): δ 1.59 (s, 9H), 4.37 (d, 2H, J=4.8 Hz), 7.55 (t, 1H, J=4.8 Hz), 7.68 (t, 1H, J=4.5 Hz), 7.78 (d, 1H, J=8.2 Hz), 7.89 (d, 1H, J=8.2 Hz), 8.16 (d, 1H, J=4.5 Hz), 8.30 (s, 1H), 8.37 (s, 1H), 8.94 (s, 1H), 9.88 (s, 1H). The urea was deprotected to afford compound 178 as yellow solid (98 mg, 89%). HPLC method B tr=13.65 nm (97.3%). ESI-MS m/z: 317.0 [M+H]$^+$.

Example 152

Preparation of 1-((6-aminopyridin-3-yl)methyl)-3-(4-oxoquinazolin-3(4H)-yl)urea (F574)(179)

The crude product was purified by flash chromatography (AcOEt/MeOH 95/5) to afford the urea protected (133 mg; 67%) as a white solid. The urea was deprotected to afford compound 179 as yellow solid (108 mg, 86%). $^1$H NMR (DMSO): δ 4.09 (d, 2H, J=5.8 Hz), 5.80 (s, 2H), 6.42 (d, 1H, J=8.6 Hz), 7.31 (d, 1H, J=8.5 Hz), 7.39 (t, 1H, J=5.5 Hz), 7.60 (t, 1H, J=7.3 Hz), 7.74 (d, 1H, J=8.0 Hz), 7.83 (s, 1H), 7.88 (t, 1H, J=7.4 Hz), 8.18 (d, 1H, J=8.0 Hz), 8.26 (s, 1H), 8.26 (s, 1H), 9.12 (s, 1H). HPLC method B tr=15.78 nm (93.8%). ESI-MS m/z: 311.0 [M+H]$^+$.

Example 153

Preparation of 1-(4-aminobenzyl)-3-(4-oxoquinazolin-3(4H)-yl)urea (F600)(180)

The crude product was purified by flash chromatography (AcOEt/MeOH 95/5) to afford the urea protected (123 mg; 62%) as a white solid. The urea was deprotected to afford compound 180 as yellow solid (102 mg, 82%). HPLC method B tr=16.49 nm (94.9%). ESI-MS m/z: 310.0 [M+H]$^+$.

XI—Synthesis of 181

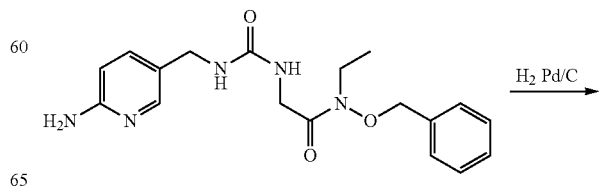

98

-continued

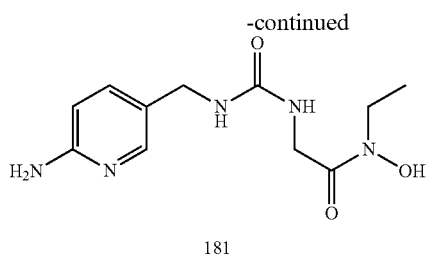

181

Example 154

Preparation of 2-(3-((6-aminopyridin-3-yl)methyl)ureido)-N-hydroxy-N-ethylacetamide (F606)(181)

A solution of 98 (38 mg) in MeOH (10 ml) was stirred for 1 h under hydrogen atmosphere in the presence of 10% Pd/C. The resulting mixture was filtered through celite and the filtrate was evaporated under reduced pressure to give 181 as white solid (16 mg, 57%). ESI-MS m/z: 268.1 [M+H]$^+$.

XI—Synthesis of Ureas 182-185

General Procedure.

Ethyl isocyanatoacetate (1 equivalent, 64 mg, 56 μA 0.49 mmol) was dissolved in DMF (0.4M). Then the amine (1 equivalent) was added in one portion and the reaction mixture was let 24 h at room temperature. After the reaction was complete (TLC control), the reaction mixture was concentrated and the crude product was purified by flash chromatography (AcOEt/MeOH 90/10) to afford the urea:

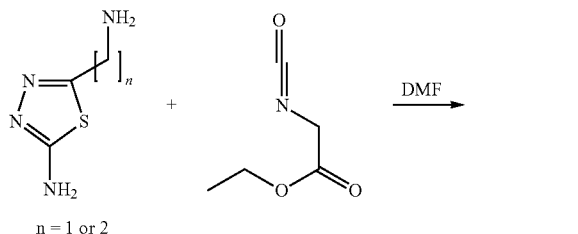

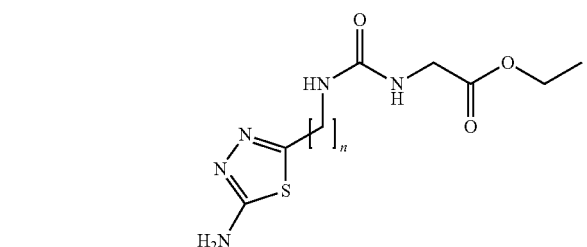

182-183
n = 1 or 2

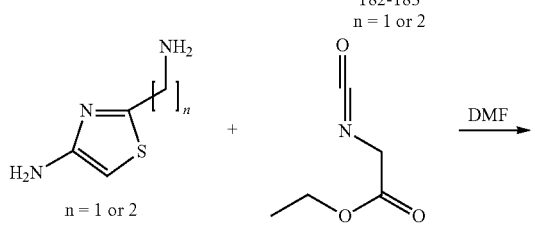

-continued

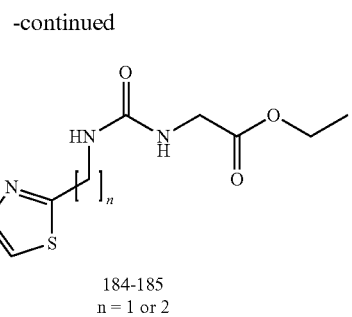

184-185
n = 1 or 2

Example 155

Preparation of ethyl 2-(3-(2-(5-amino-1,3,4-thiadiazol)methyl)ureido)acetate (F615)(182)

182 was purified to afford 86 mg of a yellow solid (68%). $^1$H NMR (DMSO): δ 1.20 (t, 3H, J=7.1 Hz), 3.78 (d, 2H, J=6.0 Hz), 4.10 (q, 2H, J=7.1 Hz), 4.31 (d, 2H, J=6.0 Hz), 6.43 (t, 1H, J=6.0 Hz), 6.92 (t, 1H, J=6.0 Hz), 7.06 (s, 2H). HPLC method A tr=4.66 nm (92.70%). ESI-MS m/z: 260.1 [M+H]$^+$.

Example 156

Preparation of ethyl 2-(3-(2-(2-(5-amino-1,3,4-thiadiazol)ethyl))ureido)acetate (F616)(183)

183 was purified to afford 87 mg of a yellow solid (64%). $^1$H NMR (DMSO): δ 1.19 (t, 3H, J=7.1 Hz), 2.88 (t, 2H, J=6.7 Hz), 3.29 (m, 2H), 3.74 (d, 2H, J=6.0 Hz), 4.09 (q, 2H, J=7.1 Hz), 6.32 (m, 2H), 7.03 (s, 2H). HPLC method A tr=4.83 nm (98.08%). ESI-MS m/z: 274.1 [M+H]$^+$.

Example 157

Preparation of ethyl 2-(3-(2-(4-amino-1,3-thiazol)methyl)ureido)acetate F617)(184)

184 was purified to afford 60 mg of a yellow solid (47%). $^1$H NMR (DMSO): δ 1.19 (t, 3H, J=7.1 Hz), 3.77 (d, 2H, J=6.0 Hz), 3.98 (d, 2H, J=5.6 Hz), 4.09 (q, 2H, J=7.1 Hz), 6.19 (s, 1H), 6.30 (t, 1H, J=6.0 Hz), 6.43 (t, 1H, J=5.6 Hz), 6.87 (s, 2H). HPLC method A tr=4.77 nm (98.97%). ESI-MS m/z: 259.1 [M+H]$^+$.

Example 158

Preparation of ethyl 2-(3-(2-(2-(4-amino-1,3-thiazol)ethyl) ureido)acetate (F618)(185)

185 was purified to afford 64 mg of a yellow solid (48%). $^1$H NMR (DMSO): δ 1.19 (t, 3H, J=7.1 Hz), 3.22 (m, 2H), 3.34 (m, 2H), 3.74 (d, 2H, J=6.0 Hz), 4.09 (q, 2H, J=7.1 Hz), 6.13 (m, 2H), 6.23 (t, 1H, J=6.0 Hz), 6.82 (s, 2H). HPLC method A tr=5.22 nm (96.30%). ESI-MS m/z: 273.1 [M+H]$^+$.

XII—Synthesis of Urea 187

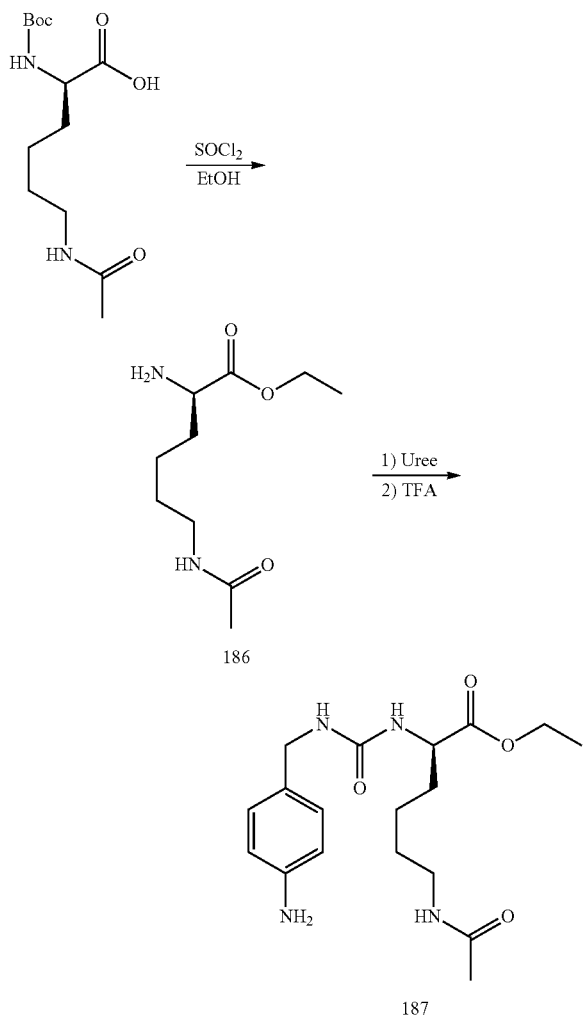

(R)-ethyl 6-acetamido-2-aminohexanoate (186)

Boc-Lys(Ac)-OH (1 equivalent, 0.2 g, 0.69 mmol) was dissolved in EtOH (2 mL). The reaction mixture was cooled at −10° C., and SOCl$_2$ (1.5 equivalent, 76 μl, 1.035 mmol) was added dropwise. The mixture was allowed to warm to room temperature, then heated at 40° C. for 20 h (TLC control). The reaction mixture was concentrated and the crude was purified by flash chromatography (CH$_2$Cl$_2$/MeOH) to afford the compound (120 mg, 80%) as a white solid Rf=0.62 (CH$_2$Cl$_2$/MeOH 70/30).

Example 159

(R)-ethyl 6-acetamido-2-(3-(4-aminobenzyl)ureido)hexanoate (F699)(187)

(R)-ethyl 6-acetamido-2-aminohexanoate 186 (1 equivalent, 120 mg, 0.55 mmol) was dissolved in anhydrous THF (4 mL) and trisphosgene (0.33 equivalent, 55 mg, 0.18 mmol) was added while stirring at −10° C. The mixture was allowed to warm to room temperature, then refluxed for 2 h. tert-butyl-N-[4-(aminomethyl)phenyl]carbamate (1 equivalent, 123 mg, 0.55 mmol) and triethylamine (2 equivalent, 154 μl, 1.1 mmol) were added successively and the resulting solution was stirring at room temperature overnight. The reaction mixture was concentrated, washed by 30 ml of NaHCO$_3$ and extracted by 3×30 ml EtOAc. The organic phase was dried over Na$_2$SO$_4$, filtered and concentrated. The crude product was purified by flash chromatography (CH$_2$Cl$_2$/MeOH) to afford the urea protected (21 mg, 8%) Rf=0.18 (CH$_2$Cl$_2$/MeOH 95/5). $^1$H NMR (200 MHz, CDCl$_3$) δ 7.30 (d, J=8.6 Hz, 2H), 7.18 (d, J=8.5 Hz, 2H), 6.68 (s, 1H), 6.10-5.90 (m, 1H), 5.43 (d, J=7.7 Hz, 1H), 5.30 (t, J=5.7 Hz, 1H), 4.51-4.35 (m, 1H), 4.35-4.25 (m, 2H), 4.15 (q, J=7.1 Hz, 2H), 3.26-3.08 (m, 2H), 1.91 (s, 3H), 1.85-1.15 (m, 6H), 1.50 (s, 9H), 1.25 (t, J=7.1 Hz, 3H). Finally, the urea was dissolved in 2 ml of DCM and 2 ml of TFA was added then the reaction mixture was let 1 h at room temperature. The reaction mixture was concentrated and purified on reverse phase (H$_2$O/MeCN) to afford the urea deprotected (7 mg, 44%) as a colorless oil Rf=0.42 (CH$_2$Cl$_2$/MeOH 90110). $^1$H NMR (200 MHz, CDCl$_3$): δ 7.06 (d, J=8.4 Hz, 2H), 6.62 (d, J=8.4 Hz, 2H), 6.15-5.92 (m, 1H), 5.36 (d, J=8.1 Hz, 1H), 5.16 (t, J=5.8, 1H), 4.55-4.35 (m, 1H), 4.22 (d, J=5.6 Hz, 2H), 4.14 (q, J=7.2 Hz, 2H), 3.28-3.10 (m, 2H), 1.92 (s, 3H), 1.90-1.27 (m, 6H), 1.25 (t, J=7.1 Hz, 3H). HPLC method A tr=6.75 nm (91.30%). ESI-MS m/z: 365.2 [M+H]$^+$.

XIII—Synthesis of Urea 191

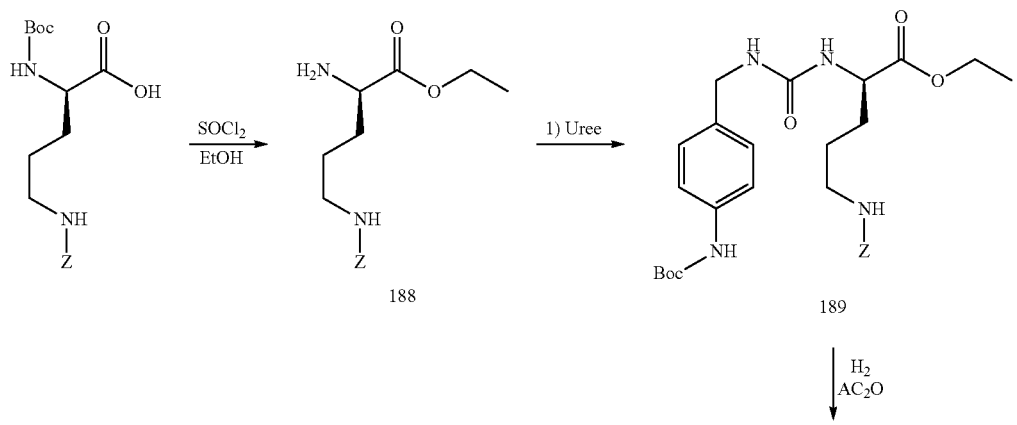

-continued

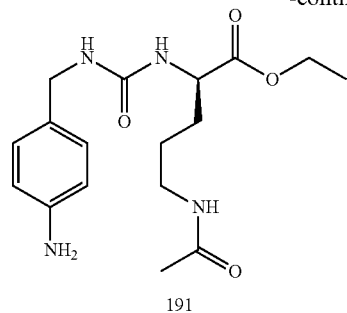

191

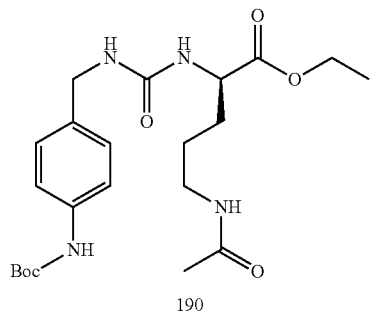

190

(R)-ethyl 2-amino-
5-(benzyloxycarbonylamino)pentanoate (188)

Boc-Orn(Z)—OH (1 equivalent, 0.4 g, 1.1 mmol) was dissolved in EtOH (4 mL). The reaction mixture was cooled at −10° C., and SOCl$_2$ (1.5 equivalent, 119 µl, 1.65 mmol) was added dropwise. The mixture was allowed to warm to room temperature, then heated at 40° C. for 20 h (TLC control). The reaction mixture was concentrated and the crude was purified by flash chromatography (CH$_2$Cl$_2$/MeOH) to afford the compound 188 (178 mg, 55%) as a white solid Rf=0.23 (CH$_2$Cl$_2$/MeOH 90/10). $^1$H NMR (300 MHz, CDCl$_3$): δ 7.37-7.27 (m, 5H), 5.54 (broad s, 1H), 5.05 (s, 2H), 4.17 (q, J=6.9 Hz, 2H), 3.95 (broad s, 1H), 3.30-3.13 (m, 2H), 2.10-1.85 (m, 2H), 1.85-1.55 (m, 2H), 1.22 (t, J=7.1 Hz, 3H).

(R)-ethyl 5-(benzyloxycarbonylamino)-2-(3-(4-(tert-butoxycarbonylamino)benzyl)ureido)pentanoate (189)

(R)-ethyl 2-amino-5-(benzyloxycarbonylamino)pentanoate (1 equivalent, 146 mg, 0.50 mmol) was dissolved in anhydrous THF (4 mL) and trisphosgene (0.33 equivalent, 49 mg, 0.17 mmol) was added while stirring at −10° C. The mixture was allowed to warm to room temperature, and then refluxed for 2 h. Tert-butyl-N-[4-(aminomethyl)phenyl]carbamate (1 equivalent, 110 mg, 0.50 mmol) and triethylamine (2 equivalent, 138 µl, 1 mmol) were added successively and the resulting solution was stirring at room temperature overnight. The reaction mixture was concentrated, washed by 30 ml of NaHCO$_3$ and extracted by 3×30 ml EtOAc. The organic phase was dried over Na$_2$SO$_4$, filtered and concentrated. The crude product was purified by flash chromatography (EDP/EtOAc) to afford the urea protected (146 mg, 54%) as a colourless oil Rf=0.59 (EtOAc). $^1$H NMR (300 MHz, CDCl$_3$) δ 7.30-7.23 (s, 5H), 7.20 (d, J=8.4 Hz, 2H), 7.09 (d, J=8.4 Hz, 2H), 6.84-6.66 (m, 1H), 5.62-5.42 (m, 2H), 5.28-5.10 (m, 1H), 5.00 (s, 2H), 4.46-4.29 (m, 2H), 4.18 (d, J=5.5 Hz, 2H), 4.05 (q, J=7.1 Hz, 3H), 3.16-3.00 (m, 2H), 1.82-1.28 (m, 4H), 1.43 (s, 9H), 1.16 (t, J=7.2 Hz, 3H).

(R)-ethyl 5-acetamido-2-(3-(4-(tert-butoxycarbonylamino)benzyl)ureido)pentanoate (190)

(R)-ethyl 5-(benzyloxycarbonylamino)-2-(3-(4-(tert-butoxy-carbonylamino)benzyl)ureido)pentanoate (1 equivalent, 115 mg, 0.21 mmol) was dissolved in 50 ml of MeOH. The Pd/C (12 mg) and the acetic anhydride (3 equivalent, 60 µl, 0.63 mmol). The reaction mixture was stirred under hydrogen at room temperature for 4 h. Then the mixture was filtrated on celite and the filter was concentrated. the crude was washed by 30 ml NaHCO$_3$ and extracted by 3×30 ml EtOAc. The organic phase was dried over Na$_2$SO$_4$, filtered and concentrated. The crude was purified by flash chromatography (CH$_2$Cl$_2$/MeOH) to afford the amide (84 mg, 78%) a colourless oil Rf=0.27 (CH$_2$Cl$_2$/MeOH 95/5). $^1$H NMR (200 MHz, CDCl$_3$): δ 7.30 (d, J=8.6 Hz, 2H), 7.18 (d, J=8.6 Hz, 2H), 6.63 (broad s, 1H), 6.28-6.10 (m, 1H), 5.45 (d, J=7.6 Hz, 1H), 5.34-5.20 (m, 1H), 4.52-4.35 (m, 1H), 4.29 (d, J=5.8 Hz 2H), 4.15 (q, J=7.1 Hz, 2H), 3.32-3.12 (m, 2H), 1.94 (s, 3H), 1.90-1.36 (m, 4H) 1.50 (s, 9H), 1.25 (1, J=7.5 Hz, 3H).

Example 160

(R)-ethyl 5-acetamido-2-(3-(4-aminobenzyl)ureido)pentanoate (F700)(191)

The urea was dissolved in 2 ml of DCM and 2 ml of TFA was added then the reaction mixture was let 1 h at room temperature. The reaction mixture was concentrated and purified on reverse phase (H$_2$O/MeCN) to afford the urea deprotected (43 mg, 61%) as a white solid Rf=0.4 (CH$_2$Cl$_2$/MeOH 90/10). HPLC method A tr=5.52 nm (98.2%). ESI-MS m/z: 351.3 [M+H]$^+$.

XIV—Synthesis of Urea 192-197

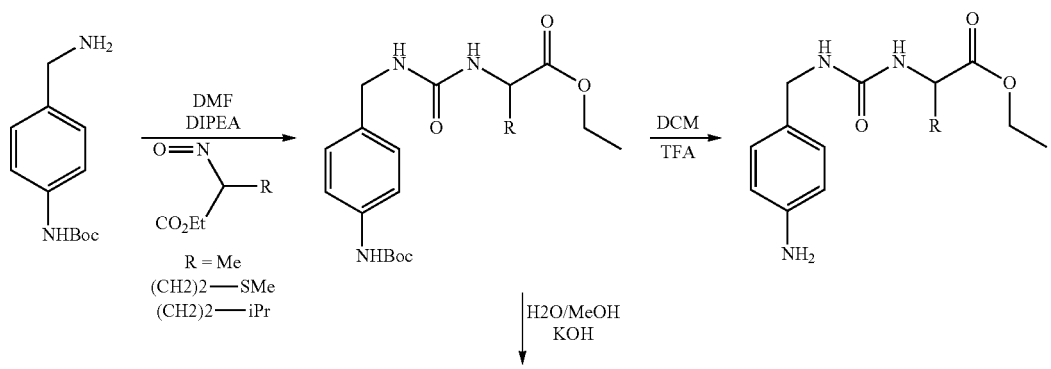

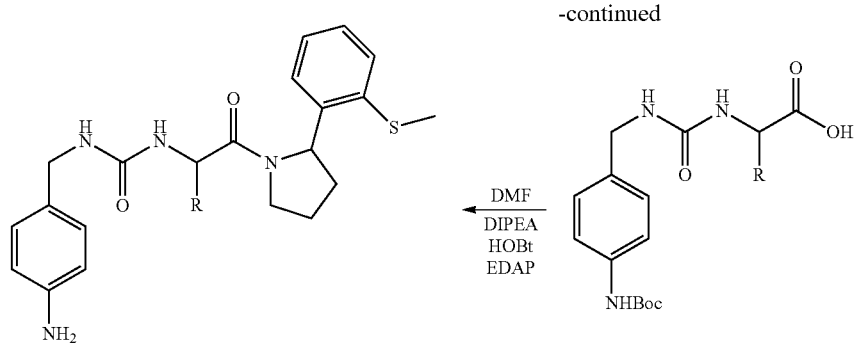

Synthesis of Urea (192-194)

General Protocol

Tert-butyl 4-(aminomethyl)phenylcarbamate (1 equivalent), isocyanate (1.2 equivalent) and DIPEA (1.2 equivalent) were dissolved in DMF. The reaction mixture was stirred at room temperature for 20 h. The mixture was washed by 30 ml of NaHCO$_3$ and extracted by 3×20 ml of EtOAc. The organic phase was dried over Na$_2$SO$_4$, filtered and concentrated. The crude was purified by flash chromatography to afford the amide. Finally, the amide was dissolved in 4 ml of DCM and 2 ml of TFA was added then the reaction mixture was let 1 h at room temperature. The reaction mixture was concentrated and purified on reverse phase (H$_2$O/MeCN) to afford the amide deprotected.

Example 161 ethyl 2-(3-(4-aminobenzyl)ureido)-4-methylpentanoate (F698)(192)

The crude was purified by flash chromatography (EDP/EtOAc) to afford the amide (612 mg, 83%) as a white solid, Rf=0.48 (EDP/EtOAc 50/50), $^1$H NMR (200 MHz, CDCl$_3$): δ 7.28 (d, J=8.6 Hz, 2H), 7.16 (d, J=8.6 Hz, 2H), 6.60 (broad s, 1H), 5.17-5.01 (m, 2H), 4.55-4.38 (m, 1H), 4.26 (d, J=5.6 Hz, 2H), 4.11 (q, J=7.2 Hz, 2H), 1.79-1.33 (m, 3H), 1.50 (s, 9H), 1.23 (t, J=7.1 Hz, 3H), 0.97-0.86 (m, 6H). The amide (200 mg, 0.49 mmol) was deprotected to afford amine 192 (130 mg, 100%) as a white solid, Rf=0.64 (CH$_2$Cl$_2$/MeOH 90/10). HPLC method A tr=8.91 nm (100%). ESI-MS m/z: 308.2 [M+H]$^+$.

Example 162 ethyl 2-(3-(4-aminobenzyl)ureido)-4-(methylthio)butanoate (F702)(193)

The crude was purified by flash chromatography (EDP/EtOAc) to afford the amide (569 mg, 74%) as a white solid, Rf=0.32 (EDP/EtOAc 50/50). $^1$H NMR (200 MHz, CDCl$_3$): δ 7.27 (d, J=8.6 Hz, 2H), 7.15 (d, J=8.6 Hz, 2H), 6.67 (broad s, 1H), 5.43 (d, J=8.1 Hz, 1H), 5.26 (t, J=5.6 Hz, 1H), 4.62-4.36 (m, 1H), 4.25 (d, J=5.6 Hz, 2H), 4.13 (q, J=7.1 Hz, 2H), 2.54-2.42 (m, 2H), 2.20-1.75 (m, 3H), 2.04 (s, 3H), 1.49 (s, 9H), 1.24 (t, J=7.1 Hz, 3H). The amide (200 mg, 0.47 mmol) was deprotected to afford amine 193 (101 mg, 94%) as a white solid, Rf=0.68 (CH$_2$Cl$_2$/MeOH 90/10). HPLC method A tr=7.72 nm (94.6%). ESI-MS m/z: 326.2 [M+H]$^+$.

Example 163 ethyl 2-(3-(4-aminobenzyl)ureido)propanoate (F720) (194)

The crude was purified by flash chromatography (EDP/EtOAc) to afford the amide (562 mg, 86%) as a white solid, Rf=0.25 (EDP/EtOAc 50/50). $^1$H NMR (200 MHz, CDCl$_3$): δ 7.28 (d, J=8.6 Hz, 2H), 7.17 (d, J=8.6 Hz, 2H), 6.57 (broad s, 1H), 5.15 (d, J=7.6 Hz, 1H), 4.98 (t, J=5.6 Hz, 1H), 4.46 (p, J=7.2 Hz, 1H), 4.27 (d, J=5.6 Hz, 2H), 4.14 (q, J=7.1 Hz, 3H), 1.50 (s, 9H), 1.35 (d, J=7.2 Hz, 3H), 1.25 (t, J=7.1 Hz, 3H). The amide (200 mg, 0.55 mmol) was deprotected to afford amine (72 mg, 100%) as a white solid, Rf=0.75 (MeOH). $^1$H NMR (300 MHz, DMSO): δ 6.95 (d, J=8.3 Hz, 2H), 6.55 (d, J=8.3 Hz, 2H), 6.32-6.21 (m, 2H), 4.99 (broad s, 2H), 4.21 (q, J=7.2 Hz, 1H), 4.13 (q, J=7.3 Hz, 2H), 4.05 (d, J=5.7 Hz, 2H), 1.28 (d, J=7.3 Hz, 3H), 1.24 (t, J=7.2 Hz, 3H). HPLC method A tr=5.38 nm (100%). ESI-MS m/z: 266.2 [M+H]$^+$.

Synthesis of Urea (195-197)

General Protocol

The ester (1 equivalent), and KOH (2.5 equivalent) were dissolved in H$_2$O/MeOH 1/1. The reaction mixture was heated at 50° C. for 1 h 30. Then the reaction was allowed cool at room temperature and the MeOH was evaporated. The mixture was washed by 30 ml of brine and extracted by 30 ml of EtOAc (impurities were eliminated in the organic phase). The aqueous phase was acidified at pH=3 by citric acid, and extracted by 3×30 ml of EtOAc. The organic phase was dried over Na$_2$SO$_4$, filtered and concentrated to afford the carboxylic acid.

The carboxylic acid (1 equivalent), 2-(2-(methylthio)phenyl)pyrrolidine (1.2 equivalent) DIPEA (1.2 equivalent), HOBt (1.2 equivalent) were dissolved in 2 ml of DMF and the mixture was stirred at room temperature for 20 minutes. Then EDAP (1.2 equivalent) was added and the reaction mixture was stirred over night. The mixture was washed by 60 ml of NaHCO$_3$ and extracted by 3×40 ml of EtOAc. The organic phase was dried over Na$_2$SO$_4$, filtered and concentrated. The crude was purified by flash chromatography to afford the amide (the amide was isolated as two diastereoisomers). Finally, the amide was dissolved in 2 ml of DCM and 1 ml of TFA was added then the reaction mixture was let 1 h at room temperature. The mixture was concentrated and purified on reverse phase (H$_2$O/MeCN) to afford the amine.

Example 164

3 1-(4-aminobenzyl)-3-(4-methyl-1-(2-(2-(methylthio)phenyl) pyrrolidin-1-yl)-1-oxopentan-2-yl) urea (F712)(195)

The ester (1 equivalent, 332 mg, 0.81 mmol), LiOH (2.5 equivalent, 50 mg, 2.08 mmol) were dissolved in $H_2O$/MeOH 4 ml/4 ml, and the reaction mixture was stirred at room temperature for 45 minutes (the intermediate product was obtained). NaOH (2.5 equivalent, 82 mg, 2.08 mmol) was added, and the reaction mixture was refluxed for 2 h. The carboxylic acid was isolated in the second organic phase (207 mg, 67%) as a white solid. $^1$H NMR (300 MHz, DMSO): δ 9.31 (broad s, 1H), 7.41 (d, J=8.4 Hz, 2H), 7.15 (d, J=8.5 Hz, 2H), 6.60 (t, J=4.9 Hz, 1H), 6.06 (d, J=7.2 Hz, 1H), 4.18-4.11 (m, 2H), 3.99-3.85 (m, 1H), 1.80-1.27 (m, 3H), 1.51 (s, 9H), 0.95-0.87 (m, 6H). The carboxylic acid was put in reaction to afford the amide. The amide was isolated as two diastereoisomer by flash chromatography (EDP/EtOAc). 108 mg, yellow solid, Rf=0.17 (EDP/EtOAc 30/70). The amide was deprotected to afford the amine 195 (50 mg, 56%) as an orange solid, Rf=0.64 (MeOH). HPLC method A tr=11.18 nm (98.8%). ESI-MS m/z: 455.2 [M+H]$^+$.

Example 165

1-(4-aminobenzyl)-3-(1-(2-(2-(methylthio)phenyl) pyrrolidin-1-yl)-1-oxopropan-2-yl)urea (F714)(196)

The carboxylic acid was isolated in the second organic phase (283 mg, 93%) as a white solid. $^1$H NMR (200 MHz, DMSO): δ 12.48 (broad s, 1H), 9.31 (s, 1H), 7.41 (d, J=8.5 Hz, 2H), 7.15 (d, J=8.5 Hz, 2H), 6.42 (t, J=5.9 Hz, 1H), 6.24 (d, J=7.8 Hz, 1H), 4.23-4.05 (m, 3H), 1.50 (s, 9H), 1.24 (d, J=7.2 Hz, 3H). The carboxylic acid was put in reaction to afford the amide. The amide was isolated as two diastereoisomer by flash chromatography (EDP/EtOAc). 118 mg, Rf=0.13 (EDP/EtOAc 30/70). The amide was deprotected to afford the amine 196 (57 mg, 95%) as a white solid, Rf=0.72 (MeOH). HPLC method A tr=9.63 nm (93.5%). ESI-MS m/z: 413.2 [M+H]$^+$.

Example 166

1-(4-aminobenzyl)-3-(4-(methylthio)-1-(2-(2-(methylthio)phenyl)pyrrolidin-1-yl)-1-oxobutan-2-yl)urea (F716)(197)

The carboxylic acid was isolated in the second organic phase (159 mg, 53%) as a white solid. $^1$H NMR (200 MHz, DMSO)/δ 12.63 (broad s, 1H), 9.30 (s, 1H), 7.41 (d, J=8.4 Hz, 2H), 7.15 (d, J=8.4 Hz, 2H), 6.42 (t, J=5.9 Hz, 1H), 6.30 (d, J=8.5 Hz, 1H), 4.33-4.20 (m, 1H), 4.16 (d, J=5.8 Hz, 2H), 2.54-2.44 (m, 2H), 2.08 (s, 3H), 2.05-1.70 (m, 2H), 1.50 (s, 9H). The carboxylic acid was put in reaction to afford the amide. The amide was isolated as two diastereoisomer by flash chromatography (EDP/EtOAc), 51 mg, Rf=0.15 (EDP/EtOAc 30/70). The amide was deprotected to afford the amine 197 (30 mg, 71%) as a solid, Rf=0.71 (MeOH). HPLC method A tr=10.55 nm (95.0%). ESI-MS m/z: 473.2 [M+H]$^+$.

XV—Synthesis of Urea 201

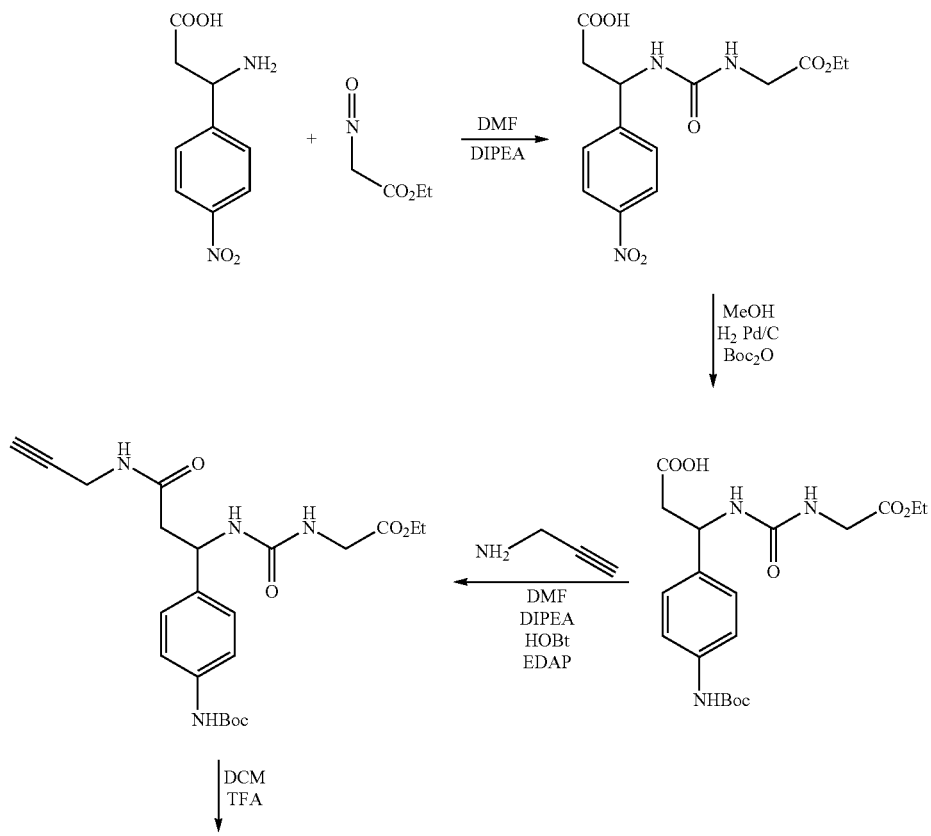

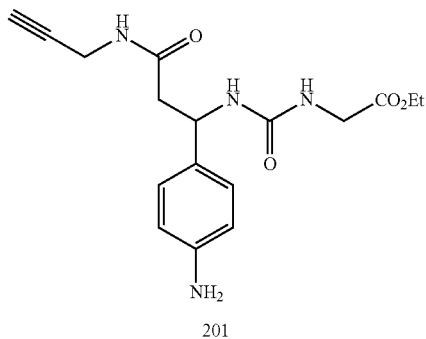

201

3-(3-(2-ethoxy-2-oxoethyl)ureido)-3-(4-nitrophenyl) propanoic (198)

acid 3-amino-3-(4-nitrophenyl)propanoic acid (1 equivalent, 500 mg, 2.38 mmol), ethyl isocyanatoacetate (1 equivalent, 267 µl, 2.38 mmol), and DIPEA (2 equivalent, 830 µl, 4.76 mmol) were dissolved in 2 ml of DMF. The reaction mixture was stirred at room temperature overnight. The mixture was concentrated, washed by 100 ml H$_2$O, extracted by 100 ml EtOAc (the impurities were eliminated). The aqueous phase was acidified at pH3 by HCl 5%, and extracted by 2×100 ml EtOAc. The organic phase was dried over Na$_2$SO$_4$, filtered and concentrated. The crude was purified by flash chromatography (EtOAc/MeOH) to afford the compound 198 (420 mg, 52%) as a white solid, Rf=0.25 (EtOAC/MeOH 95/5). $^1$H NMR (200 MHz, DMSO): δ 12.45 (s, 1H), 8.23 (d, J=8.7 Hz, 2H), 7.62 (d, J=8.7 Hz, 2H), 7.06 (d, J=8.1 Hz, 1H), 6.47 (t, J=6.0 Hz, 1H), 5.14 (q, J=7.3 Hz, 1H), 4.09 (q, J=7.1 Hz, 4H), 3.84-3.72 (m, 2H), 2.77 (d, J=6.9 Hz, 2H), 1.19 (t, J=7.1 Hz, 5H).

3-(4-(tert-butoxycarbonylamino)phenyl)-3-(3-(2-ethoxy-2-oxoethyl)ureido)propanoic acid (199)

3-(3-(2-ethoxy-2-oxoethyl)ureido)-3-(4-nitrophenyl)propanoic (197 mg, 0.58 mmol), was dissolved in 100 ml of MeOH. Pd/C (20 mg) was added under argon, followed by Boc$_2$O (1.2 equivalent, 152 mg, 0.70 mmol). The reaction mixture was stirred at room temperature and at 10 bars under hydrogen for 20 h. Then the mixture was filtrated on celite, washed by MeOH and the filter was concentrated. The crude was purified by flash chromatography (CH$_2$Cl$_2$/MeOH) to afford the compound 199 (155 mg, 65%) as a white solid, Rf=0.2 (CH$_2$Cl$_2$/MeOH 90/10). $^1$H NMR (200 MHz, CDCl$_3$) δ 7.30 (d, J=8.6 Hz, 2H), 7.19 (d, J=8.6 Hz, 2H), 6.83 (s, 1H), 6.56-6.42 (m, 1H), 5.81-5.64 (m, 1H), 5.20-5.02 (m, 1H), 4.15 (q, J=7.1 Hz, 2H), 3.99-3.86 (m, 2H), 2.87-2.74 (m, 2H), 1.50 (s, 9H), 1.23 (t, J=7.2 Hz, 3H).

ethyl 2-(3-(1-(4-(tert-butoxycarbonylamino)phenyl)-3-oxo-3-(prop-2-ynyl-amino)propyl)ureido)acetate (200)

3-(4-(tert-butoxycarbonylamino)phenyl)-3-(3-(2-ethoxy-2-oxoethyl)ureido)propanoic acid (1 equivalent, 150 mg, 0.37 mmol), propargylamin hydrocholoride (1 equivalent, 33 mg, 0.37 mmol), DIPEA (2.2 equivalent, 140 µl, 0.81 mmol), and HOBt (1.2 equivalent, 60 mg, 0.45 mmol) were dissolved in 2 ml of DMF. The reaction mixture was stirred at room temperature for 20 minutes. Then EDAP (1.2 equivalent, 84 mg, 0.45 mmol) was added and the reaction mixture was stirred at room temperature overnight. The mixture was washed by 30 ml of NaHCO$_3$, and extracted by 3×20 ml of EtOAc. The organic phase was dried over Na$_2$SO$_4$, filtered and concentrated. The crude was purified by flash chromatography (EDP/EtOAc) to afford the compound 200 (108 mg, 66%) as a white solid, Rf=0.25 (EtOAc). $^1$H NMR (200 MHz, DMSO) δ 9.28 (s, 1H), 8.29 (t, J=5.2 Hz, 1H), 7.37 (d, J=8.5 Hz, 2H), 7.16 (d, J=8.5 Hz, 2H), 6.72 (d, J=8.5 Hz, 1H), 6.34 (t, J=6.1 Hz, 1H), 4.99 (q, J=7.0 Hz, 1H), 4.09 (q, J=7.2 Hz, 2H), 3.86-3.78 (m, 2H), 3.76 (d, J=5.9 Hz, 2H), 3.41-3.32 (m, 2H), 3.13-3.08 (m, 1H), 1.50 (s, 9H), 1.20 (t, J=7.1 Hz, 3H).

Example 167 ethyl 2-(3-(1-(4-aminophenyl)-3-oxo-3-(prop-2-ynylamino) propyl)ureido)acetate (F711)(201)

ethyl 2-(3-(1-(4-(tert-butoxycarbonylamino)phenyl)-3-oxo-3-(prop-2-ynylamino)propyl)ureido)acetate (108 mg) was dissolved in 4 ml of DCM and 2 ml of TFA was added then the reaction mixture was let 2 h at room temperature. The mixture was concentrated and the crude was purified on reverse phase (H$_2$O/MeCN) to afford the amine 201 (50 mg, 60%) as a white solid, Rf=0.45 (EtOAc/MeOH 90/10). $^1$H NMR (200 MHz, DMSO) δ 8.25 (t, J=5.5 Hz, 1H), 6.94 (d, J=8.3 Hz, 2H), 6.56 (d, J=8.5 Hz, 1H), 6.50 (d, J=8.3 Hz, 2H), 6.27 (t, J=6.0 Hz, 1H), 5.05-4.79 (m, 3H), 4.10 (q, J=7.1 Hz, 2H), 3.86-3.71 (m, 4H), 3.14-3.08 (m, 2H), 2.58-2.45 (m, 2H), 1.21 (t, J=7.1 Hz, 3H). HPLC method A tr=5.12 nm (98.1%). ESI-MS m/z: 347.1 [M+H]$^+$.

XVI—Synthesis of Urea 202-208

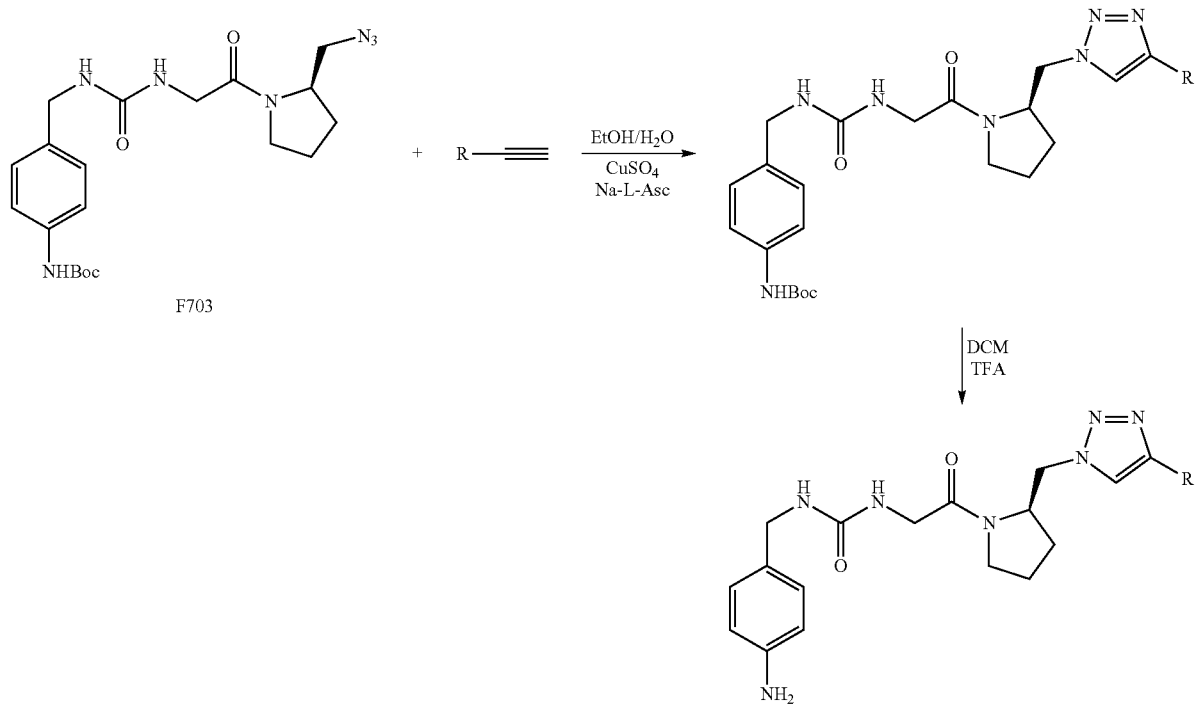

Synthesis of Ureas

General Procedure

F703 (1 equivalent), the alcyne (1 equivalent), $CuSO_4$ (0.2 equivalent; solution at 20 mM in $H_2O$), Na-L-Asc (0.5 equivalent, solution at 50 mM in $H_2O$) were dissolved in 8 ml of EtOH (reaction solution EtOH/$H_2O$ 8/2). The reaction mixture was heated at 45° C. for 1 h and at room temperature overnight. The mixture was concentrated. The crude product was purified by flash chromatography to afford the amide. Finally, the amide was dissolved in 2 ml of DCM and 2 ml of TFA was added then the reaction mixture was let 1 h at room temperature. The reaction mixture was concentrated and purified on reverse phase ($H_2O$/MeCN) to afford amide deprotected.

Example 168

(R)-1-(4-aminobenzyl)-3-(2-oxo-2-(2-((4-(phenoxymethyl)-1H-1,2,3-triazol-1-yl)methyl)pyrrolidin-1-yl)ethyl)urea (F730)(202)

The crude product was purified by flash chromatography (EtOAc/MeOH) to afford the amide protected (19 mg, 36%) Rf=0.26 (EtOAc/MeOH 95/5). $^1$H NMR (300 MHz, $CDCl_3$) δ 7.51 (s, 1H), 7.27-7.09 (m, 6H), 6.96-6.83 (m, 3H), 6.44 (s, 1H), 5.57-5.46 (m, 1H), 5.20-5.12 (m, 3H), 4.60-4.45 (m, 1H), 4.44-4.33 (m, 1H), 4.26 (d, J=5.6 Hz, 2H), 4.22-4.09 (m, 1H), 3.89-3.80 (m, 2H), 3.25-3.09 (m, 1H), 3.05-2.89 (m, 1H), 1.91-1.61 (m, 4H), 1.44 (s, 9H). The amide was deprotected and purified on reverse phase ($H_2O$/MeCN) to afford the amine (7.2 mg, 45%) Rf=0.11 (EtOAc/MeOH 95/5). HPLC method A tr=9.02 nm (98.2%). ESI-MS m/z: 464.3 [M+H]$^+$.

Example 169

1-(4-aminobenzyl)-3-(2-((2R)-2-(4-(2-(3-chlorophenoxy)-1-hydroxyethyl)-1H-1,2,3-triazol-1-yl)methyl)pyrrolidin-1-yl)-2-oxoethyl)urea (F731)(203)

The crude product was purified by flash chromatography (EtOAc/MeOH) to afford the amide protected (21 mg, 36%) Rf=0.37 (EtOAc/MeOH 95/5). $^1$H NMR (300 MHz, $CDCl_3$) δ 7.66-7.56 (m, 1H), 7.32-7.10 (m, 5H), 6.98-6.86 (m, 2H), 6.81 (m, 1H), 6.65 (s, 1H), 5.88-5.74 (m, 1H), 5.67-5.54 (m, 1H), 5.34-5.16 (m, 1H), 4.72-3.91 (m, 8H), 3.78-3.63 (m, 1H), 3.35-3.19 (m, 1H), 3.18-3.01 (m, 1H), 2.03-1.54 (m, 4H), 1.49 (s, 9H). The amide was deprotected and purified on reverse phase ($H_2O$/MeCN) to afford the amine (9.3 mg, 52%) Rf=0.08 (EtOAc/MeOH 95/5). HPLC method A tr=9.72 nm (98.7%). ESI-MS m/z: 528.3/530.3 [M+H]$^+$.

Example 170

(R)-1-(4-aminobenzyl)-3-(2-(24(4-(benzyloxymethyl)-1H-1,2,3-triazol-1-yl)methyl)pyrrolidin-1-yl)-2-oxoethyl)urea (F732)(204)

The crude product was purified by flash chromatography (EtOAc/MeOH) to afford the amide protected (23 mg, 43%) Rf=0.26 (EtOAc/MeOH 95/5). $^1$H NMR (300 MHz, $CDCl_3$): 7.43 (s, 1H), 7.25-7.13 (m, 7H), 7.09 (d, J=8.5 Hz, 2H), 6.68 (broad s, 1H), 5.95-5.85 (m, 1H), 5.67 (t, J=5.4 Hz, 1H), 4.57 (s, 2H), 4.51 (s, 2H), 4.47-4.14 (m, 4H), 4.11-4.00 (m, 1H), 3.91-3.83 (m, 2H), 3.30-3.07 (m, 2H), 2.05-1.57 (m, 4H), 1.40 (s, afford the amine (8.2 mg, 43%). HPLC method A tr=8.50 nm (95.8%). ESI-MS m/z: 478.3 [M+H]$^+$.

Example 171

(R)-1-(4-aminobenzyl)-3-(2-(24(4-benzyl-1H-1,2,3-triazol-1-yl)methyl)pyrrolidin-1-yl)-2-oxoethyl)urea (F733)(205)

The crude product was purified by flash chromatography (EtOAc/MeOH) to afford the amide protected (8.5 mg, 17%) Rf=0.17 (EtOAc/MeOH 95/5). The amide was deprotected and purified on reverse phase ($H_2O$/MeCN) to afford the amine (1.4 mg, 52%) Rf=0.11 (EtOAc/MeOH 95/5). HPLC method A tr=8.31 nm (96.8%). ESI-MS m/z: 448.3 [M+H]$^+$.

Example 172

(R)-1-(4-aminobenzyl)-3-(2-(2-((4-((4-(3-chlorophenyl) piperazin-1-yl)methyl)-1H-1,2,3-triazol-1-yl)methyl)pyrrolidin-1-yl)-2-oxoethyl) urea (F734) (206)

1-(3(chlorophenyl)piperazine hydrochloride (1 equivalent, 200 mg, 0.86 mmol), propargyl bromide (1 equivalent, 102 mg, 0.86 mmol), $K_2CO_3$ (3 equivalent, 356 mg, 3 mmol) were dissolved in 4 ml of DMF. The reaction mixture was stirred at 90° C. overnight (TLC control). The mixture was washed by 60 ml of $NaHCO_3$, extracted by 3×30 ml EtOAc. The organic phase was dried over $Na_2SO_4$, filtered and concentrated. The crude was purified by flash chromatography (EDP/EtOAc) to afford the compound (150 mg, 63%) as a colourless oil, Rf=0.37 (EDP/EtOAc 70/30). $^1$H NMR (300 MHz, CDCl$_3$): δ 7.16 (t, J=8.1 Hz, 1H), 6.92-6.85 (m, 1H), 6.85-6.75 (m, 2H), 3.35 (d, J=2.4 Hz 2H), 3.29-3.18 (m, 4H), 2.72 (m, 4H), 2.28 (t, J=2.4 Hz, 1H). The product was put in reaction as the general description. The crude product was purified by flash chromatography (EtOAc/MeOH) to afford the amide protected (54 mg, 87%) Rf=0.11 (EtOAc/MeOH 95/5). $^1$H NMR (300 MHz, CDCl$_3$) δ 7.52 (s, 1H), 7.29 (d, J=8.6 Hz, 2H), 7.21 (d, J=8.7 Hz, 2H), 7.14 (t, J=8.1 Hz, 1H), 6.87-6.82 (m, 1H), 6.82-6.72 (m, 2H), 6.54 (s, 1H), 5.58-5.50 (m, 1H), 5.22-5.11 (m, 1H), 4.66-4.55 (m, 1H), 4.52-4.41 (m, 1H), 4.37-4.24 (m, 3H), 4.03-3.93 (m, 2H), 3.74 (s, 2H), 3.40-3.22 (m, 2H), 3.22-3.15 (m, 4H), 2.71-2.60 (m, 4H), 2.02-1.54 (m, 4H), 1.50 (s, 9H). The amide was deprotected and purified on reverse phase ($H_2O$/MeCN) to afford the amine (25 mg, 54%) Rf=0.44 (MeOH). HPLC method A tr=8.27 nm (92.3%). ESI-MS m/z: 566.4/568.4 [M+H]$^+$.

Example 173

(R)-1-(4-aminobenzyl)-3-(2-oxo-2-(2-((4-((4-phenylpiperazin-1-yl)methyl)-1H-1,2,3-triazol-1-yl)methyl)pyrrolidin-1-yl)ethyl)urea (F735)(207)

1-phenylpiperazine (1 equivalent, 200 mg, 1.26 mmol), propargyl bromide (1 equivalent, 147 mg, 1.23 mmol), $K_2CO_3$ (3 equivalent, 510 mg, 3.69 mmol) were dissolved in 4 ml of DMF. The reaction mixture was stirred at 90° C. overnight (TLC control). The mixture was washed by 60 ml of $NaHCO_3$, extracted by 3×30 ml EtOAc. The organic phase was dried over $Na_2SO_4$, filtered and concentrated. The crude was purified by flash chromatography (EDP/EtOAc) to afford the compound (205 mg, 82%) as a white solid, Rf=0.32 (EDP/EtOAc 70/30). $^1$H NMR (300 MHz, CDCl$_3$): δ 7.33-7.24 (m, 2H), 6.96 (d, J=7.8 Hz, 2H), 6.88 (t, J=7.3 Hz, 1H), 3.38 (d, J=2.4 Hz, 2H), 3.29-3.22 (m, 4H), 2.80-2.71 (m, 4H), 2.30 (t, J=2.4 Hz, 1H). The product was put in reaction as the general description. The crude product was purified by flash chromatography (EtOAc/MeOH) to afford the amide protected (50 mg, 85%) Rf=0.1 (EtOAc/MeOH 95/5). $^1$H NMR (300 MHz, CDCl$_3$) δ 7.52 (s, 1H), 7.29 (d, J=8.7 Hz, 2H), 7.25-7.23 (m, 1H), 7.23-7.18 (m, 3H), 6.90 (d, J=7.9 Hz, 2H), 6.84 (t, J=7.3 Hz, 1H), 6.54 (s, 1H), 5.60-5.51 (m, 1H), 5.22-5.10 (m, 1H), 4.66-4.54 (m, 1H), 4.51-4.41 (m, 1H), 4.35-4.26 (m, 3H), 3.97 (t, J=4.6 Hz, 2H), 3.78-3.73 (m, 2H), 3.40-3.23 (m, 2H), 3.22-3.15 (m, 4H), 2.74-2.60 (m, 4H), 2.01-1.57 (m, 4H), 1.50 (s, 9H). The amide was deprotected and purified on reverse phase ($H_2O$/MeCN) to afford the amine (12.4 mg, 30%) Rf=0.58 (MeOH). HPLC method A tr=7.13 nm (100%). ESI-MS m/z: 532.4 [M+H]$^+$.

Example 174

(R)-1-(4-aminobenzyl)-3-(2-(2-((4-(hydroxymethyl)-1H-1,2,3-triazol-1-yl)methyl)pyrrolidin-1-yl)-2-oxoethyl)urea (F736)(208)

The crude product was purified by flash chromatography (EtOAc/MeOH) to afford the amide protected (22 mg, 49%) Rf=0.16 (EtOAc/MeOH 95/5). $^1$H NMR (300 MHz, CDCl$_3$) δ 7.39 (s, 1H), 7.21 (d, J=8.5 Hz, 2H), 7.13 (d, J=8.5 Hz, 2H), 6.82-6.64 (m, 1H), 5.92-5.79 (m, 1H), 5.79-5.66 (m, 1H), 4.67 (s, 2H), 4.56-4.42 (m, 1H), 4.33-4.10 (m, 4H), 4.01-3.89 (m, 1H), 3.75-3.62 (m, 1H), 3.30-3.16 (m, 1H), 3.15-3.01 (m, 1H), 1.94-1.59 (m, 4H), 1.43 (s, 9H). The amide was deprotected and purified on reverse phase ($H_2O$/MeCN) to afford the amine (11.3 mg, 42%) Rf=0.36 (MeOH). HPLC method A tr=6.51 nm (100%). ESI-MS m/z: 388.3 [M+H]$^+$.

B—Biological Results

B.1. Cyclophilin Expression and Purification

Expression and Purification of the Protein Cyclophilin A and B:

Cyclophilin A, B protein carrying a hexahistidine tag (His-Tag) at the C-terminus, were expressed in *Escherichia coli* and purified. Briefly, cultures of C41(DE3) cells were grown at 37° C. for ~1 h until the culture reached an optical density of 0.6 at 600 nm, and induced with 1 mM isopropyl β-D-thiogalactoside for 4 h at 37° C. or overnight at 22° C. for cylophilin A and cyclophilin B, respectively. Cell pellets (1 L) were resuspended in a lysis buffer (20 mM $NaH_2PO_4$ (pH 7.8), 300 mM NaCl, 7 mM β-mercaptoethanol, 1 mg/ml lysozyme, 0.1 U/µl Desoxyribonuclease and complete protease inhibitor tablets (Roche)). The sonicated cell lysates were clarified by centrifugation at 10 000 g for 45 min at 4° C., chromatographed on a Ni-NTA column and washed with buffer: (20 mM $NaH_2PO_4$ (pH7.8), 300 mM NaCl, 50 mM imidazole, 7 mM β-mercaptoethanol, 10% glycerol). The bound protein was eluted in 1 ml fractions with buffer: (20 mM $NaH_2PO_4$ (pH7.8), 300 mM NaCl, 250 mM imidazole, 7 mM β-mercaptoethanol, 10% glycerol) and monitored by the Bradford colorimetric assay. The purity of each cyclophilin was determined by Coomassie-stained SDS-PAGE analysis. Fractions enriched in cyclophilin (>95% purity) were pooled and dialysed against buffer: (20 mM $NaH_2PO_4$ (pH7.8), 300 mM NaCl, 1 mM DTT, 1 mM EDTA, 10% glycerol).

Expression and Purification of the Protein Cyclophilin D(K133I):

The protein was expressed in *E. coli* strain BL21(DE3). Bacteria were grown in LB medium at 37° C. and induced during 2 h with isopropyl-β-D-thiogalactopyranoside (IPTG) around OD 0.8. Cells were lysed by sonication in a buffer consisting of 50 mM Tris at pH 7.5, 2 mM EDTA and 2 mM β-mercaptoethanol (buffer A). The lysate was centrifuged at 40000 g for 30 min. The supernatant was loaded on a Q-Sepharose and S-Sepharose columns in series equilibrated with buffer A. The S-Sepharose column was washed with equilibrium buffer and bound proteins were eluted with a linear gradient from 0 to 1M NaCl. The combined peak fractions were loaded on a 575 column equilibrated with 20 mM Tris at pH 7.5, 200 mM NaCl, 2 mM EDTA and 1 mM dithiothreitol. This two-step purification protocol was sufficient to obtain pure protein.

To achieve the $^{15}$N labelling for the NMR experiment, bacteria were grown in M9 medium and $^{15}$N-labeled ammonium chloride was present as the sole nitrogen source. The protein was purified as describe above.

Cyclophilin Enzymatic Assay

Cyclophilin PPlase activity was measured at 20° C. by using the standard chymotrypsin coupled assay (Kofron J L, Kuzmic P, Kishore V, Colon-Bonilla E, Rich D H. Determination of kinetic constants for peptidyl prolyl cis-trans isomerases by an improved spectrophotometric assay. Biochemistry. 1991 Jun. 25; 30(25):6127-34). The assay buffer (25 mM Hepes, 100 mM NaCl, pH 7.8) and CypA, B or D (1900 nM stock solution) were pre-cooled to 4° C., to which then was added 5 µL of 50 mg/ml chymotrypsin in 1 mM HCl. The reaction was initiated by adding 20 µL of 3.2 mM peptide substrate (Suc-Ala-Ala-cis-Pro-Phe-pNA) in LiCl/TFE solution with rapid inversion. After a delay from the onset of mixing, the absorbance of p-nitroaniline was followed at 390 nM until the reaction was complete (1 min). The final concentration of LiCl in the assay was 20 mM; TFE was present at a concentration of 4% (v/v). Absorbance readings were collected every 1 s by spectrophotometer. The inhibition assays of compounds were performed in the same manner as mentioned above. A 5 µL aliquot of the compounds in DMSO was added to the cyclophilin solution in the assay buffer. The assay was started by the addition of the substrate. Cyclosporine A was used as control in all measurement. The percentage inhibition of cyclophilin PPiase activity were calculated from slopes and values obtained represent an average of at least two independent measurements. The mean of +/−SD were <10%.

Assessment Of Antiviral Activity in the Replicon Model

The genotype 1b bicistronic replicon was transfected in Huh7 cells (Krieger, N., V. Lohman, and R Bartenschlager. 2001. J. Virol. 75:4614-4624) grown in Dulbecco's modified Eagle's Medium Glutamax II (Invitrogen, Carlsbad, Calif.) supplemented with 10% fetal bovine serum, 50 IU/mL penicillin, 100 µg/mL streptomycin, 0.1 µg/mL fungizone and 600 µg/mL Geneticin (G418, Invitrogen).

HCV replicon harboring cells were seeded at a low density of 5000 cells per well in 96-well plates. The cells were treated with increasing concentrations of the tested compounds in Dulbecco modified Eagle medium containing 10% fetal bovine serum and 1% DMSO without G418 and cultured for 3 days. Total RNA was extracted using the RNeasy 96 kit (Qiagen). HCV RNA levels were measured by means of a quantitative real-time polymerase chain reaction assay using the Taqman technology with HCV-specific primers (sense 5'-CGCCCAAACCAGAATACGA-3' and antisense 5'-AGATAGTACACCCTTTTGCCAGATG-3' SEQ ID NO: 1 and SEQ ID NO: 2) and probe (5'-6-FAM-CAATGTGT-CAGTCGCG-TAMRA-3' SEQ ID NO: 3) on an ABI 7003 device (Applied Biosystems, Foster City, Calif.). HCV RNA levels were measured by means of Nanodrop 1000 spectrophotometer (Nanodrop Technologies, Wilmington, Del.). The results were normalized to GAPDH gene. Each data point represents the average of at least three replicates in cell culture. HCV RNA level reductions after treatment were assessed by comparing the level of HCV RNA in compound-treated cells to that of control cells treated with 1% DMSO.

Assessment of Antiviral Activity in the JFH1 Infection Model in Cell Culture

Plasmid pJFH1, containing the full-length cDNA of the JFH1 HCV genotype 2a isolate and the *Renilla luciferase* gene, was used to generate infectious HCV particles (HCVcc) in Huh7 cell culture, as previously described (Wakita T, Pietschmann T, Kato T, Date T, Miyamoto M, Zhao Z, Murthy K, Habermann A, Krausslich H G, Mizokami M, Bartenschlager R, Liang T J. Production of infectious hepatitis C virus in tissue culture from a cloned viral genome. Nat Med 2005; 11:791-6) Huh7 cells were seeded in 24-well plates at a density of 30,000-50,000 cells/well and infected 24 h later with 200 µl of HCVcc for 2 h at 37° C. After incubation, the supernatants were removed and JFH1-infected cells were washed with fresh medium. Increasing concentrations of the tested compounds were added in a medium containing 2% DMSO, and cells were incubated at 37° C. At 44 h post-infection, cells were washed once with Dulbecco's PBS (Invitrogen) and 100 µl *Renilla* lysis buffer (Promega, Madison, Wis.) was added to each well. Lysates were frozen at −80° C. The frozen samples were thawed for reading in one batch and 20 µl was mixed with luciferase assay substrate as specified by the manufacturer (Promega). Luciferase activity was measured for 10 s in a luminometer.

Assessment of Compound Cytotoxicity

Huh7 and HEK293 cells were seeded at a density of 2000 and 1000 cells per well, respectively, in 96-well microliter plates in DMEM glutamax-II-10% FBS. Twenty-four hours later, serial dilutions of the tested compounds were added. Cells were allowed to proliferate for 3 days at 37° C. Cell viability was then assessed with a 3-(4,5-dimethylthiazol-2-yl)-2,5-diphenyltetrazolium bromide colorimetric assay as previously described (Mosmann T. Rapid colorimetric assay for cellular growth and survival: application to proliferation and cytotoxicity assays. J Immunol Methods 1983; 65:55-63).

Acute Toxicity in Mice

The acute toxicity of F684 was evaluated in mice. In this study, female mice (n=3/group) were administered with the negative control (PBS) or F684 (1 mg/kg, 10 mg/kg, 50 mg/kg and 150 mg/kg of body weight dissolved in PBS), one time by intraperitonal injection. At the time of injection, animals were approximately 5 month old and body weights ranged from 27 to 33 g. All animals survived to scheduled sacrifice. No differences in body weights, feed consumption, clinical observations or gross organ necropsy were observed between mice administered with F684 or the vehicle control groups. These results indicate that F684 is not acutely toxic.

Results

Inhibition of Cyclophilin A (CypA)

The below results indicate the activity test at 100 µM on CypA.

| | Compounds | | | | | | | | |
|---|---|---|---|---|---|---|---|---|---|
| | F428 | F537 | F538 | F540 | F542 | F543 | F544 | F545 | F547 |
| Inhibition (%) | 77.0 | 33.4 | 15.5 | 32.6 | 60.1 | 27.7 | 12.2 | 49.2 | 22.5 |
| SD (%) | 3.3 | 5.1 | 2.2 | 1.8 | 5.9 | 0.5 | 1.0 | 0.2 | 2.9 |

| Compounds | | | | | | | | |
|---|---|---|---|---|---|---|---|---|
| | F549 | F554 | F555 | F557 | F606 | F608 | F609 | F611 | F612 |
| Inhibition (%) | 14.8 | 67.2 | 65.1 | 63.4 | 18.9 | 26.3 | 100.0 | 72.8 | 26.3 |
| SD (%) | 1.8 | 3.7 | 6.1 | 0.2 | 7.6 | 7.3 | 0.3 | 2.2 | 2.0 |

Inhibition of Cyclophilin B (CypB)

The below results indicate the activity test at 100 μM on CypB.

| Compounds | | | | | | | | |
|---|---|---|---|---|---|---|---|---|
| | F428 | F490 | F494 | F512 | F513 | F514 | F515 | F517 |
| Inhibition (%) | 83.6 | 33.1 | 22.7 | 16.6 | 23.3 | 19.5 | 18.2 | 20.0 |
| SD (%) | 0.0 | 10.4 | 2.6 | 1.4 | 0.6 | 0.0 | 4.5 | 9.1 |

| Compounds | | | | | | | | |
|---|---|---|---|---|---|---|---|---|
| | F520 | F524 | F525 | F526 | F528 | F536 | F537 | F542 |
| Inhibition (%) | 18.9 | 15.4 | 21.6 | 21.2 | 38.9 | 47.6 | 24.5 | 58.5 |
| SD (%) | 6.6 | 6.7 | 1.0 | 12.5 | 4.4 | 3.1 | 3.6 | 2.6 |

| Compounds | | | | | | | | |
|---|---|---|---|---|---|---|---|---|
| | F543 | F544 | F545 | F547 | F548 | F549 | F551 | F554 |
| Inhibition (%) | 37.5 | 26.0 | 65.7 | 15.2 | 20.8 | 48.9 | 20.8 | 70.9 |
| SD (%) | 1.5 | 2.6 | 9.1 | 3.6 | 0.0 | 5.4 | 3.6 | 9.5 |

| Compounds | | | | | | | | |
|---|---|---|---|---|---|---|---|---|
| | F555 | F557 | F558 | F559 | F561 | F562 | F563 | F565 | F566 |
| Inhibition (%) | 73.8 | 76.0 | 25.9 | 21.9 | 15.1 | 28.0 | 16.4 | 34.5 | 26.5 |
| SD (%) | 3.5 | 6.6 | 7.2 | 2.0 | 3.5 | 4.1 | 0.0 | 0.0 | 2.1 |

| Compounds | | | | | | | | |
|---|---|---|---|---|---|---|---|---|
| | F569 | F572 | F576 | F577 | F585 | F586 | F587 | F588 |
| Inhibition (%) | 17.1 | 27.6 | 18.4 | 47.3 | 35.0 | 38.4 | 99.0 | 23.2 |
| SD (%) | 23.7 | 9.5 | 5.1 | 7.2 | 0.6 | 9.9 | 4.5 | 0.8 |

| Compounds | | | | | | | |
|---|---|---|---|---|---|---|---|
| | F590 | F592 | F593 | F594 | F595 | F596 | F597 | F599 |
| Inhibition (%) | 18.2 | 18.9 | 23.4 | 37.0 | 29.1 | 19.8 | 46.3 | 71.8 |
| SD (%) | 4.0 | 5.2 | 6.0 | 2.8 | 2.8 | 8.8 | 3.8 | 3.0 |

| Compounds | | | | | | | |
|---|---|---|---|---|---|---|---|
| | F600 | F606 | F607 | F608 | F609 | F611 | F612 |
| Inhibition (%) | 65.8 | 17.3 | 95.3 | 38.7 | 100.9 | 73.3 | 26.7 |
| SD (%) | 5.0 | 4.2 | 4.3 | 5.3 | 3.7 | 7.4 | 2.5 |

Inhibition of Cyclophilin D (CypD)

The below results indicate the activity test at 100 μM on CypD.

| Compounds | F428 | F509 | F511 | F512 | F548 | F549 | F554 | F555 | F557 | F566 |
|---|---|---|---|---|---|---|---|---|---|---|
| Inhibition (%) | 88.9 | 18.3 | 12.9 | 26.5 | 25.5 | 24.5 | 20.9 | 26.1 | 42.9 | 22.7 |
| SD (%) | — | 9.3 | 14.7 | 7.1 | 3.9 | 1.0 | 4.2 | 5.1 | 7.9 | 6.0 |

The below result indicate the activity test at 1 mM on CypD.

| Compounds | F429 |
|---|---|
| Inhibition (%) | 42.1 |
| SD (%) | — |

Inhibition of Cyclophilin A, B and D (CypA, CypB and CypD)

The below results indicate the IC$_{50}$ on CypA, CypB and CypD.

| | CypA | | CypB | | CypD | |
|---|---|---|---|---|---|---|
| Compounds | IC$_{50}$ (μM) | SD (μM) | IC$_{50}$ (μM) | SD (μM) | IC$_{50}$ (μM) | SD (μM) |
| F428 | 16.8 | 8.8 | 6.1 | 3.8 | 6.2 | 4.7 |
| F542 | n.d. | n.d. | 36.6 | 22.9 | n.d. | n.d. |
| F545 | n.d. | n.d. | 75.1 | 23.7 | n.d. | n.d. |
| F554 | n.d. | n.d. | 24.6 | 10.2 | n.d. | n.d. |
| F555 | n.d. | n.d. | 27.8 | 16.3 | n.d. | n.d. |
| F557 | n.d. | n.d. | 44.5 | n.d. | n.d. | n.d. |
| F587 | n.d. | n.d. | 5.2 | 2.5 | n.d. | n.d. |
| F607 | 9.0 | 6.9 | 4.8 | 2.2 | 30.0 | 8.0 |
| F609 | 2.8 | 0.6 | 1.2 | 0.1 | 11.4 | 3.0 |
| F671 | 1.5 | 0.4 | n.d. | n.d. | 1.8 | 0.2 |
| F673 | 3.4 | 0.7 | n.d. | n.d. | 6.2 | 2.3 |
| F680 | 0.56 | 0.3 | 0.76 | 0.1 | 1.1 | 0.2 |
| F684 | 0.37 | 0.07 | 0.65 | 0.04 | 0.64 | 0.06 |
| F712 | 3.3 | 1.4 | n.d. | n.d. | 3.0 | 0.6 |

-continued

| Compounds | CypA IC$_{50}$ (μM) | CypA SD (μM) | CypB IC$_{50}$ (μM) | CypB SD (μM) | CypD IC$_{50}$ (μM) | CypD SD (μM) |
|---|---|---|---|---|---|---|
| F714 | 3.1 | 1.2 | n.d. | n.d. | 1.1 | 0.4 |
| F716 | 0.79 | 0.12 | n.d. | n.d. | 0.66 | 0.15 |

Inhibition of Virus Replication in the Replicon Model and JFH1 Model
The below results indicate the EC50 activity.

| Compounds | EC$_{50}$ replicon (μM) | EC$_{50}$ JFH1 (μM) |
|---|---|---|
| F428 | 12 | 37 |
| F609 | 20 | n.d. |
| F671 | 4.3 | n.d. |
| F680 | 3.1 | n.d. |
| F684 | 0.8 | n.d. |

The invention claimed is:

1. A compound having formula (I-bis):

(I-bis)

wherein:

$R_1$ is selected from the group consisting of H, alkyl groups, and aralkyl groups, said alkyl or aralkyl groups being possibly substituted;

$R_2$ is a group of formula $NR_3R_4$ or $OR_5$, wherein $R_3$ and $R_4$ are independently selected from the group consisting of H, $OR_a$, alkyl groups, aralkyl groups, and aryl groups, $R_a$ being selected from the group consisting of H, alkyl groups, aryl groups, and aralkyl groups, wherein $R_3$ and $R_4$ may form, together with the nitrogen atom carrying them, a heterocyclyl group comprising from 5 to 20 atoms, possibly substituted, and $R_5$ is selected from the group consisting of alkyl groups, aryl groups, and aralkyl groups, wherein $R_5$ may form together with the oxygen atom carrying it, a heterocyclyl group from 5 to 20 atoms, possibly substituted;

A is CH or N, or A is C and form, together with $R_1$ and $R_2$ and CO, a heterocyclyl group comprising from 5 to 20 atoms, possibly substituted;

X is CO, $SO_2$, or CS;

$R_6$ is H or an alkyl group, or may form together with $R_2$ a heterocyclyl group from 20 to 30 atoms, or may form together with $R_1$ a heterocyclyl group from 10 to 30 atoms; and $R_7$ is chosen from the group consisting of aryl groups and heteroaryl groups comprising 5 or 6 ring atoms, substituted by at least one $NH_2$ group, or their pharmaceutically acceptable salts, hydrates or hydrated salts or its polymorphic crystalline structures, racemates, diastereomers or enantiomers, with the exclusion of the following compounds:

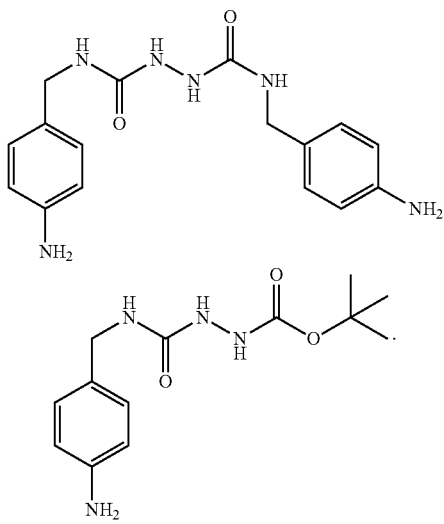

2. The compound of claim 1 having formula (I-ter):

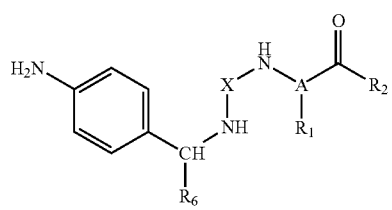
(I-ter)

wherein $R_1$, $R_2$, A, X and $R_6$ are as defined in claim 1, with the exclusion of the following compounds:

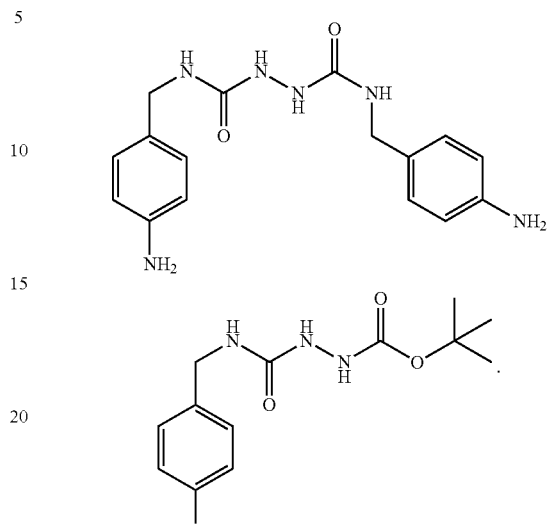

3. A pharmaceutical composition comprising the compound according to claim 1, in association with a pharmaceutically acceptable vehicle.

4. The pharmaceutical composition of claim 3, wherein said compound is the compound according to claim 2.

* * * * *

SEQUENCE LISTING

<160> NUMBER OF SEQ ID NOS: 3

<210> SEQ ID NO 1
<211> LENGTH: 19
<212> TYPE: DNA
<213> ORGANISM: Hepatitis C virus

<400> SEQUENCE: 1
cgcccaaacc agaatacga                    19

<210> SEQ ID NO 2
<211> LENGTH: 25
<212> TYPE: DNA
<213> ORGANISM: Hepatitis C virus

<400> SEQUENCE: 2
agatagtaca ccctttttgcc agatg             25

<210> SEQ ID NO 3
<211> LENGTH: 16
<212> TYPE: DNA
<213> ORGANISM: artificial sequence
<220> FEATURE:
<223> OTHER INFORMATION: probe

<400> SEQUENCE: 3
caatgtgtca gtcgcg                       16